United States Patent [19]
DeHaven-Hudkins et al.

[11] Patent Number: 5,631,264
[45] Date of Patent: May 20, 1997

[54] SUBSTITUTED 6,11-ETHANO-6,11-DIHYDROBENZO[B]QUINOLIZINIUM SALTS AND COMPOSITIONS AND METHODS OF USE THEREOF

[75] Inventors: Diane L. DeHaven-Hudkins, West Pikeland Township, Chester County; John A. Dority, Jr., Upper Providence Township, Montgomery County; William G. Earley, East Vincent Township, Chester County; Virendra Kumar, Tredyffrin Township, Chester County; John P. Mallamo, Uwchlan Township, Chester County; Matthew S. Miller, Lower Makefield Township, Bucks County; Chakrapani Subramanyam, Towamencin Township, Montgomery County, all of Pa.

[73] Assignee: Sanofi Winthrop, Inc., New York, N.Y.

[21] Appl. No.: 449,125

[22] Filed: May 24, 1995

Related U.S. Application Data

[60] Division of Ser. No. 283,317, Jul. 7, 1994, Pat. No. 5,554,620, which is a continuation-in-part of Ser. No. 121,127, Sep. 14, 1993, abandoned.

[51] Int. Cl.$^6$ .............. A61K 31/44; C07D 455/03; C07D 471/00
[52] U.S. Cl. .............. 514/289; 514/279; 514/281; 546/34; 546/35; 546/39; 546/40; 546/43; 546/44; 546/46; 546/72
[58] Field of Search .............. 546/72, 34, 35, 546/39, 40, 43, 44, 46; 514/286, 279, 281

[56] References Cited

U.S. PATENT DOCUMENTS 4,888,347  12/1989  Woodruff .............. 514/289

OTHER PUBLICATIONS

Cotman CW and Iversen L.L. (1987). TINS 10(7) 263–272.
Choi DW 1988) Neuron 1, 623–634.

*Primary Examiner*—C. Warren Ivy
*Assistant Examiner*—Evelyn Huang
*Attorney, Agent, or Firm*—Paul E. Dupont; William J. Davis

[57] ABSTRACT

Substituted 6,11-ethano-6,11-dihydrobenzo[b]quinolizinium salts, pharmaceutical compositions containing them, and methods for the treatment or prevention of neurodegenerative disorders or neurotoxic injuries utilizing them.

26 Claims, No Drawings

SUBSTITUTED 6,11-ETHANO-6,11-DIHYDROBENZO[B]QUINOLIZINIUM SALTS AND COMPOSITIONS AND METHODS OF USE THEREOF

CROSS REFERENCE TO RELATED APPLICATIONS

This application is a division of Ser. No. 08/283,317, filed on Jul. 7, 1994, U.S. Pat. No. 5,554,620, which in turn is a continuation-in-part of our prior application Ser. No. 08/121,127, filed Sep. 14, 1993, abandoned.

BACKGROUND OF THE INVENTION (a) Field of the Invention

The invention relates to substituted 6,11-ethano-6,11-dihydrobenzo-[b]quinolizinium salts, to pharmaceutical compositions containing the same and to the method of use thereof in the treatment or prevention of neurodegenerative disorders or neurotoxic injuries.

(b) Information Disclosure Statement

Fields, U.S. Pat. No. 3,517,073 issued Jun. 23, 1970, discloses compounds of the formula:

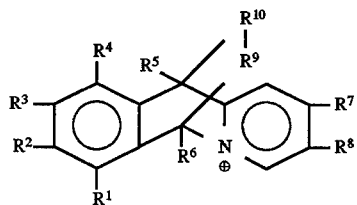

wherein each of $R^1$, $R^2$, $R^3$ and $R^4$ when taken separately, is hydrogen, lower alkyl, lower aryl, lower acyloxy, lower alkoxy, nitro, halogen, lower acylamino, di(lower alkyl) amino; one group of $R^1$ and $R^2$, $R^2$ and $R^3$, and $R^3$ and $R^4$, preferably $R^1$ and $R^2$, and $R^3$ and $R^4$, each group when taken together, represents a fused ring system containing up to three 6-member carbocyclic and nitrogen-containing heterocyclic rings at least one of which is an aromatic ring, and having no more than two nuclear nitrogens in any ring, which may be unsubstituted or substituted with one or more of the substituents defined by $R^1$, $R^2$, $R^3$ and $R^4$; each of $R^5$ and $R^6$, when taken separately is hydrogen, lower alkyl or lower aryl; each of $R^7$ and $R^8$, when taken separately, is hydrogen; $R^7$ and $R^8$, when taken together, represent a fused ring system as defined hereinbefore; $R^9$, when taken individually, is methylene or lower alkyl, lower aryl, lower alkenyl, halogen, or cyano substituted methylene; $R^{10}$, when taken individually, is a protected carbonyl group; $R^9$ and $R^{10}$, when taken together, represent a fused aromatic carboxcyclic or heterocyclic ring system, whose valence bonds are from adjacent carbons, containing up to three 6-membered carbocyclic and nitrogen-containing heterocyclic rings having no more than two nitrogens in any ring and which may be substituted with one or more of the substituents defined by $R^1$, $R^2$, $R^3$ and $R^4$. Among the compounds specifically disclosed are 12,12-diethoxy-11-methyl-9,10-ethano-9,10-dihydro-4a-azoniaanthracene perchlorate and 9,10-(O-benzeno)-9,10-dihydro-5-methyl-4a-azoniaanthracene perchlorate. Also disclosed are compounds of the formula:

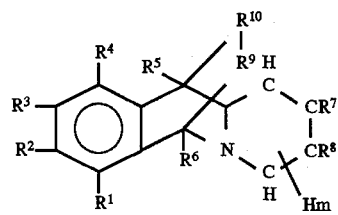

wherein $R^1$–$R^{10}$ are as defined above and m is an odd integer having a value of from 1 to 5, inclusive. Among the compounds specifically disclosed are 12,12-diethoxy-11-methyl-9,10-ethano-4a-aza-1,2,3,4,4a,9,9a,10-octahydroanthracene perchlorate acid salt, 9,10-(O-benzeno)-5-methyl-4a-aza-1,2,3,4,4a,9,9a,10-octahydroanthracene and 12,12-diethoxy-9,10-ethano-11-bromo-4a-aza-1,2,3,4,4a,9,9a,10-octahydroanthracene. The above-described compounds are disclosed as being intermediates in the synthesis of 2-napthol derivatives and various anthracene derivatives.

Fields et al., J. Org. Chem. 1968, 33(1), 390–395, disclose a series of sixteen Diels-Alder adducts prepared from a 4a-azoniaanthracene ion and various dienophiles. Among the compounds specifically disclosed are 12-ethyl,12-hydroxymethyl and 12-ethylene-9,10-dihydro-4a-azonia-9,10-ethanoanthracene bromides; 12-phenyl-12-(4-morpholinyl), 12-methyl-12-(1-methylethylene), 12,12-diethoxy-11-bromo and 12-diethylamino-11-phenyl-9,10-dihydro-4a-azonia-9,10-ethanoanthracene perchlorates, as well as 9,10[1',2'-]cyclopentyl and 9,10[2',3']-tetrahydropyranyl-9,10-dihydro-4a-azoniaanthracene perchlorates. No utility is disclosed for these compounds.

Fields and Regan, J. Org. Chem. 1971, 36(20), 2986–2990, disclose compounds of the formula:

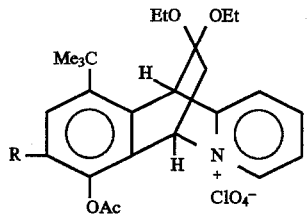

wherein R is H, Br, or OAc, as intermediates in the synthesis of substituted 8-tert-butyl-1-(2-pyridyl)napthalenes.

Fields and Regan, J. Org. Chem. 1971, 36(20), 2991–2994, disclose compounds of the formula:

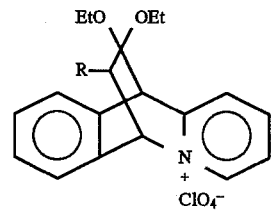

wherein R is H, $CH_3$, $C_6H_5$, or Br, as intermediates in the synthesis of 2-pyridylnapthols.

Fields, J. Org. Chem. 1971, 36(20), 3002–3005, discloses a series of substituted 12,12-diethoxy-9,10-ethano-9,10-dihydro-4a-azoniaanthracenes and the corresponding derivatives wherein the pyridinium moiety is partially or completely reduced, as intermediates in the synthesis of substituted 2-napthols. Among the compounds specifically disclosed is 12,12-diethoxy-5,11-dimethyl-9,10-ethano-9,10-dihydro-4a-azoniaanthracene perchlorate. Also disclosed is a series of substituted 9,10-(O-benzeno)-9,10-dihydro-4a-azoniaanthracenes and the corresponding derivatives wherein the pyridinium moiety is partially or completely reduced, as intermediates in the synthesis of substituted anthracenes. Among the compounds specifically disclosed is 9,10-(O-benzeno)-9,10-dihydro-4a-azoniaanthracene perchlorate.

Westerman and Bradsher, J. Org. Chem. 1971, 36(7), 969–970, disclose compounds of the formula:

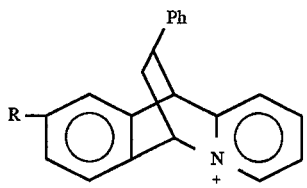

wherein R is CH$_3$, CH(CH$_3$)$_2$, H, F, I, Cl, Br, CO$_2$H, CO2CH$_3$, or NO$_2$. No utility is disclosed for these compounds.

Bradsher and Day, J. Het. Chem. 1973, 10, 1031–1033, disclose four Diels-Alder adducts prepared from acridizinium perchlorate and cyclopentadiene, methyl vinyl ether, norbornadiene and maleic anhydride. No utility is disclosed for these compounds.

Fields and Regan, J. Org. Chem. 1970, 35(6), 1870–1875, disclose compounds of the formula:

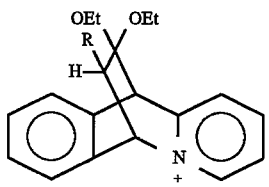

wherein R is H, CH$_3$ or C$_6$H$_5$. Also specifically disclosed are 9,10-dihydro-12,12-dimethoxy-11,11-dimethyl-4a-azonia-9,10-ethanoanthracene perchlorate and 9,10-dihydro-9,11-dimethyl-12,12-diethoxy-4a-azonia-9,10-ethanoanthracene perchlorate. The compounds are said to be intermediates in the synthesis of 9,10-dihydro-12-oxo-4a-azonia-9,10-ethanoanthracenes.

Fields et al., J. Org. Chem. 1971, 36(20), 2995–3001, disclose 9,10-dihydro-4a-azonia-9,10-O-benzenoanthracene perchlorate and several analogs as intermediates in the synthesis of various 9-(2-pyridyl)anthracenes.

Fields and Miller, J. Het. Chem. 1970, 7, 91–97, disclose a compound of the formula:

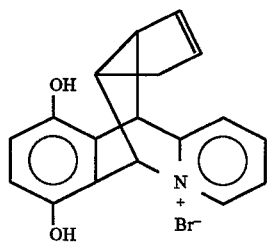

as an intermediate in the synthesis of the corresponding 5,8-dione salt.

Bradsher and Stone, J. Org. Chem. 1968, 33(2), 519–523, disclose a series of Diels-Alder adducts prepared from an acridizinium ion and maleic anhydride, maleate esters, fumarate esters and various para-substituted styrenes in which the para substituent is H, CH$_3$, OCH$_3$ or NO$_2$. No utility is disclosed for these compounds. A substantially similar disclosure for the preparation of Diels-Alder adducts from acridizinium bromide and maleic anhydride, maleate or fumarate esters can be found in Bradsher and Solomons, J. Am. Chem. Soc. 1958, 80, 933–934.

Bradsher and Stone, J. Org. Chem. 1969, 34(6), 1700–1702, disclose compounds of the formula:

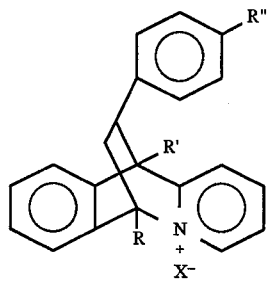

wherein R is H, or CH$_3$; R' is H, or CH$_3$; R" is OCH$_3$, CH$_3$, H, or NO$_2$; and X— is perchlorate; without an indication of utility. Also disclosed are the Diels-Alder adducts obtained from acridizinium perchlorate and diethyl maleate, diethyl fumarate or dimethyl maleate, without an indication of utility.

Burnham and Bradsher, J. Org. Chem. 1972, 37(3), 355–358, disclose compounds of the formula:

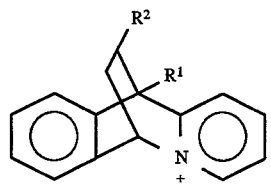

wherein R$^1$ is Ph, and R$^2$ is OEt; or R$^1$ is H, and R$^2$ is OEt, OBu, OAc, N-carbazolyl or 1-pyrrolidin-2-one, without an indication of utility Parham et at., J. Org. Chem. 1972, 37(3), 358–362, disclose compounds of the formula:

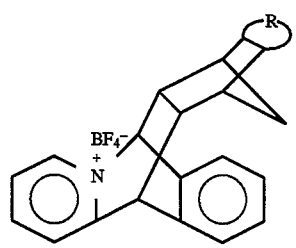

wherein R is H$_2$, (CH$_2$)$_3$, C(O)NHC(O), C(O)N(CH$_3$)C(O), C(O)OC(O), CH$_2$OCH$_2$, or CH$_2$NH$_2$+CH$_2$, without an indication of utility.

Bradsher et al., J. Am. Chem. Soc. 1977, 99(8), 2588–2591, disclose compounds of the formula:

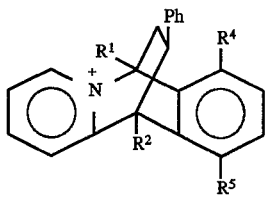

wherein: $R^1=R^2=R^4=R^5=H$; $R^1=Me$, and $R^2=R^4=R^5=H$; $R^1=R^4=R^5=H$, and $R^2=Me$; and $R^1=H$, and $R^2=R^4=R^5=Me$. No utility is disclosed for these compounds.

Bradsher et al., J. Org. Chem. 1978, 43(5), 822–827, disclose compounds of the formula:

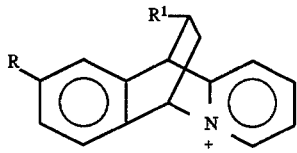

wherein: $R^1$ is OEt and R is Me, H, F, Cl, $CO_2Me$ or $NO_2$; $R^1$ is O—Ph—p—X, wherein X is $CH_3$, $OCH_3$, H, C(O)$CH_3$, or $NO_2$, and R is hydrogen; and $R^1$ is N-carbazolyl and R is hydrogen. No utility is disclosed for these compounds.

Westerman and Bradsher, J. Org. Chem. 1978, 43(15), 3002–3006, disclose a series of Diels-Alder adducts prepared from an acridizinium ion and various unsymmetrical alkenes, without an indication of utility. Among the compounds specifically disclosed are 6,11[2',3']indanyl-6,11-dihydroacridizinium tetrafluoroborate, and 12-phenyl-13-(2-pyridyl)-6,11-dihydro-6,11-ethanoacridizinium tetrafluoroborate.

Westerman and Bradsher, J. Org. Chem. 1979, 44(5), 727–733, disclose a series of Diels-Alder adducts prepared from a substituted or unsubstituted acridizinium cation and various polarizable alkenes without an indication of utility. Among the compounds specifically disclosed are 12,12-diphenyl-6,11-dihydro-6,11-ethanoacridizinium perchlorate or bromide, 9-methyl-6,11[2',3']indanyl-6,11-dihydroacridizinium tetrafluoroborate, and 7,10-dimethyl-12-phenyl-12-(4-morpholinyl), 9-methyl-12-phenyl-12-(4-morpholinyl), 12-(2-pyridyl), and 9-methyl-12-(2-pyridyl)-6,11-dihydro-6,11-ethanoacridizinium tetrafluoroborates.

Bradsher et al., J. Org. Chem. 1979, 44(8), 1199–1201, disclose a series of Diels-Alder adducts prepared from a substituted or unsubstituted acridizinium ion and cyclopropene or 1-methylcyclopropene, without an indication of utility. Hart et al., Tetrahedron Letters 1975, 52, 4639–4642, disclose a compound of the formula:

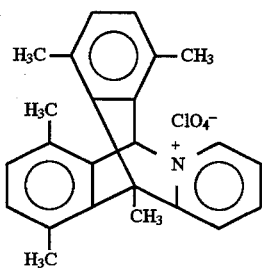

as an intermediate in the synthesis of 1,4,5,8,9-pentamethylanthracene.

SUMMARY OF THE INVENTION

The invention relates to compounds of the Formula I:

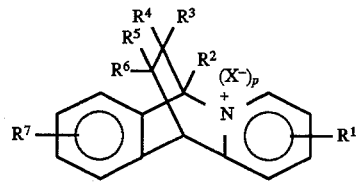

$R^1$ is hydrogen, or from one to four, the same or different, substituents in any of the 1-,2-,3- or 4-positions selected from the group consisting of lower-alkoxy, lower-alkyl, halogen, hydroxy, OC(O) alkyl-CH═CH-alkyl, OC(O) alkyl, OC(O)-lower-alkenyl-C(O)Oalkyl, alkoxy, OC(O) alkylC(O)Oalkyl, hydroxymethyl, nitro, amino and lower-alkylsulfonylamino or $R^1$ is a fused benzene ring;

$R^2$ is hydrogen, lower-alkyl, cyano or lower-alkoxycarbonyl;

$R^3$ and $R^4$ are independently hydrogen, or lower-alkyl; or $R^3$ and $R^4$ together form a cycloalkyl ring, or a lower-alkylidene group;

$R^5$ and $R^6$ are independently phenyl (or phenyl substituted by lower-alkoxy, halogen, lower-alkyl, polyfluorolower-alkyl, lower-alkoxyphenyl-lower-alkyl-N(lower-alkylsulfonyl)-, hydroxy, or polychlorolower-alkyl), a 5- or 6-membered monocyclic or 9- or 10-membered bicyclic aromatic heterocyclic ring system or a 5- or 6-membered monocyclic nonaromatic heterocyclic ring system (or said 5- or 6-membered monocyclic or 9- or 10-membered bicyclic aromatic heterocyclic ring system or said 5- or 6-membered monocyclic nonaromatic heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl (or said phenyl lower-alkyl group substituted on the phenyl group by lower-alkoxy, lower-alkyl, or halogen), trilower-alkylsilyl, lower-alkylphenylsulfonyl, or triloweroalkylsilyl-lower-alkoxy-lower-alkyl), lower-alkoxy, or lower-alkynyl; or $R^5$ and $R^6$ together form a fluorene ring;

or $R^3$ and $R^5$, and/or $R^4$ and $R^6$ taken together with the carbon atoms to which they are attached form a bicyclic ring system of the formula A:

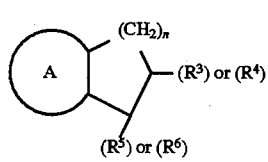

wherein A is phenyl, or a 5- or 6-membered monocyclic aromatic heterocyclic ring system and n is an integer from one to three (or said A ring substituted on any available carbon atom thereof by lower-alkoxy, or lower-alkyl);

$R^7$ is hydrogen, or from one to four, the same or different, substituents in any of the 7-, 8-,9-, or 10-positions selected from the group consisting of lower-alkyl, lower-alkanoyloxy, halogen, nitro, hydroxy, lower-alkoxy, methylene-dioxy, polyfluorolower-alkyl, OCO(CH$_2$)mC(O)Oalkyl, OC(O)alkyl, C(O)Oalkyl, CO$_2$—, carboxy, sulfo, SO$_3$—, PO$_3$H; PO$_3$— cyano, polychlorolower-alkyl, OC(O) alkyl-CH═CH-alkyl, OC(O)-lower-alkenyl-C(O)Oalkyl, alkoxy, OC(O)alkylC(O)Oalkyl, halomethyl, hydroxymethyl, amino and lower-alkylsulfonylamino wherein m is an integer from one to four and/or $R^7$ is a fused pyrazole ring;

$X^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; with the following provisos a) at least one of $R^5$ and $R^6$ when taken individually must be a substituted or unsubstituted phenyl group, or a substituted or unsubstituted 5- or 6-membered monocyclic or 9- or 10-membered bicyclic aromatic heterocyclic ring system or a substituted or unsubstituted 5- or 6-membered nonaromatic heterocyclic ring system; b) when $R^3$ and $R^5$ or $R^4$ and $R^6$ together form a bicyclic ring system of formula A wherein A is phenyl and n is 1; $R^1, R^2, R^4$, and $R^6$ or $R^1, R^2, R^3$ and $R^5$, respectively are hydrogen and $X^-$ is $BF_4^-$, $R^7$ is other than hydrogen or 9-methyl; c) when $R^1, R^2, R^3$, and $R^4$ are hydrogen; $R^5$ and $R^6$ are phenyl, and X— is $ClO_4^-$ or $Br^-$; $R^7$ is other than hydrogen, d) when $R^1, R^2, R^3$, and $R^4$ are hydrogen; one of $R^5$ or $R^6$ is phenyl, and one of $R^5$ or $R^6$ is methoxy; and $X^-$ is $BF_4^-$, $R^7$ is other than hydrogen or 9-methyl; and e) when $R^1, R^2, R^3$, and $R^4$ are hydrogen; $R^5$ is 4-morpholinyl and $R^6$ is phenyl or $R^5$ is phenyl and $R^6$ is 4-morpholinyl; and $X^-$ is $ClO_4^-$, $Br^-$ or $BF_4^-$, $R^7$ is other than hydrogen, 9-methyl, or 7,10-dimethyl.

The compounds of the Formula I bind to the PCP receptor and are thus useful in the treatment or prevention of neurodegenerative disorders or neurotoxic injuries.

Compounds within the ambit of Formula I above are those wherein:

$R^1$ is hydrogen, or from one to four, the same or different, substituents in any of the 1-,2-,3- or 4-positions selected from the group consisting of lower-alkoxy, lower-alkyl, and halogen;

$R^2$ is hydrogen, or lower-alkyl;

$R^3$ and $R^4$ are independently hydrogen, or lower-alkyl; or $R^3$ and $R^4$ together form a cycloalkyl ring, or a lower alkylidene group;

$R^5$ and $R^6$ are independently phenyl (or phenyl substituted by lower-alkoxy, halogen, lower-alkyl, polyfluorolower-alkyl, lower-alkoxyphenyl-lower-alkyl-N(lower-alkylsulfonyl)-, hydroxy, or polychlorolower-alkyl), a 5- or 6-membered monocyclic or 9- or 10-membered bicyclic aromatic heterocyclic ring system or a 5- or 6-membered monocyclic nonaromatic heterocyclic ring system (or said 5- or 6-membered monocyclic or 9- or 10-membered bicyclic aromatic heterocyclic ring system or said 5- or 6-membered monocyclic nonaromatic heterocyclic ring system substituted on any available carbon atom thereof by lower-alkyl, oxo, nitro, halogen, or lower-alkoxy; or on any available nitrogen atom thereof by loweroalkyl, phenyl-lower-alkyl (or said phenyl lower-alkyl group substituted on the phenyl group by lower-alkoxy, lower-alkyl, or halogen), trilower-alkylsilyl, or trilower-alkylsilyl-lower-alkoxy-lower-alkyl), lower-alkoxy, or lower-alkynyl; or $R^5$ and $R^6$ together form a fluorene ring;

or $R^3$ and $R^5$, and/or $R^4$ and $R^6$ taken together with the carbon atoms to which they are attached form a bicyclic ring system of the formula A:

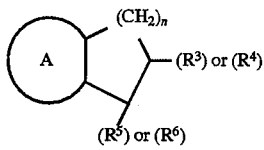

wherein A is phenyl, or a 5- or 6-membered monocyclic aromatic heterocyclic ring system and n is an integer from one to three (or said A ring substituted on any available carbon atom thereof by lower-alkoxy, or lower-alkyl);

$R^7$ is hydrogen, or from one to four, the same or different, substituents in any of the 7-, 8-,9-, or 10-positions selected from the group consisting of lower-alkyl, lower-alkanoyloxy, halogen, nitro, hydroxy, lower-alkoxy, methylenedioxy, polyfluorolower-alkyl, $OCO(CH_2)_mC(O)$Oalkyl, OC(O)alkyl, C(O)Oalkyl, $CO_2$—, carboxy, sulfo, $SO_3$—, $PO_3H$, $PO_3$—, cyano, and polychlorolower-alkyl, wherein m is an integer from one to four, $X^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; with the following provisos a) at least one of $R^5$ and $R^6$ when taken individually must be a substituted or unsubstituted phenyl group, or a substituted or unsubstituted 5- or 6-membered monocyclic or 9- or 10-membered bicyclic aromatic heterocyclic ring system or a substituted or unsubstituted 5- or 6-membered nonaromatic heterocyclic ring system; b) when $R^3$ and $R^5$ or $R^4$ and $R^6$ together form a bicyclic ring system of formula A wherein A is phenyl and n is 1; $R^1, R^2, R^4$, and $R^6$ or $R^1, R^2, R^3$ and $R^5$, respectively are hydrogen and $X^-$ is $BF_4^-$, $R^7$ is other than hydrogen or 9-methyl; c) when $R^1, R^2, R^3$, and $R^4$ are hydrogen; $R^5$ and $R^6$ are phenyl, and $X^-$ is $ClO_4^-$ or $Br^-$; $R^7$ is other than hydrogen, d) when $R^1, R^2, R^3$, and $R^4$ are hydrogen; one of $R^5$ or $R^6$ is phenyl, and one of $R^5$ or $R^6$ is methoxy; and $X^-$ is $BF_4^-$, $R^7$ is other than hydrogen or 9-methyl; and e) when $R^1, R^2, R^3$, and $R^4$ are hydrogen; $R^5$ is 4-morpholinyl and $R^6$ is phenyl or $R^5$ is phenyl and $R^6$ is 4-morpholinyl; and $X^-$ is $ClO_4^-$, $Br^-$ or $BF_4^-$, $R^7$ is other than hydrogen, 9-methyl, or 7,10-dimethyl.

Preferred compounds of the Formula I above are those wherein:

$R^1, R^2, R^3$ and $R^4$, taken independently or together, and $X^-$ are as defined directly hereinabove; $R^5$ and $R^6$ are independently phenyl (or phenyl substituted by lower-alkoxy, halogen, lower-alkyl, polyfluorolower-alkyl, or lower-alkoxyphenyl-lower-alkyl-N(lower-alkylsulfonyl)-), a 5- or 6-membered monocyclic or 9-membered bicyclic aromatic heterocyclic ring system (or said 5- or 6-membered monocyclic or 9-membered bicyclic aromatic heterocyclic ring system substituted on any available carbon atom thereof by lower-alkyl, oxo, or lower-alkoxy; or on any available nitrogen atom thereof by lower-alkoxyphenyl-lower-alkyl, trilower-alkylsilyl, or trilower-alkylsilyl-lower-alkoxy-lower-alkyl), lower-alkoxy, or lower-alkynyl; or $R^5$ and $R^6$ together form a fluorene ring;

$R^3$ and $R^5$, and/or $R^4$ and $R^6$ taken together with the carbon atoms to which they are attached form a bicyclic ring system of the Formula A:

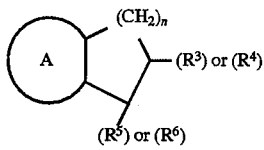

wherein A is phenyl, or a 5-membered monocyclic aromatic heterocyclic ring system and n is an integer from one to two (or said A ring substituted on any available carbon atom thereof by lower-alkoxy, or lower-alkyl) and $R^7$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, perfluorolower-alkyl, $SO_3$-, and polychlorolower-alkyl.

Particularly preferred compounds of the Formula I above are those wherein:

$R^2$, $R^3$ and $R^4$ taken independently or together, and $X^-$ are as defined directly hereinabove;

$R^1$ is hydrogen, or one lower-alkyl substituent in any of the 1-,2-,3- or 4-positions;

$R^7$ is hydrogen, or from one to two, the same or different, substituents in any of the 7-, 8-,9-, or 10-positions selected from the group consisting of halogen, hydroxy, lower-alkoxy, $SO_3$- and polyfluorolower-alkyl; $R^5$ and $R^6$ are independently phenyl (or phenyl substituted by lower-alkoxy, halogen, lower-alkyl, trifluoromethyl, or lower-alkoxyphenyl-lower-alkyl-N(lower-alkylsulfonyl)-), a 5- or 6-membered monocyclic or 9-membered bicyclic aromatic heterocyclic ring system selected from the group consisting of furanyl, benzofuranyl, pyddinyl, thienyl, oxazolyl, thiazolyl, pyrazolyl, triazolyl and pyrrolyl (or said 5- or 6-membered monocyclic or 9-membered bicyclic aromatic heterocyclic ring system substituted on any available carbon atom thereof by lower-alkyl, oxo or lower-alkoxy; or any available nitrogen atom thereof by lower-alkoxyphenyl-lower-alkyl, or trilower-alkylsilyl, trilower-alkylsilyl-lower-alkoxy-lower-alkyl), lower-alkoxy, or lower-alkynyl; or $R^5$ and $R^6$ together form a fluorene ring; and $R^3$ and $R^5$, and/or $R^4$ and $R^6$ taken together with the carbon atoms to which they are attached form a bicyclic ring system of the Formula A:

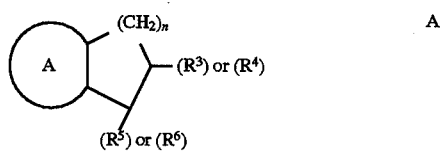

wherein A is phenyl, or a 5-membered monocyclic aromatic heterocyclic ring system selected from the group consisting of furanyl, isoxazoyl and thienyl (or said A ring substituted on any available carbon atom thereof by lower-alkoxy, or lower-alkyl).

Other preferred compounds of the Formula I above are those wherein:

$R^1$ is hydrogen or one lower-alkoxy or halogen substituent in any of the 1-, 2-, 3-, or 4-positions;

$R^2$ is hydrogen or lower-alkyl;

$R^3$ and $R^4$ are independently hydrogen, or lower-alkyl; or $R^3$ and $R^4$ together form a cycloalkyl ring, or a lower-alkylidene group;

$R^5$ and $R^6$ are independently phenyl substituted by hydroxy or a 5- or 6-membered monocyclic aromatic heterocyclic ring system selected from the group consisting of pyrazolyl, triazolyl, pyridinyl, furanyl, imidazolyl, and pyrrolyl (or said 5- or 6-membered monocyclic aromatic heterocyclic ring system substituted on any available carbon atom thereof by lower-alkoxy, or on any available nitrogen atom thereof by lower-alkyl, lower-alkoxyphenyllower-alkyl, or trilower-alkylsilyl);

$R^7$ is hydrogen, or from one to two, the same or different, substituents in any of the 7-, 8-, 9- or 10-positions selected from the group consisting of OC(O)alkyl, $OCO(CH_2)_m C(O)$ alkyl, hydroxy, lower-alkoxy, methylenedioxy, halogen and nitro; and X and p are as defined hereinabove.

Other compounds of the Formula I above are those wherein:

$R^1$ is from one to four, the same or different, substituents in any of the 1-, 2-, 3- or 4-positions selected from the group consisting of hydroxy, OC(O)alkyl-CH=CH-alkyl, OC(O) alkyl, OC(O)-lower-alkenyl-C(O)Oalkyl, alkoxy, OC(O) alkylC(O)Oalkyl, hydroxymethyl, nitro, amino and lower-alkylsulfonylamino; or $R^1$ is a fused benzene ring; and $R^2$, $R^3$, $R^4$, $R^5$, $R^6$, $R^7$, m, n, $x^-$ and p are as defined hereinabove on pages 8–9.

Preferred compounds of the Formula I within this latter group are those wherein:

$R^1$ is one substituent in any of the 1-, 2-, 3-, or 4-positions selected from the group consisting of hydroxy and OC(O) alkyl; or $R^1$ is a fused benzene ring;

$R^2$, $R^3$, $R^4$ and $R^7$ are hydrogen;

$R^5$ and $R^6$ are independently a 5- or 6-membered monocyclic aromatic heterocyclic ring system selected from the group consisting of furanyl, pyridinyl, thienyl, oxazolyl, thiazolyl, pyrazolyl, triazolyl, pyrrolyl and imidazolyl; and $X^-$ is an anion.

Still other compounds of the Formula I above are those wherein:

$R^2$ is cyano or lower-alkoxycarbonyl; and $R^1$, $R^3$, $R^4$, $R^5$, $R^6$, $R^7$, n, m, $x^-$, and p are as defined hereinabove on pages 8–9.

Preferred compounds of the Formula I within this latter group are those wherein:

$R^2$ is cyano or lower-alkoxycarbonyl;

$R^1$, $R^3$, $R^4$ and $R^7$ are hydrogen;

$R^5$ and $R^6$ are independently selected from the group consisting of furanyl, pyridinyl, thienyl, oxazolyl, thiazolyl, pyrazolyl, triazolyl, pyrrolyl and imidazolyl; and $X^-$ is an anion.

Still other compounds of the Formula I above are those wherein:

$R^1$, $R^2$, $R^3$, $R^4$, $R^5$, $R^6$, n, m, $x^-$ and p are as defined hereinabove on pages 8–9; and, $R^7$ is from one to four, the same or different, substituents in any of the 7-, 8-, 9- or 10-positions selected from the group consisting of OC(O)alkyl-CH=CH-alkyl, OC(O)-lower-alkenyl-C(O)Oalkyl, alkoxy, OC(O)alkylC(O)O alkyl, halomethyl, hydroxymethyl, amino and lower-alkylsulfonylamino; and/or $R^7$ is a fused pyrazole ring.

Preferred compounds of the Formula I within this layer group are those wherein:

$R^1$, $R^2$, $R^3$ and $R^4$ are hydrogen;

$R^5$ and $R^6$ are independently a 5- or 6-membered monocyclic aromatic heterocyclic ring system selected from the group consisting of furanyl, pyridinyl, thienyl, oxazolyl, thiazolyl, pyrazolyl, triazolyl, pyrrolyl and imidazolyl;

$R^7$ is as defined directly hereinabove; and $X^-$ is an anion.

The invention further relates to pharmaceutical compositions which comprise a compound of the Formula I:

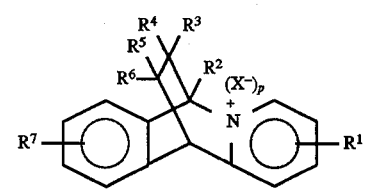

wherein:

$R^1$ is hydrogen, or from one to four, the same or different, substituents in any of the 1-,2-,3- or 4-positions selected from the group consisting of lower-alkoxy, lower-alkyl, halogen, hydroxy, OC(O) alkyl-CH=CH-alkyl, OC(O) alkyl, OC(O)-lower-alkenyl-C(O)Oalkyl, alkoxy, OC(O) alkylC(O)Oalkyl, hydroxymethyl, nitro, amino and lower-alkylsulfonylamino or $R^1$ is a fused benzene ring;

$R^2$ is hydrogen, lower-alkyl, cyano or lower-alkoxycarbonyl;

$R^3$ and $R^4$ are independently hydrogen, or lower-alkyl; or $R^3$ and $R^4$ together form a cycloalkyl ring, or a lower-alkylidene group;

$R^5$ and $R^6$ are independently phenyl (or phenyl substituted by lower-alkoxy, halogen, lower-alkyl, polyfluorolower-alkyl, lower-alkoxyphenyl-lower-alkyl-N(lower-alkylsulfonyl)-, hydroxy, or polychlorolower-alkyl), a 5- or 6-membered monocyclic or 9- or 10-membered bicyclic aromatic heterocyclic ring system or a 5- or 6-membered monocyclic nonaromatic heterocyclic ring system (or said 5- or 6-membered monocyclic or 9- or 10-membered bicyclic aromatic heterocyclic ring system or said 5- or 6-membered monocyclic nonaromatic heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl (or said phenyl-lower-alkyl group substituted on the phenyl group by lower-alkoxy, lower-alkyl, or halogen), trilower-alkysilyl, lower-alkylphenylsulfonyl, or trilower-alkylsilyl-lower-alkoxy-lower-alkyl), lower-alkoxy, or lower-alkynyl; or $R^5$ and $R^6$ together form a fluorene ring;

or $R^3$ and $R^5$, and/or $R^4$ and $R^6$ taken together with the carbon atoms to which they are attached form a bicyclic ring system of the formula A:

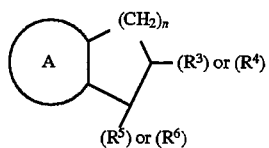

wherein A is phenyl, or a 5- or 6-membered monocyclic aromatic heterocyclic ring system and n is an integer from one to three (or said A ring substituted on any available carbon atom thereof by lower-alkoxy, or lower-alkyl);

$R^7$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylenedioxy, polyfluorolower-alkyl, $OCO(CH_2)_mC(O)Oalkyl$, $OC(O)alkyl$, $C(O)Oalkyl$, $CO_2$—, carboxy, sulfo, $SO_3$—, $PO_3H$; $PO_3$— cyano, polychlorolower-alkyl, $OC(O)alkyl-CH=CH-alkyl$, $OC(O)$-lower-alkenyl-$C(O)Oalkyl$, alkoxy, $OC(O)alkylC(O)Oalkyl$, halomethyl, hydroxymethyl, amino and lower-alkylsulfonylamino; wherein m is a integer from one to four; and/or $R^7$ is a fused pyrazole ring;

$X^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; together with a pharmaceutically acceptable carrier, adjuvant, diluent or vehicle, with the proviso that at least one of $R^5$ and $R^6$ when taken individually must be a substituted or unsubstituted phenyl group, or a substituted or unsubstituted 5- or 6-membered monocyclic or 9- or 10-membered bicyclic aromatic heterocyclic ring system or a substituted or unsubstituted 5- or 6-membered monocyclic nonaromatic heterocyclic ring system.

The invention further relates to a method for the treatment or prevention of neurodegenerative disorders, or neurotoxic injuries which comprises administering to a patient in need of such treatment an effective amount of a compound of the formula I:

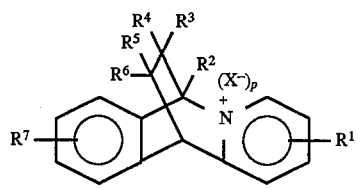

wherein:

$R^1$ is hydrogen, or from one to four, the same or different, substituents in any of the 1-,2-, 3- or 4-positions selected from the group consisting of lower-alkoxy, lower-alkyl, halogen hydroxy, $OC(O)$ alkyl-$CH=CH$-alkyl, $OC(O)$ alkyl, $OC(O)$-lower-alkenyl-$C(O)Oalkyl$, alkoxy, $OC(O)$ alkylC(O)Oalkyl, hydroxymethyl, nitro, amino and lower-alkylsulfonylamino or $R^1$ is a fused benzene ring;

$R^2$ is hydrogen, lower-alkyl, cyano or lower-alkoxycarboxy;

$R^3$ and $R^4$ are independently hydrogen, or lower-alkyl; or $R^3$ and $R^4$ together form a cycloalkyl ring, or a lower-alkylidene group;

$R^5$ and $R^6$ are independently phenyl (or phenyl substituted by lower-alkoxy, halogen, lower-alkyl, polyfluorolower-alkyl, lower-alkoxyphenyl-lower-alkyl-N(lower-alkylsulfonyl)-, hydroxy, or polychlorolower-alkyl), a 5- or 6-membered monocyclic or 9- or 10-membered bicyclic aromatic heterocyclic ring system or a 5- or 6-membered monocyclic nonaromatic heterocyclic ring system (or said 5- or 6-membered monocyclic or 9- or 10-membered bicyclic aromatic heterocyclic ring system or said 5- or 6-membered monocyclic nonaromatic heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl (or said phenyl-lower-alkyl group substituted on the phenyl group by lower-alkoxy, lower-alkyl, or halogen), trilower-alkysilyl, lower-alkylphenylsulfonyl, or trilower-alkylsilyl-lower-alkoxy-lower-alkyl), lower-alkoxy, or lower-alkynyl; or $R^5$ and $R^6$ together form a fluorene ring;

or $R^3$ and $R^5$, and/or $R^4$ and $R^6$ taken together with the carbon atoms to which they are attached form a bicyclic ring system of the formula A:

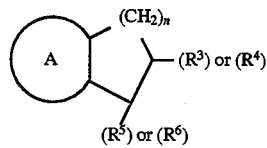

wherein A is phenyl, or a 5- or 6-membered monocyclic aromatic heterocyclic ring system and n is an integer from one to three (or said A ring substituted on any available carbon atom thereof by lower-alkoxy, or lower-alkyl);

$R^7$ is hydrogen, or from one to four, the same or different, substituents in any of the 7-, 8-, 9-, or 10-positions selected from the group consisting of lower-alkyl, lower-alkanoyloxy, halogen, nitro, hydroxy, lower-alkoxy, methylene-dioxy, polyfluorolower-alkyl, $OCO(CH_2)_mC(O)Oalkyl$, $OC(O)alkyl$, $C(O)Oalkyl$, $CO_2$—, carboxy, sulfo, $SO_3$—, $PO_3H$, $PO_3$—, cyano, polychlorolower-alkyl, $OC(O)alkyl-CH=CH-alkyl$, $OC(O)$-lower-alkenyl-$C(O)Oalkyl$, alkoxy, $OC(O)$ alkyl $C(O)O$ alkyl, halomethyl, hydroxymethyl, amino and lower-alkylsulfonylamino; wherein m is an integer from one to four; and/or $R^7$ is a fused pyrazole ring;

$X^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; with the proviso that at least one of $R^5$ and $R^6$ when taken individually must be a substituted or unsubstituted phenyl group, or a substituted or unsubstituted 5- or 6-membered monocyclic or 9- or 10-membered bicyclic aromatic heterocyclic ring system or a substituted or unsubstituted 5- or 6-membered monocyclic nonaromatic heterocyclic ring system.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, propyl, isopropyl, n-butyl, sec-butyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term alkyl as used herein means linear or branched hydrocarbon chains having one to about sixteen carbon atoms and thus includes methyl, ethyl, 1,1-dimethylethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, n-heptyl, 2-heptyl, n-octyl, 2,4,4-trimethylpentyl, n-nonyl, 3,5,5-trimethylhexyl, n-decyl, 3,7-dimethyloctyl, n-undecyl, n-dodecyl, n-tridecyl, n-tetradecyl, n-pentadecyl, n-hexadecyl, and the like.

The term alkoxy as used herein means linear or branched alkyloxy substituents having from one to about sixteen carbon atoms and thus includes methoxy, ethoxy, propoxy, isopropoxy, butoxy, sec-butoxy, t-butoxy, n-pentyloxy, 2-methyl-3-butyloxy, 1-methylbutyoxy, 2-methylbutyloxy, neopentyloxy, n-hexyloxy, 1-methylpentyloxy, 3-methylpentyloxy, 1-ethylbutyloxy, 2-ethylbutyloxy, 2-hexyloxy, 3-hexyloxy, n-heptyloxy, 2-heptyloxy, n-octyloxy, 2,4,4-trimethylpentyloxy, n-nonyloxy, 3,5,5-trimethylhexyloxy, n-decyloxy, 3,7-dimethyloctyloxy, n-undecyloxy, n-dodecyloxy, n-tridecyloxy, n-tetradecyloxy, n-pentadecyloxy, n-hexadecyloxy, and the like.

The term halogen, halo, or halide as used herein means bromine, chlorine, iodine, or fluorine.

The term lower-alkanoyloxy as used herein means linear or branched hydrocarbon chains having two to about four carbon atoms and thus includes acetyloxy, propionyloxy, isobutyryloxy, and the like.

The term cycloalkyl as used herein means $C_3$ to $C_7$ unsaturated monocyclic hydrocarbon residues and thus includes cyclopropyl, cyclobutyl, cyclopentyl, cyclohexyl and cycloheptyl.

The term lower-alkylidene as used herein means linear or branched hydrocarbon chains having one to about four carbon atoms and thus includes methylidene, ethylidene, propylidene, isopropylidene, sec-butylidene, and the like.

The term lower-alkenyl as used herein means linear or branched unsaturated hydrocarbon radicals having two to about four carbon atoms and thus includes ethenyl, 1-propenyl, 2-propenyl, isopropenyl, 1-methyl-2-propenyl, 2-butenyl, isobutenyl and the like.

The term lower-alkynyl as used herein means linear or branched unsaturated radicals having two to about four carbon atoms and thus includes ethynyl, 1-propynyl, 2-propynyl, 1-methyl-2-propynyl, 2-butynyl and the like.

The term anion (X-) as used herein means the anion of an organic acid (includes anions of organic monoacids, as well as monoanions of organic diacids) which is at least as strong as acetic acid, and thus includes anions of such acids as acetic acid, trifluoroacetic acid methanesulfonic acid, tolenesulfonic acid, trifluoromethanesulfonic acid, (−)-dibenzoyl-L-tartaric acid [(−)-DBT], (+)dibenzoyl-D-tartaric acid [(+)-DBT], and the like; or it means an inorganic acid anion such as chloride, bromide, perchlorate, $PF_6$— and the like, preferably chloride.

The term 5- or 6-membered monocyclic aromatic heterocyclic ring system as used herein means 5- or 6-membered monocyclic aromatic heterocyclic ring systems containing from one to three, the same or different, heteroatoms selected from the group consisting of nitrogen, oxygen and sulfur (or said 5- or 6-membered monocyclic aromatic heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl (or said phenyl-lower-alkyl group substituted on the phenyl group by lower-alkoxy, lower-alkyl, or halogen), trilower-alkylsilyl, lower-alkylphenylsulfonyl, or trilower-alkylsilyl-lower-alkoxy-lower-alkyl). Representative examples of such 5- or 6-membered monocyclic aromatic heterocyclic ring systems include, but are not limited to, furan, pyridine, thiophene, oxazole, thiazole, pyrazole, triazole, pyrrole, imidazole, isoxazole, oxadiazole, pyrazine, pyridazine, pyrimidine, triazine, thiadiazole and the like; or said 5- or 6-membered monocyclic aromatic heterocyclic ring systems substituted on any available carbon or nitrogen atom thereof as described hereinabove.

The term 5- or 6-membered monocyclic nonaromatic heterocyclic ring system as used herein means 5- or 6-membered nonaromatic heterocyclic ring systems containing from one to two, the same or different, heteroatoms selected from the group consisting of nitrogen, oxygen and sulfur (or said 5- or 6-membered monocyclic nonaromatic heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl (or said phenyl-lower-alkyl group substituted on the phenyl group by lower-alkoxy, lower-alkyl, or halogen), trilower-alkylsilyl, lower-alkylphenylsulfonyl, or trilower-alkylsilyl-lower-alkoxy-lower-alkyl). Representative examples of such 5- or 6-membered monocyclic nonaromatic heterocyclic ring systems include, but are not limited to, pyrrolidine, thiazolidine, tetrahydrofuran, tetrahydrothiophene, thiomorpholine, morpholine, piperazine, piperidine, tetrahydropyran, 1,4-thioxane, and the like; or said 5- or 6-membered monocyclic nonaromatic heterocyclic ring system substituted on any available carbon or nitrogen atom thereof as described hereinabove.

The term 9- or 10-membered bicyclic aromatic heterocyclic ring system as used herein means 9- or 10-membered bicyclic aromatic heterocyclic ring systems containing from one to three, the same or different, heteroatoms selected from the group consisting of oxygen, nitrogen and sulfur (or said 9- or 10-membered bicyclic aromatic heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl (or said phenyl-lower-alkyl group substituted on the phenyl group by lower-alkoxy, lower-alkyl, or halogen), trilower-alkylsilyl, lower-alkylphenylasulfonyl, or trilower-alkylsilyl-lower-alkoxy-lower-alkyl). Representative examples of such 9- or 10-membered bicyclic aromatic heterocyclic ring systems include, but are not limited to, benzofuran, benzimidazole, thianaphthene, benzisothiazole, quinoline, isoquinoline, quinoxaline, quinazoline, indole, 1,8-naphthyridine, benzothiazole, benzoxazole, indazole, benzotriazole and the like; or said 9- or 10-membered bicyclic aromatic heterocyclic ring system substituted on any available carbon or nitrogen atom thereof as described hereinabove.

It will be appreciated that in the compounds of the formulas I and II, $X^-$ is an anion when p, in the term $(X^-)_p$, is one; however, when the compounds of the formula I and II contain a negatively charged radical, e.g. when $R^7$ is $CO_2-$, $SO_3-$, or $PO_3-$, p, in the term $(X^-)_p$, is zero and the compounds exist as zwitterionic species.

The numbering system used throughout the specification is shown in the ring system which is illustrated below. This ring system is usually named in the chemical literature as a 6,11-ethano-6,11-dihydrobenzo[b]quinolizinium or a 6,11-dihydro-6,11-ethanoacridizinium. It should be noted, however, that in some

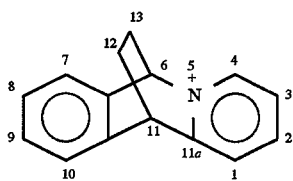

of the earlier chemical literature references (see references cited in Information Disclosure Statement) this ring system was numbered as shown below, and was named as a 9,10-ethano-9,10-dihydro-4a-azoniaanthracene, or a 9,10-dihydro-4a-azonia-9,10-ethanoanthracene.

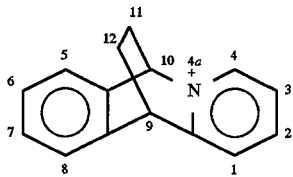

Throughout this specification, however, we will use the former numbering system, and we will name the compounds as 6,11-ethano-6,11-dihydrobenzo[b]-quinolizinium salts.

The synthesis of the compounds of the invention may be outlined as shown in Scheme A:

Scheme A

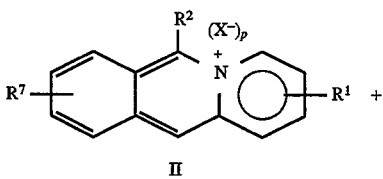

-continued
Scheme A

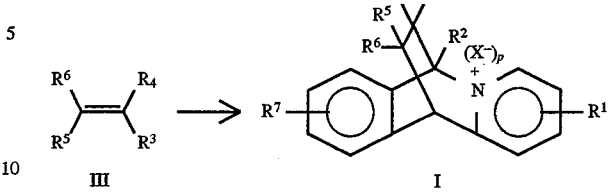

A suitably substituted benzo[b]quinolizinium salt (II) in an appropriate organic solvent, e.g. nitromethane, acetonitrile, nitropropane and lower-alkanols (e.g. methanol and ethanol) or mixtures thereof, is treated with at least one molar equivalent of a suitably substituted olefin (III), at a temperature in the range of about 50° C. up to the boiling point of the solvent or solvent mixture used to afford the compounds of the Formula I.

If desired, the compounds of Formula I can be converted into other compounds of Formula I which possess various different anions ($X^-$) by a) treating a compound of the Formula I with at least one molar equivalent of the alkali metal salt of an organic acid anion or an inorganic acid anion, $M^+X^-$, wherein the acid of the salt used is a stronger acid than the corresponding acid of the initial acid anion ($X^-$), and wherein $M^+$ is an alkali metal, e.g. lithium, sodium or potassium; b) passing a compound of the Formula I wherein $X^-$ is other than $Cl^-$ through a Dowex® 1x2-200 ion-exchange resin (Dowex®-1-chloride) column to produce the compounds of the Formula I wherein $X^-$ is $Cl^-$; or c) by passing a compound of the Formula I through a suitable ion-exchange resin column (prepared; for example, by treating Dowex® 1X2-200 ion-exchange resin with a suitable organic acid or inorganic acid) to provide various compounds of Formula I wherein $X^-$ is other than $Cl^-$, $ClO_4^-$ or $PF_6^-$.

It will be appreciated that the compounds of Formula I can possess one or more asymmetric carbon atoms and are thus capable of existing in a number of stereoisomeric forms, e.g. enantiomers, diastereomers, and geometric isomers. Unless otherwise specified herein, the invention is intended to extend to each of these stereoisomeric forms, and to mixtures thereof, including the racemates. In some cases, there may be advantages, e.g. greater potency, to using a particular enantiomer when compared to the other enantionmer or the racemate in the treatment or prevention of neurodegenerative disorders or neurotoxic injuries, and such advantages can be readily determined by those skilled in the art. The different stereoisomeric forms may be separated one from the other by the methods described hereinbelow.

The diastereomers/geometric isomers can be separated by conventional procedures which are well known in the art of chemistry such as chromatography, fractional crystallization and the like. The separation of enantiomers can be accomplished by a) chiral chromatography, or b) treating a racemic mixture of a compound of Formula I with the potassium salt of (+)-dibenzoyl-D-tartaric acid (K+[(+)-DBT]) to afford a compound of Formula I as the ⁻[(+)-DBT] salt; fractional crystallization of the ⁻[(+)-DBT] salt to afford a single diastereomer of the ⁻[(+)-DBT] salt, and then conversion of the single diastereomer of the ⁻[(+)-DBT] salt into various other non-chiral anions (X⁻) by following the procedures described hereinabove for the conversion of compounds of the Formula I into other compounds of the Formula I with various different anions (X⁻), to produce the compounds of the Formula I as a single enantiomer; or c) treating a racemic mixture of a compound of Formula I with the potassium salt of (−)-dibenzoyl-L-tartaric acid (K⁻[(−)-DBT]) to afford a compound of Formula I as the ⁻[(−)-DBT] salt and then proceeding as described hereinabove in part b to afford the compounds of Formula I as the other enantiomer.

Simple chemical transformations which are conventional and well known to those skilled in the art of chemistry can be used for effecting changes in the functional groups of the compounds of the Formula I. For example, removal of N-(lower-alkyl-lower-alkoxy-trilower-alkylsilyl), N-lower-alkoxy-phenyl-lower-alkyl, N-lower-alkylphenylsulfonyl and N-trilower-alkylsilyl protecting groups to afford the corresponding N—H derivatives; treatment of 2-lower-alkoxy pyridine derivatives with an acid to produce the corresponding 2-oxopyridine derivatives, treatment of alcohols with acylating agents to afford the corresponding esters, hydrolysis of nitriles to afford the corresponding acids, treatment of acids with alcohols in the presence of a dehydrating agent to afford the corresponding ester, treatment of halides with dialkylphosphites in the presence of a catalyst to produce phosphonates which in turn can be hydrolyzed to afford the corresponding phosphonic acid derivatives, treatment of alcohols with alkyl halides to afford the corresponding alkoxy derivatives, dealkylation of ethers to afford the corresponding alcohols, hydrolysis of alkyl halides to afford the corresponding alcohols, dehalogenation of aryl halides to afford the corresponding aryl derivatives, reduction of nitro derivatives to afford the corresponding amino derivatives and treatment of amino derivatives with sulfonyl halides to afford the corresponding sulfonamide derivatives.

The suitably substituted benzo[b]quinolizinium salts of the Formula II, which are required for the synthesis of the compounds of the Formula I, are either known and can thus be prepared by procedures which are known in the art of chemistry (see for example, Bradsher and Parham, J. Org. Chem., 1963, 28, 83–85; Bradsher and Jones, J. Am. Chem. Soc., 1957, 79, 6033–34; Bradsher et al., J. Het. Chem. 1964, 1, 30–33; and Bradsher and Parham, J. Het. Chem. 1964, 1, 121–124); or if they are novel, they can be prepared by the procedures described in the art or those described hereinbelow and illustrated in Schemes B,C and D. In Scheme B, at least one molar equivalent of an appropriately substituted benzyl halide (IV), wherein Z is a halogen, preferably chlorine, bromine, or iodine, is treated with at least one mole of an appropriately substituted 2-(1,3-dioxolan-2-yl)pyridine (V) in the presence or absence of a suitable organic solvent, e.g. sulfolane, at a temperature of about room temperature up to about 146° C., to produce the pyridinium salts of Formula VI. If desired, the pyridinium salt (VI) can then be converted into other pyridinium salts of the Formula VII, wherein X⁻ has the meanings given hereinabove, by utilizing procedures similar to those described hereinabove for the preparation of compounds of the Formula I with various anions (X⁻). The pyridinium salt (VII), or if conversion into various anions (X⁻) was not effected, the pyridinium salt (VI) can then be treated with an excess of an acid, e.g. polyphosphoric acid, 48% hydrobromic acid, acetic acid, methanesulfonic acid, or mixtures thereof, at a temperature of about room temperature up to the boiling point of the acid or acid mixture used, to afford the benzo[b]quinolizinium salts of Formula II.

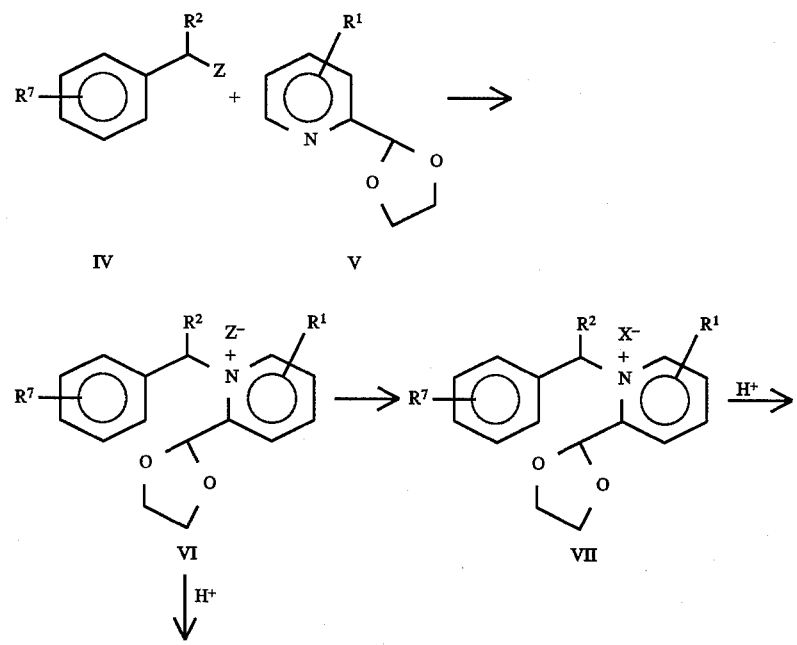

Scheme B

-continued
Scheme B

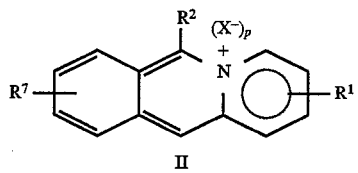

II

Alternatively, the benzo[b]quinolizinium salts of Formula II can be prepared as shown in Scheme C. At least one molar equivalent of a suitably substituted benzyl alcohol (VIII), wherein Y is hydrogen, or halogen, especially hydrogen or bromine, is treated with at least two molar equivalents of a lower-alkyl alkali metal, preferably n-BuLi, optionally in the presence of at least one mole of a second base, e.g. tetramethylethylenediamine, followed by the Scheme C

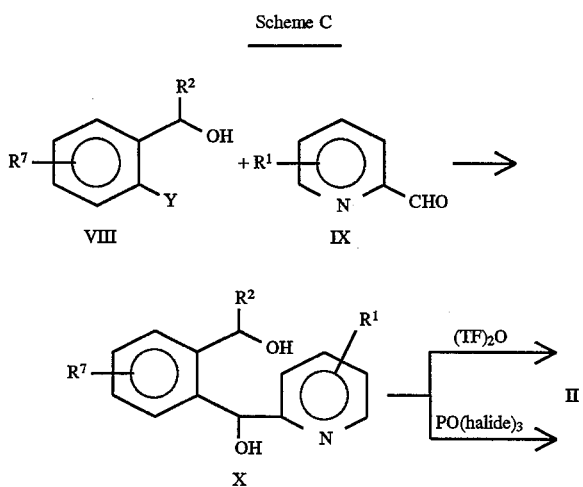

addition of at least one molar equivalent, or preferably an excess of a suitable pyridine derivative (IX), in an organic solvent, such as ether, at room temperature or below, preferably at a temperature in the range of about room temperature to about −45° C. to afford the diol (X). The diol (X) can then be treated with (a) an excess of trifluoromethanesulfonic anhydride ((TF)$_2$O), in a suitable solvent, e.g. benzene, at a temperature in the range of about room temperature up to the boiling point of the solvent used to afford a compound of the Formula II wherein X$^-$ is $^-$OTF; or (b) at least one molar equivalent of a phosphorous oxyhalide, preferably phosphorous oxychloride, at a temperature in the range of about room temperature up to the boiling point of the phosphorous oxyhalide, to afford a compound of the Formula II wherein X$^-$ is halogen. It will be noted that the methods described hereinabove in Scheme C are the preferred methods when it is desired to prepare benzo[b]quinolizinium salts of Formula II which contain substituents in the 6- and/or 10-positions.

Alteratively, the benzo[b]quinolizinium salts of Formula II can be prepared as shown in Scheme D.

Scheme D

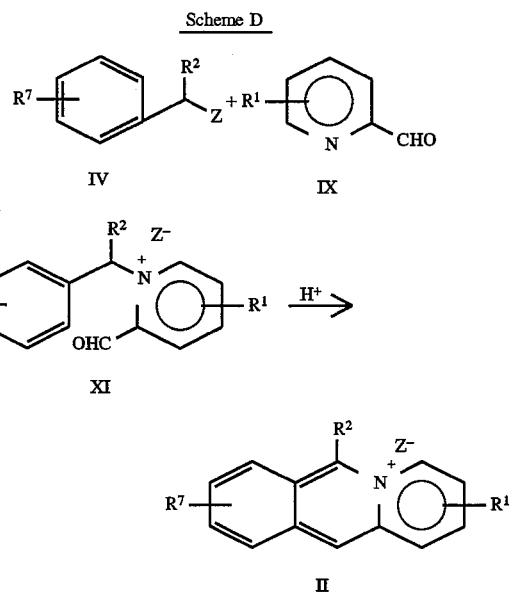

A suitably substituted benzyl halide (IV), is treated with at least one mole of suitably substituted pyridine derivative (IX), in the presence of a suitable organic solvent, e.g. sulpholane, at a temperature of about room temperature up to the boiling point of the solvent used, to produce a pyridinium salt (XI). The pyridinium salt (XI) can then be treated with an excess of an acid, e.g. 48% hydrobromic acid, in the absence of a solvent, at a temperature of about room temperature up to the boiling point of the acid used to produce the benzo[b]quinolizinium salt of Formula II (Z$^-$=X$^-$=halogen).

Alternatively, if a benzo[b]quinolizinium salt of the Formula II wherein R$^1$ is 3-hydroxy is desired, it is convenient to proceed as shown in Scheme E. A suitably substituted isoquinoline derivative of the Formula XII is treated with an excess of a haloacetone derivative of the Formula XIII, wherein Z' is a halogen, preferably chlorine or bromine, in a suitable organic solvent, such as acetone at a temperature of about room temperature up to the boiling point of the solvent used, to afford the isoquinolinium salts of the Formula XIV. The isoquinolinium salts of the Formula XIV can then be treated with an excess of an acid, e.g. 48% hydrobromine acid, in the absence of a solvent, at a temperature of about room temperature up to the boiling point of the acid used to product the 3-hydroxybenzo[b]quinolizinium salt of the Formula II (Z$^-$=X$^-$=halogen).

Scheme E

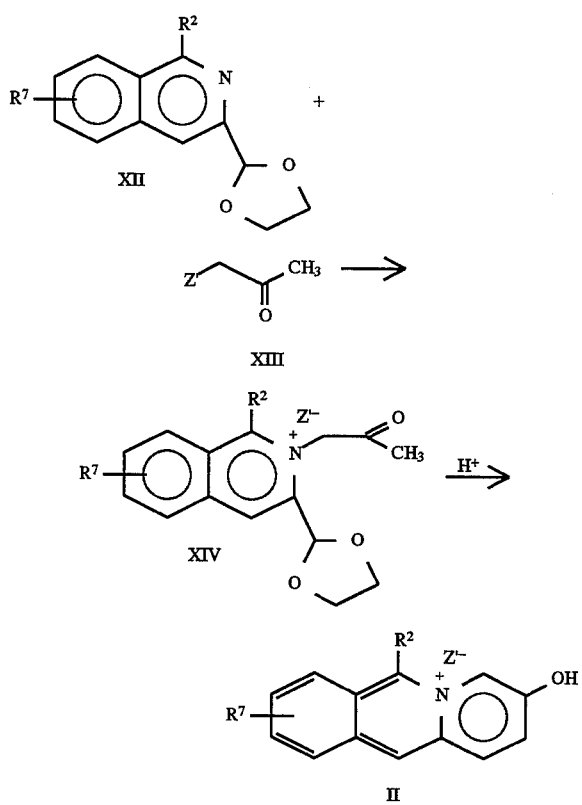

If desired, the benzo[b]quinolizinium salts of Formula II can be converted into other compounds of the Formula II which possess various different anion groups, $X^-$, by following procedures similar to those described hereinabove for the conversion of the compounds of the Formula I to various other anion groups, $X^-$.

Simple chemical transformations which are conventional and well known to those skilled in the art of chemistry can be used for effecting changes in functional groups of the compounds of Formula II. For example, dealkylation of ethers to produce the corresponding alcohols, halogenation of aryl rings to produce the corresponding aryl halides, acetylation of alcohols to produce the corresponding acetates, treatment of alcohols with halogenating reagents to afford the corresponding halogen derivative, and nitration of aryl rings to afford the corresponding nito derivatives.

The appropriately substituted olefin (III), alkali metal salts of an inorganic acid anion or an organic acid anion ($M^+X^-$), benzyl halide (IV), 2-(1,3-dioxolan-2-yl) pyridine (V), benzyl alcohol derivative (VIII), pyridine derivative (IX), isoquinoline derivative (XII) and haloacetone derivative (XIII) are commercially available, or they can be prepared by procedures well known in the art, or by the procedures described hereinbelow in the examples.

The compounds of Formula I which contain basic substituents are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The compounds of Formula I are quinolizinium salts in which it is preferred that the salts are pharmaceutically acceptable salts, that is, salts whose anions ($X^-$) are relatively innocuous to the animal organism in pharmaceutical doses of the salts, so that the beneficial properties inherent in the compounds of the Formula I are not vitiated by side effects ascribable to the anions ($X^-$). In practicing the present invention it is convenient to use the anions ($X^-$) of organic acids such as methanesulfonic acid and tolenesulfonic acid, or the anions ($X^-$) of inorganic acids such as hydrobromic acid and hydrochloric acid. However, other appropriate pharmaceutically acceptable salts within the scope of the invention are those derived from the anions ($X^-$) of other organic acids, organic diacids, or inorganic acids.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees C (°C.) and are uncorrected. The abbreviation E/PAW as used herein means ethyl acetate in pyridine/acetic acid/water (55/20/25); TEA stands for triethylamine, TEOF stands for triethylorthoformate, DME stands for dimethoxyethane, THF stands for tetrahydrofuran, LAH stands for lithium aluminum hydride, MDC stands for dichloromethane, TBME stands for tert-butylmethyl ether, TMEDA stands for N,N,N',N'-tetramethylethylene diamine, and DMPU stands for 1,3-dimethyl-3,4,5,6-tetrahydro-2(1H)-pyrimidinone.

EXAMPLE 1(a)

To a solution of 1-indanone (23.78 g, 0.18 mol) in 250 mL of ether at 0° C. was added dropwise over 30 min, 100 mL of phenyllithium in ether (1.8M in ether) and the mixture was allowed to warm to room temperature and stirred for 1 h. The reaction mixture was poured into a cold saturated ammonium chloride solution, extracted with ether (2×200 mL), and the combined organic layer was washed with brine and dried over sodium sulfate. The organic solvent was removed under reduced pressure, 70 mL of 20% sulfuric acid in acetic acid was added to the residue and stirred 2 min. To the above solution water (100 mL) and ether (3×200 mL) were added. The organic layer was washed with sodium bicarbonate solution, dried over sodium sulfate, filtered, and concentrated. Toluene (300 mL) was added to the residue and the mixture was distilled (azeotropic removal of acetic acid) to afford a brown oil. The brown oil was purified by chromatography (silica; (2:1 hexane/methylene chloride)) to afford 15.58 g (45.82%) of 1-phenyl-indene as a colorless oil. In addition 11 g of 1-phenyl-1-acetoxy-indane was isolated as a by-product.

(b)

A mixture of 2-pyridinecarboxaldehyde (500 g, 4.67 mol), 561 mL of ethylene glycol, and 234 g of p-toluenesulfonic acid monohydrate in 5.8 L of toluene was heated to reflux while distilling (azeotropic) water formed during the reaction. The solvent was removed in vacuo and the residue was distilled to afford 475 g (67%) of 2-(1.3-dioxolan-2-yl) pyridine (Formula V: $R^1$=H)

(c)

A mixture of 716 g (4.74 mol) of 2-(1,3-dioxolan-2-yl) pyridine and 859 g (5 mol) of benzyl bromide in a 5 L flask was heated on a steam-bath to 80° C. where an exothermic reaction caused the reaction temperature to reach 146° C. The reaction mixture was allowed to cool to 90° C. and the mixture was heated on a steam-bath for 2 h. The reaction mixture was cooled to room temperature, the resulting solid product was heated on a steam-bath with ethyl acetate, and ethyl acetate was decanted. The treatment with ethyl acetate was repeated three times to afford 1526.8 g of 2-(1,3-dioxolan-2-yl)-1-benzylpyridinium bromide (Formula VI: $R^1=R^2=R^7=H; Z^-=Br^-$).

(d)

A mixture of 1526.8 g (4.74 mol) of 2-(1,3-dioxolan-2-yl)-1-benzylpyridinium bromide in 9 L of 48% HBr solution was heated on a steam-bath until the bromide dissolved. The mixture was heated (heating mantle) in vacuo (aspirator) to remove HBr solution. The dry residue was suspended in 800 mL of HBr solution, cooled, and 4 L of THF was slowly added. The reaction mixture was filtered to afford 1080 g (87%) of benzo[b]quinolizinium bromide as a green solid. Benzo[b]quinolizinium bromide (586 g) was dissolved in 2.4 L of hot water and filtered to remove an insoluble dark material. The filtrate was cooled in ice-water for 4 h, filtered, and the residue was washed with water, dried in vacuo at room temperature for 9 days to afford 508.8 g (86.8%) of benzo[b]quinolizinium bromide (Formula II: $R^1=R^2=R^7=H$ ;$X^-=Br^-$).

(e)

Benzo[b]quinolizinium bromide (508.5 g, 1.95 mol) was dissolved in 5 L of distilled water with heating (steam-bath). Potassium hexafluorophosphate (367.2 g, 1.95 mol) was dissolved in 1.1 L of water with heating and the resulting solution was poured in portions into the above bromide solution with steam-bath heating (20 min). The precipitate was formed immediately and the mixture was stirred at room temperature for 3 h, then stirred 1 h in an ice-water bath. The solid was filtered, washed with cold water (800 mL), dried (50°–60° C.) in vacuo for 3 days to afford 601 g (94.8%) of benzo[b]quinolizinium hexafluorophosphate (Formula II: $R^1=R^2=R^7=H; X^-=PF_6^-$).

(f)

To a solution of benzo[b]quinolizinium hexafluorophosphate (4 g, 0.013 mol) in 60 mL of nitromethane was added 1-phenyl-indene (3.78 g, 0.0196 mol) and the mixture was heated to reflux for 3 h. The reaction mixture was cooled, filtered, the filtrate concentrated in vacuo, and the residue was dissolved in ether and cooled to yield a gray/white solid. The solid was filtered, dissolved in ethyl acetate/methylene chloride, and the solution was refluxed while distilling off methylene chloride. The solution was cooled, the filtered solid (NMR indicated 2.3:1 isomeric mixture) was dried in vacuo at (45° C./48 h) to afford 6.95 g (94.3%) of 6,11[[2', 3']-3'phenyl-indanyl]6,11-dihydrobenzo[b]quinolizinium hexafluorophosphate (Formula I: $R^1=R^2=R^3=R^7=H$;

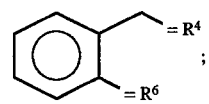

$R^5$=phenyl;$X^-=PF_6^-$; and Formula I: $R^1=R^2=R^4=R^7=H$;

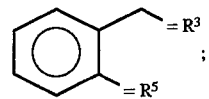

$R^6$=phenyl; $X^-=PF_6^-$).

EXAMPLES 2(a) AND (b)

A mixture of 4 g (0.013 mol) of benzo[b]quinolizinium hexafluorophosphate and 2.12 g (0.0183 mol) of indene in 55 mL of nitromethane was allowed to reflux for 36 h, cooled, and filtered to obtain a brown solid product. The solid was triturated in ether, decanted, and the residue was dried in vacuo to yield 5.6 g (87%) of a solid product (3:1 isomeric ratio). The isomeric mixture was purified by chromatography (silica/E/PAW)(2:1) and each isomer (isomer 1 and isomer 2) was convened to the corresponding chloride salt by passing the hexafluorophosphate adducts through Dowex® 1x2-200 to afford 176.9 mg of 6,11[[2',3']-indanyl] 6,11-dihydrobenzo[b]quinolizinilium chloride (Formula I: $R^1=R^2=R^4=R^7=H$;

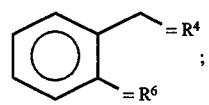

$X^-=Cl^-$; Example 2(a)) isomer 1 (m.p. 134°–143° C., isomeric ratio 1:15) and 178.0 mg 6,11[[2',3']indanyl]6,11-dihydrobenzo[b]quinolizinium chloride (Formula I: $R^1=R^2=R^4=R^6=R^7=H$;

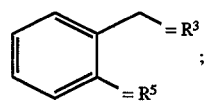

$X^-=Cl^-$; Example 2(b)) isomer 2 (m.p.240° C., isomeric ratio 10:1).

EXAMPLE 3

(a)

To a solution of 3-(4-methoxyphenyl)propionic acid (50.34 g, 0.279 mol) in 500 mL of methylene chloride cooled to 0° C. was added slowly at 0° C. 30.5 mL (0.418 mol) of thionyl chloride, the mixture was stirred 10 h at room temperature and the solvent was removed in vacuo. The residue was dissolved in 1000 mL of methylene chloride, cooled to 0° C., and 40.92 g (0.306 mol) of aluminum chloride was added in small portions and the resulting mixture was stirred at room temperature for 1 h. The above mixture was poured onto ice, the resulting mixture was filtered through celite, and the aqueous layer was extracted with methylene chloride (2×200 mL). The combined organic layer was dried over sodium sulfate, concentrated in vacuo, and the residue was extracted with hexane to afford 40 g (88%) of 6-methoxy-1-indanone.

(b)

To a solution of 20 g (0.123 mol) of 6-methoxy-1-indanone in 500 mL of ether cooled to −20° C. was added 72 mL (0.129 mol) of 1.8M phenyllithium in cyclohexane/ether and the mixture was stirred at room temperature for 1 h. An additional (10 mL) phenyllithium solution was added and stirred at room temperature for 1 h. To the reaction mixture was added saturated ammonium chloride solution and the resulting mixture was extracted with ethyl acetate (3×250 mL), and the organic layer was dried over sodium sulfate and concentrated in vacuo to afford 32.3 g of crude (contains solvent) 6-methoxy-1-phenyl-indan-1-ol.

(c)

To 1.5 L of toluene was added 32 g (0.133 mol) of 6-methoxy-1-phenyl-indan-1-ol and 100 mg of p-toluenesulfonic acid monohydrate and the mixture was placed on a Rotovap and the solvent was distilled in vacuo (40 mm) until a brown oil residue was obtained. The brown oil was chromatographed (silica, 1:1 hexane/methylene chloride) to afford 17.47 g (60.2%) of 1-phenyl-6-methoxy-indene as a pale yellow oil.

(d)

A mixture of 5.6 g (0.0183 mol) of benzo[b]quinolizinium hexafluorophosphate and 6.09 g (0.027 mol) of 1-phenyl-6-methoxyindene in 100 mL of nitromethane was heated to reflux for 12 h. The reaction mixture was cooled in ice, filtered, and concentrated in vacuo to yield a brown oil which was further concentrated in vacuo. The above brown foam was triturated in ether, decanted, and the residue in ether was filtered and dried in vacuo to yield 10.0 g (99%) of 6,11[[2',3']-3'-phenyl-6'-methoxyindanyl[6,11-dihydrobenzo[b]quinolizinium hexafluorophosphate (Formula I: $R^1=R^2=R^3=R^7=H$;

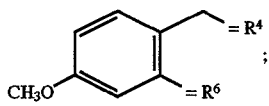

$R^5$=phenyl;$X^-=PF_6^-$; and Formula I: $R^1=R^2=R^4=R^7=H$;

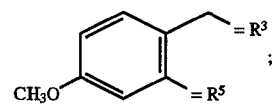

$R^6$=phenyl;$X^-=PF_6^-$; isomeric ratio 2.39:1), as a white solid, m.p. 210°–216° C.

EXAMPLE 4

(a)

Dihydrocoumarin (35 g, 0.236 mol) was added to 62.9 g (0.472 mol) of aluminum chloride and the mixture was heated in an oil-bath at 200° C. for 2.5 h with stirring. The reaction mixture was cooled, poured into ice (300 g), 300 mL of methylene chloride added to the mixture, cooled, and 400 mL of methylene chloride was added. The mixture was filtered and the solid residue was dissolved in hot methanol, filtered, and the filtrate was cooled to afford 14.5 g (41%) of 4-hydroxy-indan-1-one.

(b)

To a mixture of 4-hydroxy-indan-1-one (14.5 g, 0.0979 mol) and 27.08 g (0.195 mol) of potassium carbonate was added 500 mL of acetone and 48.7 mL (0.78 mol) of methanol with stirring and the resulting mixture was heated to reflux for 4 h, cooled, and allowed to stand at room temperature for 10 h. The above mixture was filtered, concentrated under vacuo, the solid residue was dissolved in methanol, heated and filtered. The filtrate was concentrated to a volume of 100 mL, cooled and filtered to afford 12.6 g (79 of 4-methoxy-indan-1-one.

(c)

To a solution of 9.38 g (0.057 mol) of 4-methoxy-1-indanone in 250 mL of ether cooled to 0° C. was added dropwise over 5 rain 33.72 mL (0.0607 mol) of 1.8 M phenyllithium in cyclohexane/ether and the mixture was stirred at room temperature for 1 h. An additional (10 mL) phenyllithium solution was added and stirred at room temperature for 1 h. To the reaction mixture was added saturated ammonium chloride solution and the resulting mixture was extracted with ethyl acetate (3×100 mL), and the organic layer was washed with brine, dried over sodium sulfate and concentrated in vacuo to afford 14.3 g of crude 4-methoxy-1-phenyl-indan-1-ol which was used directly in the next step without further purification.

(d)

To 1 L of toluene was added 14 g (0.058 mol) of 4-methoxy-1-phenyl-indan-1-ol and 100 mg of p-toluenesulfonic acid monohydrate and the solvent was distilled in vacuo (40 mm) until an oily residue was obtained. The oil was chromatographed (silica, 1:1 hexane/methylene chloride followed by ether) to afford 8.6 g (60.2 %) of 1-phenyl-4-methoxy-indene as a pale red oil.

(e)

A mixture of 5.6 g (0.0183 mol) of benzo[b]quinolizinium hexafluorophosphate and 6.09 g (0.027 mol) of 1-phenyl-4-methoxy-indene in 100 mL of nitromethane was heated to reflux for 6 h, cooled and filtered. The filtrate was concentrated in vacuo, 100 mL of ether was added to the brown foamy residue and the resulting mixture was triturated, a solid powder was filtered and washed with ether. After drying, 9.8 g (97%) of 6,11[[2',3']-3'-phenyl-7'-methoxy-indanyl]6,11-dihydrobenzo[b]quinolizinium hexafluorophosphate (Formula I: $R^1=R^2=R^3=R^7=H$;

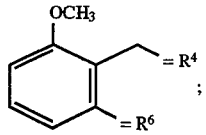

$R^5$=phenyl;$X^-$=$PF_6^-$; and Formula I: $R^1=R^2=R^4=R^7=H$;

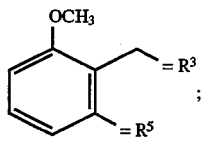

$R^6$=phenyl;$X^-$=$PF_6^-$) as a brown solid, m.p. 120°–125° C., isomeric ratio, 2.7:1, was obtained.

EXAMPLE 5

(a)

To a solution of 13.17 mL (0.104 mol) of 3-bromoanisole in 150 mL of ether cooled to −78° C. was added 10.4 mL (0.104 mol) of 10M n-butyllithium in hexane and the mixture was allowed to warm to room temperature (10 min). The above mixture was cooled to −20° C. and 12.5 g (0.094 mol) of indanone in 20 mL of THF was added and the mixture was allowed to warm to room temperature, and then stirred for 1 h. To the mixture was added saturated ammonium chloride solution and the resulting mixture was extracted with ethyl acetate (3×50 mL), and the organic layer was washed with brine, dried over sodium sulfate and concentrated in vacuo to afford 23.3 g of crude 1-(3-methoxy)-phenyl-indan-1-ol, as a brown oil, which was used directly in the next step without further purification.

(b)

To a mixture of 23 g (0.095 mol) of 1-(3-methoxyphenyl)-indan-1-ol and 100 mg of p-toluene sulfonic acid monohydrate was added 1 L of toluene and the solvent was distilled in vacuo (40 mm) until an oil residue was obtained. The oil was chromatographed (silica, 1:1 hexane/methylene chloride) to afford 17.0 g (80.1%) of 1-(3-methoxyphenyl)-indene as a pale yellow oil.

(c)

A mixture of 5.6 g (0.0183 mol) of benzo[b]quinolizinium hexafluorophosphate and 6.09 g (0.027 mol) of 1-(3-methoxyphenyl)-indene in 100 mL of nitromethane was heated to reflux for 14 h, cooled and concentrated in vacuo. The residue was triturated in ether, and a solid product was filtered to afford 9.8 g (98%) of 6,11[[2',3']-3'-(3-methoxyphenyl)-indanyl]6,11-dihydrobenzo[b] quinolizinium hexafluorophosphate (Formula I: $R^1=R^2=R^3=R^7=H$;

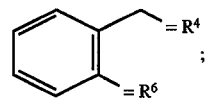

$R^5$=3-$CH_3$O-phenyl;$X^-$=$PF_6^-$; and Formula I: $R^1=R^2=R^4=R^7=H$;

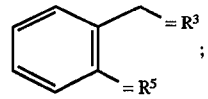

$R^6$=3-$CH_3$O-phenyl;$X^-$=$PF_6^-$) as a grey solid, m.p. 178°–185° C., isomeric ratio, 2.27:1.

(d)

The product of example 5 (C) was taken up in methanol (300 mL) and $CH_2Cl_2$ (100 mL) and heated to reflux. The mixture was cooled to room temperature and a solid was collected by filtration. The solid was fractionally crystallized several times from hot methanol to afford 6,11[2',3']-3'-(3-methoxyphenyl)-indanyl]6,11-dihydrobenzo[b] quinolizinium hexafluorophosphate (Formula I: $R^1=R^2=R^3=R^7=H$;

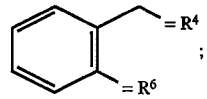

$R^5$=3-$CH_3$O-phenyl;$X^-$=$PF_6^-$) as a single geometric isomer.

EXAMPLE 6

(a)

To a solution of 2.7 mL (0.027 mol) of 10M n-butyllithium in hexane in 70 mL of ether cooled to −78° C. was added 4 g (0.027 mol) of 3-bromofuran and the mixture was stirred for 15 min. To the above cooled mixture was added 3.17 g (0.024 mol) of indanone in 10 mL of THF and the mixture was allowed to warm to room temperature, and then stirred for 20 min. To the mixture was added saturated ammonium chloride solution and the resulting mixture was extracted with ethyl acetate (3×100 mL), and the organic layer was washed with brine, dried over sodium sulfate and concentrated in vacuo to afford 5 g of crude 1-(3-furyl)-indan-1-ol, as an orange oil, which was used directly in the next step.

(b)

To a mixture of 5 g (0.024 mol) of 1-(3-furyl)-indan-1-ol in 500 mL of toluene was added 50 mg of p-toluenesulfonic acid monohydrate and the solvent was distilled in vacuo (40 mm) until a residue was obtained. The residue was chromatographed (silica, 1:1 hexane/methylene chloride) to afford 2.7 g (61.3 %) of 1-(3-furyl)-indene as a clear oil.

(c)

A mixture of 4.28 g (0.014 mol) of benzo[b]quinolizinium hexafluorophosphate and 2.6 g (0.0143 mol) of 1-(3-furyl)-indene in 75 mL of nitromethane was heated to reflux for 2 h, cooled to 0° C., filtered, and concentrated in vacuo. The brown foamy residue was triturated in ether, a tan solid product was filtered to afford 6.5 g of 6,11[[2',3']-3'-(3-furyl)

-indanyl]6,11-dihydrobenzo[b]quinolizinium hexafluorophosphate (Formula I: $R^1=R^2=R^3=R^7=H$;

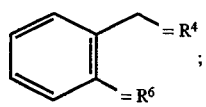

$R^5$=3-furanyl;$X^-$=$PF_6^-$; and Formula I: $R^1=R^2=R^4=R^7=H$;

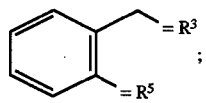

$R^6$=3-furanyl;$X^-$=$PF_6^-$), as a tan solid, m.p.155°–161° C., isomeric ratio, 1.1:1.

(d)

6,11[[2',3']-3'-(3-Furyl)-indanyl]6,11-dihydrobenzo[b] quinolizinium hexafluorophosphate (1.3 g, 0.00256 mol) was converted to the corresponding chloride salt by passing the hexafluorophosphate adduct through Dowex® 1x2-200 to afford, after by drying in vacuo for 12 h, 420 mg of 6,11[[2',3']-3'-(3-furyl)indanyl]6,11-dihydrobenzo[b] quinolizinium chloride, (Formula I: $R^1=R^2=R^3=R^7=H$;

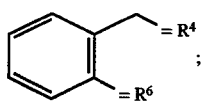

$R^5$=3-furanyl;$X^-$=$Cl^-$), m.p. 188°–193° C., as a white solid.

EXAMPLE 7

(a)

To a solution of 10.2 mL (0.102 mol) of 10M n-butyllithium in hexane in 200 mL of ether cooled to –78° C. was added dropwise 15 g (0.102 mol) of 3-bromofuran and the mixture was stirred for 15 min. To the above cooled mixture was added 12.61 g (0.092 mol) of 4',5',6',7'-tetrahydrobenzofuran-7-one in 50 mL of THF and the mixture was allowed to warm to room temperature, and then stirred for 15 min. To the mixture was added saturated ammonium chloride solution and the resulting mixture was extracted with ethyl acetate (3×100 mL), and the organic layer was washed with brine, dried over sodium sulfate and concentrated in vacuo to afford 16.3 g (86%) of 4',5',6',7'-tetrahydro-7-(3-furyl)-benzofuran-7-ol, a red oil.

To a mixture of 16.3 g of the above alcohol in 400 mL of toluene was added 100 mg of p-toluenesulfonic acid monohydrate and the mixture was placed on a Rotovap and the solvent was distilled in vacuo (40 mm/50° C.) until a brown-red residue was obtained yielding 14.3 g (96%) of 4,5-dihydro-7-(3-furyl)-benzofuran as a red oil.

(b)

To a mixture of 19 g (0.062 mol) of benzo[b] quinolizinium hexafluorophosphate and 200 mg of potassium carbonate in 200 mL of acetonitrile was added 14.3 g (0.0768 mol) of 4,5-dihydro-7-(3-furyl)-benzofuran and the mixture was heated to reflux for 10 min, cooled, and concentrated in vacuo. The residue was triturated in ether (300 mL), a brown solid product was filtered and dissolved in 300 mL of isopropanol, heated to 50° C. and cooled. The solid was filtered and chromatographed on silica (13% acetonitrile/methylene chloride) to afford 13.8 g of 6,11[[5', 4']-4'-(3-furyl)-4',5',6',7'-tetrahydrobenzofuryl]6,11-dihydrobenzo[b]quinolizinium hexafluorophosphate (Formula I: $R^1=R^2=R^3=R^7=H$;

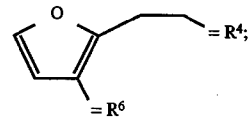

$R^5$=3-furanyl;$X^-$=$PF_6^-$; and Formula I: $R^1=R^2=R^4=R^7=H$;

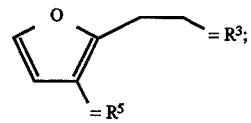

$R^6$=3-furanyl;$X^-$=$PF_6^-$), as a tan solid, m.p. 203°–210° C. (1:1.8 mixture of isomers). The solid was further purified by dissolving in 400 mL of methylene chloride/ethanol (1:1) with heating, distilling methylene chloride, followed by cooling to yield the product as an enriched 5.6:1 mixture of the geometric isomers.

(c)

6,11-[5',4"]-4'-(3-Furyl)-4',5',6',7'-tetrahydrobenzofuryl]6,11-dihydrobenzo[b]quinolizinium hexafluorophosphate, enriched isomer, (1.3 g, 0.00256 mol) was converted to the corresponding chloride salt by passing the hexafluorophosphate through Dowex® 1x2-200 (65 g) after placing the hexafluorophosphate salt with 10 mL of acetonitrile. The residue obtained was dissolved in acetonitrile, heated to reflux, ethyl acetate was added, cooled and filtered to afford 2.2 g (70.9%) of 6,11-[5',4"]-4'-(3-furyl)-4',5',6',7'-tetrahydrobenzofuryl]-6,11-dihydrobenzo[b]quinolizinium chloride, (Formula I: $R^1=R^2=R^3=R^7=H$;

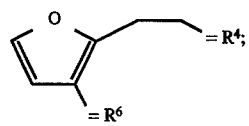

$R^5$=3-furanyl;$X^-$=$Cl^-$) m.p. 253°–256° C., as a tan solid.

EXAMPLE 8

(a)

To a solution of 4 mL (0.04 mol) of 10M n-butyllithium in hexane cooled to –78° C. was added 3.59 mL (0.04 mol) of 3-bromofuran in 100 mL of ether and the mixture was stirred for 10 min. To the above cooled solution was added 5.49 g (0.036 mol) 4',5',6',7'-tetrahydro-3-methyl-benzisoxazol-7-one and the mixture was allowed to warm to room temperature, and then stirred for 1 h. To the mixture was added saturated ammonium chloride solution and the resulting mixture was extracted with ethyl acetate (3×100 mL), and the organic layer was washed with brine, dried over sodium sulfate and concentrated in vacuo to afford 7.6 g (96%) of 7-(3-furyl)-3-methyl-4',5',6',7'-tetrahydrobenzisoxazol-7-ol, as a brown oil.

(b)

To a mixture of 7.6 g (0.034 mol) of 7-(3-furyl)-3-methyl-4',5',6',7'-tetrahydrobenzisoxazol-7-ol in 300 mL of toluene was added 100 mg of p-toluenesulfonic acid and the mixture was placed on a Rotovap, and the solvent was distilled in vacuo (80° C.) until an oil residue was obtained. Toluene (200 mL) was added to the above residue, the mixture was placed on a Rotovap, and the solvent was distilled in vacuo to complete the reaction. The oil was chromatographed (silica, 1:1 hexane/methylene chloride) to afford 3.36 g (95%) of 7-(3-furyl)-3-methyl-4,5-dihydrobenzisoxazole, (Formula III: $R^3$=H;

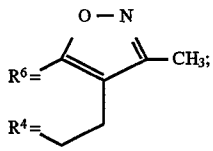

A mixture of 3.86 g (0.0124 mol) of benzo[b]quinolizinium hexafluorophosphate and 3 g (0.0149 mol) of 7-(3-furyl)-3-methyl-4,5-dihydrobenzisoxazole in 50 mL of nitromethane was heated to reflux for 14 h, cooled, and concentrated in vacuo. The residue was triturated in ether (100 mL), and a tan solid product was filtered. This solid was chromatographed (silica, 9% methanol/methylene chloride) and dried to afford 1.6 g of 6,11[6',7'[-7'-(3-furyl)-3'-methyl-4',5',6',7'-tetrahydrobenzisoxazolyl]6,11-dihydrobenzo[b]quinolizinium hexafluorophosphate, (Formula I:

$R^1=R^2=R^3=R^7$=H;

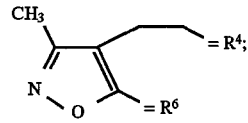

$R^5$=3-furanyl;$X^-$=$PF_6^-$; and Formula I: $R^1=R^2=R^4=R^7$=H;

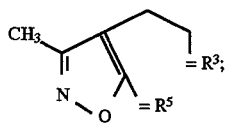

$R^6$=3-furanyl; $X^-$=$PF_6^-$), m.p.150°–156° C., (1:2.29 mixture of isomers).

EXAMPLE 9

(a)

To a solution of 20 g (0.147 mol) of 4,5,6,7-tetrahydrobenzofuryl-4-one was added 31.8 mL of triethylorthoformate, 34.5 mL of ethanol, and 100 mg of p-toluenesulfonic acid monohydrate and the mixture was stirred for 16 h. To the above mixture was added 2 g of potassium carbonate, and the mixture was stirred for 5 min, filtered and concentrated in vacuo to afford 24.1 g of a 2:1 mixture of 4-ethoxy-6,7-dihydrobenzofuran and starting 4',5',6',7'-tetrahydro-benzofuryl-4-one.

(b)

A mixture of 5 g (0.0163 mol) of benzo[b]quinolizinium hexafluorophosphate and 8.5 g (0.0407 mol) of 4-ethoxy-6,7-dihydrobenzofuran, and 100 mg of p-toluenesulfonic acid monohydrate in 100 mL of acetonitrile was heated to reflux for 10 h, cooled, and concentrated in vacuo. The brown residue was triturated in ether (30 min), a tan solid product was filtered and chromatographed on silica (15% acetonitrile/methylene chloride) to afford 3.69 g (46%) of 6,11[[5',4']-4'-ethoxy-4',5',6',7'-tetrahydrobenzofuryl]-6,11-dihydrobenzo[b]quinolizinium hexafluorophosphate, (Formula I: $R^1=R^2=R^3=R^7$=H;

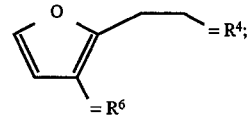

$R^5$=$CH_3CH_2O$;$X^-$=$PF_6^-$; and Formula I: $R^1=R^2=R^3=R^7$=H;

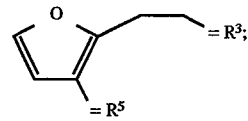

$R^6$=$CH_3CH_2O$;$X^-$=$PF_6^-$), as a yellow foam, m.p.101°–107° C., (1:1.36 mixture of isomers).

EXAMPLE 10

(a)

To a solution of 11.1 g (0.0939 mol) of benzofuran in 150 mL of ether cooled to −20° C. was added a solution of 9.39 mL (0.0939 mol) of 10M n-butyllithium in hexane, and the mixture was heated to warm to 0° C. and stirred for 30 min. The mixture was cooled to −78° C. and 10.6 g (0.078 mol) of 4',5',6',7'-tetrahydrobenzofuran-4-one in 20 mL of ether was added dropwise and the mixture was heated to warm to room temperature, and then stirred for 1 h. To the mixture was added saturated ammonium chloride solution and the resulting mixture was extracted with ethyl acetate (3×100 mL). The organic layer was washed with brine, dried over sodium sulfate and concentrated in vacuo to afford 19.3 g (97%) of 4',5',6',7'-tetrahydro-4-(2-benzofuryl)-benzofuran-7-ol, an oil which crystallized on standing as a yellow solid.

(b)

To a mixture of 19.3 g of 4,5,6,7-tetrahydro-4-(2-benzofuryl)-benzofuran-7-ol in 400 mL of toluene was added 100 mg of p-tolenesulfonic acid monohydrate, and the mixture was placed on a Rotovap, and the solvent was distilled in vacuo (60° C.) until a residue was obtained. The residue was chromatographed on silica (hexane/methylene chloride 1.5:1) to afford 15.3 g (86%) of 6,7-dihydro-4-(2-benzofuryl)-benzofuran, (Formula III: $R^3$=H;

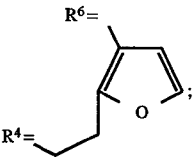

$R^5$=2-benzofuryl) as an orange oil.

(c)

To a mixture of 5.5 g (0.0179 mol) of benzo[b]quinolizinium hexafluorophosphate in 100 mL of acetonitrile was added 5.51 g (0.0768 mol) of 6,7-dihydro-4-(3-benzofuryl)-benzofuran and the mixture was heated to reflux for 2 h, cooled, and concentrated in vacuo. The residue was triturated in ether, a tan solid product was filtered and chromatographed on silica (13% acetonitrile/methylene chloride) to afford 16 g of 6,11[[5',4']-4'-(2-benzofuryl)-4',5',6',7'-tetrahydrobenzofuryl]6,11-dihydrobenzo[b]quinolizinium hexafluorophosphate (Example 10(c): isomeric ratio 1:1.3) as a yellow foam, m.p.146°–150° C. Isomeric separation was achieved by dissolving the mixture in 400 mL of methanol with heating, followed by cooling, and separating a solid (methanol insoluble G-isomer) via filtration and a methanol soluble isomer K. The solid G was fractionally recrystallized from methanol/methylene chloride to afford 2.0 g of 6,11[[5',4']-4'-(2-benzofuryl)-4',5',6',7'-tetrahydrobenzofuryl]6,11-dihydrobenzo[b]quinolizinium hexafluorophosphate (Formula I: $R^1=R^2=R^4=R^7=H$;

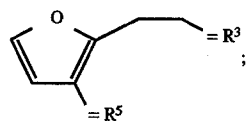

$R^6$=2-benzofuryl;$X^-$=$PF_6^-$; Example 10(c)-G), m.p. 238°–242° C., as a white solid. The filtrate containing methanol soluble isomer K was concentrated to 100 mL, and the insoluble G-isomer was removed. The purification procedure of retaining methanol soluble K-isomer and removing the methanol insoluble G-isomer was repeated to afford 1.4 g of 6,11[[5',4']-4'-(2-benzofuryl)-4',5',6',7'-tetrahydrobenzofuryl]6,11-dihydrobenzo[b]quinolizinium hexafluorophosphate, (Formula I: $R^1=R^2=R^3=R^7=H$;

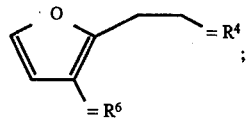

$R^5$=2-benzofuryl;$X^-$=$PF_6^-$; Example 10(c)-K), m.p. 170°–176° C., as a pale-yellow solid.

EXAMPLE 11

(a)

To a solution of furan-3-carboxylic acid (26 g, 0.23 mol) in 250 mL of toluene was added 24.15 mL (0.276 mol) of oxalyl chloride and 1 drop of pyridine and the mixture was heated on a steam-bath for 2 h. The mixture was cooled to room temperature, and N,O-dimethylhydroxamine hydrochloride (24.66 g, 0.253 mol), 4-dimethylaminopyridine (DMAP, 1.2 g, 0.01 mol), and 600 mL of methylene chloride were added. The mixture was cooled to 0° C., 50.1 mL of pyridine in 50 mL of methylene chloride was added slowly, the mixture was heated to warm to room temperature (3 h), and 2 g of N,O-dimethyl-hydroxamine hydrochloride and 1 g of 4-dimethylaminopyridine (DMAP) were added. The resulting mixture was stirred for 12 h. The above mixture was cooled to 0° C., filtered, and the filtrate was washed with 3 N HCl, brine, dried over sodium sulfate, and concentrated in vacuo to yield 14 g (39%) of 3-(N-methyl-N-methoxycarbamoyl)furan.

(b)

To a solution of 3-(N-methyl-N-methoxycarbamoyl)furan (14 g, 0.09 mol) in 150 mL of THF cooled to −78° C. was added in portions 36.1 mL (0.108 mol) of 3M methylmagnesium bromide in ether and the mixture was heated to warm to room temperature, and then stirred for 30 min. To the above mixture was added a cold 2N HCl (100 mL) and the aqueous layer was extracted with ether (3×100 mL), the combined organic layer was washed with brine, dried over sodium sulfate, and concentrated in vacuo to yield a pale-yellow oil. The above oil was chromatographed on silica (methylene chloride/hexane 2:1) to afford 6.95 g (70.2 %) of 1-(3-furyl)-1-propanone as a colorless oil which crystallized as a white solid.

(c)

To a stirring mixture of 1-(3-furyl)-1-propanone (6.75 g, 0.0612 mol) in 150 mL of methylene chloride was added TEOF (13.2 mL, 0.079 mol) with stirring followed by 100 mg of p-toluenesulfonic acid monohydrate and the resulting mixture was stirred for 126 h. Potassium carbonate (2 g) was added to the above reaction mixture, stirred for 10 min, filtered, and concentrated in vacuo. The residue was distilled (35 mm, 82°–85° C.) to afford 2.5 g (29%) of 1-(3-furyl)-1-ethoxy-ethylene (Formula III: $R^3=R^4=H$; $R^5=CH_3CH_2O$;$R^6$=3-furanyl), as a clear oil.

(d)

To a mixture of 4.59 g (0.015 mol) of benzo[b]quinolizium hexafluorophosphate in 50 mL of acetonitrile was added 1-(3-furyl)-1-ethoxy-ethylene (2.5 g, 0.018 mol) and the mixture was heated to reflux for 20 min, cooled, filtered, and concentrated in vacuo. The brown residue was triturated in ether for 1 h, a tan solid product was filtered and dried in vacuo to yield 6.3 g (90%) of 6,11-ethano-12-(3-furyl)-12-ethoxy-6,11-dihydrobenzo[b]quinolizinium hexafluorophosphate, as a tan solid, m.p.143°–147° C., (1.59:1 mixture of isomers).

(e)

isomeric separation 6,11-Ethano-12-(3-furyl)-12-ethoxy-6,11-dihydrobenzo[b]quinolizinium hexafluorophosphate (6.0 g) was dissolved in hot methanol/isopropanol (1:3) and filtered while hot, separating insoluble solid isomer P and soluble isomer R. Isomer P - the solid insoluble in hot methanol/isopropanol (1:3) was fractionally recrystallized from methanol/isopropanol (1:5), followed by dissolving the solid in methylene chloride/methanol/isopropanol (1:1:4) and distilling methylene chloride to isolate 1.75 g of 6,11-ethano-12-(3-furyl)-12-ethoxy-6,11-dihydrobenzo[b]quinolizinium hexafluorophosphate (isomer P). Isomer R - the solid soluble in hot methanol/isopropanol (1:3) was successively treated with hot methanol/isopropanol (1:5) to remove the insoluble solid, while retaining the soluble product and then distilling methanol to ½ of its original volume to yield upon cooling and filtration 629 mg of 6,11-ethano-12-(3-furyl)-12-ethoxy-6,11-dihydrobenzo[b]quinolizinium hexafluorophosphate (isomer R).

(f)

6,11-Ethano-12-(3-furyl)-12-ethoxy-6,11-dihydrobenzo[b]quinolizinium hexafluorophosphate (isomer R, 629 mg, 0.00135 mol) was converted to the corresponding chloride salt by passing the hexafluorophosphate dissolved in $CH_3CN$ (5 mL) through Dowex® 1x2-200 (45 g) eluting with $H_2O$. The aqueous fractions were concentrated and the residue obtained was dried in vacuo (0.1 mm/40° C./12 h) to afford 460 mg (95.8%) of 6,11-ethano-12-(3-furyl)-12-ethoxy-6,11-dihydrobenzo[b]quinolizinium chloride, (Formula I: $R^1=R^2=R^3=R^4=R^7=H; R^6=3$-furanyl; $R^5=CH_3CH_2O$; X-Cl⁻), m.p. 178°–182° C., as a white solid.

(g)

6,11-Ethano-12-(3-furyl)-12-ethoxy-6,11-dihydrobenzo[b] quinolizinium hexafluorophosphate (isomer P, 1.75 g, 0.0037 mol) was converted to the corresponding chloride salt by passing the hexafluorophosphate dissolved in $CH_3CN$ (10 mL) through Dowex® 1x2-200 (65 g) eluting with $H_2O$, and concentration of residue. The residue obtained was dried in vacuo (0.1 mm/40° C./12 h) to afford 1.2 g (90.2%) of 6,11-ethano-12-(3-furyl)-12-ethoxy-6,11-dihydrobenzo[b]quinolizinium chloride, (Formula I: $R^1=R^2=R^3=R^4=R^7=H; R^5=CH_3CH_2O; R^6=3$-furanyl; X⁻Cl⁻), m.p. 132°–136° C., as an off-white solid.

EXAMPLE 12

(a)

A mixture of (2,5-dimethyl-3-acetyl)-furan (12.5 g, 0.09 mol), 300 mg of p-toluenesulfonic acid monohydrate, 21.2 mL (0.35 mol) of ethanol, and 29.9 mL (0.18 mol) of triethylorthoformate in 250 mL of methylene chloride was stirred at room temperature 72 h, then 1 g of potassium carbonate, was added. The mixture was stirred for 5 min, filtered, and concentrated in vacuo. The residue was distilled (40–45 mm/115°–125° C.) to afford 7.94 g (53.2%) of 1-[(2,5-dimethyl)-3-furyl]-1-ethoxy-ethylene. (Formula III: $R^3=R^4=H; R^5=CH_3CH_2O; R^6=2,5$-dimethyl-3-furanyl); as a clear oil.

(b)

To a mixture of 6 g (0.0196 mol) of benzo[b] quinolizinium hexafluorophosphate in 100 mL of acetonitrile was added 1-[(2,5-dimethyl)-3-furyl]ol-ethoxyethylene (3.9 g, 0.0235 mol) and 100 mg of p-toluenesulfonic acid monohydrate and the mixture was heated to reflux for 24 h, cooled, filtered, and concentrated in vacuo. The brown residue was triturated in ether (150 mL) for 1 h, and a tan solid product was filtered and dried in vacuo. The solid residue was chromatographed on silica (13% acetonitrile/methylene chloride) to yield, after crystallization from isopropanol, 6,11-ethano-12-[(2,5-dimethyl)-3-furyl]-12-ethoxy-6,11-dihydrobenzo[b] quinolizinium hexafluorophosphate (Formula I: $R^1=R^2=R^3=R^4=R^7=H; R^5=CH_3CH_2O; R^6=2,5$-dimethyl-3-furyl; X⁻=$PF_6^-$ and Formula I: $R^1=R^2=R^3=R^4=R^7=H; R^5=2,5$-dimethyl-3-furyl; $R^6=CH_3CH_2O$; X⁻=$PF_6^-$) as a tan solid, (1:1.33 mixture of isomers).

EXAMPLE 13

(a)

To a mixture of 8 g of 6-methyl-benzo[b]quinolizinium perchlorate (Bradsher and Parham J. Het. Chem. 1964, 1, 121–124) in 200 mL of ethanol was added 7.86 g (0.057 mol) of 1-(3-furyl)-1-ethoxy-ethylene and 75 mL of acetonitrile and the mixture was heated to reflux, cooled, filtered (to remove the perchlorate salt) and the solvent was heated to evaporate at room temperature. The residue was triturated in 50 mL of methylene chloride, filtered, and the filtrate was concentrated in vacuo and the resulting residue was chromatographed on silica (methylene chloride/ethyl acetate/methanol, 7:2:1) to afford 7.5 g of 6,11-ethano-12-(3-furyl)-12-ethoxy-6-methyl -6,11-dihydrobenzo[b]quinolizinium perchlorate, (Formula I: $R^1=R^3=R^4=R^7=H; R^2=CH_3$; $R^5=CH_3CH_2O; R^6=3$-furyl; X⁻=$ClO_4^-$ and Formula I: $R^1=R^3=R^4=R^7=H; R^2=CH_3; R^5=3$-furyl; $R^6=CH_3CH_2O$; X⁻=$ClO_4$-) as a white solid (isomeric ratio, 1:1).

(b)

6,11-Ethano-12-(3-furyl) -12-ethoxy-3-methyl-6,11-dihydrobenzo-[b]quinolizinium perchlorate of Example 13(a) (5.4 g), was converted to the corresponding chloride salt by passing the perchlorate through Dowex® 1x2-200 to afford 5.4 g (0.0125 mol) of the chloride salt which was treated with 4.955 g (0.0125 mol) of potassium monobenzoyl-D-tartarate in methylene chloride to afford 10.05 g of the monobenzoyl-D-tartarate salt as a white solid. The monobenzoyl-D-tartarate salt was recrystallized (3x) from ethanol to yield 100 mg of 6,11-ethano-12-(3-furyl)-12-ethoxy-3-methyl-6,11-dihydrobenzo[b]-quinolizinium monobenzoyl-D-tartarate, (Formula I: $R^1=R^3=R^4=R^7=H; R^2=CH_3; R^5=3$-furyl; $R^6=CH_3CH_2O$; X⁻=(−)$C_{18}H_{14}O_8$), as a white solid, m.p.150° C.

EXAMPLE 14

(a)

To a solution of 3,3-difurylmethanone (3 g, 0.0185 mol) in 50 mL of THF cooled to 0° C. was added 7.4 mL (0.022 mol) of 3 Methylmagnesium bromide in ether and the mixture was heated to warm to room temperature, and then stirred for 30 min. To the above mixture was added ammonium chloride solution, the mixture was extracted with ethyl acetate, and the organic layer was dried over sodium sulfate and concentrated in vacuo to yield 2.5 g (70.4%) of 1,1-(di-3-furyl)-propanol, a brown oil.

(b)

A mixture of 1,1-(di-3-furyl)-propanol (2.95 g. 0.0153 mol) and 150 mL of p-toluenesulfonic acid monohydrate in toluene was heated to 70° C. and the mixture was distilled to remove toluene in vacuo to yield a pale-yellow oil. The above oil was chromatographed on silica (hexane/methylene chloride 3:1) to afford 500 mg (18.7%) of 1,1-(di-3-furyl)-2-methyl-ethylene, (Formula III: $R^3=CH_3; R^4=H; R^5=R^6=3$-furyl), as a clear oil.

(c)

A mixture of 0.78 g (0.00256 mol) of benzo[b] quinolizinium hexafluorophosphate and 1,1-(di-3-furyl)-2-methyl-ethylene (0.49 g, 0.0028 mol) in 25 mL of nitromethane was heated to reflux for 8 h, and 50 mL of methylene chloride was added. The mixture was cooled to 0° C., filtered, and the filtrate was concentrated in vacuo. The solid residue was triturated in ether, filtered, and chromatographed on silica (15% acetonitrile/methylene chloride) to afford 150 mg (11%) of 6,11-ethano-12,12-difuryl-13-methyl-6,11-dihydrobenzo[b]-quinolizinium hexafluorophosphate (Formula I: $R^1=R^2=R^3=R^7=H; R^4=CH_3; R^5=R^6=3$-furyl; X⁻=$PF_6^-$ and Formula I: $R^1=R^2=R^4=R^7=H; R^3=CH_3; R^5=R^6=3$-furyl; X⁻=$PF_6^-$) as a tan solid, m.p.122°–126° C.

EXAMPLE 15

(a)

To a solution of 7.22 mL (0.0722 mol) of 10M n-butyllithium in hexane in 150 mL of ether cooled to −78° C. was added 10.62 g (0.0722 mol) of 3-bromofuran and the mixture was stirred for 15 min. To the above cooled mixture was added 10 g (0.0656 mol) of 4,5,6,7-tetrahydrothianaphthen-4-one in 25 mL of THF and the mixture was heated to warm to room temperature, and then stirred. To the mixture was added saturated ammonium chloride solution and the resulting mixture was extracted with ethyl acetate (3×100 mL), and the organic layer was washed with brine, dried over sodium surf ate and concentrated in vacuo to afford 13.6 g (94.2%) of 4-(3-furyl)-4,5,6,7-tetrahydrothianaphthen-4-ol, as a brown oil.

(b)

To a mixture of 13.6 g (0.0618 mol) of 4-(3-furyl)-4,5,6,7-tetrahydrothianaphthen-4-ol in 250 mL of toluene was added 600 mg of p-toluenesulfonic acid monohydrate. The mixture was placed on a Rotovap and toluene was distilled in vacuo (60° C.) until a residue was obtained. The residue was chromatographed (silica, 3:1 hexane/methylene chloride) to afford 11.6 g (92.9%) of 4-(3-furyl)-6,7-dihydrothianaphthene as a pale-yellow oil.

(c)

A mixture of 6 g (0.0196 mol) of benzo[b]quinolizinium hexafluorophosphate and 5.12 g (0.023 mol) of 4-(3-furyl)-6,7-dihydrothianaphthene in 100 mL of nitromethane was heated to reflux for 14 h, cooled, and concentrated in vacuo. The residue was dissolved in ethyl acetate (200 mL), filtered, and the filtrate was concentrated in vacuo, the residue was dissolved in ether, and the ether solution was cooled to yield 11 g of 6,11[[5',4']-4'-(3-furyl)-4',5',6',7'-tetrahydrothianaphthyl]6,11-dihydrobenzo[b]quinolizinium hexafluorophosphate as a gray solid, (1:1.03 mixture of isomers). The gray solid, product was dissolved in 500 mL of isopropanol/methylene chloride (3:2) on a steam-bath while distilling 150 mL of methylene chloride and cooled to afford 6,11[[5',4']-4'-(3-furyl)-4',5',6',7'-tetrahydrothianaphthyl]6,11-dihydrobenzo[b]quinolizinium hexafluorophosphate, (Formula I: $R^1=R^2=R^3=R^7=H$;

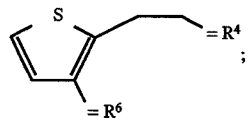

$R^5$=3-furyl;$X^-$=$PF_6^-$; and Formula I: $R^1=R^2=R^4=R^7=H$;

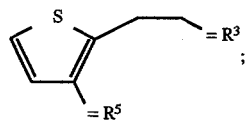

$R^6$=3-furyl;$X^-$=$PF_6^-$), as a tan solid (1:1 mixture of isomers).

EXAMPLE 16

(a)

A mixture of 0.52 g of benzo[b]quinolizinium bromide and 1.02 g of 1,1-diphenylethylene in 50 mL of nitromethane was heated to reflux under argon for 16 h, cooled, and concentrated in vacuo. The residue was chromatographed on silica (methylene chloride/methanol 9:1), the solid product was dissolved in 50 mL of warm water, filtered, and the filtrated was treated with 10% sodium perchlorate solution. The solid precipitate was filtered, washed with hexane, ether, and dried in vacuo for 72 h to afford 6,11-ethano-12,12-diphenyl-6,11-dihydrobenzo[b]quinolizinium perchlorate, (Formula I: $R^1=R^2=R^3=R^4=R^7=H$;$R^5=R^6$=phenyl;$X^-=ClO_4^-$), m.p. 150° C.(d).

EXAMPLE 17

(a)

A mixture of 4.6 g (0.0165 mol) of benzo[b]quinolizinium perchlorate and 9 g of 1,1-diphenylethylene (0.05 mol) in 250 mL of nitromethane was heated to reflux under nitrogen for 16 h. The reaction mixture was poured into 100 mL of water, shaken, and the organic layer was separated and washed with 100 mL of water, and the nitromethane layer was concentrated in vacuo to 50 mL of its volume. To the above nitromethane layer was added 100 mL of water, the resulting mixture was concentrated in vacuo, and the residue was dissolved in 200 mL of acetonitrile and 500 mL of water. The above mixture was extracted with hexane (3×100 mL; a black oil insoluble in both hexane and acetonitrile/water was removed), and the aqueous layer was steam distilled to remove acetonitrile to yield an oil which crystallized on standing. The solid product was washed with 200 mL of ether, 200 mL of hexane, and 200 mL of ether to afford 5.1 g (67%) of 6,11-ethano-12,12-diphenyl-6,11-dihydrobenzoro]quinolizinium perchlorate, as a tan solid.

(b)

A Dowex® column was prepared with 150 g of Dowex® 1x2-200 in 0.5 N HCl, washed with 0.5 N HCl, followed by water until the pH was 4–5. 6,11-Ethano-12,12-diphenyl-6,11-dihydrobenzo[b]quinolizinium perchlorate (5.1 g) was dissolved in 40 mL of acetonitrile and was placed on the column, eluted with water, and the aqueous eluent was concentrated in vacuo (45° C.). The residue was dissolved in 50 mL of warm acetonitrile, treated with activated charcoal, filtered through diatomaceous earth, and the filtrate triturated in isopropyl acetate to yield an insoluble solid (0.5 g). The above filtrate (isopropyl acetate) was concentrated, the residue was triturated in acetonitrile, and filtered to yield 1.6 g of an amorphous solid. The mother liquor (acetonitrile) was concentrated further to obtain 2.0 g of an amorphous solid. All solid products were combined and dried in vacuo (48 h) to give 4.036 g of a white solid which was recrystallized from 100 mL of water and dried in vacuo to afford 3.57 g of 6,11-ethano-12,12-diphenyl-6,11-dihydrobenzo[b]quinolizinium chloride, (Formula I: $R^1=R^2=R^3=R^4=R^7=H$; $R^5=R^6$=phenyl;$X^-=Cl^-$), as a white solid, m.p. 169°–174° C.

EXAMPLE 18

(a)

A mixture of 0.5 g of benzo[b]quinolizinium perchlorate and 1 g of 1,1-diphenyl-2-methyl-ethylene in 40 mL of nitropropane was heated to reflux under nitrogen for 2 h. An additional 1,1-diphenyl-2-methyl-ethylene (0.3 g) was added and the mixture was refluxed for 48 h. The reaction mixture was concentrated in vacuo, the residue was triturated in ether/hexane (1:1), and the solid was filtered. The above solid was resuspended with methylene chloride/hexane (1:1), and filtered. The filtrate was concentrated in vacuo, and the resulting residue was chromatographed on silica (methylene chloride and then methylene chloride/methanol 9:1) to afford 0.52 g of 6,11-ethano-12,12-diphenyl-13-methyl-6,11-dihydrobenzo[b]quinolizinium perchlorate, as a foamy solid.

The above perchlorate was purified by dissolving the solid in methanol/ethyl acetate (9:1), treating the solution with activated charcoal, and concentrating the filtrate in vacuo to yield a foamy solid. The purified solid was converted to the corresponding chloride salt by passing the perchlorate through Dowex® 1x2-200 exchange resin. The chloride salt residue obtained was dissolved in 10 mL of methanol, treated with 10% sodium perchorate solution (10 mL), stirred for 10 min, and methanol was removed in vacuo to yield a solid product. The above perchlorate salt was washed with water, ether, and hexane and dried in vacuo to afford 0.12 g of 6,11-ethano-12,12-diphenyl-13-methyl-6,11-dihydrobenzo[b]quinolizinium perchlorate, (Formula I: $R^1=R^2=R^3=R^7=H;R^4=CH_3;R^5=R^6=phenyl;X^-=ClO_4^-$; and Formula I: $R^1=R^2=R^4=R^7=H;R^3=CH_3;R^5=R^6=phenyl;X^-=ClO_4^-$), m.p. 197°–199° C.

EXAMPLE 19

(a)

A mixture of 0.52 g of 6-methylbenzo[b]quinolizinium perchlorate and 1.02 g of 1,1-diphenylethylene in 40 mL of nitromethane was heated to reflux under nitrogen for 16 h. An additional 1,1-diphenylethylene (0.5 g) was added, and the mixture was refluxed for an additional 72 h, cooled, and concentrated. The residue was triturated in hexane/ether (1:1), filtered, dried, and chromatographed on silica (methylene chloride/methanol 9:1) to afford 0.88 g of 6,11-ethano-12,12-diphenyl-6-methyl-6,11-dihydrobenzo[b] quinolizinium perchlorate as a solid.

(b)

6,11-Ethano-12,12-diphenyl-6-methyl-6,11-dihydrobenzo[b]quinolizinium perchlorate (850 mg) was converted to the corresponding chloride salt by passing the perchlorate through 100 g of Dowex® 1x2-200 exchange resin to afford 580 mg (79.4%) of 6,11-ethano-12,12-diphenyl-6-methyl-6,11-dihydro-benzo[b]quinolizinium chloride, (Formula I: $R^1=R^3=R^4=R^7=H; R^2=CH_3;R^5=R^6=phenyl;X^-=Cl^-$) as a solid, m.p. 160° C.(d).

EXAMPLE 20

(a)

A mixture of 1-(1-methyl-benzyl)2-(1,3-dioxolan-2-yl) pyridinium perchlorate (18 g) and 100 g of polyphosphoric acid was heated to heat at 100° C. for 5 h and then the mixture was allow to stand at room temperature overnight. To the mixture was added 200 mL of water, the reaction mixture was stirred for 30 min, filtered, and sodium perchlorate solution (a slight excess) was added to the above filtrate. The precipitated solid was filtered and dried to afford 10.5 g (70%) of 6-methyl-benzo[b]quinolizinium perchlorate (Formula II: $R^1=R^7=H;R^2=CH_3;X^-=ClO_4^-$) as a yellow solid.

(b)

A mixture of 9.5 g (0.032 mol) of 6-methyl-benzo[b] quinolizinium perchlorate and 16.2 g (0.09 mol) of 1,1-diphenylethylene in 100 mL of nitromethane was heated to reflux for 3 days. The reaction mixture was filtered through a pad of silica gel, washed with 150 mL of acetonitrile, the filtrate was triturated with ether, and the crystalline white solid was filtered, washed with ether, and dried to afford 18.3 g (100%) of 6,11-ethano-12,12-diphenyl-6-methyl-6,11-dihydrobenzo[b]quinolizinium perchlorate, (Formula I: $R^1=R^3=R^4=R^7=H;R^2=CH_3;R^5=R^6-phenyl;X^-=ClO_4^-$) as a white solid.

(c)

To a solution of dibenzoyl-L-tartrate (64 g, 0.17 mol) in 450 mL of methanol was added dropwise a solution of potassium hydrogen carbonate (17.2 g, 0.17 mol) in 100 mL of water in 4 min and the mixture was stirred overnight. The white solid formed was filtered, washed with 100 mL of methanol, dried in an oven in vacuo to afford 67.4 g (86.5%) of monopotassium monobenzoyl-L-tartarate.

(d)

A mixture of 6,11-ethano-12,12-diphenyl-6-methyl-6,11-dihydrobenzo[b]quinolizinium perchlorate (15.8 g, 0.033 mol) and mono-potassium monobenzoyl-L-tartarate (13.2 g, 0.033 mol) in 2 L of methanol was gently warmed on a steam bath to dissolve the solids, and then filtered. The filtrate was concentrated, the residue was combined with 2 L of methylene chloride with stirring, and re-filtered to remove potassium perchlorate. The methylene chloride filtrate on standing at room temperature yielded a white solid which was recrystallized from methylene chloride/methanol to afford 5.7 g of 6,11-ethano-12,12-diphenyl-6-methyl -6,11-dihydrobenzo[b]quinolizinium monobenzoyl-L-tartarate, (Formula I: $R^1=R^3=R^4=R^7=H;R^2=CH_3;R^5=R^6-phenyl; X^-=[(-)-DBT]$) as a white solid, m.p. 160°–161° C.

(e)

The mother liquor from the above recrystallization (methylene chloride/methanol) containing 6,11-ethano-12, 12-diphenyl-6-methyl-6,11-dihydrobenzo[b]quinolizinium perchlorate was passed through 100 g of Dowex® 1x2-200. The residue obtained was dissolved in 4 L warm water/ methanol (1:1), the solution was stirred, 14 g of sodium perchlorate in 100 mL of water was added, methanol was removed in vacuo, and a crystalline solid was filtered and washed with water. The above solid was dissolved in 75 mL of methylene chloride, the solution was extracted with 50 mL of water containing 1 g of sodium perchlorate, and washed with water. The organic layer was concentrated in vacuo, the residue was flash chromatographed on silica (methylene chloride/acetonitrile to afford 8.7 g of 6,11-ethano-12,12-diphenyl-6-methyl-6,11-dihydrobenzo[b] quinolizinium perchlorate, as an amorphous solid.

(f)

To a solution of dibenzoyl-D-tartarate (49.2 g, 0.1307 mol) in 345 mL of methanol was added dropwise a solution of potassium hydrogen carbonate (13.09 g, 0.1307 mol) in 77 mL of water in 4 min and the mixture was stirred overnight. The white solid formed was filtered, washed with 100 mL of methanol, dried in vacuo to afford 51.6 g (84%) of mono-potassium monobenzoyl-D-tartarate.

(g)

A mixture of 6,11-ethano-12,12-diphenyl-6-methyl-6,11-dihydrobenzo[b]quinolizinium perchlorate (8.5 g, 0.0179 mol) and mono-potassium monobenzoyl-D-tartarate (7.11 g, 0.0179 mol) in 1 L of methanol was gently warmed on a steam bath to dissolve the solids, the mixture was concentrated, the residue was dissolved in 500 mL of methylene chloride with stirring, and filtered to remove potassium perchlorate. The methylene chloride filtrate was concentrated to 200 mL of its volume, cooled, filtered, and the solid obtained was washed with methylene chloride (2×20 mL) to afford 6.8 g (51.9 %) of 6,11-ethano-12,12-diphenyl-6-methyl -6,11-dihydrobenzo[b]quinolizinium monobenzoyl-D-tartarate, (Formula I: $R^1=R^3=R^4=R^7=H;R^2=CH_3;R^5=R^6=$-phenyl; $X^-=[(+)$-DBT]), as a white solid, m.p. 160°–161° C.

(h)

6,11-Ethano-12,12-diphenyl-6-methyl-6,11-dihydrobenzo[b]quinolizinium monobenzoyl-D-tartarate (6.8 g) was passed through Dowex® 1x2-200 (100 g). The residue obtained was dried in vacuo to afford 3.84 g of 6,11-ethano-12,12-diphenyl-6-methyl-6,11-dihydrobenzo[b]quinolizinium chloride ½ hydrate, (Formula I: $R^1=R^3=R^4=R^7=H;R^2=CH_3;R^5=R^6=$phenyl;$X^-=Cl^-$; as (−)-isomer), as an amorphous solid, $[\alpha]_D^{25}=-50.7°$ in $CHCl_3$,C=10 mg/mL.

EXAMPLE 21

6,11-Ethano-12,12-diphenyl-6-methyl-6,11-dihydrobenzo [b]quinolizinium monobenzoyl-L-tartarate (11 g) was converted to the corresponding chloride salt by passing the mono benzoyl-L-tartrate through Dowex® 1x2-200 (100 g) after placing the salt in 50 mL of methanol. The amorphous residue obtained was dried in vacuo to afford 2.7 g of 6,11-ethano-12,12-diphenyl-6-methyl-6,11-dihydrobenzo[b]quinolizinium chloride hydrate (Formula I: $R^1=R^3=R^4=R^7=H;R^2=CH_3;R^5=R^6=$phenyl;$X^-=Cl^-$; as (+)-isomer) as a solid, $[\alpha]_D^{25}=+50.9°$ in $CHCl_3$,C=10 mg/mL.

EXAMPLE 22

(a)

A mixture of 1.0 g of benzo[b]quinolizinium perchlorate and 1.28 g of 1,1-diphenylmethylenecyclopropane in 40 mL of nitromethane was heated to reflux under nitrogen for 16 h. The mixture was concentrated in vacuo and the residue was triturated in hexane/ether (1:1), filtered, dried, and chromatographed on silica (methylene chloride/methanol 9:1) to afford 2.4 g of 6,11-ethano-12,12-diphenyl-13,13-spirocyclopropyl-6,11-dihydrobenzo[b]quinolizinium perchlorate as a solid.

(b)

6,11-Ethano-12,12-diphenyl-13,13-spirocyclopropyl-6,11-dihydrobenzo[b]quinolizinium perchlorate (2.4 g) was converted to the corresponding chloride salt by passing the perchlorate through Dowex® 1x2-200 ion exchange resin to afford 2.7 g of 6,11-ethano-12,12-diphenyl-13,13-spirocyclopropyl-6,11-dihydrobenzo[b]quinolizinium chloride, (Formula I: $R^1=R^2=R^7=H$; $R^3$ and $R^4$ together form a cyclopropyl ring;$R^5=R^6=$phenyl;$X^-=Cl^-$), as a solid.

EXAMPLE 23

(a)

To a solution of bromobenzene (100 g, 0.63 mol) in 300 mL of dichloroethane cooled to 0° C. was added 169.6 g (1.27 mol) of aluminum chloride. The mixture was stirred (1 min), and 37.6 g (0.378 mol) of 1,1,1-trichloroethane in 50 mL of dichloroethene was added and stirred at 0° C. for 1 h. The above mixture was diluted with 500 g of ice, basified with 30% sodium hydroxide solution, filtered, the aqueous layer was extracted with methylene chloride (2×500 mL), and the combined organic layer was dried over sodium sulfate and concentrated in vacuo to yield a brown oil. The brown oil was crystallized from hexane (2×150 mL) to afford 10.5 g of 1,1-di(4-bromo)-phenylethylene (Formula III: $R^3=R^4=H;R^5=R^6=$4-bromophenyl) as a white solid. The mother liquor was concentrated in vacuo and chromatographed on silica (hexane) to yield 18.5 g (total 29 g, 27%) of an additional white solid.

(b)

A mixture of 3.0 g (0.0098 mol) of benzo[b]quinolizinium hexafluorophosphate and 4.9 g (0.0147 mol) of 1,1-di-p-bromophenylethylene in 50 mL of nitromethane was heated to reflux for 8 h. After adding 0.5 g of 1,1-di-p-bromophenylethylene, the mixture was refluxed for an additional 12 h. The mixture was cooled, concentrated in vacuo and the residue was triturated in hexane/ether (1:1), filtered, and dried to afford 6.25 g (99.2%) of 6,11-ethano-12,12-di-p-bromophenyl-6,11-dihydrobenzo[b]quinolizinium hexafluorophosphate, (Formula I: $R^1=R^2=R^3=R^4=R^7=H;R^5=R^6=$4-bromophenyl;$X^-=PF_6^-$) as a white solid.

(c)

6,11-Ethano-12,12-di-p-bromophenyl-6,11-dihydrobenzo[b]quinolizinium hexafluorophosphate (6.2 g, 0.0096 mol)) was converted to the corresponding chloride shk by passing the salt through Dowex® 1x2-200 (80 g) by placing the salt in 20 mL of acetonitrile. The eluent was concentrated in vacuo, and the residue obtained was dried by dissolving in 200 mL of toluene and concentrating the solution. The resulting residue was crystallized from ethyl acetate to afford 4.4 g (83%) of 6,11-ethano-12,12-di-p-bromophenyl-6,11-dihydrobenzo[b]quinolizinium chloride, (Formula I: $R^1=R^2=R^3=R^4=R^7=H;R^5=R^6=$4-bromophenyl;$X^-=Cl^-$), as a white solid.

EXAMPLE 24

(a)

A mixture of 0.5 g of benzo[b]quinolizinium perchlorate and 0.77 g of 1,1-di-(2-pyridyl)ethylene in 30 mL of nitromethane was heated under nitrogen at 100° C. for 8 h. The mixture was cooled, concentrated in vacuo, the dark residue was dissolved in 100 mL of methanol, treated with activated charcoal, filtered, and concentrated in vacuo to afford 0.55 g (62.5%) of 6,11-ethanol-12,12-di-(2-pyridyl)-6,11-dihydrobenzo[b]quinolizinium perchlorate (Formula I: $R^1=R^2=R^3=R^4=R^7=H;R^5=R^6=$2-pyridyl;$X^-=ClO_4^-$), as a brown foamy solid.

(b)

6,11-Ethano-12,12-di-(2-pyridyl)-6,11-dihydrobenzo[b]quinolizinium perchlorate (750 mg) was purified by passing through a pad of silica gel (dichloromethane/methanol) to yield 450 mg of the perchlorate, and the perchlorate was converted to the corresponding chloride salt by passing the salt through Dowex® 1x2-200 ion exchange resin. The eluent was concentrated in vacuo, and the residue obtained was dried to afford 250 mg (40%) of 6,11-ethano-12,12-di-(2-pyridyl)-6,11-dihydrobenzo[b]quinolizinium chloride hydrate (Formula I: $R^1=R^2=R^3=R^4=R^7=H;R^5=R^6=$2-pyridyl;$X^-=Cl^-$), as a pale-yellow solid.

EXAMPLE 25

(a)

To a mixture of 63.55 g (0.46 mol) of m-methoxybenzyl alcohol in 1.5 L of ether cooled to −40° C. was added in 2 portions (100 mL, 1.0 mol) 10M of n-butyllithium over a 30 min period and the reaction mixture was slowly (removing a bath) warmed to room temperature by removal of the cooling bath and stirred for 30 minutes. The above reaction mixture was cooled to −20° C., 69.7 g (0.651 mol) of 4-pyridinecarboxaldehyde was added to the mixture, and the resulting reaction mixture was heated to warm to room temperature. After 1 h, ammonium chloride solution was added to the mixture. The diol was extracted with ethyl acetate, dried over sodium sulfate, and the solvent was removed in vacuo. Recrystallization (2x) from ethyl acetate/ether afforded 68.5 g (60.7%) of 2-[1-hydroxy-(2'-methoxy-6'-hydroxymethyl)-benzyl]pyridine (Formula X: $R^1=R^2=H;R^7=6'-OCH_3$).

(b)

To 25 g (0.102 mol) of 2-[1-hydroxy-(2'-methoxy-6'-hydroxymethyl)benzyl]-pyridine was added rapidly with stirring 30 mL of $POCl_3$ and the resulting mixture was placed in an oil bath preheated to 110° C. The exothermic reaction mixture (with evolution of HCl gas) was cooled, 250 mL of methylene chloride was added, and the solvent was decanted to yield an oil. The oil was dissolved in water, treated with 5 g of sodium perchlorate, in 100 mL of water and the precipitated perchlorate was isolated by filtration. The above decanted organic solvent was concentrated, the residual chloride was triturated with 100 mL of methylene chloride, and the precipitated solid was filtered and converted to the perchlorate by treating with sodium perchlorate solution. The combined perchlorate salts were crystallized from methanol to afford 12.2 g (38.7%) of 10-methoxybenzo[b]quinolizinium perchlorate (Formula II: $R^1=R^2=H;R^7=10-OCH_3;X^-=ClO_4^-$).

(c)

A mixture of 5 g (0.016 mol)) of 10-methoxybenzo[b]quinolizinium perchlorate and 3.49 g (0.0194 mol) of 1,1-di-phenylethylene in 100 mL of nitromethane was heated to reflux for 14 h. The mixture was cooled, filtered, and the filtrate was concentrated in vacuo. The residue was dissolved in methanol, and filtered to afford 7.29 g (92.2%) of 6,11-ethano-12,12-diphenyl-10-methoxy-6,11-dihydrobenzo[b]quinolizinium perchlorate (Formula I: $R^1=R^1=R^3=R^4=H;R^7=10-OCH_3;X^-=ClO_4^-$), as a white solid, m.p. 227°–230° C.

EXAMPLE 26

6,11-Ethano-12,12-diphenyl-10-methoxy-6,11-dihydrobenzo[b]-quinolizinium perchlorate (0.0143 mol) was converted to the corresponding chloride salt by passing the salt dissolved in $CH_3CN$ (20 mL) through Dowex® 1x2-200 ion exchange resin (70 g) elutate with $H_2O$. The eluent was concentrated in vacuo, and the residue obtained was dried by dissolving in toluene and distilling the solvent followed by triturating with ethyl acetate to afford 4.4 g (72.3%) of 6,11-ethano-12,12-diphenyl-10-methoxy-6,11-dihydrobenzo[b]quinolizinium chloride (Formula I: $R^1=R^2=R^3=R^4=-H;R^7=10^- OCH_3;X^-=Cl^-$), as a white amorphous solid m.p. 158°–164° C.

EXAMPLE 27

(a)

A mixture of pyridine-2-carboxaldehyde (151 g, 1.41 mol), ethylene glycol (157 mL), and 56 g (0.29 mol) of p-toluenesulfonic acid monohydrate in 1.4 L of toluene placed in a 5 L flask fitted with a Dean Stark trap was heated to reflux for 16 h, removing 50 mL of water. The mixture was concentrated in vacuo to a 800 mL volume, cooled, saturated sodium hydrogen carbonate solution was added (to pH 8–9), the layers were separated and the aqueous layer was washed with 100 mL of toluene. The combined organic layer was dried over magnesium sulfate, concentrated in vacuo, and distilled (with a short distilling head) to afford 119.5 g of 2-(1.3-dioxolan-2-yl-pyridine (Formula V: $R^1=H$) as a pale oil, b.p. 100° C./1 mm.

(b)

A mixture of 20 g of 2-(1,3-dioxolan-2-yl)-pyridine and p-methoxybenzyl chloride (21.2 g) was stirred at room temperature overnight, then left to stand six days. The mixture was dissolved in 100 mL of water and extracted with 30 mL ether/hexane (1:1). To the aqueous solution was added a solution of potassium hexafluorophophate (excess) in 250 mL of water. The solid product precipitate was filtered and dried (2 days) to afford 67g of 1-(p-methoxybenzyl)-2-(1,3-dioxolan-2-yl)pyridinium hexafluorophosphate (Formula VII: $R^1=R^2=H; R^7=4-CH_{3O};X^-=PF_6^-$).

(c)

To a mixture of 50 g of polyphosphoric acid and 125 mL of methanesulfonic acid heated to 40° C. was added with stirring 52 g (0.125 mol) of 1-(p-methoxybenzyl)-2(1,3-dioxolan-2-yl)pyridinium hexafluorophosphate and the resulting reaction mixture was heated at 105° C. with stirring for 2 hours. The mixture was cooled to room temperature and poured into 2 L of ice-water. To the resulting solution was added 55 g of potassium hexafluorophosphate with stirring, the solid precipitate was filtered and dried to afford 56.2 g of 9-methoxy-benzo[b]quinolizinium hexafluorophosphate (Formula II: $R^1=R^2=H; R^7=9-OCH_3;X^-=PF_6^-$).

(d)

A mixture of 5.82 g (0.0165 mol) of 9-methoxybenzo[b]quinolizinium hexafluorophosphate and 9 g (0.05 mol) of 1,1-diphenylethylene in 250 mL of nitromethane was heated at reflux overnight. An additional 1,1-diphenylethylene (5 g) was added and the mixture was heated for an additional 72 h, cooled, and 200 mL of water was added with stirring. The organic layer was washed with 100 mL of water and concentrated at 55° C. The residue was triturated in a mixture of 200 mL of water, 150 mL of acetonitrile, and 50 mL of hexane. The aqueous layer was extracted with 50 mL of ether, and concentrated in vacuo to afford 4 g of 6,11-ethano-12,12-diphenyl-9-methoxy-6,11-dihydro-benzo[b]quinolizinium hexafluorophosphate (Formula I: $R^1=R^2=R^3=R^4=H;R^7=9-CH_{3O};R^5=R^6=phenyl;X^-=PF_6^-$) as a solid.

(e)

6,11-Ethano-12,12-diphenyl-9-methoxy-6,11-dihydrobenzo[b]quinolizinium hexafluorophosphate (4 g) was converted to the corresponding chloride salt by passing the above salt through Dowex® 1x2-200 (150 g) after placing the salt in acetonitrile (15 mL). The residue obtained was dried in vacuo to afford 0.97 g of 6,11-ethano-12,12-diphenyl-9-methoxy-6,11-dihydrobenzo[b]quinolizinium chloride ½ hydrate (Formula I: $R^1=R^2=R^3=R^4=H; R^5=R^6=phenyl;R^5=9-CH_{3O};X^-=Cl^-$) as a solid.

EXAMPLE 28

(a)

A mixture of 4 g of 10-methoxybenzo[b]quinolizinium perchlorate in 50 mL of 48% HBr was heated at 100° C. for 20 h, cooled to room temperature, and the resulting mixture was poured into 100 mL of 50% sodium perchlorate solution and stirred for 5 min. The precipitate was filtered, washed with ice-water, ether, ethyl acetate and air dried to afford 2.9 g of 10-hydroxybenzo[b]quinolizinium perchlorate, (Formula II: $R^1=R^2=H; R^7=10\text{-}OH$; $X^-=ClO_4^-$) m.p. 218°–229° C.(d).

(b)

A mixture of 1.4 g (4.7 mmol) of 10-hydroxybenzo[b]quinolizinium perchlorate and 1.28 g (7.1 mmol) of 1,1-diphenylethylene in 50 mL of nitromethane was heated to heat at 100° C. for 15 h, cooled to room temperature, and the resulting mixture was concentrated in vacuo. The above residue was purified by chromatography on silica (methylene dichloride/methanol 9:1) to yield a yellow foamy solid which was triturated with isopropanol to afford, after filtration, 1.7 g (75.5%) of 6,11-ethano-12,12-diphenyl-10-hydroxy-6,11-dihydrobenzo[b]quinolizinium perchlorate (Formula I: $R^1=R^2=R^3=R^4=\text{-}H; R^5=R^6=$phenyl; $R^7=10\text{-}OH; X^-=ClO_4^-$) as a solid.

(c)

6,11-Ethano-12,12-diphenyl-10-hydroxy-6,11-dihydrobenzo [b]quinolizinium perchlorate (1.7 g) was converted to the corresponding chloride salt by passing the above salt through Dowex® 1x2-200 (100 g) to afford 1.28 g (87%) of 6,11-ethano-12,12-diphenyl-10-hydroxy-6,11-dihydrobenzo [b] quinolizinium chloride (Formula I: $R^1=R^2=R^3=R^4=H; R^5=R^6=$phenyl; $R^7=10\text{-}OH; X^-=Cl^-$) as a solid, m.p. >260° C.(d).

EXAMPLE 29

(a)

To a solution of 1,1-di(N-methylsulfonylaminophenyl) ketone (10 g, 0.027 mol) in 200 mL of DMF was added 2.6 g (0.065 mol) of 60% NaH dispersion, and the mixture was stirred at room temperature under nitrogen for 1 h, and then p-methoxybenzyl chloride (9.34 g, 0.057 mol) and n-tetra-n-butylammonium bromide (870 mg) were added. The resulting mixture was stirred for 1 h at room temperature, heated at 100° C. under nitrogen for 2 h, cooled to room temperature and poured into 600 mL of water. The solid mixture was stirred, 1 N HCl solution was added, and the product was filtered, washed with water, hexane, ether, and dried to afford 16 g (96.9%) of 1,1-di[4-(N-p-methoxybenzyl-N-methylsulfonylamino)phenyl]ketone, as a solid.

(b)

To a suspension of methyl triphenylphosphonium bromide (2.2 g; 6.1 mmol) in 50 mL of DME, was added at room temperature n-butyllithium in hexane (3.8 mL; 6.1 mmol) and the mixture was stirred for 30 min. To the S above reaction mixture was added 3.0 g (4.9 mmol) of 1,1-di[4-(N-p-methoxybenzyl-N-methylsulfonylamino) phenyl]ketone in 40 mL of DME/-DMPU (2:1), and the mixture was stirred at room temperature for 30 minutes and then was heated to reflux under nitrogen for 2 h. The mixture was poured into 250 mL of water, the solid product was filtered, and washed with water and ether respectively, and purified by chromatography on silica eluting with hexane/ethyl acetate (1:1) to afford 1.4 g (46.6%) of 1,1-di[4-(N-p-methoxy-benzyl-N-methylsulfonyl-amino)phenyl] ethylene (Formula III: $R^3=R^4=\text{-}H; R^5=R^6\text{-}4\text{-}[N(SO_2CH_3)(4\text{-}CH_3Obenzyl)]$phenyl) as a solid.

(c)

A reaction mixture containing benzo[b]quinolizinium perchlorate (1.45 g; 5.18 mmol) and 1,1-di [4-(N-p-methoxybenzyl-N-methylsulfonylamino) phenyl]ethylene (3 g; 4.94 mmol) in 100 mL of nitromethane was heated to reflux under nitrogen for 24 h. The reaction mixture was cooled, concentrated in vacuo, and the residue was purified by chromatography on silica eluting with methylene chloride/methanol (9:1). The perchlorate was treated with warm acetonitrile (200 mL), filtered, and the filtrate was concentrated in vacuo to afford 2.0 g (45%) of 6,11-ethano-12,12-di[4-(N-p-methoxybenzyl-N-methylsulfonylamino) phenyl]-6,11-dihydrobenzo[b]quinolizinium perchlorate ½ ethyl acetate (Formula I: $R^1=R^2=R^3=R^4=R^7=H; R^5=R^6=4\text{-}[N(SO_2CH_3)(4\text{-}CH_3Obenzyl)]$phenyl; $X^-=ClO_4^-$), m.p. 174°–77° C.

EXAMPLE 30

(a)

To a suspension of methyl triphenylphosphonium bromide (17.83 g; 49.9 mmol) in 150 mL of ether was added at −10° 10M n-butyllithium in hexane (4.99 mL; 49.4 mmol) and the mixture was stirred at room temperature for 1 h. To the above mixture was added 10 g (47 mmol) of 1,1-di(p-tolyl)ketone in 50 mL of ether/tetrahydrofuran (3:2), and the mixture was heated to reflux for 2 h, cooled, 20 mL of THF added, and filtered. To the filtrate was added ammonium chloride solution and the resulting mixture was extracted with ethyl acetate (2x), dried over sodium sulfate and concentrated in vacuo to yield a yellow oil. The oil was purified through flash chromatography on silica (hexane/methylene chloride 3:1) to afford 9.3 g (95.1%) of 1,1-di(p-tolyl)ethylene (Formula III: $R^3=R^4=H; R^5=R^6=4\text{-}CH_3$phenyl).

(b)

A reaction mixture containing benzo[b]quinolizinium hexafluorophosphate (3.5 g; 11.4 mmol) and 1,1-di(p-tolyl) ethylene (2.85 g; 13.7 mmol) in 50 mL of nitromethane was heated to reflux under nitrogen for 5 h. The reaction mixture was cooled, filtered, and the filtrate was concentrated in vacuo to yield a brown foamy solid. The solid product was triturated with ether, filtered, and dried to yield 5.8 g (95.4%) of 6,11-ethano-12,12-di(p-tolyl)-6,11-dihydrobenzo[b] quinolizinium hexafluorophosphate (Formula I: $R^1=R^2=R^3=R^4=\text{-}R^7=H; R^5=R^6=4\text{-}CH_3$phenyl; $X^-=PF_6^-$) as a solid.

(c)

6,11-Ethano-12,12-di(p-tolyl)-6,11-dihydrobenzo[b] quinolizinium hexafluorophosphate (5.8g: 10.8 mmol) was converted to the corresponding chloride salt by passing the hexafluorophosphate salt through Dowex® 1x2-200 (60 g) eluting with $H_2O$ to afford 4.18 g (91.6%) of 6,11-ethano-12,12-di(p-methylphenyl)-6,11-dihydrobenzo[b] quinolizinium chloride (Formula I: $R^1=R^2=R^3=R^4=R^7=H; R^5=R^6=4\text{-}CH_3$phenyl; $X^-=Cl^-$), as an off-white solid, m.p. 180°–85° C.

EXAMPLE 31

(a)

To a suspension of methyl triphenylphosphonium bromide (42.94 g; 120 mmol) in 500 mL of ether was added at −30° C. 10M n-butyllithium in hexane (12.02 mL; 120 mmol) and the mixture was stirred at room temperature for 1 h. To the above mixture was added 25 g (114.5 mmol) of 1,1-di(p-fluorophenyl)ketone in 100 mL of THF during a 5 min period, and the mixture was heated to reflux for 2 h, cooled, and filtered. To the filtrate was added ammonium chloride solution and the resulting mixture was extracted with ethyl acetate (2x), dried over sodium sulfate and concentrated in vacuo to yield a red oil which was purified through flash chromatography on silica (hexane/methylene chloride 5:1) to afford 21.2 g (85.7%) of 1,1-di(p-fluorophenyl)ethylene (Formula III: $R^3=R^4=H;R^5=R^6=$4-F-phenyl).

(b)

A reaction mixture containing benzo[b]quinolizinium hexafluorophosphate (3 g, 9.8 mmol) and 1,1-di(p-fluorophenyl)ethylene (3.17 g; 14.7 mmol) in 50 mL of nitromethane was heated to reflux under nitrogen for 6 hours. The reaction mixture was cooled, filtered, and the filtrate was concentrated in vacuo to yield a foamy solid. The solid product was triturated with ether, filtered, and dried to yield 5.07 g (87.4%) of 6,11-ethano-12,12-di(p-fluorophenyl)-6,11-dihydrobenzo[b]quinolizinium hexafluorophosphate (Formula I: $R^1=R^2=R^3=R^4=-R^7=H;R^5=R^6=$4-F-phenyl;$X^-=PF_6^-$), as a solid.

(c)

6,11-Ethano-12,12-di(p-fluorophenyl)-6,11-dihydrobenzo[b]quinolinium hexafluorophosphate (5 g: 8.4 mmol) was converted to the corresponding chloride by passing through Dowex® 1x2-200 (60 g) to afford 2.84 g (77.3%) of 6,11-ethano-12,12-di(p-fluorophenyl)-6,11-dihydrobenzo[b]-quinolizinium chloride (Formula I: $R^1=R^2=R^3=R^4=R^7=H;R^5=R^6=$4-F-phenyl; $X^-=Cl^-$), m.p. 155°–161° C.

EXAMPLE 32

(a)

A mixture of isopropyl bromide (36.8 mL, 0.39 mol), m-hydroxybenzaldehyde (40 g, 0.327 mol), and potassium carbonate (53.9 g, 0.39 mol) in 200 mL of DMF was stirred at room temperature for 12 h. After adding additional isopropyl bromide (20 mL) and potassium carbonate (10 g), the reaction mixture was stirred at room temperature for 18 h and then heated at 50° C. for 1 h. Water (500 mL) was added to the mixture, the red oil formed was removed by decantation, and the aqueous layer was extracted with methylene chloride (3×250 mL) and the combined organic layers were washed with 200 mL of 2N NaOH solution, brine, dried over sodium sulfate, filtered, and concentrated in vacuo. The residue was distilled (0.75 mm/80°–100° C.) to afford 44.2 g (82%) of m-isopropoxybenzaldehyde as a colorless oil.

(b)

To m-isopropoxybenzaldehyde (38 g, 0.23 mol) in 500 mL of ethanol was added slowly sodium borohydride (12.2 g, 0.32 mol) over a period of 1 h and the mixture was stirred for 2 h, filtered, and concentrated to 100 mL of its volume. The above mixture was diluted with 50 mL of water, neutralized with sulfuric acid solution with cooling, and was extracted with ether (4×100 mL). The organic layer was dried over sodium sulfate, filtered, and concentrated in vacuo to afford 36.32 g (95%) of m-isopropoxybenzyl alcohol.

(c)

To a mixture of 30 g (0.18 mol) of 3-isopropoxybenzyl alcohol in 600 mL of ether cooled to −20° C. was added in portions 38.7 mL (0.387 mol) of n-butyllithium (10M) in hexane over a 20 min period, and the reaction mixture was heated to warm to room temperature and stirred for 2 h. The above reaction mixture was cooled to −20° C., 23.13 g (0.216 mol) of pyridine-2-carboxaldehyde was added in one portion to the mixture, and the resulting reaction mixture was heated to warm to room temperature and stirred for 1 h. Ammonium chloride solution (200 mL) and 100 mL of ethyl acetate were added to the mixture. The aqueous layer was extracted with methylene chloride (2×200 mL), the combined organic layer was washed with brine, dried over sodium sulfate, and concentrated. The diol was purified by chromatography on silica eluting with ethyl acetate/hexane (9:1; and 0.05% TEA). The solvent was concentrated in vacuo, the brown oil was dissolved in methylene chloride/hexane, and removal of methylene chloride in vacuo to ½ of its volume afforded 11.1 g (22.6%) of 2-[1-hydroxy-(6'-hydroxymethyl-2'-isopropoxy)benzyl]pyridine (Formula X: $R^1=R^2=H;R^7=$2'-OCH(CH$_3$)$_2$), as a tan solid.

(d)

To 11.1 g (0.0406 mol) of 2-[1-hydroxy-(6'-hydroxymethyl-2'-isopropoxy)benzyl]pyridine was added 25 mL of POCl$_3$ in 1 min, the mixture was heated at 110° C. for 5 min and then cooled. The reaction mixture was concentrated in vacuo, 100 mL of toluene was added and concentrated to yield an oil. Water and sodium perchlorate were added to the above oil, water was decanted, and the residue was dried under reduced pressure to yield a foam. The foam was dissolved in methanol/water, potassium hexafluorophosphate was added, and the mixture was heated on a steam-bath and then cooled. The aqueous mixture was concentrated in vacuo, the residue was dissolved in methylene chloride/methanol, cooled and filtered to remove potassium perchlorate. The mixture was concentrated in vacuo to 10 mL of its volume, ethyl acetate was added and the mixture was cooled. The product was filtered to afford 5.32 g (34.3%) of 10-isopropoxy-benzo[b]quinolizinium hexafluorophosphate (Formula II: $R^1=R^2=H;R^7=$10-OCH(CH$_3$)$_2$; $X^-=PF_6^-$), as an orange solid.

(e)

A reaction mixture containing 10-isopropoxy-benzo[b]quinolizinium hexafluorophosphate (2 g; 5.2 mmol) and 1,1-diphenylethylene (1.129 g; 6.2 mmol) in 50 mL of nitromethane was heated to reflux under nitrogen for 16 hours. The reaction mixture was cooled, filtered, and the filtrate was concentrated in vacuo to yield a foamy solid. The solid product was triturated with ether, filtered, and dried to yield 2.63 g (89.4%) of 6,11-ethano-12,12-diphenyl-10-isopropoxy-6,11-dihydrobenzo[b]quinolizinium hexafluorophosphate (Formula I: $R^1=R^2=R^3=R^4=H;R^5=R^6=$phenyl;$R^7=$10-OCH(CH$_3$)$_2$; $X^-=PF_6^-$).

(f)

6,11-Ethano-12,12-diphenyl-10-isopropoxy-6,11-dihydrobenzo[b]-quinolizinium hexafluorophosphate(2.6 g: 4.6 mmol) was converted to the corresponding chloride by passing through Dowex® 1x2-200 (60 g) to afford 1.66 g (79.4%) of 6,11-ethano-12,12-diphenyl-10-isopropoxy-6,11-dihydro-benzo[b]quinolizinium chloride (Formula I: $R^1=R^2=R^3=R^4=H;R^5=R^6=$phenyl; $R^7$=10-OCH(CH$_3$)2;$X^-$= Cl$^-$), m.p. 226°–30° C.

EXAMPLE 33

(a)

A mixture of 5 g (0.024 mol) of 3,5-difluorobenzyl bromide and 3.6 g (0.024 mol) of 2-(2'-pyridyl)-1,3-dioxolane was heated to stir at room temperature overnight and then filtered. The reaction mixture was partitioned between water and ether, the aqueous phase was separated and treated with a solution of potassium hexafluorophosphate in water. The solid residue was filtered and dried in vacuo to afford 9 g (76.9%) of 1-(3,5-difluorobenzyl)-2-(2'-1,3-dioxolane)-pyridinium hexafluorophosphate (Formula VI: $R^1=R^2=H; R^7=3,5-F_2;Z^-=Br^-$).

(b)

A mixture of 1-(3,5-difluorobenzyl-2-(2'-1,3-dioxolane)-pyridinium hexafluorophosphate (9 g; 0.021 mol), polyphosphoric acid (90 g), and 9 mL of methanesulfonic acid was heated at 110° C. for 7 hours and then stirred at room temperature overnight. The reaction mixture was poured into 200 mL of water and a warm solution of 9 g of potassium hexafluorophosphate in water was added with stirring. The resulting pale yellow solid product was filtered and dried to afford 6.5 g (86%) of 8,10-difluoro-benzo[b] quinolizinium hexafluorophosphate (Formula II: $R^1=R^2=H;R^7=8,10-F_2;X^-=PF_6^-$).

(c)

A reaction mixture containing 8,10-difluoro-benzo[b] quinolizinium hexafluorophosphate (4 g; 11 mmol) and 1,1-diphenylethylene (4 mL; 22 mmol) in 40 mL of nitromethane was heated to reflux under nitrogen for 3 days. The reaction mixture was cooled, concentrated in vacuo, and the residue was purified by chromatography on silica eluting with acetonitrile. The hexafluorophosphate was converted to the corresponding chloride by passing through Dowex® 1x2-200 to afford 1.68 g (35.5%) of 6,11-ethano-12,12-diphenyl-8,10-difluoro-6,11-dihydrobenzo[b]quinolizinium chloride ¼ hydrate (Formula I: $R^1=R^2=R^3=R^4=H;R^5=R^6=$phenyl;$R^7=8,10-F_2;X^-=Cl^-$).

EXAMPLE 34

(a)

A mixture of 9-methoxy-benzo[b]quinolizinium hexafluorophosphate (4 g) and 25 mL of 48% HBr was stirred and heated to 110° C. overnight. The above reaction mixture was filtered and the residue was washed with water and dried to yield 1.8 g of 9-hydroxybenzo[b]quinolizinium bromide (Formula II: $R^1=R^2=H;R^7=9-OH;X^-=Br^-$).

(b)

A reaction mixture containing 9-hydroxybenzo[b] quinolizinium bromide (1.35 g; 4.9 mmol) and 1,1-diphenylethylene (2.64 g; 14.7 mmol) in 20 mL of nitromethane was heated to reflux under nitrogen for 3 days. The reaction mixture was cooled and the solid product was filtered, triturated with hexane (40 mL×3), and isolated by filtration. The solid product was dissolved in a mixture of 2 N-HCl solution (150 mL), methanol (500 mL), and water (100 mL), filtered, and the solvent was removed in vacuo to yield the residue. The residual product was washed with 20 mL of water and dried to afford 1.0 g (45.5%) of 6,11-ethano-12,12-diphenyl-9-hydroxy-6,11-dihydrobenzo[b] quinolizinium chloride (Formula I: $R^1=R^2=R^3=R^4=H;R^5=R^6=$phenyl;$R^7$=9-OH;$X^-$ =Cl$^-$), as a gray solid, m.p. 270° C.(d).

EXAMPLE 35

(a)

To a suspension of methyltriphenylphosphonium bromide (7.14 g; 20 mmol) in ether was added at 0° C. n-butyllithium in hexane (8 mL; 20 mmol) and the mixture was stirred at room temperature for 1 h. To the above mixture was added 2.8 g (8.2 mmol) of 1,1-di(m-methoxyphenyl)ketone in ether and the mixture was stirred for 10 minutes. The above reaction mixture was quenched with acetone (5 mL), stirred for 5 minutes, filtered, and the filtrate was concentrated in vacuo. The residue was purified by chromatography on silica eluting with hexane/ether (9:1) to afford 3.6 g (90%) of 1,1-di(3-methoxyphenyl)ethylene (Formula III: $R^3=R^4=H;R^5=R^6$=3-CH$_3$O-phenyl).

(b)

A reaction mixture containing benzo[b]quinolizinium perchlorate (2.5 g; 8.9 mmol) and 1,1-di(3-methoxyphenyl) ethylene (3.0 g;12.5 mmol) in 100 mL of nitromethane was heated to reflux under nitrogen for 48 h. The reaction mixture was cooled, concentrated in vacuo, and the residue was purified by chromatography on silica eluting with methylene chloride/ethyl acetate/methanol (7:2:1). The perchlorate was dissolved in 200 mL of warm acetonitrile/methanol (2:1), treated with activated charcoal, filtered, and the filtrate was concentrated in vacuo to afford 3.8 g (81.7%) of 6,11-ethano-12,12-di(m-methoxyphenyl)-6,11-dihydrobenzo[b]quinolizinium perchlorate (Formula I: $R^1=R^2=R^3=R^4=R^7=H;R^5=R^6$=3-CH$_{3O}$-phenyl;$X^-$=ClO$_4^-$).

(c)

6,11-Ethano-12,12-di(m-methoxyphenyl)-6,11-dihydrobenzo[b]quinolizinium perchlorate (3.8 g) was converted to the corresponding chloride by passing through Dowex® 1x2-200 to afford 2.8 g (84.8%) of 6,11-ethano-12,12-di(m-methoxyphenyl)-6,11-dihydrobenzo[b] quinolizinium chloride (Formula I: $R^1=R^2=R^3=R^4=R^7=$H;$R^5=R^6$=-3-CH$_{3O}$-phenyl;$X^-$=Cl$^-$), m.p. 164°–68° C.

EXAMPLE 36

(a)

To a suspension of methyltriphenylphosphonium bromide (3.25 g; 9.05 mmol) in 100 mL of ether was added at 0° C. n-butyllithium in hexane (3.7 mL; 9.05 mmol) and the mixture was heated to stir at room temperature for 1 h. To the above mixture was added 2.8 g (8.2 mmol) of 1,1-di(m-bromophenyl)ketone in 30 mL of tetrahydrofuran and the mixture was stirred for 10 min. The above reaction mixture was quenched with acetone (5 mL), stirred for 5 minutes, filtered, and the filtrate was concentrated in vacuo. The residue in hexane/methylene chloride (3:1) was purified by chromatography on silica eluting with hexane to afford 2.2 g (78.6%) of 1,1-di(m-bromophenyl)ethylene (Formula III: $R^3=R^4=H;R^5=R^6=3$-Br-phenyl).

(b)

A reaction mixture containing 1.51 g (5.4 mmol) of benzo[b]quinolizinium perchlorate and 1,1-di(m-bromophenyl)ethylene (2.2 g; 6.5 mmol) in 70 mL of nitromethane was heated to reflux under nitrogen for 40 hours. The reaction mixture was cooled, concentrated in vacuo, and the residue was triturated with ether. The solid product was filtered and purified by chromatographic separations on silica (methylene chloride/ethyl acetate/methanol (9:2:1)). The perchlorate was treated with warm acetonitrile/methanol and activated charcoal, filtered, and the filtrate was concentrated in vacuo to afford 2.7 g (81.8%) of 6,11-ethano-12,12-di-(m-bromophenyl)-6,11-dihydrobenzo[b]quinolizinium perchlorate (Formula I: $R^1=R^2=R^3=R^4=R^7=H;R^5=R^6=3$-Br-phenyl;$X^-=ClO_4^-$).

(c)

6,11-Ethano-12,12-di(m-bromophenyl)-6,11-dihydrobenzo[b]quinolizinium perchlorate (2.7g; 4.5 mmol) was converted to the corresponding chloride by passing through Dowex® 1x2-200 (50 g) to afford 2.16 g (86.4%) of 6,11-ethano-12,12-di(m-bromophenyl)-6,11-dihydrobenzo[b]quinolizinium chloride (Formula I: $R^1=R^2=R^3=R^4=R^7=H;R^5=R^6=3$-Br-phenyl;$X^-=Cl^-$), m.p. 194°–98° C.

EXAMPLE 37

(a)

To m-methoxyacetophenone (100 g, 0.665 mol) in 400 mL of methanol was added with cooling sodium borohydride (30.22 g, 0.799 mol) over a period of 1 h and the mixture was stirred, poured into ice-water, and neutralized with conc. HCl. The above mixture was extracted with ether (3×400 mL), the organic layer was dried over sodium sulfate, and concentrated. The residue was then distilled (149°–151° C. @ 25 mm)(short path column) to afford 95.6 g (94%) of m-methoxy-1-methyl-benzyl alcohol as a clear oil.

(b)

To a mixture of 71 g (0.467 mol) of m-methoxy-1-methyl-benzyl alcohol in 800 mL of ether cooled to –20° C. was added in portions 100.4 mL (1.004 mol) of n-butyllithium (10M) in hexane over a 40 min period, and the reaction mixture was heated to warm to room temperature and stirred for 3 h. The above reaction mixture was cooled to –20° C., 59.98 g (0.56 mol) of pyridine-2-carboxaldehyde was added to the mixture, and the resulting reaction mixture was heated to warm to room temperature and stirred for 2 h. Ammonium chloride solution and ethyl acetate were added to the mixture. The aqueous layer was extracted with ethyl acetate, the combined organic layer was dried over sodium sulfate, and concentrated to afford 63 g (53%) of 2-[1-hydroxy-[6'-(1'-hydroxyethyl)-2'-methoxy]-benzyl]pyridine (Formula X: $R^1=H;R^2=CH_3;R^7=2'$-methoxy), as an oil which was recrystallized from ethyl acetate/hexane as a tan solid.

(c)

A mixture of 5.4 g (0.021 mol) of 2-[1-hydroxy-[6'-(1'-hydroxyethyl)-2'-methoxy]-benzyl]pyridine in POCl$_3$ was refluxed for 1 h and then cooled. The reaction mixture was poured into ice with stirring, warmed, and 20 g of sodium perchlorate was added with stirring. The solid product precipitated was filtered, washed with water, hexane, ethyl acetate, and ether, and then air dried to afford 4.12 g (61.4%) of 10-methoxy-6-methyl-benzo[b]quinolizinium perchlorate (Formula II: $R^1=H;R^2=CH_3;R^7=10$-OCH$_3$; $X^-=ClO_4^-$), as a solid, m.p. 300°–302° C. (d) (recrystallization from methanol/acetonitrile).

(d)

A reaction mixture containing 10-methoxy-6-methyl-benzo[b]quinolizinium perchlorate (1.5 g; 4.63 mmol) and 1,1-diphenylethylene (1.1.7 g; 9.2 mmol) in 50 mL of nitromethane was heated to reflux under nitrogen for 72 hours. After adding additional 1,1-diphenylethylene (0.5 g), the mixture was heated to reflux overnight. The reaction mixture was cooled and concentrated in vacuo to yield a foamy solid. The solid product was treated with activated charcoal in boiling methanol/acetonitrile (3:1), filtered and the filtrate was concentrated in vacuo to afford 2.1 g (90.1%) of 6,11-ethano-12,12-diphenyl-10-methoxy-6-methyl-6,11-dihydrobenzo[b]quinolizinium perchlorate (Formula I: $R^1=R^3=R^4=H;R^2=CH_3;R^5=R^6=$phenyl;$R^7=10$-OCH$_3$; $X^-$-ClO$_4^-$).

(e)

6,11-Ethano-12,12-diphenyl-10-methoxy-6-methyl-6,11-dihydrobenzo[b]quinolizinium perchlorate (2.1 g: 4.2 mmol) was convened to the corresponding chloride by passing through Dowex®1x2-200 (100 g) to afford 1.54 g (84.1%) of 6,11-ethano-12,12-diphenyl-10-methoxy-6-methyl-6,11-dihydrobenzo[b]quinolizinium chloride (Formula I: $R^1=R^3=R^4=H$; $R^2=CH_3;R^5=R^6=$phenyl;$R^7=10$-OCH$_3$;$X^-$-ClO$_4^-$), m.p. 184°–188° C.

EXAMPLE 38

(a)

A mixture of 2.3 g of 10-methoxy-6-methylbenzo[b]quinolizinium perchlorate in 35 mL of 48% HBr was heated at 100° C. for 14 h, cooled to room temperature, and was diluted with water. The resulting mixture was heated to dissolve the solid product, filtered while hot, and the filtrate was treated with 20 g of sodium perchlorate. The precipitated solid product was filtered, washed with ether, air dried to afford 2 g (90.9%) of 10-hydroxy-6-methyl-benzol[b]quinolizinium perchlorate (Formula II: $R^1=H;R^2=CH_3;R^7=10$-OH; $X^-ClO_4^-$), m.p. 246°–248° C.(d).

(b)

A mixture of 1.5 g (5.5 mmol) of 10-hydroxy-6-methyl-benzo[b]-quinolizinium perchlorate and 1.98 g (10 mmol) of 1,1-diphenylethylene in 75 mL of nitromethane was heated to reflux under nitrogen for 48 h. After adding additional 1,1-diphenylethylene (0.5 g), the mixture was heated to reflux under nitrogen for an additional 48 h. The reaction mixture was cooled and concentrated in vacuo to yield a yellow foam. The solid product was treated with activated charcoal in boiling methanol/acetonitrile (3:1), filtered and the filtrate was concentrated in vacuo. The residue was crystallized from isopropanol to afford 1.7 g (62.9%) of 6,11-ethano-12,12-diphenyl-10-hydroxy-6-methyl-6,11-dihydrobenzo[b]quinolizinium perchlorate (Formula I: $R^1=R^3=R^4=H;R^2=CH_3;R^5=R^6=$phenyl;$R^7=10$-OH;$X^-$ClO$_4^-$).

(c)

6,11-Ethano-12,12-diphenyl-10-hydroxy-6-methyl-6,11-dihydrobenzo[b]quinolizinium perchlorate (1.7 g) was convened to the corresponding chloride salt by passing the above salt through Dowex® 1x2-200 (100 g) to afford 1.05 g (75%) of 6,11-ethano-12,12-diphenyl-10-hydroxy-6-methyl-6,11-dihydrobenzo[b]quinolizinium chloride (Formula I: $R^1=R^3=R^4=H; R^2=CH_3$; $R^5=R^6$=phenyl;$R^7$=10-OH;$X^-Cl^-$)as a solid, m.p. 208°–212° C.(d).

EXAMPLE 39

(a)

To a suspension of methyltriphenylphosphonium bromide (6 g; 16.8 mmol) in 75 mL of ether was added at −20° C. n-butyllithium in hexane (6.8 mL; 17 mmol) and the mixture was heated to stir at room temperature for 1 h. To the above mixture was added 2.5 g (15.4 mmol) of 1,1-di(3-furyl) ketone in 50 mL of tetrahydrofuran in 10 minutes and the mixture was stirred at room temperature for 2 h. To the above reaction mixture was added saturated ammonium chloride solution, and the mixture was diluted with hexane. The organic layer was separated, washed with water, dried, and concentrated in vacuo. The residue was purified by chromatography on silica eluting with hexane to afford 1 g (40%) of 1,1-di(3-furyl)ethylene (Formula III: $R^3=R^4=H; R^5=R^6$=3-furyl).

(b)

A reaction mixture containing benzo[b]quinolizinium perchlorate (1.4 g; 4.95 mmol) and 1,1-di(3-furyl)ethylene (0.95 g; 5.9 mmol) in 50 mL of nitromethane was heated to reflux under nitrogen for 3 h. The reaction mixture was cooled, concentrated in vacuo, and the residue was purified by chromatography on silica eluting with methylene chloride/ethyl acetate/methanol (7:2:1) to yield a pale yellow solid. The solid product was treated with warm methanol and activated charcoal, filtered, and the filtrate was concentrated to give 1.9 g (86.3%) of 6,11-ethano-12,12-di (3-furanyl)-6,11-dihydrobenzo[b]quinolizinium perchlorate (Formula I: $R^1=R^2=R^3=R^4=R^7$=H; $R^5=R^6$=3-furyl;$X^-ClO_4^-$), as a colorless solid.

(c)

6,11-Ethano-12,12-di(3-furanyl)-6,11-dihydrobenzo[b] quinolizinium perchlorate (1.9 g; 4.3 mmol) was converted to the corresponding chloride by passing the salt through Dowex® 1x2-200 (50 g) to afford 1.3 g (80.2%) of 6,11-ethano-12,12-di(3-furanyl)-6,11-dihydrobenzo[b] quinolizinium chloride (Formula I: $R^1=R^2=R^3=R^4=R^7$=H;$R^5=R^6$=3-furyl;$X^-Cl^-$), m.p. 168°–71° C.

EXAMPLE 40

(a)+(h)

6,11-Ethano-12,12-di (3-furanyl)-6,11-dihydrobenzo [b]quinolizinium perchlorate (3.5 g) dissolved in 50 mL of acetonitrile (hot) was passed through Dowex® 1x2-200 ion exchange resin (OH$^-$), collecting 500 mL of aqueous eluate. This eluate was extracted with 50 mL of ether, and the aqueous layer was treated with excess dibenzoyl-L(−)-tartaric acid monohydrate. The aqueous layer was concentrated in vacuo, a pale-yellow residue was triturated in 40 mL of ethanol with heating to afford 2.6 g (2 crops) of 6,11-ethano-12,12-di(3-furanyl)-6,11-dihydrobenzo[b] quinolizinium o,o'-dibenzoyl-L(−)-tartarate (Example 40 (a)). The above O,O'-dibenzoyl L(−)-tartrate salt was recrystallized from 20 mL of hot ethanol, was convened to the corresponding chloride salt by passing the salt through Dowex® 1x2-200 to afford 0.67 g of (+)-6,11-ethano-12,12-di(3-furanyl)-6,11-dihydrobenzo[b]quinolizinium chloride 3/2 hydrate (Formula I: $R^1=R^2=R^3=R^4=R^7$=H;$R^5=R^6$=3-furyl;$X^-Cl^-$;Example 40(b)) as a white solid. $[\alpha]_D^{25}$=+10.1°, in 10% DMSOd$_6$ in CDCl$_3$,C=10 mg/mL.

EXAMPLE 41

(a)+(b)

The residue obtained on evaporation of all mother liquor from Example 40 in methanol/acetonitrile (minimum) was made acidic by the addition of 2N HCl solution, diluted with 300 mL of water, and extracted with ether (3×75 mL). The aqueous layer was concentrated in vacuo, the residue was dissolved in acetonitrile, and passed through Dowex® 1X2-200 ion exchange resin (OH$^-$), then treated with 2.5 g of dibenzoyl-D(+)-tartaric acid monohydrate in acetonitrile. The solvent was concentrated to ⅓ its volume and water was added to the mixture. The solid precipitate was filtered and recrystallized from ethanol to afford 6,11-ethano -12,12-di (3-furanyl)-6,11-dihydrobenzo[b]quinolizinium dibenzoyl-D(+)-tararate (Example 41(a)). The above D(+)-tartarate salt was convened to the corresponding chloride salt by passing the salt through Dowex® 1x2-200 to afford 0.67 g of (−)-6,11-ethano-12,12-di(3-furanyl)-6,11-dihydrobenzo[b] quinolizinium chloride (Formula I: $R^1=R^2=R^3=R^4=R^7$=H;$R^5=R^6$=3-furyl;$X^-Cl^-$;(−)-isomer), Example 41 (b)) as a white solid, $[\alpha]_D^{25}$,=+9.37° in DMF or $[\alpha]_D^{25}$=−10.0° in 10% DMSOd$_6$ in CDCl$_3$,C=10 mg/mL.

EXAMPLE 42

(a)

To a solution of 3-bromopyridine (9.84 g, 0.062 mol) in 300 mL of ether cooled to −78° C. was added n-butyllithium (1.6M, 41 mL, 0.066 mol) and stirred for 30 min. N-Methyl, N-methoxy-urethane (3.76 g, 0.028 mol) in 20 mL of ether was added in 10 min, the mixture was stirred (−78° C.) for 1 h, allowed to warm to room temperature and stirred for 2 h. The reaction mixture was quenched with 6 N HCl (100 mL) and stirred. The aqueous layer was basified with 10% NaOH solution, extracted with ethyl acetate (2x) and methylene dichloride. The organic layer was dried over sodium sulfate, concentrated in vacuo, and the residue was purified by chromatography on silica (ethyl acetate, 10% methanol/ ethyl acetate) to afford 1.7 g (33%) of di-(3-pyridyl)ketone.

(b)

To a suspension of methyl-triphenylphosphonium bromide (3.6 g; 10.1 mmol) in 50 mL of ether was added at −20° C. 2.5M n-butyllithium in hexane (4 mL; 10.1 mmol) and the mixture was heated to stir at room temperature for 1 hour. To the above mixture was added 1.7 g (9.3 mmol) of 1,1-di(3-pyridyl)ketone in 50 mL of tetrahydrofuran and the mixture was stirred at room temperature for 2 h. Ammonium chloride solution and ethyl acetate (250 mL) were added to the above mixture, the organic phase was washed with water, brine, dried, and concentrated in vacuo. The residue was purified by chromatography on silica (ether/hexane/ methanol, 5:4.5:0.5) to afford 0.9 g (52.9%) of 1,1-di(3-pyridyl)-ethylene (Formula III: $R^3=R^4$=H; $R^5=R^6$=3-pyridyl).

(c)

A reaction mixture containing benzo[b]quinolizinium perchlorate (1.15 g; 4.12 mmol) and 1,1-di(3-pyridyl)ethylene (0.9 g; 4.94 mmol) in nitromethane was heated to reflux under nitrogen for 120 h. The reaction mixture was cooled, concentrated in vacuo, the residue was treated with 300 mL of warm methanol/acetonitrile (3:1) and activated charcoal, and the mixture was filtered. The filtrate was concentrated in vacuo and the residue was triturated with ether to yield 1.2 g (63.1%) of 6,11-ethano-12,12-di(3-pyridyl)-6,11-dihydrobenzo[b]quinolizinium perchlorate (Formula I: $R^1=R^2=R^3=R^4=R^7=H; R^5=R^6=3$-pyridyl;$X^-=ClO_4^-$).

(d)

6,11-Ethano-12,12-di(3-pyridyl)-6,11-dihydrobenzo[b]quinolizinium perchlorate (1.2 g; 2.6 mmol) was further purified by chromatography on silica (1:2 ethanol/PAW), passed through Dowex® 1x2-200 resin (Cl⁻), and then treated with 10% potassium hexafluorophosphate solution to yield 1.1 g (83.3%) of 6,11-ethano-12,12-di(3-pyridyl)-6,11-dihydrobenzo[b]quinolizinium hexafluorophosphate (Formula I: $R^1=R^2=R^3=R^4=R^7=H; R^5=R^6=3$-pyridyl; $X^-=PF_6^-$).

(e)

The above hexafluorophosphate (1.05 g, 2.06 mmol) was converted to the corresponding chloride by passing the salt through Dowex® 1x2-200 resin (Cl⁻) to afford 540 mg (65.8%) of 6,11-ethano-12,12-di(3-pyridyl)-6,11-dihydrobenzo[b]quinolizinium chloride (Formula I: $R^1=R^2=R^3=R^4=R^7=H; R^5=R^6=3$-pyridyl;$X^-=Cl^-$), m.p. 225° C.(d).

EXAMPLE 43

(a)

To a suspension of methyl-triphenylphosphonium bromide (31.36 g; 0.0878 mol) in 500 mL of ether was added at −30° C. 10M n-butyllithium in hexane (8.78 mL; 0.078 mol), the mixture was heated to warm and then stirred at room temperature for 1 h. To the above mixture was added 21 g (0.0836 mol) of 1,1-di(p-chlorophenyl)ketone in 50 mL of tetrahydrofuran and the mixture was refluxed for 1 h, cooled, and filtered. The above filtrate was added to ammonium chloride solution, the resulting mixture was extracted with ethyl acetate (3×150 mL), the organic layer was dried over sodium sulfate, and concentrated in vacuo to afford 22 g of crude 1,1-di-(p-chlorophenyl)ethylene, (Formula III: $R^3=R^4=H; R^5=R^6=4$-Cl-phenyl), as an off-white solid.

(b)

A reaction mixture containing benzo[b]quinolizinium hexafluorophosphate (3 g; 9.8 mmol) and 1,1-di(p-chlorophenyl)ethylene (3.64g; 14.7 mmol) in 60 mL of nitromethane was heated to reflux under nitrogen for 3 h. The reaction mixture was cooled, filtered, and the filtrate was concentrated in vacuo. The dark residue was triturated with ether, filtered, and dried to give a pale brown solid product which was recrystallized from methylene chloride/ethyl acetate to afford 3.8 g (62.3%) of 6,11-ethano-12,12-di(p-chlorophenyl)-6,11-dihydrobenzo[b]quinolizinium hexafluorophosphate (Formula I: $R^1=R^2=R^3=R^4=R^7=H; R^5=R^6=4$-Cl-phenyl;$X^-=PF_6^-$), as a white solid, m.p. 212°–15° C.

EXAMPLE 44

(a)

To a suspension of methyltriphenylphosphonium bromide (30.96 g; 0.0825 mol) in ether (500 mL) was added at −30° C. 10M n-butyllithium in hexane (8.66 mL; 0.0866 mol) and the mixture was heated to stir at room temperature for 1 h. To the above mixture was added 20 g (0.0825 mol) of 1,1-di(p-methoxyphenyl)ketone in 50 mL of THF over a 4 rain period and the mixture was refluxed for 1 h and cooled. The above reaction mixture was filtered and ammonium chloride solution was added to the filtrate. The above mixture was extracted with ethyl acetate (3×150 mL), the organic layer was dried over sodium sulfate and concentrated in vacuo to afford 20.2 g of crude 1,1-di-(p-methoxyphenyl)ethylene (Formula III: $R^3=R^4=H; R^5=R^6=4$-OCH$_3$-phenyl).

(b)

A reaction mixture containing benzo[b]quinolizinium hexafluorophosphate (3.52 g; 14.7 mmol) and 1,1-di(p-methoxyphenyl)-ethylene (3.52 g, 14.7 mmol) in 60 mL of nitromethane was heated to reflux under nitrogen for 18 h. The reaction mixture was cooled, filtered, and the filtrate was concentrated in vacuo. The resulting brown residue was triturated in ether, the gray powder was dissolved in 10 mL of methylene chloride, 100 mL of ethyl acetate, and hexane and the resulting solution was concentrated in vacuo to remove methylene chloride. Upon cooling the solution, an off-white solid formed, was filtered and dried to afford 4 g (66%) of 6,11-ethano-12,12-di(p-methoxyphenyl)-6,11-dihydrobenzo[b]quinolizinium hexafluorophosphate (Formula I: $R^1=R^2=R^3=R^4=R^7=H; R^5=R^6=4$-OCH$_3$-phenyl;$X^-=PF_6^-$).

EXAMPLE 45

(a)

To a mixture of 5 g (0.024 mol) of p-trifluoromethylbenzoyl chloride in 100 mL of THF was added in portions 3 g (0.027 mol) of LAH, stirred at room temperature for 2 h, then refluxed for 2 h and cooled. To the reaction mixture was added 3 mL of water, 3 mL of 15% NaOH solution, and 9 mL of water and the resulting mixture was refluxed for 10 min, cooled, and filtered. The filtrate was concentrated in vacuo to afford 5.5 g (100%) of p-trifluoromethyl-benzyl alcohol, as a clear oil.

(b)

A mixture of 5.5 g of p-trifluoromethyl-benzyl alcohol in 50 mL of 48% HBr was heated on a steam-bath for 6 h with stirring, and cooled. Water (100 mL) was added to the above mixture, and the aqueous layer was extracted with ether, and the organic layer was concentrated in vacuo to afford 4.8 g of p-trifluoromethyl-benzyl bromide.

(c)

A mixture of 4.8 g (0.02 mol) of p-trifluoromethylbenzyl bromide and 3 g (0.019 mol) of 2-(2'-pyridyl)-1,3-dioxolane was heated to stir at room temperature 2 days, then filtered. The solid residue was washed with ether and dried in vacuo to afford 6 g (76.9%) of 1-(p-trifluoromethylbenzyl)-2-(1,3-dioxolon-2-yl)-pyridinium bromide (Formula VI: $R^1=R^2=H; R^7=4$-CF$_3$;$Z^-=Br^-$)

(d)

A mixture of 1-(p-trifluoromethylbenzyl)-2-(1,3-dioxolan-2-yl)pyridinium bromide (5 g; 12.8 mmol) in 50 g of polyphosphoric acid and 5 g of methanesulfonic acid was heated to 110° C. overnight. The reaction mixture was cooled, poured into water, and treated with 6 g of potassium hexafluorophosphate in water. The solid product was filtered and dried to afford 3.05 g (60%) of 9-trifluoromethyl-benzo[b]quinolizinium hexafluorophosphate (Formula II: $R^1=R^2=H; R^7=9-CF_3; X^-=PF_6^-$).

(e)

A reaction mixture containing 9-trifluoromethylbenzo[b]quinolizinium hexafluorophosphate (2 g; 5 mmol) and 1,1-diphenylethylene (1.8 mL; 10 mmol) in 30 mL of nitromethane was heated to reflux under nitrogen for 3 days. The reaction mixture was cooled and filtered through a plug of silica gel (with 150 mL of acetonitrile), the filtrate was concentrated in vacuo, and the resulting residue dissolved in 10 mL of acetonitrile was passed through Dowex® 1x2-200 (Cl⁻). The eluate was treated with 1 g of activated charcoal, filtered, and the filtrate was washed with 50 mL of ether, and the aqueous solution was concentrated in vacuo. The white solid residue was crystallized from water and dried in vacuo to afford 3.04 g of 6,11-ethano-12,12-diphenyl-9-trifluoromethyl-6,11-dihydrobenzo[b]quinolizinium chloride ¼ hydrate (Formula I: $R^1=R^2=R^3=R^4=H; R^5=R^6=$phenyl; $R^7=9-CF_3; X^-=Cl^-$), as a white solid, m.p. 180° C. (softens).

EXAMPLE 46

(a)

To a suspension of methyl triphenylphosphonium bromide (29.44 g; 0.0785 mol) in 500 mL of ether was added at −30° C. 10M n-butyllithium in hexane (8.24 mL; 0.0824 mol) and the mixture was heated to warm and stir at room temperature for 1 h. To the above mixture was added 25 g (0.0785 mol) of 3,3'-bis(trifluoromethyl)benzophenone in 50 mL of tetrahydrofuran and the mixture was refluxed for 1 h, cooled, filtered, and concentrated in vacuo. The above residue was chromatographed on silica (hexane:$CH_2Cl_2$ 2:1) to afford 22.3 g (89.9%) of 1,1-di-(m-trifluoromethylphenyl)ethylene (Formula III: $R^3=R^4=H; R^5=R^6=3-CF_3$-phenyl), as a yellow liquid.

(b)

A reaction mixture containing benzo[b]quinolizinium hexafluorophosphate (4 g; 13 mmol) and 1,1-di(m-trifluoromethylphenyl)ethylene (4.95 g; 15.6 mmol) in 55 mL of nitromethane was heated to reflux under nitrogen for 24 h. The reaction mixture was cooled, filtered, and the filtrate was concentrated in vacuo. The solid product was triturated with ether, filtered, and dried to yield a tan powder. The product was purified by chromatography on silica eluting with methanol/methylene chloride (8:92) to afford 8.1 g (90.3 %) of 6,11-ethano-12,12-di(m-trifluoromethylphenyl)-6,11-dihydroben[b]quinolizinium hexafluorophosphate (Formula I: $R^1=R^2=R^3=R^4=R^7=H; R^5=R^6=3-CF_3$-phenyl; $X^-=PF_6^-$).

(c)

6,11-Ethano-12,12-di(m-trifluoromethylphenyl)-6,11-dihydrobenzo[b]quinolizinium hexafluorophosphate (8 g: 11.5 mmol) was converted to the corresponding chloride by passing the salt through Dowex® 1x2-200 (Cl⁻) (70 g) to afford 2.63 g (42.7%) of 6,11-ethano-12,12-di(m-trifluoromethylphenyl)-6,11-dihydrobenzo[b]quinolizinium chloride (Formula I: $R^1=R^2=R^3=R^4=R^7=H; R^5=R^6=3-CF_3$-phenyl; $X^-=Cl^-$), as a tan powder, m.p. 155°–160° C.

EXAMPLE 47

(a)

To a mixture of 12.7 g (0.099 mol) of 2-thienylcarboxylic acid, 8.33 g (0.099 mol) of thiophene, and 34.9 mL of Ambedyst-15 in 250 mL of nitromethane was added 34.9 mL (0.247 mol) of trifluoroacetic acid at room temperature and stirred for 14 h. The reaction mixture was filtered, the filtrate was concentrated in vacuo, and a green oil residue was chromatographed on silica (hexane/methylene chloride 1:1) to afford 8 g (41.6%) of di-(2-thienyl)ketone, as white needles.

(b)

To a suspension of methyl triphenylphosphonitun bromide (15.46 g; 16.8 mmol) in 250 mL of ether was added at −30° C. 10M n-butyllithium in hexane (4.3 mL; 43 mmol) and the mixture was heated to stir at room temperature for 1 h. To the above mixture was added 8 g (41 mmol) of 1,1-di(2-thienyl)ketone in 30 mL of tetrahydrofuran over a 3 min period, the mixture was stirred at room temperature for 1 h and then filtered. To the above reaction mixture was added saturated ammonium chloride solution, and the mixture was extracted with ethyl acetate (3×100 mL). The organic layer was separated, washed with water, dried, and concentrated in vacuo to afford 1,1-di(2-thienyl)ethylene (Formula III: $R^3=R^4=H; R^5=R^6=2$-thienyl), as a brown oil.

(c)

A reaction mixture containing 6-methylbenzo[b]quinolizinium perchlorate (0.84 g; 2.86 mmol) and 1,1-di(2-thienyl)ethylene (0.768 g; 4 mmol) in 50 mL of nitromethane was heated to reflux under nitrogen for 14 h. The reaction mixture was cooled, filtered, and the solid product was triturated with ether, filtered, and dried. The solid product was recrystallized from methylene chloride/ethyl acetate to yield 6,11-ethano-12,12-di(2-thienyl)-6-methyl-6,11-dihydrobenzo[b]quinolizinium perchlorate (Formula I: $R^1=R^3=R^4=R^7=H; R^2=CH_3; R^5=R^6=2$-thienyl; $X^-=ClO_4^-$).

(d)

6,11-Ethano-12,12-di(thienyl)-6-methyl-6,11-dihydrobenzo[b]quinolizinium perchlorate was converted to the corresponding chloride by passing the salt through Dowex® 1x2-200 (Cl⁻) (55 g) to afford 0.595 g (49.4%) of 6,11-ethano-12,12-di(2-thienyl)-6-methyl-6,11-dihydrobenzo [b]quinolizinium chloride (Formula I: $R^1=R^3=R^4=R^7=H; R^2=CH_3; R^5=R^6=2$-thienyl; $X^-=Cl^-$), as an off-white solid, m.p. 173°–180° C.

EXAMPLE 48

(a)

A reaction mixture containing benzo[b]quinolizinium hexafluorophosphate (3.06 g; 10 mmol) and 1,1-di(2-thienyl)ethylene (2.2 g; 11.4 mmol) in 50 mL of nitromethane was heated to reflux under nitrogen for 14 h. The reaction mixture was cooled, filtered, and the brown solid product was triturated with ether, filtered, and dried to yield a brown powder which was triturated with ethyl acetate/ether. The solid product was dissolved in acetonitrile, treated with activated charcoal, filtered and the solvent was concentrated to afford 2.3 g (40.5%) of (6,11-ethano-12,12-di(2-thienyl)-6,11-dihydrobenzo[b] quinolizinium hexafluorophosphate (Formula I: $R^1=R^2=R^3=R^4=R^7=H;R^5=R^6=$2-thienyl;$X^-=PF_6^-$).

(b)

6,11-Ethano-12,12-di(2-thienyl)-6,11-dihydrobenzo[b] quinolizinium hexafluorophosphate (2.3 g; 4 mmol) was converted to the corresponding chloride by passing the salt through Dowex® 1-2-200. (Cl⁻) (60 g) to afford 0.86 g (53%) of 6,11-ethano-12,12-di(2-thienyl)-6,11-dihydrobenzo[b]quinolizinium chloride (Formula I: $R^1=R^2=R^3=R^4=R^7=H;R^5=R^6=$2-thienyl;$X^-=Cl^-$), as an off-white solid, m.p. 162°–168° C.

EXAMPLE 49

(a)

To a suspension of 4-bromopyridine hydrochloride (21 g, 0.1 mol) in 300 mL of ether was added 200 mL of saturated sodium bicarbonate and the mixture was stirred for 5 min. The organic layer was dried over sodium sulfate and concentrated in vacuo to afford 15.1 g (89.3%) of 4-bromopyridine.

(b)

To a solution of n-butyllithium (2.5 M, 39 mL, 0.096 mol) in 300 mL of ether cooled to –75° C. was added 4-bromopyridine (15.1 g, 0.095 mol) in 100 mL of ether at such a rate to maintain the internal temperature below –50° C. The resulting mixture was stirred at –75° C. for 15 min, and N-methyl,N-methoxyurethane (5.8 g, 0.043 mol) in 25 mL of ether was added over a 20 min period, and the mixture was warmed to room temperature and then stirred for 2 h. The mixture was quenched with 300 mL of water and the layers were separated. The organic layer was extracted with 6 N HCl solution, and the aqueous layer was basified with 10% NaOH solution. The basic solution was extracted with chloroform, the organic layer dried over sodium sulfate, concentrated in vacuo, and purified by chromatography on silica (ethyl acetate) to afford 3.9 g (48.7%) of di-(4-pyridyl) ketone.

(c)

A suspension of methyl triphenylphosphonium bromide (6.4 g; 18 mmol) in 75 mL of ether was added at 0° C. to n-butyllithium in hexane (7.2 mL; 18 mmol) and the mixture was heated to stir at room temperature under nitrogen for 1 h. To the above mixture was added 3 g (16 mmol) of 1,1-di(4-pyridyl)ketone in 20 mL of tetrahydrofuran over a 10 min period and the mixture was stirred at room temperature for 30 minutes. The above reaction mixture was quenched with water and stirring. The organic layer was separated, dried over sodium sulfate, and concentrated in vacuo. The residue was purified by chromatography on silica eluting with ethyl acetate/methylene chloride/methanol (7:2:1) to afford 2.2 g (73.3%) of 1,1-di(4-pyridyl)ethylene (Formula III: $R^3=R^4=H;R^5=R^6=$4-pyridyl).

(d)

A reaction mixture containing benzo[b]quinolizinium perchlorate (1.8 g; 6.4 mmol) and 1,1-di(4-pyridyl)ethylene (2.1 g; 11.5 mmol) in 75 mL of nitromethane was heated to reflux under nitrogen for 48 h. The reaction mixture was cooled, concentrated, the residue was treated with boiling water and the mixture was filtered. The residual mixture was treated with charcoal and hot methanol, filtered, and the filtrate was concentrated in vacuo. The residue was further purified by chromatography on silica to afford 280 mg (9.4%) of 6,11-ethano-12,12-di(4-pyridyl)-6,11-dihydrobenzo[b]quinolizinium perchlorate (Formula I: $R^1=R^2=R^3=R^4=R^7=H;R^5=R^6=$4-pyridyl;$X^-=ClO_4^-$).

(e)

6,11-Ethano-12,12-di(4-pyridyl)-6,11-dihydrobenzo[b] quinolizinium perchlorate (280 mg; 0.61 mmol) was converted to the corresponding chloride by passing the salt through Dowex® 1x2-200 resin to afford 220 mg (9.4%) of 6,11-ethano-12,12-di(4-pyridyl)-6,11-dihydrobenzo[b] quinolizinium chloride (Formula I: $R^1=R^2=R^3=R^4=R^7=H;R^5=R^6=$4-pyridyl;$X^-=Cl^-$).

EXAMPLE 50

(a)

A reaction mixture containing 6-methylbenzo[b] quinolizinium perchlorate (2.1 g; 7.1 mmol) and 1,1-di(3-furyl)ethylene (1.7 g; 10.1 mmol) in 50 mL of nitromethane was heated to reflux under nitrogen for 16 h. The reaction mixture was cooled, concentrated in vacuo, and the residue was triturated with 100 mL of ethyl acetate/methanol (5:1). The solid product was filtered, washed with methanol, water, ether, and methanol to afford 1.5 g (46.8 %) of 6,11-ethano-12,12-di(3-furanyl)-6-methyl-6,11-dihydrobenzo[b] quinolizinium chloride (Formula I: $R^1=R^3=R^4=R^7=H;R^2=CH_3;R^5=R^6=$3-furanyl; $X^-=ClO_4^-$).

(b)

6,11-Ethano-12,12-di(3-furanyl)-6-methyl-6,11-dihydrobenzo [b]-quinolizinium perchlorate (1.5 g; 3.3 mmol) was converted to the corresponding chloride by passing the salt through Dowex® 1x2-200 (Cl⁻) resin to afford 1.0 g (77.5%) of 6,11-ethano-12,12-di(3-furanyl)-6-methyl-6,11-dihydrobenzo[b]quinolizinium chloride (Formula I: $R^1=R^3=R^{11}=R^7=H;$ $R^2=CH_3;R^5=R^6=$3-furanyl;$X^-=Cl^-$), m.p. 180°–84° C.(d).

EXAMPLE 51

(a)

To a suspension of NaH (4.7 g of 60% disp in oil) in DME (150 mL) was added cyclopropyl triphenylphosphonium bromide (44 g) and anhydrous ethanol (10 drops). The resulting mixture was heated at 68° C. for 4 h and then 23 g of benzophenone was added in one portion and the reaction mixture was stirred under nitrogen at 70° C. for 5 h. The mixture was cooled to room temperature and stirred overnight under nitrogen. Water (300 mL) and 500 mL of hexane were added to the mixture, stirred for 10 min, and the organic layer was dried over sodium sulfate and concentrated in vacuo to afford 6.8 g (28.8% in 2 crops) of diphenylmethylenecyclopropane (Formula III: $R^3$ and $R^4$ together form a cyclopropyl ring; $R^5=R^6=$phenyl) after chromatography on silica (hexane).

(b)

A reaction mixture of 6-methylbenzo[b]quinolizinium perchlorate (2.4 g; 8.2 mmol) and diphenylmethylenecyclopropane (3.12 g; 15 mmol) in nitromethane (75 mL) was heated to reflux under nitrogen for 48 h. The reaction mixture was cooled, concentrated in vacuo, and the residue was triturated with ether/ethyl acetate (5:1), and filtered. The solid product was purified by chromatography on silica eluting with methylene chloride/ethyl acetate/methanol (7:2:1) to yield a brown foamy solid. The product was treated with warm methanol/acetonitrile (5:1) and activated charcoal and filtered. The filtrate was concentrated in vacuo to give 2.0 g (48.8%) of 6,11-ethano-12,12-diphenyl-6-methyl-13,13-(spiropropane)-6,11-dihydrobenzo[b] quinolizinium perchlorate (Formula I: $R^1=R^7=H; R^2=CH_3; R^3$ and $R^4$ together form a cyclopropyl ring; $R^5=R^6=$ phenyl; $X^-=ClO_4^-$).

(c)

6,11-Ethano-12,12-diphenyl-6-methyl-13,13-(spiropropane)-6,11-dihydrobenzo[b]quinolizinium perchlorate (2.0 g; 4 mmol) was converted to the corresponding chloride by passing the salt through Dowex® 1x2-200 (Cl$^-$) resin to afford 6,11-ethano-12,12-diphenyl-6-methyl-13,13-(spirocyclopropane)-6,11-dihydrobenzo[b]quinolizinium chloride (Formula I: $R^1=R^7=H; R^2=CH_3; R^3$ and $R^4$ together form a cyclopropyl ring; $R^5=R^6=$phenyl; $X^-=Cl^-$), m.p. 184°–189° C.

EXAMPLE 52

(a)

A mixture of 2-pyridinecarboxaldehyde (300 g), 300 mL of ethylene glycol, 3 L of toluene and 100 g of p-toluenesulfonic acid in a 5 L 3 neck-flask equipped with a Dean-Stark head was refluxed for 4 h, separating the water formed. The mixture was concentrated in vacuo to ½ of its volume, and poured into a 5 L flask containing a cold (5° C.) sodium bicarbonate solution. The aqueous layer was extracted with methylene chloride (3×500 mL), the combined organic layer was dried over sodium sulfate, and concentrated in vacuo to yield a dark oil. The oil was distilled (1 mm/100°–110° C.) to afford 349.1 g (82.4%) of 2-(1,3-dioxolan-2-yl)pyridine.

(b)

A reaction mixture of 249.5 g (1.65 mol) of 2-(1,3-dioxolan-2-yl) pyridine and 339 g (1.98 mol) of benzyl bromide was heated briefly with stirring on a steam-bath to 50° C. After an exothermic reaction (125° C.), the mixture was heated at 100° C. on a steam-bath for 1 h to afford 533 g (1.65 mol) of 1-benzyl-2-(1,3-dioxolan-2-yl)pyridinium bromide (Formula VI: $R^1=R^2=R^7=H; Z^-=Br^-$).

(c)

To 1-benzyl-2-(1,3-dioxolan-2-yl)pyridinium bromide (1.65 mol) was added 1 L of 48% HBr and 1 L of acetic acid with stirring and the mixture was heated on a steam-bath at 95° C. for 7 h. The mixture was concentrated in vacuo, the oil residue was combined with 2 L of isopropyl acetate/isopropyl alcohol (1:1), and the solution was cooled. The yellow solid was filtered, washed with ethyl acetate and dried to afford 292 g (68%) of benzo[b]quinolizinium bromide, (Formula II: $R^1=R^2=R^7=H; X^-Br^-$), as a light yellow solid.

(d)

To cooled (−78° C.) solution of 3-bromothiophene (16.3 g, 0.1 mol) in THF (100 mL) was added under nitrogen, n-butyllithium (2.5M, 40 mL) and to the above mixture was added N-methyl-N-methoxyurethane (6.28 g, 0.047 mol) in 5 mL of THF over a 0.5 h period and the mixture was allowed to warm to room temperature. The mixture was quenched with saturated ammonium chloride solution and the aqueous layer was extracted with ether. The combined organic layer was dried over magnesium sulfate, concentrated in vacuo, and the oil residue was crystallized from methanol to afford 1.465 g (16%) of 1,1-di-(3-thienyl) ketone, m.p. 78°–80° C. Alternatively, 1,1-di-(3-thienyl) ketene was prepared as follows: To 100 mL of THF cooled to −78° C. under nitrogen was added 2.5M n-butyllithium (36 mL), and 14.67 g (0.09 mol) of 3-bromothiophene was added and the resulting mixture was stirred for 30 min. To the above mixture was added 3-thiophenecarboxaldehyde (10 g, 0.089 mol) in 10 mL of THF and the mixture was stirred, allowing it to reach room temperature. Saturated ammonium chloride solution was added to the reaction mixture, the aqueous layer was extracted with ether, and the combined organic layer was concentrated in vacuo to yield 17.26 g (98.9%) of 1,1-di(3-thienyl)methanol, as an oil. Chromium trioxide (1.4 g) was dissolved in 12 mL of water and 24 mL of acetic acid, and the resulting mixture was added dropwise to 1,1-di(3-thienyl)-methanol in 30 mL of acetic acid over a 1 h period. The above mixture was stirred for 1 h with cooling (20° C.) in an ice-water bath. The mixture was diluted with 150 mL of water, extracted with methylene chloride, and the organic layer was washed with saturated sodium bicarbonate solution, dried over sodium sulfate, and concentrated in vacuo to yield an oil, which was crystallized in methanol to afford 1.85 g (47.7%) of 1,1-di (3-thienyl)ketone, as a solid, m.p. 79°14 81° C.

(e)

To a suspension of methyl triphenylphosphonium bromide (15.7 g; 44 mmol) in 75 mL of ether was added under nitrogen at 0° C. 2.5M n-butyllithium in hexane (17.6 mL; 43 mmol) dropwise (<5° C.) and the mixture was allowed to warm and stir at room temperature for ½ h. To the above mixture was added 7.85 g (44 mmol) of di(3-thienyl)ketone in 50 mL of tetrahydrofuran dropwise and the mixture was stirred at room temperature for ½ h. To the above reaction mixture was added 20 mL of acetone, concentrated in vacuo, and the residue was partitioned in water/methylene chloride and methylene chloride was distilled in vacuo. The oil residue was distilled (0.02 mm/95°–100° C.) to afford 5.944 g (77.3%) of 1,1-di(3-thienyl)ethylene (Formula III: $R^3=R^4=H; R^5=R^6=$3-thienyl), as a colorless oil.

(f)

A reaction mixture containing benzo[b]quinolizinium perchlorate (0.839 g; 3 mmol) and 1,1-di(3-thienyl)ethylene (0.68 g; 3.54 mmol) in 2 mL of acetonitrile was allowed to reflux under nitrogen with stirring for 21 h. The reaction mixture was concentrated in vacuo, the residue was stirred in methylene chloride, and the white solid (975 mg) was filtered. The above solid was triturated in methanol (15 mL), dissolved in water and passed through Dowex® 1x2x200 (Cl$^-$) resin, the eluent was concentrated, and the residue was washed with acetonitrile and ether to afford 459 mg (58.6%) of 6,11-ethano-12,12-di(3-thienyl-6,11-dihydrobenzo[b] quinolizinium Chloride (Formula I: $R^1=R^2=R^3=R^4=R^7=H; R^5=R^6=$3-thienyl; $X^-=Cl^-$).

EXAMPLE 53

(a)

To a suspension of 1,1-carbonyldiimidazole (90 g, 0.555 mol) in 400 mL of THF at 0° C. was added dropwise formic acid 25.5 g (0.555 mol) in 100 mL of THF over a 15 min period. The mixture was warmed to room temperature and stirred for 1.5 h. The resulting solution was added via a canula to the anion of methyl isocyanoacetate (generated by addition of the methyl isocyanoacetate in 75 mL of THF to a suspension of potassium t-butoxide at 0° C. and stirring for 15 min) at 0° C. During the addition (exothermic), the reaction mixture reached to 20° C. and the ice-bath was removed, stirring was continued at room temperature for 1 h. The above mixture was quenched with 100 mL of acetic acid followed by 200 mL of water, THF was removed in vacuo, and 1000 mL of chloroform was added to the residual mixture. The organic layer was washed with water (2×200 mL), saturated sodium bicarbonate solution (1×100 mL), water, brine, and dried over sodium sulfate and concentrated in vacuo. The resulting residue was chromatographed on silica (methylene chloride/hexane/ether 7:2:1) to afford 23.5 g (37%) of methyl 4-oxazolecarboxylate.

(b)

To a suspension of methoxy-methylamine hydrochloride (2.3 g, 23.6 mmol) in 30 mL of dichloroethane at 0° C. was added dropwise 11.8 mL (23.6 mmol) of trimethylaluminum. The mixture was stirred at 0° C. for 20 min, and methyl 4-oxazolecarboxylate (1 g, 7.9 mmol) in 20 mL of dichloroethane was added in one portion. The mixture was poured into an ice-cold solution of 0.5 N HCl/methylene chloride (2:1) and stirred for 10 min. The aqueous layer was extracted with methylene chloride (2×50 mL), and the combined organic layer was washed with saturated ammonium chloride solution, dried over sodium sulfate, and concentrated in vacuo. The resulting residue was purified by chromatography on silica (methylene chloride/ethyl acetate/methanol 6:3:1) to afford 1.0 g (81.9%) of 4-oxazolyl-N-methyl-N-methoxy-carboxamide.

(c)

To a solution of 4-oxazolyl-N-methyl-N-methoxy-carboxamide (2.76 g, 17.6 mmol) in 250 mL of DME/THF (2:1) and 100 mL of DME cooled to −78° C., was added a 1M solution of LAH (35.3 mL, 35.3 mmol) in THF over a 15 min period and the mixture was stirred at −78° C. for 1 h. After an additional addition of 35 mL of LAH solution, the mixture was stirred for 15 min, quenched with 2.6 mL of water, followed by 2 mL of 10% NaOH solution and 2.6 mL of water. The above mixture was stirred at room temperature for 15 min, filtered, and the residue was washed with 600 mL of MDC/acetone (2:1). The combined filtrate was concentrated in vacuo, and the residue was purified by chromatography on silica (MDC/ethyl acetate 6:1) to afford 0.62 g (36%) of 4-oxazolylcarboxaldehyde.

(d)

To a solution of oxazole (0.4 mL (6.2 mmol) in 20 mL of THF cooled to −78° C. under nitrogen was added 2.5M n-butyllithium (2.5 mL, 6.2 mmol). The mixture was stirred at −78° C. for 30 min and a solution of 4-oxazolylcarboxaldehyde (0.6 g, 6.2 mmol) in 25 mL of THF was added dropwise. The resulting mixture was warmed to room temperature and stirred overnight. The reaction mixture was quenched with a suspension of Dowex® 50x2-200 in methanol (20 mL) and stirred for 30 min, filtered, and the filtrate was concentrated in vacuo. The residue was dissolved in methylene chloride, dried over magnesium sulfate, and concentrated in vacuo. The resulting residue was purified by chromatography on silica (5% methanol in MDC) to afford 0.35 g (33.9%) of 1,1-di(4-oxazolyl)methanol.

(e)

To a suspension of chromium trioxide (1.35 g, 13.5 mmol) in 75 mL of methylene chloride at 0° C. was added 2.1 g (12.6 mmol) of pyridine and the mixture was allowed to warm to room temperature and stirred for 30 min. To the mixture was added 1,1-di(4-oxazolyl)methanol (0.35 g, 2.1 mmol) in 10 mL of MDC, and the mixture was stirred at room temperature under nitrogen for 15 min. The mixture was diluted with 100 mL of ethyl acetate, stirred, filtered through a pad of florisil (4 inches) eluting with 300 mL of ethyl acetate to afford 0.15 g (43.4%) of 1,1-di(4-oxazolyl) ketone, as a white solid.

(f)

To a suspension of methyltriphenylphosphonium bromide (0.36 g; 1.01 mmol) in 10 mL of THF was added under nitrogen at 0° C. 2.5M n-butyllithium (0.4 mL, 1.01 mmol), and the mixture was stirred for 30 min. To the above mixture was added di(4-oxazolyl)ketone (0.15 g, 0.92 mmol) in 10 mL of THF and the mixture was stirred for 1 h. The mixture was quenched with 25 mL of saturated ammonium chloride solution and 50 mL of MDC was added and stirred. The organic layer was dried over sodium sulfate, concentrated in vacuo, and the residue was purified by chromatography on silica (hexane/ethyl acetate 2:1) to afford 0.05 g (33.3%) of 1.1-di(4-oxazolyl)ethylene (Formula III: $R^3=R^4=H; R^5=R^6=$ 4-oxazolyl).

(g)

A reaction mixture containing benzo[b]quinolizinium perchlorate (71 mg; 0.25 mmol) and 1,1-di(4-oxazolyl)ethylene (0.05 g; 0.3 mmol) in 10 mL of nitromethane was heated at 100° C. for 2 h under nitrogen. The reaction mixture was concentrated in vacuo and the residue was dissolved in 5 mL of methanol and concentrated. The residue was triturated in 1 mL of methanol, the solid product was filtered, washed with 2 mL of cold methanol and 10 mL of ether to afford 85 mg (75.8%) of 6,11-ethano-12,12-di(4-oxazolyl)-6,11-dihydrobenzo[b]quinolizinium perchlorate (Formula I: $R^1=R^2=R^3=R^4=R^7=H; R^5=R^6=$4-oxazolyl;$X^-=ClO_4^-$), as a white solid, m.p. 236°–238° C.

EXAMPLE 54

(a)

To a solution of 4-picoline-N-oxide (20 g) in $CH_2Cl_2$ (360 mL) was added TMSCN (26.5 mL), stirred 5 minutes, added dimethyl carbamyl chloride (16.6 mL) was added slowly dropwise. The mixture was stirred at RT overnight, poured onto 400 mL $H_2O$, and 40 g $NaCO_3$. Separation of layers and evaporation of $CH_2Cl_2$ gave 17.25 g of 2-Cyano-4-methylpyridine-N-oxide, recrystallized from hexane, m.p. 95°–98° C.

(b)

To a solution of 2-cyano-4-methylpyridine-N-oxide (3.29 g, 0.0279 mol) in 164 mL of methylene chloride at −78° C.

was added 27.6 mL of DIBAL(H) and the mixture was stirred at −78° C. for 2 h. To the above mixture was added 13 mL of HCl (conc.) and 52 mL of water, and the mixture was warmed to room temperature. To the aqueous layer was added sodium bicarbonate solution, the solution was extracted with ether, and the combined organic layer was concentrated in vacuo. The residue was purified by chromatography on silica (ether) to afford 0.5 g (14.8%) of 4-methylpyridine-2-carboxaldehyde, as an oil.

(c)

A mixture of 1 g (8.26 mmol) of 4-methylpyridine-2-carboxaldehyde, and 1.41 g (8.3 mmol) of benzyl bromide in 10 mL of sulfolane was stirred and heated on a steam-bath overnight. The resulting mixture was triturated (repeatedly) with ethyl acetate and the solvent was decanted to isolate a dark gum. This residue was dissolved in water, and washed with ether, and the aqueous solution was concentrated in vacuo to afford 1-benzyl-4-methyl-2-formyl-pyridinium bromide, which was used without additional purification.

(d)

A mixture of 1-(benzyl)-2-(formyl)-4-methylpyridinium bromide in 50 mL of 48% HBr was heated to 100° C. overnight. The reaction mixture was cooled and the solvent removed in vacuo. The residue was added to water (20 mL), and treated with 6 g of sodium perchlorate in water (100 mL). The solid product was filtered, dissolved in methylene chloride/methanol, and was purified by chromatography on silica eluting with methylene chloride/methanol (1:1) to afford 2-methyl-benzo[b]quinolizinium perchlorate, (Formula II: $R^1$=2-$CH_3$;$R^2$=$R^7$=H;$X^-$=$Br^-$) as a brown oil.

(e)

The above 2-methylbenzo[b]quinolizinium perchlorate and 1,1-diphenylethylene (2 mL) in 50 mL of nitromethane was heated at 110° C. under nitrogen overnight. The reaction mixture was cooled, concentrated in vacuo, and the residue was purified by chromatography on silica eluting with acetonitrile/methylene chloride (from 1:9 to 4:6) to afford 170 mg of 6,11-ethano-12,12-diphenyl-2-methyl-6,11-dihydrobenzo[b]quinolizinium perchlorate (Formula I: $R^1$=2-$CH_3$;$R^2$=$R^3$=$R^4$=$R^7$=H;$R^5$=$R^6$=phenyl;$X^-$=$ClO_4^-$), as a brown oil.

EXAMPLE 55

(a)

To a suspension of methyl triphenylphosphonium bromide (15.6 g; 44 mmol) in 200 mL of ether cooled to −10° C. was added dropwise 2.2M n-butyllithium in hexane (20 mL; 44 mmol) at −10° C. and the mixture was allowed to warm to room temperature. To the above mixture cooled to −10° C. was added 10 g (44 mmol) of 1,1-di(m-chlorophenyl)ketone in one portion, and the mixture was stirred overnight at room temperature. The mixture was quenched with water, extracted with ethyl acetate, and the organic layer was washed with water, dried over sodium sulfate, and concentrated in vacuo to afford 11.55 g of an oil. The oil was purified by chromatography on silica eluting with hexane to afford 6.5 g (65.3%) of 1,1-di(m-chlorophenyl)ethylene (Formula III: $R^3$=$R^4$=H;$R^5$=$R^6$=3-Cl-phenyl), as a colorless oil.

(b)

A reaction mixture containing 1.7 g (6.5 mmol) of benzo[b]quinolizinium bromide and 1,1-di(m-chlorophenyl)ethylene (6.5 g; 26 mmol) in 25 mL of acetonitrile/methanol (1:1) was allowed to reflux under nitrogen for 40 hours. The reaction mixture was cooled, concentrated in vacuo, and the residue was purified by chromatography on silica (ethyl acetate/ethanol 1:1) to afford 2.15 g (65%) of a white solid. The white solid was added to a mixture of 75 mL of water,75 mL of methanol, and Dowex® 1x2-200 (Cl$^-$), and the resulting mixture was heated with stirring and poured on Dowex® 1x2-200 (Cl$^-$) resin column to afford 1.2 g (36.3%) of 6,11-ethano-12,12-di(m-chlorophenyl)-6,11-dihydrobenzo[b]quinolizinium chloride (Formula I: $R^1$=$R^2$=$R^3$=$R^4$=$R^7$=H;$R^5$=$R^6$=3-Cl-phenyl;$X^-$=$Cl^-$).

EXAMPLE 56

A reaction mixture containing 0.5 g (1.6 mmol) of benzo[b]quinolizinium hexafluorophosphate, 0.001 g of p-tolenesulfonic acid, and 1-phenyl-1-ethynyl-methanol (0.9 g; 6.4 mmol) in 10 mL of nitromethane was heated to reflux under nitrogen for 4 h. The reaction mixture was cooled, concentrated in vacuo, and the residue (4.1:1 mixture of isomers) was purified by chromatography on silica (methanol/methylene chloride 1:10) to afford 95 mg (13.6%) of 6,11-ethano -12-phenyl-12-ethynyl-6,11-dihydrobenzo[b]quinolizinium hexafluorophosphate (Formula I: $R^1$=$R^2$=$R^3$=$R^4$=$R^7$=H; $R^5$=C=CH;$R^6$=phenyl;$X^-$=$PF_6^-$), single isomer, as a brown solid, m.p. 101°–106° C.

EXAMPLE 57

(a)

To a solution of 45.04 g (0.66 mol) of furan in 300 mL of ether was added 36.3 mL (0.363 mol) of 10M n-butyllithium at −20° C. and the mixture was warmed to 0° C. and stirred for 1 h. The above mixture was cooled to −78° C. and N-methyl-N-methoxy-urethane (22 g, 0.165 mol) in 20 mL of ether was added dropwise over a 20 min period and the resulting mixture was allowed to warm to room temperature for 1 h. The reaction mixture was quenched with 100 mL of ammonium chloride solution, extracted with ether (2 ×100 mL), and the organic layer was dried over sodium sulfate and concentrated in vacuo to yield an oil. The above oil was purified by chromatography on silica (methylene chloride) to afford 26.5 g (95%) of 1,1-di(2-furyl)ketone, as a pale oil.

(b)

A suspension of methyl triphenylphosphonium bromide (11.56 g; 32.3 mmol) in 100 mL of ether was added at −30° C. 10M n-butyllithium in hexane (3.23 mL; 32.3 mmol) and the mixture was allowed to stir at room temperature for 1 h. To the above mixture was added 5 g (30.8 mmol) of 1,1-di(2-furyl)ketone in 15 mL of tetrahydrofuran in 1 rain and the mixture was refluxed. The above mixture was cooled, filtered, and concentrated to yield 4.92 g (100%) of 1,1-di(2-furyl)ethylene (Formula III: $R^3$=$R^4$=H;$R^5$=$R^6$=2-Furyl).

(c)

A reaction mixture containing benzo[b]quinolizinium hexafluorophosphate (5 g; 16.3 mmol) and 1,1-di(2-furyl)-ethylene (4.92 g; 30 mmol) in 100 mL of nitromethane was allowed to reflux under nitrogen for 15 min. The reaction mixture was cooled, triturated in ether for 20 min, and the solvent was decanted to yield a brown powder. The above solid was purified by two chromatographic purifications on silica (acetonitrile/methylene chloride, 1:9) to afford 1.2 g (15.1%) of 6,11-ethano-12,12-di(2-furanyl)-6,11- dihydrobenzo[b]quinolizinium hexafluorophosphate (Formula I: $R^1=R^2=R^3=R^4=R^7=H$; $R^5=R^6$=2-Furyl;$X^-$= $PF_6^-$), as a solid.

(d)

6,11-Ethano-12,12-di(2-furanyl)-6,11-dihydrobenzo [b]quinolizinium hexafluorophosphate (1.2 g; 2.47 mmol) was converted to the corresponding chloride by passing the salt through Dowex® 1x2-200 (Cl⁻) (60 g) to afford 0.91 g (98.9%) of 6,11-ethano-12,12-di(2-furanyl)-6,11-dihydrobenzo[b]quinolizinium chloride (Formula I: $R^1=R^2=R^3=R^4=R^7=H;R^5=R^6$=2-Furyl;$X^-$=Cl⁻), m.p. 136°–141° C.

EXAMPLE 58

(a)

A suspension of methyl triphenylphosphonium bromide (31.22 g; 87.3 mmol) in 500 mL of ether was added at −30° C. 10M n-butyllithium in hexane (8.73 mL; 87.3 mmol) and the mixture was allowed to stir at room temperature for ½ h. To the above mixture was added 15 g (83.2 mmol) of 9-fluorenone in 50 mL of tetrahydrofuran and the mixture was refluxed for 1 h. The above mixture was cooled to 0° C., filtered, and concentrated to yield 11.3 g (76.3%) of 9-methylene-fluorine (Formula III: $R^3=R^4=H;R^5=R^6$ together form a 9-fluorene ring).

(b)

To a reaction mixture containing benzo[b]quinolizinium hexafluorophosphate (6 g; 19.6 mmol) in 100 mL of nitromethane was added 9-methylene-fluorene (6 g; 19.6 mmol) and the mixture was refluxed under nitrogen for 1 h. After the addition of another 2 g of 9-methylene-fluorene, the reaction mixture was refluxed for 1 h. To the refluxing solution an additional 4 g of 9-methylene-fluorene was added and refluxed for an additional 20 min, cooled, and filtered. The filtrate was concentrated, the residue was triturated in water, and the solvent was decanted to yield a gray powder. The above powder was chromatographed on silica (11% acetonitrile in methylene chloride) to afford 2.3 g (21.3%) of 6,11-ethano-12,12-spiro-9H-fluorenyl-6,11-dihydrobenzo[b]quinolizinium hexafluorophosphate, as a yellow foam.

(c)

6,11-Ethano-12,12-spiro-9H-fluorenyl-6,11-dihydrobenzo [b]quinolizinium hexafluorophosphate (2.3 g) was converted to the corresponding chloride by passing the salt through Dowex® 1x2-200 (Cl⁻) (60 g) to afford 6,11-ethano-12,12-spiro-9H-fluorenyl-6,11-dihydrobenzo [b]quinolizinium chloride (Formula I: $R^1=R^2=R^3=R^4=R^7$= H;

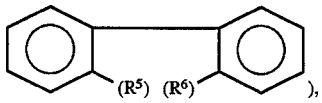

as a white solid, m.p. 236°–242° C.(d).

EXAMPLE 59

(a)

To a mixture of 10 mL (85.6 mmol) of 2-bromobenzaldehyde in 300 mL of ether cooled to -45° C. was added in portions 8.56 mL (85.6 mmol) of 10M n-butyllithium in hexane over a 20 min period, and the reaction mixture was stirred at −20 for ½ h. To the above reaction mixture cooled to −20° C., was added 8.98 mL (88.9 mmol) of 10M n-butyl-lithium in hexane over a 10 min period, and the mixture was allowed to warm to room temperature and stirred for 1 h. The mixture was cooled to −20° C., and 12.2 mL (128 mmol) of 2-pyridinecarboxaldehyde was added rapidly and the mixture was allowed to warm to room temperature and stirred for 1 h. The above reaction mixture was poured into 150 mL of saturated ammonium chloride solution with stirring, the aqueous layer was extracted with ethyl acetate (3×200 mL), the combined organic layer was washed with brine, dried over sodium sulfate, and concentrated in vacuo to yield a brown oil. The oil was purified by chromatography on silica eluting with methylene chloride and then ether/hexane (9:1). The solvent was concentrated in vacuo, the brown oil was dissolved in methylene chloride/hexane, and removal of methylene chloride in vacuo to ½ of its volume afforded 19.3 g (83.2%) of 2-[1-hydroxy-6'-(1-hydroxypentyl)-benzyl] pyridine (Formula X: $R^1=R^7=H;R^2$=n-butyl), as a yellow solid.

(b)

To a refluxing solution of 11.1 g (0.04 mol) of 2-[1-hydroxy-6'-(1-hydroxypentyl)-benzyl]pyridine in 250 mL of benzene was added 23.9 mL (0.14 mol) of triflic anhydride in 5 min, the mixture was heated for 65 min and then cooled. The reaction mixture was concentrated in vacuo, the residual oil was triturated in ether and decanted. The oil was chromatographed on silica (ethyl acetate/methylene chloride, 1:1) to afford an oil, which was treated with sodium perchlorate solution. The salt was triturated in hot water, decanted, and the residue crystallized on cooling. The above solid was crystallized (2x) from ethyl acetate/methylene chloride to afford 1.5 g (11%) of 6-butylbenzo[b] quinolizinium perchlorate (Formula II: $R^1=R^7=H;R^2$=n-butyl;$X^-=ClO_4^-$), as a pale solid, m.p. 174°–177° C.

(c)

A reaction mixture containing 6-butyl-benzo[b] quinolizinium perchlorate (0.75 g; 2.2 mmol) and 1,1-diphenylethylene (0.6 g; 3.3 mmol) in 50 mL of nitromethane was allowed to reflux under nitrogen for 16 h. The reaction mixture was cooled, concentrated in vacuo and the resulting residue was triturated in ether to yield a brown powder. The solid product was dissolved in methylene chloride, filtered, and the filtrate was chromatographed on silica (15% acetonitrile in methylene chloride) to afford 400 mg (35.3%) of 6,11-ethano-12,12-diphenyl-6-butyl-6,11-dihydrobenzo[b]quinolizinium perchlorate (Formula I: $R^1=R^3=R^4=R^7$=H; $R^2$=n-butyl;$R^5=R^6$=phenyl; $X^-=ClO_4^-$), m.p. 134°–138° C.

EXAMPLE 60

(a)

A mixture of 2-pyridinecarboxaldehyde (2678, 2.5 mol), ethylene glycol (310.35 g, 5 mol), and 118.8 g (0.62 mol) of p-toluenesulfonic acid in 1.5 L of toluene placed in a 3 L flask fined with a Dean Stark trap was allowed to reflux until the removal of water was complete. The mixture was concentrated in vacuo and the residue was poured into 800 mL of ice/10% potassium carbonate solution. The above mixture was extracted with ether (2×500 mL), and the organic layer was dried over sodium sulfate, filtered through an active charcoal/supercel and concentrated in vacuo to yield an oil. The oil was distilled (0.15 mm/90° C.) to afford 109.7 g (29.3%) of 2-(1,3-dioxolan-2-yl)-pyridine, as a pale yellow liquid.

(b)

To a solution of 75 g (0.3 mol) of 2,5-dibromotoluene in 1 L of carbon tetrachloride was added 58.73 g (0.33 mol) of NBS and 50 mg of benzyl peroxide, and the resulting mixture was refluxed with stirring for 24 h. The mixture was cooled, and concentrated in vacuo. The residue was crystallized from hot methanol and washed with hexane to afford 54.5 g (55.7%) of 2,5-dibromobenzyl bromide as a solid.

(c)

A mixture of 25.03 g (0.165 mol) of 2-(1,3-dioxolan-2-yl)-pyridine and 2,5-dibromobenzyl bromide (54 g, 0,165 mol) in 60 mL of sulfolane was heated on a steam-bath for 6 h. The mixture was diluted with 600 mL of ethyl acetate, cooled, and the resulting solid product was isolated by filtration. The above solid was triturated in 300 mL of ethyl acetate, the mixture was cooled, filtered and dried to afford 62.24 g (79%) of 1-(2,5-dibromobenzyl)-2-(1,3-dioxolan-2-yl)pyridinium bromide (Formula VI: $R^1=R^2=H;R^7=2,5-Br_2;Z^-=Br^-$), as a yellow solid, m.p.135°–139° C.

(d)

A mixture of 400 g of 48% HBr and 52 g (0.125 mol) of 1-(2,5-dibromobenzyl)-2-(1,3-dioxolan-2-yl)pyridinium bromide was heated at 100° C. with stirring for 39 h. The mixture was cooled to room temperature and poured into 400 g of ice, stirred, and filtered. The filtrate was diluted with 300 mL of water with stirring and filtered to yield a yellow solid. The solid was dissolved in hot water, filtered, and treated with sodium perchlorate solution to afford 21 g (39%) of 7,10-dibromobenzo[b]quinolizinium perchlorate (Formula II: $R^1=R^2=H;R^7=7,10-Br_2;X^-=ClO_4^-$), as a yellow solid, m.p. 270° C.

(e)

A mixture of 2.5 g (6 mmol) of 7,10-dibromobenzo[b]quinolizinium perchlorate and 1.15 g (7.2 mmol) of 1,1-di(3-furyl)ethylene in 50 mL of nitromethane was refluxed for 20 min and cooled. The mixture was concentrated in vacuo, the residue (brown oil) was triturated in ether, and the resulting solid was crystallized from methanol to afford 3.49 g (99.7%) of 6,11-ethano-12,12-di(3-furyl)-7,10-dibromo-6,11-dihydrobenzo[b]quinolizinium perchlorate (Formula I: $R^1=R^2=R^3=R^4=H;R^5=R^6=3-Furyl;R^7=7,10-Br_2;X^-=ClO_4^-$) as an off white solid, m.p. 174°–179° C.

EXAMPLE 61

(a)

To a cooled (–78° C.) ether solution containing n-butyllithium (2.5M, 13 mL, 32.5 mmol) was added 5.2 g (31 mmol) of 2-bromothiazole in 50 mL of ether over a 30 min period, and the mixture was stirred (–78° C.) for 1 h. N-Methyl-N-methoxy-urethane (2.1 g, 15 mol) in 25 mL of ether was added to the above mixture over a 15 min period, the resulting reaction mixture was stirred at –78° C. for 1 h, warmed to room temperature, and stirred for 2 h. The above mixture was quenched with 3 N HCl (200 mL) and stirred for 15 min. The aqueous layer was treated with solid sodium bicarbonate (to pH 9), the precipitated solid was filtered, and washed with water, and dried to yield a solid product. The solid product was purified by chromatography on silica (hexane/ether/methylene dichloride 4:2:1) to afford 1.7 g (54.8%) of 1,1-di(2-thiazolyl)ketone.

(b)

To a solution of 1,1-di(2-thiazolyl)ketone (1.96 g, 10 mmol) in 75 mL of THF cooled to 0° C. under nitrogen was added 15 mL (15 mmol) of 1M trimethylsilyl-methylmagnesium chloride over a 10 min period, and the resulting mixture was warmed to room temperature and stirred for 1 h. The reaction mixture was quenched with 3 mL of saturated ammonium chloride solution, diluted with 100 mL of methylene chloride, and filtered. The filtrate was washed with saturated ammonium chloride solution, and the organic layer was dried over sodium sulfate and concentrated in vacuo. The residue was purified by passing through a pad of silica, eluting with hexane/ether/methylene chloride 4:2:1) to afford 1.1 g (38.5%) of 1,1-di(2-thiazolyl)-2-trimethylsilylethanol.

(c)

A mixture of 0.18 g (0.665 mmol) of benzo[b]quinolizinium perchlorate, 0.24 g (0.85 mmol) of 1,1-di(2-thiazolyl)2-trimethylsilylethanol, and 0.21 g (0.65 mmol) of p-tolenesulfonic acid in 10 mL of nitromethane was refluxed under nitrogen for 3 h and cooled. The mixture was concentrated in vacuo, the residue was purified by chromatography on silica (ethyl acetate, and then methylene chloride/ethyl acetate/methanol 6:3:1) to yield a foamy solid which was triturated with isopropanol, filtered and dried in vacuo (65° C./60 h) to afford 30 mg (9.7%) of 6,11-ethano-12,12-di(2-thiazolyl)-6,11-dihydrobenzo[b]quinolizinium perchlorate (Formula I: $R^1=R^2=R^3=R^4=R^7=H$; $R^5=R^6=2$-thiazolyl;$X^-=ClO_4^-$) as an off white solid, m.p. 235°–237° C.

EXAMPLE 62

(a)

To a cooled (–78° C.) ether (200 mL) solution containing n-butyllithium (2.5M, 13.5 mL, 33 mmol) was added 6.43 g (40.9 mmol) of 2-trimethylsilyl-thiazole in 50 mL of ether over a 1 h period and the mixture was stirred (–78° C.) for 1 h. N-Methyl-N-methoxy-urethane (2.32 g, 17.5 mol) in 50 mL of ether was added to the above mixture over a 15 min period, the resulting reaction mixture was stirred at –78° C. for 1 h, and then warmed to room temperature with stirring. The above mixture was quenched with 3 N HCl and stirred for 2 h. The aqueous layer was treated with solid sodium bicarbonate (to pH 8), diluted with saturated ammonium chloride solution, and extracted with chloroform (3×150 mL). The combined organic layer (including the original ether layer) was dried over sodium sulfate, and concentrated in vacuo. The residue was triturated with ether (50 mL), filtered, and dried to afford 160 mg (4.6%) of 1.1-di(5-thiazolyl)ketone.

(b)

To a suspension of methyl triphenylphosphonium bromide (0.35 g; 1 mmol) in 15 mL of THF was added under nitrogen at 0° C. 2.5M n-butyllithium (0.4 mL, 1 mmol) and the mixture was stirred for 1 h. To the above mixture was added 1,1-di(5-thiazolyl)ketone (0.16 g, 0.82 mmol) in 5 mL of THF and the mixture was stirred under nitrogen at room temperature for 2 h. The mixture was quenched with 2 mL of acetone, diluted with 50 mL of ether, and filtered. The filtrate was concentrated in vacuo and the residue was purified by chromatography on silica (ether) to afford 0.035 g (21.8%) of 1,1-di(5-thiazolyl)ethylene (Formula III: $R^3=R^4=H$; $R^5=R^6=$5-thiazolyl).

(c)

A reaction mixture containing benzo[b]quinolizinium perchlorate (450 mg; 0.165 mmol) and 1,1-di(5-thiazolyl) ethylene (0.035 g; 0.18 mmol) in 8 mL of nitromethane was heated at 90° C. for 16 h under nitrogen. The reaction mixture was concentrated in vacuo and the residue was dissolved in 25 mL of boiling methanol with charcoal, filtered, and concentrated in vacuo. The residue was triturated with 10 mL of methanol/isopropanol (1:2), and the solid product was filtered and dried to afford 22 mg (28.2%) of 6,11-ethano-12,12-di(5-thiazolyl)-6,11-dihydrobenzo[b]quinolizinium perchlorate (Formula I: $R^1=R^2=R^3=R^4=R^7=H$; $R^5=R^6=$5-thiazolyl; $X^-=ClO_4^-$), as a solid.

EXAMPLE 63

(a)

To a cooled (−78° C.) 200 mL of THF solution containing 19.8 g (0.1 mol) of 1-(trimethylsilylethoxymethyl)pyrazole was added n-butyllithium (2.5M, 40 mL, 0.1 mol) over a 30 min period, and the mixture was stirred at −78° C. for 2 h. To the above mixture was added at −78° C. N-methyl-N-methoxy-urethane (6.7 g, 0.05 mol) in 30 mL of THF and the mixture was stirred for 1 h, and then was allowed to warm to room temperature and stirred for 14 h under nitrogen. The above mixture was quenched with 100 mL of saturated ammonium chloride solution and stirred for 10 min. The organic layer was dried over sodium sulfate, concentrated in vacuo, and the residue was purified by chromatography on silica (hexane/ether 4:1) to afford 15 g (71.4%) of 1,1-di[5-(1-trimethylsilyl-etholxymethyl)pyrazolyl]ketone.

(b)

To a suspension of methyl triphenylphosphonium bromide (7.3 g; 0.02 mol, dried in vacuo) in 150 mL of ether was added under nitrogen at 0° C. 2.5M n-butyllithium (8 mL, 0.02 mol) and the mixture was stirred for 1 h. To the above mixture was added 1,1-di[5-(1-trimethylsilylethoxymethyl)pyrazolyl]ketone (7.2 g, 0.017 mol) in 30 mL of ether over a 10 min period, then the mixture was stirred for 10 min at room temperature, refluxed for 15 min, and the mixture was cooled. The above mixture was quenched with 2 mL of acetone, stirred for 10 min, filtered through a pad of supercel, and washed with ether. The filtrate was concentrated in vacuo and the residue was purified by chromatography on silica (hexane/methylene chloride/ether 6:3:1) to afford 3.6 g (50.7%) of 1,1-di[5-(1-trimethylsilylethoxymethyl)pyrazolyl]ethylene (Formula III: $R^3=R^4=H$;$R^5=R^6=$5-[1-$(CH_3)_3Si(CH_2)_2OCH_2$)pyrazolyl]).

(c)

A reaction mixture containing benzo[b]quinolizinium perchlorate (1.9 g; 6.8 mmol) and 1,1-di [5-(1-trimethylsilylethoxymethyl)pyrazolyl]ethylene (3.6 g; 8.6 mmol) in 70 mL of nitromethane was heated at 105° C. for 9 h under nitrogen. The reaction mixture was concentrated in vacuo, the residue was triturated with 50 mL of isopropanol, filtered, and dried to afford 4 g (84.2%) of 6,11-ethano-12,12-di[5-(1-trimethylsilyl-ethoxymethyl)pyrazolyl]6,11-dihydrobenzo[b]quinolizinium perchlorate, (Formula I: $R^1=R^2=R^3=R^4=R^7=H$;$R^5=R^6=$5-[1-$(CH_3)_3Si(CH_2)_2OCH_2$)pyrazolyl];$X^-=ClO_4^-$), as a solid, m.p.123°–125° C.

(d)

To a solution of 525 mg (0.74 mmol) of 6,11-ethano-12,12-1,1-di[5-(1-trimethyl-silylethoxymethyl)pyrazolyl]-6,11-dihydrobenzo[b]quinolizinium perchlorate in 15 mL of dichloroethane was added 5 mL of trifluoroacetic acid and the mixture was stirred at room temperature for 2 h. The reaction mixture was concentrated in vacuo to afford 6,11-ethano-12,12-di(5-pyrazolyl)-6,11-dihydrobenzo[b]quinolizinium perchlorate (Formula I: $R^1=R^2=R^3=R^4=R^7=H$;$R^5=R^6=$5-pyrazolyl;$X^-=ClO_4^-$), as a white solid, which was dissolved in 75 mL of ethanol/isopropanol (2:1), heated with charcoal, filtered, and concentrated. The resulting residue was dissolved in 25 mL of water, filtered, and the filtrate was concentrated in vacuo to yield a white solid. The above white solid was purified by chromatography on silica (E/PAW) and the residue was dissolved in water, filtered, and the filtrate was concentrated in vacuo to afford the purified perchlorate salt, m.p. 178°–180° C.

EXAMPLE 64

(a)

To a cooled (−78° C.) solution of 46.3 g (0.3 mol) of 1-(1-pyrrolidinomethyl)pyrazole in anhydrous THF (1 L) was added n-butyllithium (2.5M, 123 mL, 0.3 mol), and the mixture was stirred at −78° C. for 1.5 h. To the above mixture was added DMPU and stirred at −78° C. for 20 min, and then N-methyl-N-methoxy-urethane (79 g, 0.612 mol) in 150 mL of THF, and the mixture was allowed to warm to room temperature and stirred overnight. The above mixture was quenched with 200 mL of water and stirred. The aqueous layer was extracted with ethyl acetate (2×100 mL), and the organic layer was dried over sodium sulfate, and concentrated in vacuo. The residue was dissolved in 500 mL of dioxane/ether (2:1), diluted with 300 mL of 6N HCl and stirred under nitrogen for 20 h. The layers were separated, the organic layer was washed with brine, and the aqueous layer was extracted with THF/ether (5×400 mL). The combined organic layer was dried over sodium sulfate and concentrated to afford 45 g of a mixture that contained 25% (by NMR) of 1,1-di-(5-pyrazolyl)-ketone.

(b)

To a suspension of 3.7 g (0.15 mol) of NaH in DMF at 0° C. was added 11.25 g (0.07 mol) of 1,1-di-(5-pyrazolyl)-ketone, and the mixture was allowed to warm to room temperature and stirred for 1 h. To the above mixture was added p-methoxybenzyl chloride (24 g, 0.15 mol) in 25 mL of DMF and the mixture was stirred at room temperature under nitrogen for 20 h. The mixture was concentrated in vacuo, and the residue was purified by chromatography on silica (hexane/ethanol) to afford 6.2 g (22%) of 1-[1-p-methoxybenzyl)-pyrazol-3-yl]-1-[(1-p-methoxybenzyl)-pyrazol-5-yl)-ketone and 18 g (63.9%) of 1,1-di-[(1-p-methoxybenzyl)-pyrazol-3-yl]-ketone.

(c)

To a suspension of potassium t-butoxide (7 g, 0.062 mol) in 650 mL of THF at 0° C. was added methyl triphenylphosphonium bromide (22.3 g; 0.062 mol) under nitrogen and the mixture was stirred at room temperature for 1.5 h. To the above mixture was added 1,1-di-[(1-p-methoxybenzyl)-pyrazol-3-yl)-ketone in 200 mL of THF and the mixture was stirred at room temperature under nitrogen for 30 min. The above mixture was quenched with 15 mL of saturated ammonium chloride solution, and 700 mL of ether was added with stirring. The organic layer was dried over sodium sulfate, concentrated in vacuo, and the residue was purified by chromatography on silica (ether/hexane 1:1) to afford 14.9 g (89.7%) of 1,1-di-[(1-p-methoxybenzyl)-pyrazol-3-yl)ethylene (Formula III: $R^3=R^4=H; R^5=R^6=1$-p-methoxybenzyl-3-pyrazolyl).

(d)

A reaction mixture containing benzo[b]quinolizinium perchlorate (9.5 g; 6.8 mmol) and 1,1-di-[(1-p-methoxybenzyl)-pyrazol-3-yl)ethylene (14.9 g; 0.034 mol) in 300 mL of nitromethane was refluxed for 16 h under nitrogen. The reaction mixture was concentrated in vacuo, the residue was triturated with 400 mL of methanol, and the solid was filtered, and dried (60° C.) to afford 22.1 g (85.6%) of 6,11-ethano-12,12-di-[(1-p-methoxybenzyl) pyrazol-3-yl)]-6,11-dihydrobenzo[b]quinolizinium perchlorate (Formula I: $R^1=R^2=R^3=R^4=R^7=H$ ; $R^5=R^6=1$-p-methoxybenzyl-3-pyrazolyl;$X^-=ClO_4^-$), as a solid.

(e)

A solution of 5.6 g (8.2 mmol) of 6,11-ethano-12,12-1, 1-di-[(1-p-methoxybenzyl)-pyrazol-3-yl)]-6,11-dihydrobenzo[b]quinolizinium perchlorate in 200 mL of trifluoroacetic acid was refluxed under nitrogen for 36 h and then stirred at room temperature overnight. The reaction mixture was concentrated in vacuo, the residue was triturated with ethyl acetate, and the solid product was filtered. The resulting solid dissolved in hot methanol/acetonitrile (3:1) was treated with activated charcoal, filtered, and the filtrate was concentrated in vacuo to afford 2.6 g (72.2%) of 6,11-ethano-12,12-di-[(pyrazol-5-yl)-6,11-dihydrobenzo[b] quinolizinium perchlorate (Formula I: $R^1=R^2=R^3=R^4=R^7=H; R^5=R^6=5$-pyrazolyl;$X^-=ClO_4^-$), as a solid. The above product was further purified by chromatography on silica (ethyl acetate/PAW, 2:1 and then ethyl acetate/PAW, 1:1) and the resulting solid was triturated with acetonitrile, the solid was filtered and recrystallized from ethyl acetate to yield 2.5 g of 6,11-ethano-12,12-di-[(pyrazol-5-yl)-6,11-dihydrobenzo[b]quinolizinium acetate (Formula I: $R^1=R^2=R^3=R^4=R^7=H$; $R^5=R^6=5$-pyrazolyl;$X^-=OAC$).

(f)

6,11-Ethano-12,12-di-[(pyrazol-5-yl)-6,11-dihydrobenzo [b]quinolizinium acetate was converted to the corresponding chloride salt by passing the acetate salt through Dowex® 1x2-200 (Cl⁻) (200 g) to afford 1.9 g (80.8%) of 11-ethano-12,12-di-[(pyrazol-5-yl)-6,11-dihydrobenzo[b] quinolizinium chloride (Formula I: $R^1=R^2=R^3=R^4=R^7=H; R^5=R^6=5$-pyrazolyl;$X^-=Cl^-$), as a solid.

EXAMPLE 65

(a)

To 300 mL of THF was added with cooling (ice-bath) 300 mL (0.3 mol) of 1M $TiCl_4$ in methylene chloride and the mixture was stirred for 10 min. To the above mixture was added at room temperature 90.5 mL (0.6 mol) of TMEDA, the mixture was stirred for 10 min, and then 44.12 g (0.675 mol) of Zn dust was added with cooling to maintain the mixture at room temperature and stirred for 40 min. To the resulting reaction mixture was added dropwise to a mixture of ethyl 3-furoate (10.5 g, 0.075 mol), 31 g (0.165 mol) of dibromoethane in 200 mL of THF, and the mixture was stirred at room temperature for 2.5 h. After adding 90 mL of aqueous potassium carbonate solution, the mixture was concentrated in vacuo, the residue was diluted with 20 g of basic alumina, passed through a basic alumina column (ether/YEA 200:1), and the eluent was concentrated. The residue was triturated in ether (200 mL), filtered, and the filtrate was distilled (80-95° C./25 mm) to afford 6.2 g (54.3%) of 1-(3-furyl)-1-ethoxy-2- methylethylene (Formula I/I: $R^3=CH_3;R^4=H$; $R^6=CH_3CH_2O;R^5=3$-Furyl; and Formula III: $R^3=H;R^4=CH_3;R^6=3$-Furyl; $R^5=CH_3H_2O$).

(b)

A reaction mixture containing benzo[b]quinnolizinium hexafluorophosphate (10.98 g; 35 mmol) and 1-(3-furyl)-1-ethoxy-2-methylethylene (6 g; 0.039 mol) in 100 mL of nitromethane was heated at 60°–100° C. for 2 h, cooled, and filtered. The reaction mixture was concentrated in vacuo, the residue was triturated in ether and decanted. The brown solid was dried, ground to powder, and treated with activated charcoal in hot ethyl acetate. The above mixture was filtered through celite, and concentrated to afford 6,11-ethanol-12-(3-furyl)-12-ethoxy-13-methyl-6,11-dihydrobenzo[b] quinolizinium hexafluorophosphate, as a brown solid [2.1:1:4.04 mixture geometries].

(c)

The mixture of Example 65(b) was subjected to fractional saturation (5x) in hot isopropanol to yield hot isopropanol insoluble 6,11-ethano-12-(3-furyl)-12-ethoxy-13-methyl-6, 11-dihydrobenzo[b]quinolizinium hexafluorophosphate, (Formula I: $R^1=R^2=R^4=R^7=H;R^3=CH_3;R^5=3$-Furyl; $R^6=CH_3CH_2O;X^-=PF_6^-$) as a single geometric isomer, m.p. 195°–197° C.

EXAMPLE 66

(a)

To a solution of furan-3-carboxylic acid (36 g, 0.32 mol) in 250 mL of toluene was added 49 mL (0.385 mol) of oxalyl chloride and 1 drop of pyridine and the mixture was heated at 80°–90° C. for 1.5 h. The mixture was cooled to room temperature, N,O-dimethylhydroxylamine hydrochloride (35 g, 0.36 mol), 4-dimethylaminopyridine (DMAP, 1.8 g, 0.0147 mol), and 600 mL of methylene chloride were added. The mixture was cooled to 0° C., 68.4 g of pyridine was added slowly, the mixture was allowed to warm to room temperature and stirred for 2 h. The mixture was filtered, and the filtrate was washed with water, 5% aqueous dimethylaminopropylamine, water, 6 N HCl solution, water, and brine. The organic layer was dried and concentrated in vacuo, and the residue was distilled (b.p. 85°–87° C./0.2 mm) to afford 44 g (88.7%) of 3-(N-methyl-N-methoxycarbamoyl)furan.

(b)

To a solution of n-butyllithium (2.5M, 28 mL, 0.07 mol) in 150 mL of ether at −78° C. was added a solution of 3-bromofuran (10 g, 0.0628 mol) in 30 mL of ether over a 20 min period and the mixture was stirred at −78° C. for 20 min. To the above mixture was added 3-(N-methyl-N-methoxycarbamoyl)furan (9.16 g, 0.059 mol) in 30 mL of ether over a 15 min period and the mixture was stirred at room temperature for ½ h. The reaction mixture was quenched with 200 mL of ammonium chloride solution, 500 mL of methylene chloride was added and the mixture was stirred. The organic layer was dried over sodium sulfate, concentrated in vacuo, and the residue was triturated with 100 mL of hexane/TBME (9:1). The solid product was filtered and washed with TBME to afford 7.5 g (78.3%) of di-(3-furyl)ketone.

(c)

A suspension of methyl triphenylphosphonium bromide (145 g; 0.405 mol, dried at 60° C.) in 1 L of ether was added at −20° C. n-butyllithium in hexane (2.5 M, 162 mL; 0.405 mol) and the mixture was allowed to stir at room temperature for 1 h. To the above mixture was added 60 g (0.37 mol) of 1,1-di(3-furyl)ketone in 450 mL of DME/THF/DMPU (2:2:0.5) in 10 minutes and the mixture was stirred at room temperature for 1 h. To the above reaction mixture was added saturated ammonium chloride solution (250 mL), and the mixture was diluted with 500 mL of water. The organic layer was separated, washed with water (2×500 mL), dried, and concentrated in vacuo. The residue was purified by chromatography on silica (hexane, then 10% ether/hexane) to afford 51 g (86%) of 1,1-di(3-furyl)ethylene (Formula III: $R^3=R^4=H$; $R^5=R^6$=3-Furanyl). This product was further distilled (b.p. 60°–63° C./0.01 mm).

(d)

To a mixture of 14 g (0.1 mol) of m-methoxybenzyl alcohol in 300 mL of ether cooled to −40° C. was added 12.8 mL (0.2 mol) of 2.5M n-butyllithium over a 30 min period and the reaction mixture was slowly (removing a bath) warmed to room temperature and stirred for 30 minutes. To the above mixture 11.77 g (0.1 mol) of TMEDA was added. The above reaction mixture was cooled to −20° C., 16.05 g (0.15 mol) of 2-pyridinecarboxaldehyde was added to the mixture, and the resulting reaction mixture was allowed to warm to room temperature with stirring. After 1 hour, ammonium chloride solution was added to the mixture. The diol was extracted with ethyl acetate, dried over sodium sulfate, and the solvent was removed in vacuo. The residue was triturated in ether, filtered and the solid was washed with ether to afford 14.6 g (58%) of 2-[1-hydroxy-(2'-methoxy-6'-hydroxymethyl)-benzyl]pyridine (Formula X: $R^1=R^2$=H;$R^7$=2'-OCH$_3$).

(e)

To a stirred POCl$_3$ (75 mL) was added slowly 14.6 g (0.059 mol) of 2-[1-hydroxy-(2'-methoxy-6'-hydroxymethyl)benzyl]-pyridine and the reaction mixture was heated on a steam-bath for 2 h and cooled. The above mixture was poured into ice-water and stirred for ½ h. Sodium perchlorate (excess) was added to the above mixture, the solid precipitate was filtered and washed with water. The solid product was recrystallized from acetonitrile to afford 4 g of 10-methoxy-benzo[b]quinolizinium perchlorate (Formula II: $R^1=R^2$=H;$R^7$=10-OCH$_3$; $X^-$=ClO$_4^-$).

(f)

A mixture of 3.1 g (0.01 mol)) of 10-methoxybenzo[b]quinolizinium perchlorate and 2.4 g (0.01 mol) of 1,1-di-(3-furyl)ethylene in 75 mL of acetonitrile was allowed to reflux for 18 h. The mixture was cooled, filtered, and the filtrate was concentrated in vacuo. The residue was triturated in ether, and filtered to yield 4.6 g of a crude product. This solid was purified by chromatography on silica (methylene chloride/ethyl acetate/methanol, 7:2:1) to afford 4.1 g (87.4%) of 6,11-ethano-12,12-di-(3-furyl)-10-methoxy-6, 11-dihydrobenzo[b]quinolizinium perchlorate. (Formula I: $R^1=R^2=R^3=R^4$=H; $R^5=R^6$=3-Furyl;$R^7$=10-OCH$_3$;$X^-$= ClO$_4^-$) as a solid.

(g)

6,11-Ethano-12,12-di-(3-furyl)-10-methoxy-6,11-dihydrobenzo [b]-quinolizinium perchlorate (4.1 g; 8.73 mmol) was converted to the corresponding chloride by passing the salt through Dowex® 1x2-200 (Cl$^-$) to afford 3.4 g (96 %) of 6,11-ethano-12,12-di(3-furanyl)-10-methoxy-6, 11-dihydrobenzo[b]quinolizinium chloride (Formula I: $R^1=R^2=R^3=R^4$=H;$R^5=R^6$=3-Furyl; $R^7$=10-OCH$_3$;$X^-$=Cl$^-$).

EXAMPLE 67

(a)

To a cooled (−78° C.) 1 L ether solution containing 25 g (0.105 mol) of 2,6-dibromopyridine was added n-butyllithium (2.5 M, 42 mL, 0.105 mol) over a 20 min period, and the mixture was stirred at −78° C. for ½ h. To the above mixture was added at −78° C. N-methyl-N-methoxyurethane (6.6 g, 0.049 mol) in 50 mL of ether and the mixture was stirred at −78° C. for 1 h, and was allowed to warm to room temperature and stirred for 3 h. The above mixture was quenched with 100 mL of saturated ammonium chloride solution and stirred overnight. The organic layer was dried over sodium sulfate, concentrated in vacuo, and the residue was triturated with ether, filtered, and the solid residue was dried to afford 11 g (65.47%) of 1,1-di[(6-bromo)-2-pyridyl]ketone. This solid product was recrystallized from ethyl acetate to yield 8.2 g of the ketone.

(b)

To 200 mL of methanol was added in portions 2.3 g (0.1 mol) of sodium and the mixture was stirred under nitrogen for 2 h. 1,1-di[(6-bromo)-2-pyridyl]ketone (8 g, 0.024 mol) was added to the above mixture, and the reaction mixture was refluxed under nitrogen for 24 h. An additional 2 g of sodium methoxide was added to the mixture and refluxed for 48 h, and cooled. The mixture was diluted with ether, washed with saturated ammonium chloride solution, and the organic layer was dried over sodium sulfate, and concentrated in vacuo. The residue was purified by chromatography on silica (ether hexane, 2:8) to afford 2.5 g (42.7%) of 1,1-di(6-methoxypyridin-2-yl)methanol. In addition, 100 mg of 1,1-di(6-methoxypyridin-2-yl)ketone was also isolated from the chromatographic fractions.

(c)

To a solution of 10.2 g (0.13 mol) of pyridine in 500 mL of methylene chloride at 0° C. was added CrO$_3$ (6.5 g, 0.011 mol) in portions, and the mixture was stirred at 0° C. for 1 h. To the above mixture was added 1,1-di(6-methoxypyridin-2-yl)methanol (2.5 g, 0.011 mol) in 50 mL of methylene chloride and the mixture was stirred for 2 h at room temperature. The reaction mixture was diluted with ethyl acetate, filtered through celite, and the filtrate was concentrated in vacuo to afford 1.65 g (66%) of 1,1-di(6-methoxypyridin-2-yl)ketone.

(d)

To a suspension of 1.25 g (0.011 mol) of potassium t-butoxide in 30 mL of THF at 0° C. was added methyl triphenylphosphonium bromide (3.57 g; 0.01 mol) and the mixture was stirred at room temperature for 1 h. To the above mixture was added 1,1-di(6-methoxypyridin-2-yl) ketone (1.6 g, 0.0657 mol) in 30 mL of THF and the mixture was stirred for 30 min at room temperature under nitrogen. The above mixture was quenched with saturated ammonium chloride solution, diluted with ether, filtered, the aqueous layer was extracted with ether, and the combined organic layer was filtered. The above filtrate was concentrated in vacuo, and the residue was chromatographed on silica (hexane/ether, 8:2) to afford 0.94 g (59.4%) of 1,1-di(6-methoxypyridin-2-yl)ethylene (Formula III: $R^3=R^4=H;R^5=R^6=6-OCH_3-2-Pyridyl$).

(e)

A mixture of 1 g (3.5 mmol) of benzo[b]quinolizinium perchlorate and 0.94 g (3.8 mmol) of 1,1-di(6-methoxypyridin-2-yl)ethylene in 30 mL of nitromethane was allowed to reflux under nitrogen for 16 h. The mixture was cooled, and concentrated in vacuo. The residue was dissolved in 200 mL of boiling methanol/acetonitrile (5:1) containing activated charcoal, filtered, and the filtrate was concentrated in vacuo. The residue was triturated with methanol, filtered and the solid residue was washed with ether and dried to afford 1.6 g (87.4%) of 6,11-ethano-12,12-di-(6-methoxypyridin-2-yl)-6,11-dihydrobenzo[b]quinolizinium perchlorate (Formula I: $R^1=R^2=R^3=R^4=R^7=H; R^5=R^6=6-OCH_3-2-Pyridyl; X^-=ClO_4^-$).

(f)

A solution of 6,11-ethano-12,12-di-(6-methoxypyridin-2-yl)-6,11-dihydrobenzo[b]quinolizinium perchlorate (0.26 g, 0.5 mmol) in 10 mL of 48% HBr was stirred under nitrogen at room temperature for 2 h, and then heated at 90° C. for 4 h, and cooled to room temperature. The mixture was concentrated in vacuo, the residue was treated with boiling methanol containing activated charcoal, filtered, and the filtrate was concentrated in vacuo. The residue was triturated with acetonitrile, filtered, and the solid product was washed with ethyl acetate, ether, and dried (73° C.) in vacuo to afford 0.22 g (91.6%) of 6,11-ethanol-12,12-di-(2-oxo-dihydropyridin-6-yl)-6,11-dihydrobenzoro]quinolizinium perchlorate (Formula I: $R^1=R^2=R^3=R^4=R^7=H;R^5=R^6=2-oxo-6-dihydropyridyl; X^-=ClO_4^-$).

(g)

6,11-Ethano-12,12-di-(2-oxo-dihydropyridin-6-yl)-6,11-dihydrobenzo[b]quinolizinium perchlorate (1.3 g) was converted to the corresponding chloride by passing the salt through Dowex® 1x2-200 (Cl⁻) to afford 1.1 g (93.2%) of 6,11-ethano-12,12-di-(2-oxo-dihydropyridin-6-yl)-6,11-dihydrobenzorb]quinolizinium chloride (Formula I: $R^1=R^2=R^3=R^4=R^7=H;R^5=R^6=2-oxo-6-dihydropyridyl; X^-=Cl^-$).

EXAMPLE 68

(a)

A mixture of 5 g (0.016 mol) of 10-methoxybenzo[b] quinolizinium perchlorate in 15 mL of 48 % HBr was refluxed with stirring for 18 h, cooled to room temperature, the resulting mixture was filtered, and the solid residue was washed with cold water to afford 4.3 g of a solid product. The above solid was redissolved in warm water and treated with excess sodium perchlorate, the resulting solid was filtered, washed with cold water and dried to afford 3.4 g (71%) of 10-hydroxybenzo[b]quinolizinium perchlorate (Formula II: $R^1=R^2=H;R^7=10-OH ; X^-=ClO_4^-$).

(b)

A mixture of 3.4 g (0.011 mol) of 10-hydroxybenzo[b] quinolizinium perchlorate and 2.72 g (0.017 mol) of 1,1-di (3-furyl)ethylene in 75 mL of acetonitrile was refluxed for 3 h, cooled to room temperature, and the resulting mixture was concentrated in vacuo. The above residue was triturated in ether, filtered, and the solid was washed with ether to afford 5.4 g of 6,11-ethano-12,12-di(3-furyl)-10-hydroxy-6,11-dihydrobenzo[b]quinolizinium perchlorate (Formula I: $R^1=R^2=R^3=R^4=H;R^5=R^6=3-Furyl;R^7=10-OH;X^-=ClO_4^-$) as a solid.

(c)

6,11-Ethano-12,12-di (3-furyl)-10-hydroxy-6,11-dihydrobenzo[b]-quinolizinium perchlorate (5.3 g, 11.63 mmol) was converted to the corresponding chloride salt by passing the above salt through Dowex® 1x2-200 after placing the salt in acetonitrile. The chloride residue obtained was triturated in water, filtered through celite, and dried in vacuo to afford 3.2 g (94.5%) of 6,11-ethano-12,12-di(3-furyl)-10-hydroxy-6,11-dihydrobenzo[b]quinolizinium chloride (Formula I: $R^1=R^2=R^3=R^4=H;R^5=R^6=3-Furyl;R^7=10-OH; X^-=Cl^-$) as a solid.

EXAMPLE 69

(a)

A mixture of 19.97 g (0.0768 mol) of benzo[b] quinolizinium bromide and 15.67 g (0.0768 mol) of 4,5,6,7-tetrahydro-7-(3-furyl)-benzofuran-7-ol in 50 mL of ethanol was heated to reflux for 4.5 h, filtered while hot, and the residue was washed with 10 mL of ethanol to yield 14.25 g, after recrystallization from water, of 6.11[[5',4']-4'-(3-furyl)-4,5,6,7-tetrahydrobenzofuryl]benzo[b]quinolizinium bromide (as a mixture of regioisomers), as a white solid.

(b)

Sodium borohydride (6 g) was added to a cold (0° C.) stirring mixture of 12.2 g (0.0275 mol) of 6,11[[5',4']-4'-(3-furyl)-4,5,6,7-tetrahydrobenzofuryl]benzo[b]quinolizinium bromide (regioisomers) in 150 mL of methanol containing 3 g of sodium bicarbonate and the mixture was stirred for 4.5 h. The mixture was concentrated in vacuo, and the residue was partitioned between 200 mL of water and 200 mL of methylene chloride. The aqueous layer was extracted with 200 mL of methylene chloride, the combined organic layer was washed with 50 mL of water, and concentrated in vacuo to yield 10.5 g of a solid. The solid product was triturated in 30 mL of methylene chloride (insoluble=2.63 g), filtered, and the filtrate was chromatographed on silica (1.8 L of Hexane/methylene chloride, 4:5) to yield 2.5 g of 6,11[[5', 4']-4'-(3-furyl)-4,5,6,7-tetrahydrobenzofuryl]-1,4,5,6,11, 11a-hexahydrobenzo[b]quinolizine bromide (pure isomer A), m.p. 177°–178° C. The 2nd regioisomer was eluted with ethyl acetate/methylene chloride (2 L) to afford 3 g of 6,11[[5',4']-4'-(3-furyl)-4,5,6,7-tetrahydrobenzofuryl]-1,4,5, 6,11,11a-hexahydrobenzo[b]quinolizine bromide (pure isomer B), m.p. 200° C.(d).

(c)

A mixture of 370 mg of 6,11[[5',4']-4'-(3-furyl)-4,5,6,7-tetrahydrobenzofuryl]-1,4,5,6,11,11a-hexahydrobenzo[b] quinolizine bromide (pure regioisomer A), 400 mg of mereuric acetate in 25 mL of 10% acetic acid in water was stirred and heated at 100° C. for 1 h. The mixture was filtered hot, the residue was washed with 10 mL of water, and the filtrate was treated with excess sodium perchlorate. The solid product was filtered, and the solid was dissolved in methylene chloride and passed through a silica gel column to yield (from the 2nd fraction) 40 mg of 6,11[[5',4']-4'-(3-furyl)-4,5,6,7-tetrahydrobenzofuryl]-6,11-dihydrobenzo[b] quinolizinium perchlorate (Formula I: $R^1=R^2=R^4=R^7=H$;

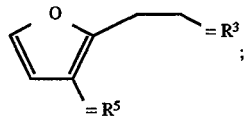

$R^6$=3-Furanyl;$X^-=ClO_4^-$). (Note that reaction yield rose to 57.5% when 2.2 eq of Hg(OAc)$_2$ was used).

EXAMPLE 70

(a)

To a suspension of 3.5 g (0.139 mol) of sodium hydride in 120 mL of DMF at 0° C. was added 8 g (0.115 mol) of 1,2,3-triazole in 50 mL of DMF dropwise, and the mixture was allowed to warm to room temperature and stirred for 1 h. The above mixture was cooled to 0° C., and 21.8 g (0.139 mol) of p-methoxybenzyl chloride was added, and the mixture was allowed to warm to room temperature and stirred for 20 h. The reaction mixture was concentrated in vacuo and the residue was purified by chromatography on silica (hexane/ethyl acetate) to afford 14 g (64.5%) of 1-(p-methoxybenzyl)-1,2,3-triazole.

(b)

To a cooled (−78° C.) 600 mL of THF solution containing 14 g (0.074 mol) of 1-(p-methoxybenzyl)-1,2,3-triazole was added n-butyllithium (2.5M, 30 mL, 0.07 mol) dropwise over a 15 min period, and the mixture was stirred at −78° C. for 2 h. The mixture was stirred at −78° C. for 1.5 h, and N-methyl-N-methoxy-urethane (4.5 g, 0.033 mol) in 25 mL of THF was added and the mixture was stirred at −78° C. for 1h, and was allowed to warm to room temperature and stirred for 2 h under nitrogen. The above mixture was quenched with saturated ammonium chloride solution and the layers were separated. The organic layer was dried over sodium sulfate, concentrated in vacuo, and the residue was triturated with ether and filtered to afford 10.4 g of 1,1-di[5-(1-p-methoxybenzyl)-1,2,3-triazolyl]ketone. The ether filtrate was purified by chromatography on silica to afford an additional 0.9 g of the above ketone.

(c)

To a suspension of methyl triphenylphosphonium bromide (14.5 g; 0.04 mol) in 300 mL of THF was added under nitrogen at −5° C. 2.5M n-butyllithium (16.2 mL, 0.04 mol) and the mixture was stirred for 1 h. To the above mixture was added 1,1-di[5-(1-p-methoxybenzyl)-1,2,3-triazolyl]ketone (10.9 g, 0.027 mol) in 100 mL of THF and the mixture was stirred for 2 h at room temperature under nitrogen. The above mixture was quenched with 10 mL of acetone, and 200 mL of ether was added and the mixture was stirred overnight. The mixture was concentrated in vacuo, and the residue was partitioned between water and methylene chloride with stirring. The mixture was filtered, the organic filter was concentrated in vacuo, and the residue was purified by chromatography on silica to afford 1.2 g (11%) of 1,1-di[5-(1-p-methoxybenzyl)-1,2,3-triazolyl]-ethylene (Formula III: $R^3=R^4=H;R^5=R^6$=1-p-methoxybenzyl-5-(1,2,3-triazoyl).

(d)

A reaction mixture containing benzo[b]quinolizinium hexafluorophosphate (0.82 g; 2.6 mmol) and 1,1-di[5-(1-p-methoxybenzyl)-1,2,3-triazolyl]-ethylene (1.27 g; 3.16 mmol) in 25 mL of nitromethane in a sealed wheaton vial was heated at 130° C. for 20 h under nitrogen. The reaction mixture was concentrated in vacuo, the residue was dissolved in boiling methanol/acetonitrile containing activated charcoal, filtered, and the filtrate was concentrated in vacuo to yield a residue. The above residue was purified by chromatography on silica (methylene dichloride/ethyl acetate/methanol) to yield a brown foam. The brown foam was dissolved in 100 mL of boiling acetonitrile/methanol (1:1) containing activated charcoal, filtered, and concentrated in vacuo. The residue was triturated with 30 mL of isopropanol/methanol (3:1), filtered, and the solid product was washed with ether and dried to afford 720 mg (38.9%) of 6,11-ethano-12,12-di[5-(1-p-methoxybenzyl)-1,2,3-triazolyl]6,11-dihydrobenzo[b]quinolizinium hexafluorophosphate (Formula I: $R^1=R^2=R^3=R^4=R^7=H;R^5=R^6$=1-p-methoxybenzyl-5-(1,2,3-triazolyl); $X^-=PF_6^-$), as a solid.

(e)

A solution of 680 mg (0.95 mmol) of 6,11-ethano-12,12-di[5-(1-p-methoxybenzyl)-1,2,3-triazolyl]5-6,11-dihydrobenzo[b]quinolizinium hexafluorophosphate in 25 mL of trifluoroacetic acid was refluxed under nitrogen for 16 h. After adding 10 mL of methanol, the mixture was concentrated in vacuo, the residue was triturated with ethyl acetate, and the solid product was filtered. The solid product was treated with 100 mL of boiling isopropanol/methanol/acetonitrile (1:1:1) and charcoal, filtered, and the filtrated was concentrated in vacuo to afford 320 mg (71.1%) of 6,11-ethano-12,12-di-(5-1,2,3-triazolyl)6,11-dihydrobenzo[b]quinolizinium hexafluorophosphate (Formula I: $R^1=R^2=R^3=R^4=R^7=H;R^5=R^6$=5-(1,2,3-triazolyl);$X^-=PF_6^-$), as a solid.

(f)

6,11-Ethano-12,12-di-(5-1,2,3-triazolyl)6,11-dihydrobenzo[b]quinolizinium hexafluorophosphate (320 mg, 0.66 mmol) was converted to the corresponding chloride salt by passing the above salt through Dowex® 1x2-200 (Cl$^-$) to afford 150 mg (60%) of 6,11-ethano-12,12-di-(5-1,2,3-triazolyl)6,11-dihydrobenzo[b]quinolizinium chloride (Formula I: $R^1=R^2=R^3=R^4=R^7=H$; $R^5=R^6$=5-(1,2,3-triazolyl);$X^-=Cl^-$), as a solid.

EXAMPLE 71

(a)

To a solution of 1-triisoproylsilyl-pyrrole (13.2 g, 0.059 mol) in 250 mL of THF at −78° C. was added 10.45 g (0.0587 mol) of N-bromosuccinamide (NBS), and the mixture was stirred at −78° C. for 3 h. The reaction mixture was warmed to room temperature and concentrated in vacuo, and the resulting residue in hexane was stirred overnight. The hexane solution was filtered through alumina eluting with hexane, the eluate was concentrated in vacuo, and the residue was distilled (b.p. 107°–108° C./0.2 mm) to afford 10.4 g (58.4%) of 3-bromo-1-triisopropylsilyl-pyrrole.

(b)

To a solution of 3-bromo-1-triisopropylsilyl-pyrrole (10.4 g, 0.0292 mol) in 150 mL of THF at −78° C. was added n-butyllithium (2.5M, 12.3 mL, 0.031 mol) and the mixture was stirred at −78° C. for ½ h. To the above mixture was added N-methyl,N-methoxy-urethane (1.9 g, 0.014 mol) in 25 mL of THF, the mixture was allowed to warm to room temperature and stirred under nitrogen for 20 h. The mixture was quenched with saturated sodium bicarbonate solution and the layers were separated. The organic layer was dried over sodium sulfate, concentrated in vacuo, and the residue was chromatographed on silica (hexane/ether, 2:1) to afford 4.25 g (64.3%) of 1,1-di[3-(1-triisopropylsilyl)-pyrrolyl]-ketone, as an oil.

(c)

To a solution of 1,1-di[3-(1-triisopropylsilyl)-pyrrolyl]-ketone (1 g, 2.1 mmol) in 30 mL of THF at room temperature was added methylmagnesium bromide in ether (3.0M, 9 mmol) and the mixture was stirred for ½ h. The above reaction mixture was quenched with 2 mL of saturated sodium bicarbonate solution. The reaction mixture was diluted with methylene chloride, stirred, passed through a florisil column, and the filtrate was concentrated in vacuo to afford 1.1 g (100%) of 1,1-di[3-(1-triisopropylsilyl)-pyrrolyl]-ethylene (Formula III: $R^3=R^4=H;R^5=R^6=1$-triisopropylsilyl-3-pyrrolyl).

(d)

A reaction mixture containing benzo[b]quinolizinium perchlorate (0.59 g; 2.11 mmol) and 1,1-di[3-(1-triisopropylsilyl)-pyrrolyl]-ethylene (1.1 g; 2.3 mmol) in 50 mL of nitromethane was refluxed for ½ h under nitrogen. The reaction mixture was concentrated in vacuo, the residue was dissolved in 10 mL of methanol and concentrated in vacuo. The resulting bright yellow solid was triturated with methanol, filtered and washed with ether to afford 1.25 g (79.1%) of 6,11-ethano-12,12-di[3-(1-triisopropylsilyl)-pyrrolyl]-6,11-dihydrobenzo[b]quinolizinium perchlorate (Formula I: $R^1=R^2=R^3=R^4=R^7=H$; $R^5=R^6=1$-triisopropylsilyl-3-pyrroyl;$X^-=ClO_4^-$), as a yellow solid.

(e)

To a solution of 1.22 g (1.62 mmol) of 6,11-ethano-12,12-di[3-(1-triisopropylsilyl)-pyrrolyl]-6,11-dihydrobenzo[b]quinolizinium perchlorate in 50 mL of methylene chloride was added tetrabutylammonium fluoride (2.8 mL, 3.08 mmol) and the mixture was stirred at room temperature under nitrogen for 15 min. The solid precipitate was filtered, washed with methylene chloride, ether, acetonitrile, methylene chloride, and hexane and dried in vacuo at 50° C. to afford 0.65 g of 6,11-ethano-12,12-di(3-pyrrolyl)-6,11-dihydrobenzo[b]quinolizinium perchlorate (Formula I: $R^1=R^2=R^3=R^4=R^7=H;R^5=R^6=3$-pyrrolyl; $X^-=ClO_4^-$) as a solid.

(f)

6,11-ethano-12,12-di(3-pyrrolyl)-6,11-dihydrobenzo[b]quinolizinium perchlorate (600 mg, 1.5 mmol) was convened to the corresponding chloride salt by passing the above salt through Dowex® 1x2-200 (Cl⁻) to afford 350 mg (69%) of 6,11-ethano-12,12-di(3-pyrrolyl) -6,11-dihydrobenzo[b]quinolizinium chloride (Formula I: $R^1=R^2=R^3=R^4=R^7=H;R^5=R^6=3$-pyrrolyl;$X^-=Cl^-$), as a solid.

EXAMPLE 72

(a)

To 3-furaldehyde (25.0 g, 0.26 mol) in THF (250 mL) at 78° C. was added ethynylmagnesium bromide (572 mL, 0.286, 0.5M THF) at the rate of 10 mL per min. The mixture was slowly warmed to room temperature, stirred for 1 h and then poured into a cooled ammonium chloride solution. The mixture was extracted with ethyl acetate, and the organic layer was dried over $Na_2SO_4$ and concentrated in vacuo. The residue was distilled at 50°–55° C. and 0.24 mm Hg to afford 1-(3-furyl)-1-hydroxy-2-propyne.

(b)

To a mixture of 1-(3-furyl)-1-hydroxy-2-propane (20.0 g, 0.163 mol), hexane (200 mL) and THF (25 mL) was added tetrabutylammonium bromide (1.05 g, 0.0032 mol), 50% NaOH (150 mL) and then diethylsulfate (30.0g, 0.195 mol) at 0° C. The mixture was stirred for 3 h at room temperature, poured into ice, and extracted with ethyl acetate. The combined organic layers were washed with brine, dried over $Na_2SO_4$ and concentrated in vacuo. The residue was distilled at 70°–84° C. and (10 mm Hg) to afford 1-(3-furyl-1-ethoxy-2-propyne.

(c)

To a mixture of benzo[b]quinolizinium hexafluorophosphate (1.69 g, 0.0055 mol), 1-(3-furyl)-1-ethoxy-2-propyne (1.0 g, 0.0066 mol) and THF (25 mL) was added potassium t-butoxide (0.06 g, 0.00055 mol) (forms 1-(3-furyl)-1-ethoxyallene in situ). The mixture was heated to reflux for 10 min, additional potassium t-butoxide (0.06 g) was added and the mixture was refluxed for 1 h. Nitromethane (5.0 mL) was added and the mixture was refluxed for another 1 h, cooled and the solvent was removed in vacuo. Ether was added to the residue, the mixture was cooled to 0° C. and the solid thus formed was collected by filtration. The solid was dissolved in ethyl acetate (150 mL), heated to reflux, cooled to room temperature and filtered to remove recovered starting material (0.42 g). The filtrate was concentrated in vacuo and the residue was purified by column chromatography on silica eluting with 10% methanol/$CH_2Cl_2$. The purified product was recrystallized from hot isopropanol (3x) to afford 0.173 g of 12-(3-furyl)-12-ethoxy-13-methylidene-6-,11-ethano-6,11-dihydrobenzo[b]quinolizinium hexafluorophosphate. (Formula I: $R^1=R^2=R^7=H;R^5=OC_2H^5;R^6=3$-furyl;$R^3$ and $R^4$ together=methylidene; $X^-=PF_6^-$), as a single geometric isomer.

EXAMPLE 73

To a solution of 6.5 g (23.6 mmol) of 10-hydroxybenzo[b]quinolizinium bromide in 400 mL of methylene chloride/pyridine (1:1) was added 100 mg of DMAP and 50 mL of acetic anhydride and the resulting reaction mixture was stirred under argon at room temperature for 2 h. The reaction mixture was concentrated in vacuo. The residue was suspended in 2:1 10%$NaClO_4$/$CH_2Cl_2$ (300 mL) and sonicated. The solid was collected by filtration to afford 4.3 g (55.9%) of 10-acetoxybenzo[b]quinolizinium perchlorate.

The above 10-acetoxybenzo[b]quinolizinium perchlorate (3.3 g) was dissolved in 500 mL of water, the solution was boiled, and filtered. To the filtrate was added 100 mL of 30% sodium perchlorate solution and the mixture was chilled. The precipitated solid was isolated by filtration and dried in vacuo to afford 1.9 g of 10-acetoxybenzo[b]quinolizinium perchlorate (Formula II: $R^1=R^2=H$; $R^7=10$-OAc; $X^-=ClO_4^-$). The filtrate was extracted with methylene chloride (3×100 mL), the organic layer was dried and concentrated to yield an additional 0.32 g of the desired acetate perchlorate.

EXAMPLE 74

(a)

A mixture of 9.4 g (60 mmol) of o-methoxybenzyl chloride and 2-(1,3-dioxolan-2-yl)pyridine in sulfolane (6 mL) was heated at 80° C. for 5 h, cooled to room temperature, and was allowed to stand overnight. The mixture was poured into 100 mL of ethyl acetate and the reaction mixture was stirred for 30 min. A gummy precipitate was isolated by decanting ethyl acetate and triturated with ethyl acetate (2x). The gummy product was dissolved in 100 mL of water, filtered, and treated with 150 mL of hot aqueous potassium hexafluorophosphate solution. The solid salt was isolated by filtration, washed successively with hot water and ether, and dried to afford 7.4 g (29.6%) of 1-(o-methoxylbenzyl-2(1,3-dioxolan-2-yl)pyridinium hexafluorophosphate (Formula VIII: $R^1=R^2=H$; $R^7=2'-OCH_3;X^-=PF_6^-$).

(b)

To 50 g of polyphosphoric acid heated to 95° C. in an oil-bath was added with stirring 5 g (12 mmol) of 1-(o-methoxybenzyl)-2(1,3-dioxolan-2-yl)pyridinium hexafluorophosphate and the resulting reaction mixture was heated at this temperature with stirring under nitrogen for 5 h. The mixture was cooled to 40° C., and 125 mL of water was added followed by an additional 125 mL of water. The resulting mixture was cooled to room temperature, potassium hexafluorophosphate (5 g, 27 mmol) was added, the precipitated solid was isolated by filtration, and the desired salt was washed successively with water and ether and then dried to afford 3.2 g (74.9 g) of 7-methoxybenzo[b]quinolizinium hexafluorophosphate (Formula II: $R^1=R^2=H$; $R^7=7-OCH_3$; $X^-=PF^-_6$).

EXAMPLE 75

(a)

Following a procedure similar to that described in Example 45, parts a–d, it is contemplated that there can be prepared 9-trichloromethylbenzo[b]quinolizinium hexafluorophosphate from p-trichloromethylbenzoyl chloride.

(b)

Following a procedure similar to that described in Example 77, parts a–b, it is contemplated that there can be prepared 4-bromobenzo[b]quinolizinium perchlorate from o-bromobenzyl alcohol, and 6-bromo-2-pyridine carboxyaldehyde.

EXAMPLE 76

(a)

A mixture of 47.6 g (0.289 mol) of p-chlorobenzyl chloride and 45 g (0.298 mol) of 2-(1,3-dioxolan-2-yl)-pyridine in 30 mL of sulfolane was heated on a steam bath for 4 hr. After adding an additional 4 g of p-chlorobenzyl chloride, the reaction mixture was heated on a steam bath for 12 h and poured into 300 mL of ethyl acetate. Ethyl acetate was decanted, and an additional 200 mL of ethyl acetate was added to the residue with stirring (20 min) and decanted to remove excess 2-(1,3-dioxolan-2-yl)-pyridine and p-chlorobenzyl chloride. The ethyl acetate wash was repeated and then the brown residue was washed with 300 mL of ether to afford 92 g of 1-(p-chlorobenzyl)-2-(1,3-dioxolan-2-yl)-pyridinium chloride (Formula VI: $R^1=R^2=H;R^7=4-Cl;Z^-=Cl^-$).

(b)

A mixture of 1-(p-chlorobenzyl-2-(1,3-dioxolan-2-yl)-pyridinium chloride and 300 mL of 48% HBr was heated at 100° C. for 24 h, cooled, concentrated in vacuo, and poured into 50 g of ice. The resulting tan solid was filtered to afford 7.9 g of 9-chlorobenzo[b]quinolizinium chloride (Formula II: $R^1=R^2=H;R^7=9-Cl;X^-=Cl^-$).

The aqueous layer was treated with sodium perchlorate solution in water and the resulting solid was cooled and filtered to afford 7.9 g (9%) of 9-chlorobenzo[b]quinolizinium perchlorate (Formula II: $R^1=R^2=H;R^7=9-Cl$; $X^-=ClO_4^-$).

EXAMPLE 77

(a)

To a mixture of 28.3 g (0.15 mol) of o-bromobenzyl alcohol in 1 L of ether cooled to −20° C. was added in portions 32.5 mL (0.32 mol) of n-butyllithium (10M) in hexane over a 20 min period and the reaction mixture was stirred 1 h.

The above reaction mixture was cooled to −20° C., 19.9 g (0.165 mol) of 6-methyl-2-pyridinecarboxaldehyde was added to the mixture, and the resulting reaction mixture was allowed to warm to room temperature. After 1 h, saturated ammonium chloride solution was added to the mixture. The diol was extracted with ethyl acetate, washed with brine, the ethyl acetate phase was dried over sodium sulfate, and the solvent was removed in vacuo to afford 21.9 g (70.5%) of 2-[1-hydroxy-(2'-hydroxymethyl3-benzyl]-6-methyl-pyridine (Formula X: $R^1=6-CH_3;R^2=R^7=H$).

(b)

To a mixture of 10.34 g (0.05 mol) of 2-[1-hydroxy-(2'-hydroxymethyl)-benzyl]-6-methyl-pyridine in 200 mL of benzene heated to 80° C. was added in one portion 50 g (0.176) of trifluoromethanesulfonic anhydride, and the reaction mixture was allowed to react at 60° C. for 10 min, and then allowed to cool to room temperature. The reaction mixture was concentrated in vacuo and the residue was purified by chomatography on silica eluting with 9% methanol/chloroform to yield a pale yellow solid. This solid was dissolved in water and reacted with excess sodium perchlorate. The solid product was filtered, washed with water, and dried to afford 5.54 g (combined yield 37%) of 4-methylbenzo[b]quinolizinium perchlorate (Formula II: $R^1=4-CH_3;R^2=R^7=H$; $X^-=ClO_4^-$), as a yellow solid, m.p. 160°–165° C.

EXAMPLE 78

To 8.22 g (0.0316 mol) of benzo[b]quinolizinium bromide was added with cooling in an ice-bath 24.4 mL (0.474 mol) of bromine and the reaction mixture was allowed to stand at room temperature 24 h. The reaction mixture was poured into ethyl acetate, refrigerated at −15° C. for 24 h, and the resulting solid was filtered. The solid product was washed with ethyl acetate, dissolved in boiling methanol/acetone (1:1), refluxed for 15 min, and the solution was concentrated in vacuo to yield a white solid. The solid was stirred at room temperature with 400 mL of water and sodium acetate for 24 h and filtered. The red filtrate was treated with sodium perchlorate (15 g) and a resulting yellow solid was filtered. The solid product was dissolved in methylene chloride/ethyl 30 acetate (1:1) and the methylene chloride was distilled (½ of the original volume) in vacuo. The reaction mixture was cooled and the solid product was filtered to afford 3.6 g (32.3%) of 10-bromobenzo[b]quinolizinium perchlorate (Formula II: $R^1=R^2=H;R^7=10\text{-Br};X^-=ClO_4^-$), m.p. 112°–115° C.

EXAMPLE 79

(a)

To a mixture of 15.0 g (0.098 mol) of 3,4-methylenedioxybenzyl alcohol in 250 mL of ether cooled to −20° C. was added in portions 21.1 mL (0.211 mol) of n-butyllithium (10M) in hexane over 10 min period, and the reaction mixture was allowed to warm to room temperature and stirred 1 h. The above reaction mixture was cooled to −20° C., 11.18 mL (0.117 mol) of 2-pyridinecarboxaldehyde was added to the mixture, and the resulting reaction mixture was allowed to warm to room temperature. Ammonium chloride solution (70 mL) was added to the mixture and the mixture was extracted with methylene chloride (3×150 mL). The organic layer was washed with brine, dried over sodium sulfate, and concentrated. The diol was purified by chomatography on silica eluting with ethyl acetate/hexane (9:1). The diol was triturated with ether and filtered to afforded 8.8 g (34.7%) of 2-[1-hydroxy-6'-hydroxymethyl-2',3'-methylenedioxy)benzyl]-pyridine (Formula X: $R^1=R^2=H; R^7=2',3'(\text{—OCH}_2\text{O—})$), as a white solid, m.p. 98°–101° C.

(b)

To a mixture of 2 g (0.0077 mol) of 2-[1-hydroxy-(6'-hydroxymethyl-2',3'-methylenedioxy)benzyl]pyridine in 80 mL of benzene heated to 50° C. was added in one portion 7.64 g (0.027 mol) of trifluoromethanesulfonic anhydride, and the mixture was allowed to cool to room temperature and stirred for 30 min. The reaction mixture was concentrated in vacuo and the residue was purified by chomatography on silica eluting with 10% methanol/methylene chloride to yield a red solid. This solid was dissolved in water to react with the excess sodium perchlorate. The solid product was filtered, washed with water, and dried to afford 0.069 g (2.4%) of 9,10-methylenedioxybenzo[b]quinolizinium perchlorate (Formula II: $R^1=R^2=H; R^7=2',3'(\text{—OCH}_2\text{O}^-);X^-=\text{-ClO}_4^-$), as an orange solid, m.p. 220°–224° C.

EXAMPLE 80

(a)

To a mixture of 3.59 g (0.019 mol) of o-bromobenzyl alcohol in 100 mL of ether cooled to −20° C. was added in portions 4.1 mL (0.0412 mol) of n-butyllithium (10M) in hexane over a 6 min period, and the reaction mixture was stirred 20 min. The above reaction mixture was cooled to −20° C., 3 g (0.021 mol) of 3-methoxy-pyridine-2-carboxaldehyde in 5 mL of THF was added in one portion to the mixture, and the resulting reaction mixture was allowed to warm to room temperature and stirred for 20 min. Ammonium chloride solution (30 mL) was added to the mixture and the mixture was extracted with ethyl acetate (3×50 mL). The organic layer was washed with brine, dried over sodium sulfate, and concentrated. The diol was triturated with 100 mL of ether, filtered, and purified by chomatography on silica eluting with 4 % methanol/hexane The solvent was concentrated in vacuo to afford 0.68 g (14.5%) of 2-[1-hydroxy-(2'-hydroxymethyl)benzyl]-3-methoxypyridine (Formula X: $R^1=3\text{-OCH}_3; R^2=R^7=H$), as a white solid, m.p.138°–140° C.

(b)

To a mixture of 0.61 g (0.00248 mol) of 2-[1-hydroxy-(2'-hydroxymethyl)-benzyl]-3-methoxypyridine in 50 mL of benzene heated to 50° C. was added in one portion 2.11 g (0.0074 mol) of trifluoromethanesulfonic anhydride, and the mixture was allowed to cool to room temperature and stirred for 30 min. The reaction mixture was concentrated in vacuo and the residue was purified by chomatography on silica eluting with 5% methanol/methylene chloride and 10% methanol/methylene chloride. The second fraction was concentrated in vacuo, the residue was dissolved in hot water (20 mL), heated to reflux, and reacted with the excess sodium perchlorate. The solid product was filtered, washed with water, and dried to afford 0.27 g (18.2%) of 1-methoxybenzo[b]quinolizinium perchlorate (Formula II: $R^1=1\text{-OCH}_3; R^2=R^7=H; X^-=ClO_4^-$), as a yellow solid, m.p. 143°–145° C.

EXAMPLE 81

(a)

A mixture of 2-(1,3-dioxolan-2-yl)-pyridine (48.7g; 0.322 mol) and p-bromobenzyl-bromide (80.52 g; 0.322 mol) in 60 mL of sulfolane was heated on a steam-bath (after 1 h a red precipitate forms) for 3 h. After cooling, 300 mL of ethyl acetate was added to the mixture, sonicated for 30 min, filtered, and the solid was dried to yield 110 g (85.2%) of 1-(p-bromobenzyl)-2-(1,3-dioxolan-2-yl)pyridinium bromide (Formula VI: $R^1=R^2=H;R^7=4\text{-Br};Z^-=Br^-$).

(b)

A mixture of 55 g (0.137 mol) of 1-(p-bromobenzyl)-2-(1,3-dioxolan-2-yl)pyridinium bromide and 300 g of 48% HBr was heated to 100° C. for 24 h and then cooled. The reaction mixture was poured into 250 g of ice and the resulting yellow precipitate was filtered and dried in vacuo (at 45° C.) to afford 32.85 g (70.8%) of 9-bromobenzo[b]quinolizinium bromide (Formula II: $R^1=R^2=H;R^7=9\text{-Br};X^-=Br^-$).

EXAMPLE 82

(a)

A mixture of 2-(1,3-dioxolan-2-yl) pyridine (36.4 g, 0.24 mol), 4-nitrobenzylbromide (51.84 g, 0.24 mol) and sulfolane (50 mL) was heated on a steam bath for 10 h. The mixture was cooled, ethyl acetate (300 mL) was added and the mixture was heated to 60° C. A precipitate formed which was collected by filtration to afford 1-(p-nitrobenzyl-2-1,3-dioxolan-2-yl) pyridinium bromide (Formula VI: $R^1=R^2=H;R^7\text{-}4\text{-NO}_2; Z^-=Br$)

(b)

To a mixture of polyphosphoric acid (250 mL) and methanesulfonic acid (55 mL) heated to 100° C. with stirring was added 71 g (0.193 mol) of 1-(p-nitrobenzyl)-2-(2'-1',3'-dioxolane)pyridinium bromide and the resuking mixture was heated to 110° C. for 4 h and cooled. The reaction mixture was poured into 500 g of ice, activated charcoal was added to the mixture, filtered, and sodium perchlorate solution added. The mixture was extracted with methylene chloride (2×500 mL), and the organic layer was concentrated to afford 5.2 g (8.3 %) of 9-nitrobenzo[b]quinolizinium perchlorate (Formula II: $R^1=R^2=H;\text{-}R^7=9\text{-NO}_2; X^-=ClO_4^-$), as a brown solid.

EXAMPLE 83

(a)

To a mixture of 12.49 g (0.0621 mol) of o-bromo-m-methylbenzyl alcohol in 400 mL of ether cooled to −20° C. was added in portions 13.3 mL (0.1335 mol) of n-butyllithium (10M) in hexane over a 20 min period, and the reaction mixture was allowed to warm to room temperature and stirred 1 h. The above reaction mixture was cooled to −20° C., 14.63 g (0.136 mol) of pyridine-2-carboxaldehyde in 50 mL of ether was added to the mixture over an 1 h period (the mixture turns purple), and the resulting reaction mixture was allowed to warm to room temperature and stirred for 1 h. Ammonium chloride solution (100 mL) and 200 mL of ethyl acetate were added to the mixture with stirring, and the mixture was extracted with ethyl acetate (2×200 mL). The combined organic layer was washed with brine, dried over sodium sulfate, and concentrated. The diol was triturated with 100 mL of ether, filtered, and the solid product was washed with hexane (yield: 6.6 g; 46%) to afford 2-[1-hydroxy-(2'-hydroxymethyl-6'-methyl)-benzyl]-pyridine (Formula X: $R^1=R^2=H$; $R^7=6'-CH_3$), as a pale yellow solid, m.p. 129°–132° C.

(b)

To a mixture of 3 g (0.013 mol) of 2-[1-hydroxy-(2'-hydroxymethyl-6'-methyl)-benzyl]-pyridine in 100 mL of benzene heated to 40° C. was added in one portion 12.96 g (0.0458 mol) of trifluoromethanesulfonic anhydride, and the mixture was allowed to cool to room temperature and stirred for 30 min. The reaction mixture was concentrated in vacuo and the residue (a red oil) was purified by chomatography on silica eluting with 9% methanol/methylene chloride. The eluate was concentrated in vacuo, the residue was dissolved in water (60 mL), heated to reflux, and reacted with 3 g of sodium perchlorate with stirring. The yellow solid product was filtered, washed with water, and dried to afford 0.926 g (24.4%) of 10-methylbenzo[b]quinolizinium perchlorate (Formula II: $R^1=R^2=H$;$R^7=10-CH_3$;$X^-=ClO_4^-$), as a pale yellow solid, mp 163°–166° C.

EXAMPLE 84

(a)

To a mixture of 10 g (0.059 mol) of 2,5-dimethoxybenzyl alcohol in 250 mL of ether cooled to −20° C. was added in portions 12.75 mL (0.127 mol) of n-butyllithium (10M) in hexane over a 10 min period, and the reaction mixture was allowed to warm to room temperature and stirred 1 h. The above reaction mixture was cooled to −20° C., 7.58 g (0.07 mol) of pyridine-2-carboxaldehyde was added to the mixture, and the resulting reaction mixture was allowed to warm to room temperature (a brown precipitate formed) and stirred for 1 h. Ammonium chloride solution (60 mL) was added, the mixture was extracted with ethyl acetate, the combined organic layer was washed with brine, dried over sodium sulfate, and concentrated. The diol was purified by chomatography on silica eluting with ethyl acetate/hexane (9:1) to afford 1.7 g (10.5%) of 2-[(2',5'-dimethoxy-6'-hydroxymethyl)benzyl]pyridine (Formula X: $R^1=R^2=H$;$R^7=$ 2',5'-$(OCH_3)_2$), as a white solid, m.p. 102°–104° C.

(b)

To a mixture of 1.25 g (0.045 mol) of 2-[(2',5'-dimethoxy-6'-hydroxymethyl)-benzyl]pyridine in 60 mL of benzene heated to 50° C. was added in one portion 4.5 g (0.0159 mol) of trifluoromethanesulfonic anhydride, and the mixture was allowed to cool to room temperature and stirred for 30 min. The reaction mixture was concentrated in vacuo and the residue (an oil) was purified by chomatography on silica eluting with 10% methanol/methylene chloride. The eluate was concentrated in vacuo, the residue was dissolved in water (30 mL), heated to reflux, and reacted with excess sodium perchlorate with stirring and then cooled (using ultrasound and ice). The orange solid product was filtered, washed with water (4 mL), and dried in vacuo to afford 0.42 g (27.6%) of 7,10-dimethoxybenzo[b]quinolizinium perchlorate (Formula II: $R^1=R^2=H$;$R^7=7,10-(OCH_3)_2$; $X^-=ClO_4^-$), as an orange solid, m.p.235°–240° C.

EXAMPLE 85

A mixture of 3-methoxybenzylchloride (5.0 g, 0.032 mol) and 2-(1,3-dioxolan-2-yl)pyridine (5.0 g, 0.032 mol) was stirred at room temperature for 5 days, then at reflux for 1 day. HCl (50 mL) was added and the mixture was heated for 3 more days. The mixture was cooled, the solvent was removed in vacuo and the residue was diluted with water and treated with $KPF_6$ (7.0 g) in water. A precipitate formed, which was collected by filtration. The solid product was purified by column chomatography on silica eluting with acetonitrile/$CH_2Cl_2$ (⅓), followed by slurrying the product in hot methanol and then collecting the product by filtration to afford 1.0 g of 8-methoxybenzol[b]quinolizinium hexafluorophosphate (Formula II: $R^1=R^2=H$;$R^7=8-OCH_3$; $X^-=PF_6^-$). Following procedures similar to those described in Example 42, parts a–b, but substituting an appropriately substituted 5- or 6-membered monocyclic aromatic heterocyclic halide, or 5- or 6-membered monocyclic nonaromatic heterocyclic halide, or 9- or 10-membered bicyclic aromatic heterocyclic halide for 3-bromopyridine in part a, it is comtemplated that the following olefins of Formula III, illustrated in Table 1 can be prepared.

TABLE 1
| Example Number | R³ | R⁴ | R⁵ | R⁶ |
|---|---|---|---|---|
| 86 | H | H | 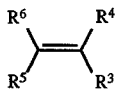 | 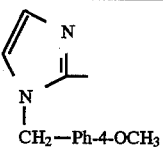 |
| 87 | H | H | 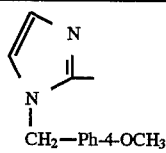 | 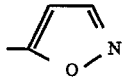 |
| 88 | H | H | 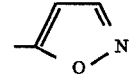 | 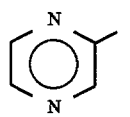 |
| 89 | H | H | 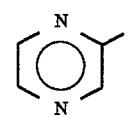 | 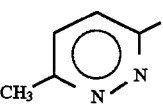 |
| 90 | H | H | 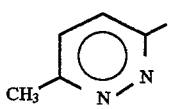 | 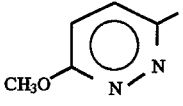 |
| 91 | H | H | 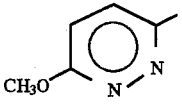 | 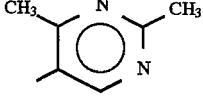 |
| 92 | H | H | 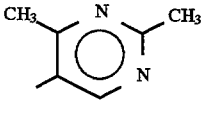 | 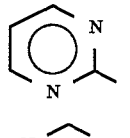 |
| 93 | H | H | 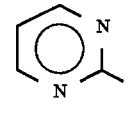 | 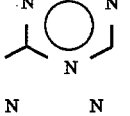 |
| 94 | H | H | 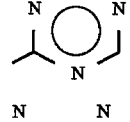 | 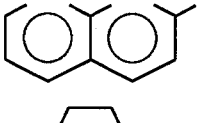 |
| 95 | H | H |  | 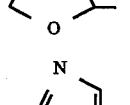 |
| 96 | H | H | 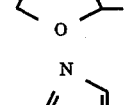 | 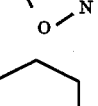 |
| 97 | H | H | 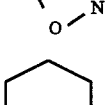 | 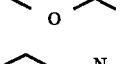 |
| 98 | H | H | 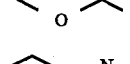 | 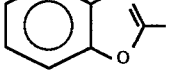 |

TABLE 1-continued
III
| Example Number | R³ | R⁴ | R⁵ | R⁶ |
|---|---|---|---|---|
| 99 | H | H | 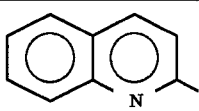 | 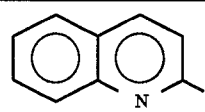 |
| 100 | H | H | 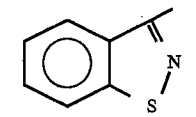 | 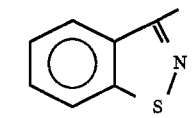 |
| 101 | H | H | 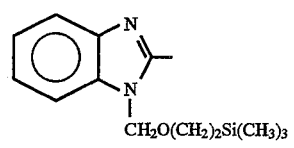<br>CH₂O(CH₂)₂Si(CH₃)₃ | 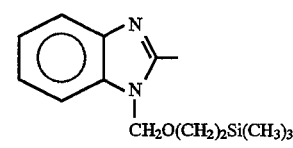<br>CH₂O(CH₂)₂Si(CH₃)₃ |
| 102 | H | H | 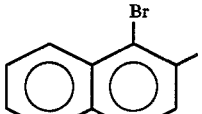 | 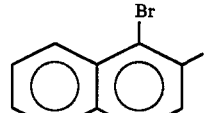 |
| 103 | H | H | 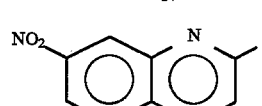 | 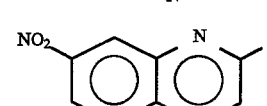 |
| 104 | H | H | 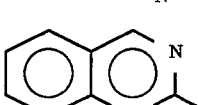 | 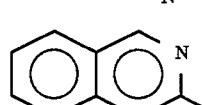 |
| 105 | H | H | 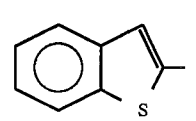 | 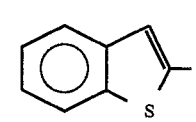 |
| 106 | H | H | 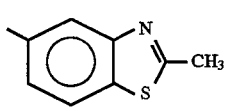 | 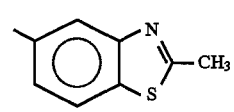 |
| 107 | H | H | 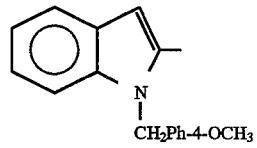<br>CH₂Ph-4-OCH₃ | 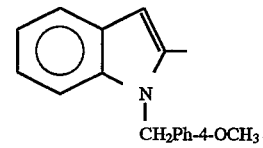<br>CH₂Ph-4-OCH₃ |
| 107a | H | H | 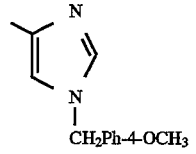<br>CH₂Ph-4-OCH₃ | 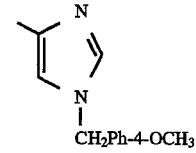<br>CH₂Ph-4-OCH₃ |
| 107b | H | H | 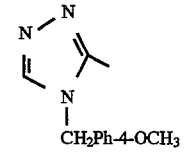<br>CH₂Ph-4-OCH₃ | 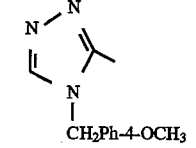<br>CH₂Ph-4-OCH₃ |

TABLE 1-continued

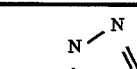

| Example Number | R³ | R⁴ | R⁵ | R⁶ |
|---|---|---|---|---|
| 107c | H | H | 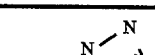 | 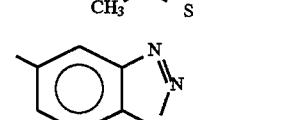 |
| 107d | H | H | 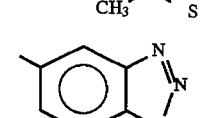 | 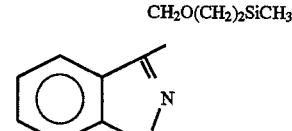 |
| 107e | H | H | 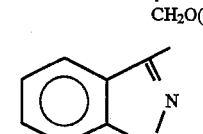 | |

EXAMPLES 108 a–b

Following procedures similar to those described in Example 64, parts b, and c, but substituting an appropriate halide for p-methoxybenzylchloride in part b, it is contemplated that there can be prepared the following olefins of the Formula III.

(a)

1,1-Di[1-(methyl)-3-pyrazolyl]ethylene (Formula III: $R^3=R^4=H$; $R^5=R^6=$-1-methyl-3-pyrazolyl)

(b)

1,1-Di[1-(benzyl)-3-pyrazolyl]ethylene (Formula III: $R^3=R^4=H$; $R^5=R^6=$1-benzyl-3-pyrazolyl)

EXAMPLES 109 a–b

Following procedures similar to those described in Example 70, parts a, b, and c, but substituting an appropriate halide for p-methoxybenzylchloride in part a, it is contemplated that there can be prepared the following olefins of the Formula III.

(a)

1,1-Di[1(4-methylbenzyl)-5-(1,2,3-triazolyl)]ethylene (Formula III: $R^3=R^4=H$; $R^5=R^6=$1-(4-methylbenzyl)-5-(1,2,3-triazolyl))

(b)

1,1-Di[1(4-chlorobenzyl)-5-(1,2,3-triazolyl)]ethylene (Formula III: $R^3=R^4=H$; $R^5=R^6=$1-(4-chlorobenzyl)-5-(1,2,3-triazolyl))

EXAMPLES 110 a–b

Following procedures similar to those described in Example 46, part a, but substituting an appropriately substituted benzophenone derivative for 3,3'-bis(trifluoromethyl)benzophenone, it is contemplated that the following olefins of the Formula III can be prepared.

(a)

1,1-Di(3-trichloromethylphenyl)ethylene (Formula III: $R^3=R^4=H$; $R^5=R^6=$3-trichloromethylphenyl)

1,1-Di(3-hydroxyphenyl)ethylene (Formula III: $R^3=R^4=$H; $R^5=R^6=$3-hydroxyphenyl)

EXAMPLE 111 (a–b)

Following procedures similar to those described hereinabove, or by utilizing procedures which are known in the art, the following known compounds (Examples 111 (a)–(b)) were prepared and, unexpectedly, they were found to bind to the PCP receptor and are thus useful in the treatment or prevention of neurodegenerative disorders or neurotoxic injuries.

(a)

6,11-Ethano-12,12-diphenyl-6,11-dihydrobenzo[b]quinolizinium perchlorate.

6,11-Ethano-12-phenyl-12-(4-morpholinyl)-6,11-dihydrobenzo[b]quinolizinium perchlorate.

Following procedures similar to those described in Example 42 (c), but substituting an appropriately substituted olefin of the Formula III for 1,1-di(3-pyridyl)ethylene and an appropriately substituted benzo[b]quinolizinium salt of the Formula II for benzo[b]quinolizinium perchlorate it is contemplated that the following compounds of the Formula I illustrated in Table 2 can be prepared.

TABLE 2
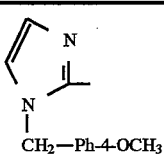
| Example Number | R¹ | R² | R³ | R⁵ | R⁴ | R⁶ | R⁷ | X⁻ |
|---|---|---|---|---|---|---|---|---|
| 112 | H | H | H | 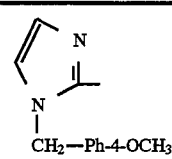 | H | 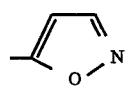 | 10-OC(O)CH₃ | ClO₄⁻ |
| 113 | H | H | H | 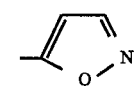 | H | 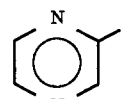 | 7-OCH₃ | PF₆⁻ |
| 114 | H | H | H | 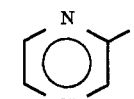 | H | 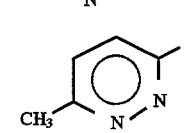 | 9-CCl₃ | PF₆⁻ |
| 115 | 4-Br | H | H | 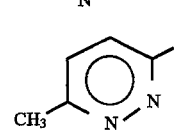 | H | 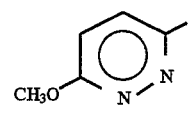 | H | ClO₄⁻ |
| 116 | H | H | H | 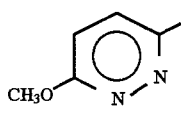 | H | 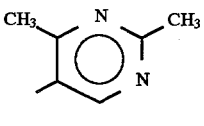 | 9-Cl | Cl⁻ |
| 117 | 4-CH₃ | H | H | 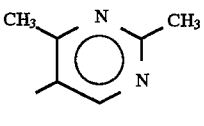 | H | 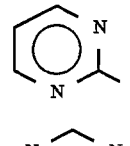 | H | ClO₄⁻ |
| 118 | H | H | H | 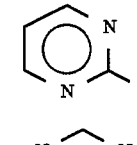 | H | 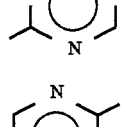 | 10-Br | ClO₄⁻ |
| 119 | H | H | H | 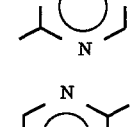 | H | 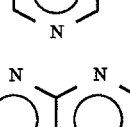 | 9,10-OCH₂O⁻ | ClO₄⁻ |
| 120 | 1-OCH₃ | H | H | 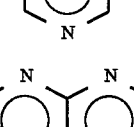 | H |  | H | ClO₄⁻ |
| 121 | H | H | H | 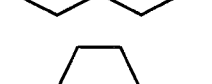 | H | 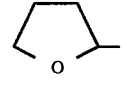 | 9-Br | Br⁻ |
| 122 | H | H | H | 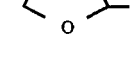 | H | 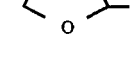 | 9-NO₂ | ClO₄⁻ |

TABLE 2-continued

I

| Example Number | R¹ | R² | R³ | R⁵ | R⁴ | R⁶ | R⁷ | X⁻ |
|---|---|---|---|---|---|---|---|---|
| 123 | H | H | H | 3-methyl-1,2,4-oxadiazol-5-yl | H | 3-methyl-1,2,4-oxadiazol-5-yl | 10-CH₃ | ClO₄⁻ |
| 124 | H | H | H | tetrahydropyran-2-yl | H | tetrahydropyran-2-yl | 7,10-(OCH₃)₂ | ClO₄⁻ |
| 125 | H | H | H | benzoxazol-2-yl | H | benzoxazol-2-yl | 8-OCH₃ | PF₆⁻ |
| 126 | H | H | H | quinolin-2-yl | H | quinolin-2-yl | 10-OC(O)CH₃ | ClO₄⁻ |
| 127 | H | H | H | benzisothiazol-3-yl | H | benzisothiazol-3-yl | 9-CCl₃ | PF₆⁻ |
| 128 | 4-Br | H | H | 1-(CH₂O(CH₂)₂Si(CH₃)₃)-benzimidazol-2-yl | H | 1-(CH₂O(CH₂)₂Si(CH₃)₃)-benzimidazol-2-yl | H | ClO₄⁻ |
| 129 | 4-CH₃ | H | H | 3-bromoquinolin-4-yl | H | 3-bromoquinolin-4-yl | H | ClO₄⁻ |
| 130 | H | H | H | 6-nitroquinoxalin-2-yl | H | 6-nitroquinoxalin-2-yl | 9,10-OCH₂O⁻ | ClO₄⁻ |
| 131 | 1-OCH₃ | H | H | quinazolin-2-yl | H | quinazolin-2-yl | H | ClO₄⁻ |
| 132 | H | H | H | benzothiophen-2-yl | H | benzothiophen-2-yl | 9-NO₂ | ClO₄⁻ |
| 133 | H | H | H | 2-methyl-5-methylbenzothiazol-? | H | 2-methyl-5-methylbenzothiazol-? | 10-CH₃ | ClO₄⁻ |

TABLE 2-continued

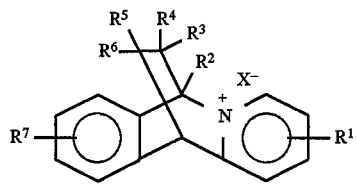

| Example Number | R¹ | R² | R³ | R⁵ | R⁴ | R⁶ | R⁷ | X⁻ |
|---|---|---|---|---|---|---|---|---|
| 134 | H | H | H | 2-(1-(CH₂Ph-4-OCH₃)-indolyl) | H | 2-(1-(CH₂Ph-4-OCH₃)-indolyl) | 7,10-(OCH₃)₂ | ClO₄⁻ |
| 135[a] | H | H | H | 2-(1H-pyrazolyl) | H | 2-(1H-pyrazolyl) | 10-OC(O)CH₃ | ClO₄⁻ |
| 136[b] | 4-Br | H | H | 2-(1H-benzimidazolyl) | H | 2-(1H-benzimidazolyl) | H | ClO₄⁻ |
| 137[c] | H | H | H | 2-(1H-indolyl) | H | 2-(1H-indolyl) | 7,10-(OCH₃)₂ | ClO₄⁻ |
| 138 | 4-Br | H | H | 3-HO-Ph | H | 3-HO-Ph | H | ClO₄⁻ |
| 139 | 4-CH₃ | H | H | 3-CCl₃-Ph | H | 3-CCl₃-Ph | H | ClO₄⁻ |
| 140 | 1-OCH₃ | H | H | 3-(1-CH₃-pyrazolyl) | H | 3-(1-CH₃-pyrazolyl) | H | ClO₄⁻ |
| 141 | 4-Br | H | H | 3-(1-CH₂Ph-pyrazolyl) | H | 3-(1-CH₂Ph-pyrazolyl) | H | ClO₄⁻ |
| 142 | 4-CH₃ | H | H | 5-methyl-1-(CH₂Ph-4-Cl)-triazolyl | H | 5-methyl-1-(CH₂Ph-4-Cl)-triazolyl | H | ClO₄⁻ |
| 143 | 1-OCH₃ | H | H | 5-methyl-1-(CH₂Ph-4-CH₃)-triazolyl | H | 5-methyl-1-(CH₂Ph-4-CH₃)-triazolyl | H | ClO₄⁻ |

TABLE 2-continued

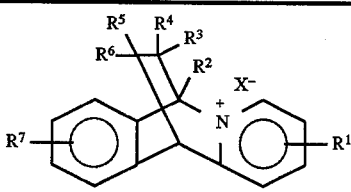

| Example Number | R¹ | R² | R³ | R⁵ | R⁴ | R⁶ | R⁷ | X⁻ |
|---|---|---|---|---|---|---|---|---|
| 144 | H | H | H | imidazolyl-CH₂Ph-4-OCH₃ | H | imidazolyl-CH₂Ph-4-OCH₃ | H | Br⁻ |
| 145 | H | H | H | triazolyl-CH₂Ph-4-OCH₃ | H | triazolyl-CH₂Ph-4-OCH₃ | H | Br⁻ |
| 146 | H | H | H | CH₃-thiadiazolyl | H | CH₃-thiadiazolyl | H | Br⁻ |
| 147 | H | H | H | methylbenzotriazolyl-CH₂O(CH₂)₂Si(CH₃)₃ | H | methylbenzotriazolyl-CH₂O(CH₂)₂Si(CH₃)₃ | H | Br⁻ |
| 148 | H | H | H | methylindazolyl-CH₂O(CH₂)₂Si(CH₃)₃ | H | methylindazolyl-CH₂O(CH₂)₂Si(CH₃)₃ | H | Br⁻ |
| 149(d) | H | H | H | imidazolyl-NH | H | imidazolyl-NH | H | Br⁻ |
| 150(e) | H | H | H | methyltriazolyl-NH | H | methyltriazolyl-NH | H | Br⁻ |
| 151(f) | H | H | H | methylbenzotriazolyl-NH | H | methylbenzotriazolyl-NH | H | Br⁻ |
| 152(g) | H | H | H | methylindazolyl-NH | H | methylindazolyl-NH | H | Br⁻ |

TABLE 2-continued

| | | | | | R⁵  R⁴  R³ | | | | I |
| | | | | | R⁶⎯⎯⎯R² | | | | |
| | | | | | ⎯⎯⎯⎯⎯ X⁻ | | | | |
| | | | | | ⎯⎯⎯+N⎯⎯⎯ | | | | |
| | | | | | R⁷⎯⎯⎯⎯⎯⎯⎯R¹ | | | | |

| Example Number | R¹ | R² | R³ | R⁵ | R⁴ | R⁶ | R⁷ | X⁻ |
|---|---|---|---|---|---|---|---|---|
| 153 | H | H | H | phenyl | H | phenyl | 10-Br | ClO₄⁻ |

(a)Prepared by treating the compound of Example 112 with trifluoroacetic acid.
(b)Prepared by treating the compound of Example 128 in dichloroethane with trifluoroacetic acid.
(c)Prepared by treating the compound of Example 134 with trifluoroacetic acid.
(d)Prepared by treating the compound of Example 144 with trifluoroacetic acid.
(e)Prepared by treating the compound of Example 145 with trifluoroacetic acid.
(f)Prepared by treating the compound of Example 147 in dichloroethane with trifluoroacetic acid.
(g)Prepared by treating the compound of Example 148 in dichloroethane with trifluoroacetic acid.

EXAMPLE 154

(a), (b), (c), and (d)

It is contemplated that by treatment of 6,11-ethano-12,12-di(3-furyl)-10-hydroxy-6,11-dihydrobenzo[b]quinolizinium chloride of Example 68(c) with heptadecanoyl chloride, propionyl chloride, ethylsuccinyl chloride, or hexadecyl succinyl chloride there can be prepared the following compounds of the Formula I, respectively, (a)

6,11-Ethano-12,12-di(3-furyl)-10-[OC(O)(CH$_2$)$_{15}$CH$_3$]-6,11-dihydrobenzo[b]quinolizinium chloride (Formula I: R$^1$ = R$^2$ = R$^3$ = R$^4$ = H; R$^5$ = R$^6$ = 3-furyl; R$^7$=10-[OC(O)(CH$_2$)$_{15}$CH$_3$];X$^-$=Cl$^-$).

(b)

6,11-Ethano-12,12-di(3-furyl)-10-[OC(O)C$_2$H$_5$]-6,11-dihydrobenzo[b]quinolizinium chloride (Formula I: R$^1$=R$^2$=R$^3$=R$^4$=H;R$^5$=R$^6$=3-furyl;R$^7$=10-[OC(O)C$_2$H$_5$]; X$^-$=Cl$^-$).

(c)

6,11-Ethano-12,12-di(3-furyl)-10-[OC(O)(CH$_2$)2C(O)OC$_2$H$_5$]-6,11-dihydrobenzo[b]quinolizinium chloride (Formula I: R$^1$=R$^2$=R$^3$=R$^4$=H;R$^5$=R$^6$=3-furyl; R$^7$=10-[OC(O)(CH$_2$)$_2$C(O)OC$_2$H$_5$];X$^-$=Cl$^-$).

(d)

6,11-Ethano-12,12-di(3-furyl)-10-[OC(O)(CH$_2$)$_2$C(O)O(CH$_2$)$_{15}$CH$_3$]-6,11-dihydrobenzo[b]quinolizinium chloride (Formula I: R$^1$=R$^2$=R$^3$=R$^4$=H;R$^5$=R$^6$=3-furyl;R$^7$=10-[OC(O)(CH$_2$)$_2$C(O)O(CH$_2$)$_{15}$CH$_3$]; X$^-$=Cl$^-$).

EXAMPLE 155

(a)

Following a procedure similar to that described in Example 82, pans a–b, but substituting 4-cyanobenzyl bromide for 4-nitrobenzyl bromide it is contemplated that there can be prepared 9-cyanobenzo[b]quinolizinium perchlorate (Formula II: R$^1$=R$^2$=H;R$^7$=9-CN;X$^-$=ClO$_4^-$).

(b)

It is contemplated that treatment of 9-cyanobenzo[b]quinolizinium perchlorate with 1,1-diphenylethylene, following a procedure similar to that described in Example 42(c), will afford 9-cyano-6,11-ethano-12,12-diphenyl-6,11-dihydrobenzo[b]quinolizinium perchlorate (Formula I: R$^1$=R$^2$=R$^3$=R$^4$=H; R$^5$=R$^6$=phenyl;R$^7$=9-CN;X$^-$=ClO$_4^-$).

(c)

It is contemplated that the treatment of the compound of Example 155(b) with aqueous sodium hydroxide containing about 6–12% of H$_2$O$_2$ with afford 9-carboxy-6,11-ethano-12,12-diphenyl-6,11-dihydrobenzo[b]quinolizinium perchlorate (Formula I: R$^1$=R$^2$=R$^3$=R$^4$=H;R$^5$=R$^6$=phenyl;R$^7$= 9-CO$_2$H;X$^-$=ClO$_4^-$).

(d) and (e)

It is contemplated that treatment of the compound of Example 155(c) with either propanol or hexadecanol in the presence of dicyclohexylcarbodiimide will afford, respectively, 9-[C(O)Opropyl]-6,11-ethano-12,12-diphenyl-6,11-dihydrobenzo[b]quinolizinium perchlorate (Example 155(d) Formula I: R$^1$=R$^2$=R$^3$=R$^4$=H;R$^5$=R$^6$=phenyl;R$^7$=9-C(O)Opropyl; X$^-$=ClO$_4^-$) and 9-[C(O)O(CH$_3$)$_{15}$CH$_3$]-6,11-ethano-12,12-diphenyl-6,11-dihydrobenzo[b]quinolizinium perchlorate (Example 155(e) Formula I: R$^1$=R$^2$=R$^3$=R$^4$= H;R$^5$=R$^6$=phenyl;R$^7$=9-[C(O)O(CH$_2$)$_{15}$CH$_3$];X$^-$=ClO$_4^-$).

EXAMPLE 156

It is contemplated that treatment of 6,11-ethano-12,12-diphenyl-10-bromo-6,11-dihydrobenzo[b]quinolizinium perchlorate of Example 153 with diethyl phosphite in the presence of a source of Pd(0) will afford 6,11-ethano-12,12-diphenyl-10-[P(O)(OC$_2$H$_5$)$_2$]-6,11-dihydrobenzo[b]quinolizinium perchlorate, which can be hydrolyzed with aqueous hydrochloric acid to afford 6,11-ethano-12,12-diphenyl-10-(PO$_3$H)-6,11-dihydrobenzo[b]quinolizinium perchlorate (Formula I: $R^1=R^2=R^3=R^4=H; R^5=R^6=$ phenyl; $R^7=10$-$PO_3H$ ; $X^-=ClO_4^-$).

EXAMPLE 157

A mixture of 10-($SO_3^-$)-benzo[b]quinolizinium (0.99 g, 3.47 mmol) (prepared as described in Bradsher and Turner, J. Org. Chem. 1965, 31,565–567), acetonitrile (20 mL) and 1,1-di-(3-furyl)ethylene (0.83 g, 5.2 mmol) was refluxed for three days. The solvent was removed in vacuo and the residue was triturated with ether, filtered and washed with ether. The residue was purified by column chromatography on silica eluting with dichloromethane/methanol (8/2) to afford crude product, which was recrystallized from acetonitrite/ethyl acetate, then water to afford 0.58 g (40%) of 10-($SO_3^-$)-6,11-ethane-12,12-di(3-furyl)-6,11-dihydrobenzo[b]quinolizinium Formula I: $R^1=R^2=R^3=R^4=H; R^5=R^6=$3-furyl; $R^7=SO_3^-$), m.p. 300 ° C. (dec).

EXAMPLE 158

(a)

To a cooled (–78° C.) solution of 1-(p-methoxyphenyl) methyl-pyrazole (110 g, 0.582 mol) in 3 L of ether/THF (2:1) was added in portions, 240 ml (0.593 mol) of n-butyllithium (2.5M) over a 1 hour period, and the mixture was stirred at –78° C. for 1.5 h. To the above mixture was added at –78° C. N-methyl-N-methoxy-urethane (37.1 g, 0.28 mol), the mixture was stirred for 1 h at –78° C., then allowed to warm to –10° C. The mixture was quenched with saturated ammonium chloride solution and stirred overnight. The organic layer was dried over sodium sulfate, concentrated in vacuo, and the residue was purified by medium pressure liquid chromatography to afford 48 g (42.8%) of 1,1-di[5-(1-(p-methoxy-phenyl)methylpyrazolyl]ketone.

(b)

A solution of 1,1-di[5-(1-(p-methoxyphenyl) methylpyrazolyl]-ketone (43.6 g, 0.108 mol) in 250 ml of trifluoroacetic acid was refluxed under nitrogen for 16 hours, cooled to room temperature, and concentrated in vacuo. The residue was suspended in methanol/ether (100 ml, 1:3), stirred, and filtered. The filtrate was concentrated in vacuo, the residue was triturated in methylene chloride, filtered, and the solid was washed with hexane to afford 16.4 g (93.7%) of 1,1-di(5-pyrazolyl)ketone.

(c)

To a solution of 1,1-di(5-pyrazolyl)ketone (3.25 g, 0.02 mol) in 100 ml of DMF cooled to 0° C. was added NaH (1.05 g, 44 mmol), the mixture was stirred, and methyl iodide (7.1 g, 0.05 mol) was added with stirring. The resulting mixture was stirred for 20 hours allowing the mixture to warm to room temperature. The reaction mixture was concentrated in vacuo, the residue was dissolved in ethyl acetate, and the organic layer was washed with water and brine. The above organic layer was dried and concentrated in vacuo and the residue was crystallized from ethyl acetate and ethyl acetate/methylene chloride/methanol (6:3:1) to afford 0.8 g (21%) of 1,1-di[3-(1-methylpyrazolyl]ketone.

(d)

To a solution of potassium t-butoxide (0.63 g, 5.9 mmol) in 50 ml of THF cooled at 0° C. was added methyltriphenyl-phosphonium bromide (2.03 g; 5.2 mmol) and the resulting mixture was allowed to warm to room temperature with stirring for 1 hour. To the above mixture was added 1,1-di [3-(1-methylpyrazolyl]ketone (0.72 g, 3.8 mmol) in 30 ml of THF, and the mixture was stirred for 2 hours at room temperature. The above mixture was quenched with saturated ammonium chloride solution, stirred, and filtered through a pad of florisil. The filtrate was concentrated in vacuo and the residue was purified by chromatography on silica (ethyl acetate, ethyl acetate/ether/methanol) to afford 0.6 g (50.7%) of 1,1-di[3-(1-methylpyrazolyl)]ethylene (Formula III: $R^3=R^4=H; R^5=R^6=$

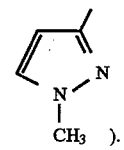

(e)

A reaction mixture containing 4a-azoniaanthracene perchlorate (0.82 g; 2.9 mmol) and 1,1-di[3-(1-methylpyrazolyl)]ethylene (0.6 g; 3.2 mmol) in 50 ml of nitromethane was refluxed for 24 h under nitrogen. The reaction mixture was concentrated in vacuo, the residue was dissolved in acetonitrile/methanol (200 ml, 1:1), treated with activated charcoal, filtered, and the filtrate was concentrated in vacuo. The above residue was triturated in isopropanol/methanol (100 ml, 9:1), filtered, and dried to afford 1.3 g (84.2%) of 6,11-ethano-12,12-di[3-(1-methylpyrazolyl]-6,11-dihydrobenzo[b]-quinolizinium perchlorate (Formula I: $R^1=R^2=R^3=R^4=R^7=H; R^5=R^6=$

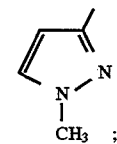

$X^-=ClO_4^-$), as a solid.

(f)

6,11-Ethano-12,12-di[3-(1-methylpyrazolyl)]-6,11-dihydrobenzo[b]quinolizinium perchlorate (1.3 g, 2.8 mmol) in ethanol/(pyridine/acetic acid/water (55/20/25)) was converted to the corresponding chloride by passing the salt through DOWEX® 1x2-200-Cl-(water/acetonitrile, 7.3) to afford 0.84 g (74.3%) of 6,11-ethano-12,12-di[3-(1-methylpyrazolyl)]-6,11-dihydrobenzo[b]quinolizinium chloride (Formula I: $R^1=R^2=R^3=R^4=R^7=H; R^5=R^6=$

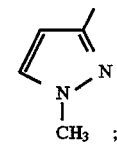

$X^-=Cl^-$), as a solid.

EXAMPLE 159

(a)

To a suspension of 4 g (0.16 mol) of sodium hydride in 200 ml of DMF 20 at 0° C. was added 10 g (0.145 mol) of 1,2,4-triazole in 75 ml of DMF dropwise over a period of 30 minutes, and the mixture was allowed to warm to room temperature and stirred for 1 h. The above mixture was cooled to 0° C., 25 g (0.16 mol) of p-methoxybenzyl chloride was added, the mixture was allowed to warm to room temperature, and stirred for 16 h. The reaction mixture was concentrated in vacuo and the residue was purified by chromatography on silica (hexane/ethyl acetate) to afford 21.9 g (64.5%) of 1-(p-methoxybenzyl)-1,2,4-triazole.

(b)

To a cooled (−78° C.) solution containing 14 g (0.074 mol) of 1-(p-methoxybenzyl)-1,2,4-triazole (21.9 g, 0.115 mol) in 500 ml of THF was added n-butyllithium (2.5M, 46.3 ml, 0.115 mol) dropwise over a 15 min period. The mixture was stirred at −78° C. for 1.5 h. To the mixture was added N-methyl-N-methoxy-urethane (6.95 g, 0.052 mol) in 20 ml of THF and the mixture was stirred at room temperature for 2 h under nitrogen. The above mixture was quenched with saturated ammonium chloride solution and 5 was diluted with 200 ml of ethyl acetate. The two layers were separated. The organic layer was dried over sodium sulfate, concentrated in vacuo, and the residue was triturated in ether, filtered, and washed with hexane to afford 20 g (95.2%) of 1,1-di[5-(1-p-methoxybenzyl)-1,2,4-triazolyl]ketone.

(c)

A solution of 1,1-di[5-(1-p-methoxyphenyl)methyl-1,2,4-triazolyl]ketone (10 g, 0.02 mol) in 150 ml of trifluoroacetic acid was refluxed under nitrogen for 18 hours, cooled to room temperature, and concentrated in vacuo. The residue was suspended in methylene chloride (200 ml), stirred, and filtered. The residue was washed with methylene chloride, ethyl acetate, and ether to afford 5.4 g of 1,1-di[5-(1,2,4-triazolyl)]ketone.

(d)

To a solution of 1,1-di[5-(1,2,4-triazolyl)ketone (5.4 g, 0.032 mol) in 200 ml of DMF cooled to 0° C. was added NaH (1.8 g, 72 mmol), and the mixture was stirred for 2 hours, and p-methoxybenzyl chloride (12.9 g, 0.082 mol) was added with stirring. The resulting mixture was stirred for 98 hours 25 at room temperature. The reaction mixture was filtered through CELITE®, the filtrate was concentrated in vacuo, the residue was dissolved in ethyl acetate, and the organic layer was washed with water and brine. The above organic layer was dried and concentrated in vacuo and the residue was crystallized from ethyl acetate and ethyl acetate/methylene chloride/methanol (6:3:1) to afford 2.5 g of 1.1-di[3-(1-p-methoxybenzyl-1,2,4-triazolyl]ketone.

(e)

To a solution of potassium t-butoxide (0.95 g, 8.4 mmol) in 75 ml of THF at 0° C. was added methyltriphenylphosphonium bromide (2.88 g; 8 mmol) under nitrogen and the mixture was stirred for 1 h at room temperature. To the above mixture was added 1,1-di[3-(1-p-methoxybenzyl)-1,2,4-triazolyl]ketone (2.57 g, 6.2 mol) in 50 ml of THF and the mixture was stirred for 2 h at room temperature under nitrogen. The above mixture was quenched with saturated ammonium chloride solution, filtered through CELITE®, and the filtrate was concentrated in vacuo. The residue was purified by crystallization from ethyl acetate and ethyl acetate/methylene chloride/methanol (6:3:1) to afford 0.9 g (36%) of 1,1-di[3-(1-p-methoxybenzyl)-1,2,4-triazolyl]-ethylene (Formula III: $R^3=R^4=H$; $R^5=R^6=$

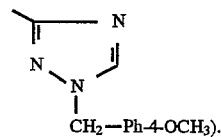
$CH_2-Ph-4-OCH_3$).

(f)

A reaction mixture containing 4a-azoniaanthracene perchlorate (0.61 g; 2.2 mmol) and 1,1-di[3-(1-p-methoxybenzyl)-1,2,4-triazolyl]-ethylene (0.85 g; 2.12 mmol) in 25 ml of nitromethane was refluxed for 20 h under nitrogen. The reaction mixture was concentrated in vacuo, the residue was dissolved in 15 boiling methanol/acetonitrile containing active charcoal, filtered, and the filtrate was concentrated in vacuo to yield a residue. The above residue was purified by chromatography on silica (methylene chloride/ethyl acetate/methanol) to yield a brown foam. The residue was triturated in water, filtered, and the solid was washed with hexane to afford 0.9 g (62%) of 6,11-ethano-12,12-di[3-(1-p-methoxybenzyl)-1,2,4-triazolyl]-6,11-dihydrobenzo[b]quinolizinium perchlorate (Formula I: $R^1=R^2=R^3=R^4=R^7=H$; $R^5=R^6=$

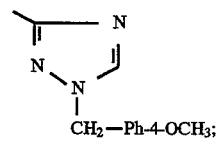
$CH_2-Ph-4-OCH_3$;

$X^-=ClO_4^-$).

(g)

A solution of 700 mg (1.32 mmol) of 6,11-ethano-12,12-di[3-(1-p-methoxybenzyl)-1,2,4-triazolyl]-6,11-dihydrobenzo[b]quinolizinium perchlorate in 50 ml of trifluoroacetic acid was refluxed under nitrogen for 28 h. The mixture was concentrated in vacuo, the residue triturated in 30 methanol, and the solid product filtered. The solid was crystallized from ethanol/PAW (1:1) to afford 170 mg (29.3%) of 6,11-ethano-12,12-di-[3-(1,2,4-triazolyl)]-6,11-dihydrobenzo[b]quinolizinium perchlorate (Formula I: $R^1=R^2=R^3=R^4=R^7=H$; $R^5=R^6=$

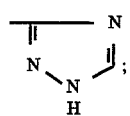

$X^-=ClO_4^-$).

(h)

6,11-Ethano-12,12-di-[3-(1,2,4-triazolyl)]-6,11-dihydrobenzo[b]quinolizinium perchlorate (170 mg) was converted to the corresponding chloride salt by passing the above salt through DOWEX® 1x20-200-Cl⁻ after placing the salt in acetonitrile. The chloride residue obtained was dried in vacuo to afford 90 mg (88.2%) of 6,11-ethano-12,12-di-[3-(1,2,4-triazolyl)]-6,11-dihydrobenzo[b]quinolizinium chloride (Formula I: $R^1=R^2=R^3=R^4=R^7=H$; $R^5=R^6=$

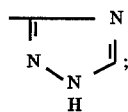

$X^-=Cl^-$), as a solid.

EXAMPLE 160

(a)

To a solution of 1 g (3.9 mmol) of 1,1-di(2-chloropyridin-3-yl)methanol in 25 ml of acetone at −30° C. was added CrO₃ (1.17 g, 0.011 mol) in portions, and the mixture was stirred at room temperature for 2 h. To the above mixture was added 25 ml of isopropanol and saturated sodium bicarbonate solution (100 ml) and the mixture was stirred, filtered through CELITE®, and washed with 200 ml of chloroform. The combined filtrate was washed with brine, the organic layer was dried and concentrated in vacuo to afford 0.81 g (81%) of 1,1-di(2-chloropyridin-3-yl)ketone.

(b)

To 20 ml of methanol was added in portions 0.22 g (9.5 mmol) of sodium and the mixture was stirred under nitrogen for 0.5 h. 1,1-di-(2-chloro)pyridin-3-yl]ketone (0.8 g, 3.16 mmol) in 20 ml of methanol was added to the above mixture, and the reaction mixture was refluxed under nitrogen for 12 h. The mixture was quenched with 2N HCl (1 ml), concentrated in vacuo, and the residue was dissolved in 100 ml of ethyl acetate. The organic layer was washed with water and brine, dried over sodium sulfate, and concentrated in vacuo. The residue was purified by chromatography on silica (ethyl acetate/hexane, 1:1) to afford 0.38 g (49.3%) of 1,1-di(2-methoxypyridin-3-yl)ketone.

(c)

To a suspension of 0.26 g (2.34 mmol) of potassium t-butoxide in 20 ml of THF at 0° C. was added methyltriphenylphosphonium bromide (0.86 g; 2.34 mmol) and the mixture was stirred at room temperature for 1 h. To the above mixture was added 1,1-di(2-methoxypyridin-3-yl)ketone (0.38 g, 1.55 mmol) in 10 ml of THF and the mixture was stirred for 1 h at room temperature under nitrogen. The above mixture was quenched with saturated ammonium chloride solution, diluted with ether, filtered, the aqueous layer was extracted with ether, and the combined organic layer was filtered. The above filtrate was concentrated in vacuo, and the residue was chromatographed on silica (hexane/ethyl acetate, 2:1) to afford 0.38 g of 1,1-di(2-methoxypyridin-3-yl)ethylene (Formula III: $R^3=R^4=H$; $R^5=R^6=$

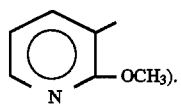

(d)

A mixture of 0.39 g (1.42 mmol)) of 4a-azoniaanthracene perchlorate and 0.38 g (1.55 mmol) of 1,1-di(2-methoxypyridin-3-yl)ethylene in 25 ml of nitromethane was allowed to reflux under nitrogen for 120 h. The mixture was cooled, and concentrated in vacuo. The residue was dissolved in 100 ml of boiling methanol/acetonitrile (5:1) containing active charcoal, filtered, and the filtrate was concentrated in vacuo. The residue was triturated in water, filtered and the solid residue washed with water and ether, and dried to afford 0.13 g (17.5%) of 6,11-ethano-12,12-di-(2-methoxypyridin-3-yl)-6,11-dihydrobenzo[b]quinolizinium perchlorate (Formula I: $R^1=R^2=R^3=R^4=R^7=H$; $R^5=R^6=$

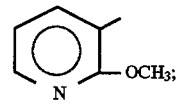

$X^-=ClO_4^-$).

EXAMPLE 161

(a)

To a suspension of NaH (0.072 g, 3 mmol) in 20 ml of DMF cooled to 0° C. under argon was added 1,1-di-(pyrazol-4-yl)ketone (0.23 g, 1.4 mmol) with stirring. p-Methoxybenzyl chloride (0.24 g, 1.5 mmol) was added to the mixture at 0° C. with stirring and the resulting mixture was stirred at room temperature. The reaction mixture was quenched with saturated ammonium chloride solution and the mixture was extracted with ethyl acetate (50 ml). The organic layer was washed with water (3×50ml) and brine (50 ml), dried and concentrated in vacuo to afford 0.4 g of 1,1-di[(1-p-methoxybenzyl)-pyrazol-4-yl]ketone.

(b)

To a solution of potassium t-butoxide (0.18 g, 1.5 mmol) in 25 ml of THF at 0° C. was added methyltriphenylphosphonium bromide (0.38 g; 1.5 mmol) under nitrogen and the mixture was stirred at room temperature. To the above mixture was added a solution of 1,1-di[(1-p-methoxybenzyl)-pyrazol-4-yl]ketone (0.4 g, 1.0 mol) in 5 ml of THF and the mixture was stirred at room temperature under nitrogen. The above mixture was quenched with saturated ammonium chloride solution, filtered through CELITE®, and the filtrate was concentrated in vacuo. The residue was extracted with ethyl acetate (3×20 ml), the organic layer was washed with brine and dried over sodium sulfate. The organic solution was concentrated in vacuo and the residue was purified by flash chromatography (ethyl acetate/hexane) to afford 0.16 g of 1,1-di[(1-p-methoxybenzyl)-pyrazol-4-yl]-ethylene (Formula III: $R^3=R^4=H$; $R^5=R^6=$

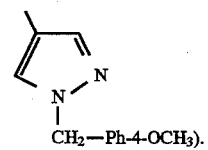

(c)

A reaction mixture containing 4a-azoniaanthracene perchlorate (0.16 g; 0.4 mmol) and 1,1-di[(1-p-methoxybenzyl)-pyrazol-4-yl]-ethylene (0.11 g; 0.4 mmol) in 10 ml of acetonitrile was refluxed for 6.5 h under nitrogen. The reaction mixture was concentrated in vacuo, the residue was purified by flash chromatography on silica (10% methanol in methylene chloride) to afford 0.25 g of 6,11-ethano-12,12-di[(1-p-methoxy-benzyl)pyrazol-4-yl]-6,11-dihydrobenzo

[b]quinolizinium perchlorate (Formula I: $R^1=R^2=R^3=R^4=R^7=H$; $R^5=R^6=$

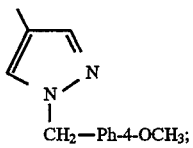

CH₂—Ph-4-OCH₃;

$X^-=ClO_4^-$), as a solid.

(d)

A solution of 250 mg of 6,11-ethano-12,12-di[(1-p-methoxy-benzyl)pyrazol-4-yl]-6,11-dihydrobenzo[b]quinolizinium perchlorate in 10 ml of trifluoroacetic acid was refluxed under nitrogen for 8 h. The mixture was concentrated in vacuo, the residue partitioned in 25 ml of water and 20 ml of ethyl acetate. The aqueous layer was concentrated in vacuo and the residue was treated with 1 g of sodium perchlorate in 10 ml of water. The solution was concentrated (to 4 ml) and the resulting solid product was filtered to afford 25 mg of 6,11-ethano-12,12-di(pyrazol-4-yl)]-6,11-dihydrobenzo-[b]quinolizinium perchlorate (Formula $R^1=R^2=R^3=R^4=R^7=H$; $R^5=R^6=$

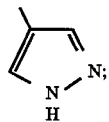

$X^-=ClO_4^-$), as a solid, m.p. 160°–170° C.

EXAMPLE 162

(a)

To a mixture of 3-bromofuran (10 g, 0.068 mol) and propargyl alcohol (4.3 ml, 0.074 mol) in 200 ml of TEA was added under argon, CuI (0.26 g, 1.4 mmol) and [(C₆H₅)₃P]₂PdCl₂ (1.05 g, 1.4 mmol) and the mixture was stirred at 0° C. for 2 hours and at room temperature for 72 hours. The reaction mixture was cooled, decanted, and the solid was washed with TEA. The combined TEA solution was concentrated in vacuo and the residue was distilled (Kugelrohr distillation) to afford 1.48 g (17.8%) of 3-(3-furyl-2-propynyl alcohol.

(b)

A mixture of 3-(3-furyl)-2-propynyl alcohol (1.45 g, 0.0118 mol), DMAP (1 mg), TEA (2.46 ml, 0.017 mol), and acetic anhydride (1.6 ml, 0.017 mol) in 25 ml of methylene chloride was stirred for 1 hour and the mixture was poured into cold 1 N HCl solution. The mixture was extracted with ether (3×50 ml), the organic layer was dried over sodium sulfate and concentrated in vacuo. The residue was purified by silica column chromatography (hexane/ether, 2:1) to afford 1.44 g (57.5%) of 3-(3-acetyloxy-1-propynyl)furan as a clear oil.

(c)

To a mixture of 3-(3-acetyloxy-1-propynyl)furan (1.44 g, 8.7 mmol), 3-bromofuran (2.55 g, 0.017 mol), and Pd(P(C₆H5)3)4 (1.0 g, 0.8 mmol) in THF was added added zinc chloride (0.5M in THF, 34 ml, 0.017 mol) and the mixture was stirred at room temperature for 4 hours. The reaction mixture was concentrated in vacuo and the residue was purified by silica column chromatography (methylene chloride/hexane, 2:1) to afford 1.25 g (85%) of [1,1-di(3-furyl)-1,2-propadiene (Formula III: $R^3$ and $R^4$ together form $=CH_2$; $R^5=R^6=$3-furanyl) as a pale yellow oil.

(d)

A reaction mixture containing 4a-azoniaanthracene hexafluorophosphate (1.48 g; 4.8 mmol) and 1,1-di(3-furyl)-1,2-propadiene (0.25 g; 7.2 mmol) in 50 ml of nitromethane was refluxed for 4 h under nitrogen. The reaction mixture was concentrated in vacuo, the residue was triturated in ether, and the brown residue was filtered. The solid was dissolved in ethyl acetate, filtered, and concentrated in vacuo. The resulting residue was dissolved in isopropanol, cooled, filtered, and the solid was dried to afford 0.386 g (16.7%) of 6,11-ethano-12,12-di(3-furyl)-13-methylene-6,11-dihydrobenzo[b]quinolizinium hexafluorophosphate (Formula I: $R^1=R^2=R^7=H$; $R^3$ and $R^4$ together form $=CH_2$; $R^5=R^6=$3-furanyl; $X^-=PF_6^-$), as a solid.

EXAMPLE 163

To a solution of 1.0 g (2.2 mmol) of 6,11-ethano-12,12-di(3-furyl)-10-hydroxy-6,11-dihydrobenzo[b]quinolizinium perchlorate in 20 ml of pyridine was added 1,8-diazabicyclo[5.4.0]undec-7-ene (0.37 g, 2.4 mmol) under nitrogen. To the above mixture was added stearic acid chloride (1,3 g, 4.4 mmol) and the mixture was stirred at room temperature overnight. The reaction mixture was concentrated in vacuo and the residue was purified by silica gel column chromatography (ethyl acetate, 20% methanol in ethyl acetate). The above product was dissolved in 20% methylene chloride in methanol and passed through AMBERLITE® A-27 column to afford 0.193 g of 6,11-ethano-12,12-di(3-furyl)-10-stearyloxy-6,11-dihydrobenzo[b]quinolizinium chloride (Formula I: $R^1=R^2=R^3=R^4=H$; $R^5=R^6=$3-furyl; $R^7=$10-OC(O)(CH₂)7 CH=CH(CH₂)₇CH₃) as a solid, m.p. 95°–100° C.

EXAMPLE 164

(a)

To a solution of t-BuLi (216 ml, 1.7M, 0.367 mol) in 1 L of THF at −78° C. was added dropwise 1-bromo-2,4,6-trimethyl-benzene (35.6 g, 0.178 mol) over a period of 45 minutes. The mixture was stirred at −78° C. for 1 hour, 3-methoxypyridine (15 g, 0.138 mol) was added and then the mixture was stirred at −23° C. for 3 hours. The above reaction mixture was cooled to −78° C. and 13 g (0.2 mol) of DMF in 25 ml of THF was added and the mixture was stirred for 1 hour. The reaction mixture was quenched with 250 ml of brine, the mixture was stirred overnight, and diluted with 1 L of ether. The aqueous layer was extracted with ethyl acetate (1 L), the combined organic layer was dried over potassium carbonate, and concentrated in vacuo to afford 7.5 g of 3-methoxypyridyl-2-carboxaldehyde.

(b)

To a solution of 4.96 g (0.0265 mol) of 2-bromobenzyl alcohol in 200 ml of ether cooled to −20° C. was added in portions 22.3 ml (55 mmol) of 2.5 M n-butyllithium in hexane and the resulting mixture was stirred at room temperature for 2 hours. The reaction mixture was cooled to 0° C., 3.08 g (26.5 mmol) of TMEDA was added. The above reaction mixture was cooled to −30° C., and 4 g (0.029 mol) of 3-methoxypyridine-2-carboxaldehyde in 30 ml of THF was added, and the resulting reaction mixture was allowed to warm to 0° C. and quenched with 10 ml of water. The resulting diol was filtered, and filtrate was extracted with ethyl acetate, dried over sodium sulfate, and the solvent was removed in vacuo. The combined residue was triturated in ether/ethyl acetate (9:1) and hexane to afford 4 g (64.5%) of 2-[1-hydroxy-(2'-hydroxymethyl-benzyl]-3-methoxy-pyridine (Formula X: $R^1$ =3-$OCH_3$; $R^2$=H; $R^7$=H).

(c)

A mixture of 4 g (16 mmol) of 2-[1-hydroxy-(2'-hydroxymethyl)benzyl]-3-methoxypyridine and 75 ml of $POCl_3$ was heated at 105° C. with stirring for 1 h. The mixture was cooled, concentrated in vacuo, and the residue was dissolved in 50 ml of water and 100 ml of 30% sodium perchlorate solution. The resulting mixture was faltered, the solid was washed with water, ethyl acetate, and hexane, and dried to afford 3.5 g (70.7%) of 1-methoxy-benzorb] quinolizinium perchlorate (Formula II: $R^1$=1-$OCH_3$; $R^2$=$R^7$=H; $X^-$=$ClO_4^-$).

(d)

A reaction mixture containing 1-methoxy-benzo[b] quinolizinium perchlorate (1.5 g; 4.85 mmol) and 1,1-di(3-furyl)-ethylene (1 g) in 75 ml of nitromethane was allowed to reflux under nitrogen with stirring for 3 hour. The reaction mixture was concentrated in vacuo and the residue was crystallized from methylene chloride/ethyl acetate/methanol (7:2:1) and charcoal. The solid product was triturated in water and dried to afford 2 g (86.9%) of 6,11-ethano-12,12-di(3-furyl-1-methoxy-6,11-dihydrobenzo[b]quinolizinium perchlorate (Formula I: $R^1$=1-$OCH_3$; $R^2$=$R^3$=$R^4$=$R^7$=H; $R^5$=$R^6$=3-furyl; $X^-$=$ClO_4^-$) as a solid.

(e)

6,11-Ethano-12,12-di(3-furyl)-1-methoxy-6,11-dihydrobenzo-[b]quinolizinium perchlorate (2 g) was converted to the corresponding chloride salt by passing the above salt through DOWEX® 1x20-200-$Cl^-$ after placing the salt in acetonitrile. The chloride residue obtained was dried in vacuo to afford 0.92 g (53.4%) of 6,11-ethano-12, 12-di(3-furyl)-1-methoxy-6,11-dihydrobenzo[b] quinolizinium chloride (Formula I: $R^1$=1-$OCH_3$; $R^2$=$R^3$=$R^4$=$R^7$=H; $R^5$=$R^6$=3-furyl; $X^-$=$Cl^-$) as a solid.

EXAMPLE 165

To a solution of 1.0 g (2.2 mmol) of 6,11-ethano-12,12-di(3-furyl)-10-hydroxy-6,11-dihydrobenzo[b]quinolizinium perchlorate in 20 ml of pyridine was added DBU (0.37 g, 2.4 mmol) under nitrogen, and to the above mixture was added octanoic acid chloride (0.71 g) and the mixture was stirred at room temperature overnight. The reaction mixture was concentrated in vacuo and the residue was triturated with ether, the resulting solid was purified by silica gel column chromatography (10% methanol/ethyl acetate, 20% methanol in ethyl acetate). The above product was dissolved in acetonitrile and passed through DOWEX® 1x20-200-$Cl^-$ column to afford 0.44 g of 6,11-ethano-12,12-di(3-furyl)-10-octanoyloxy-6,11-dihydrobenzol[b]quinolizinium chloride (Formula I: $R^1$=$R^2$=$R^3$=$R^4$=H; $R^5$=$R^6$=3-furyl; $R^7$=10-OC(O)$C_7H_{15}$; $X^-$ =$Cl^-$) as a solid, m.p. 80°–90° C.

EXAMPLE 166

A mixture of 0.5 g (1.1 mmol) of 6,11-ethano-12,12-di (3-furyl)-10-hydroxy-6,11-dihydrobenzo[b]quinolizinium perchlorate and $CS_2CO_3$ (0.39 g, 1.22 mmol) in 20 ml of acetonitrile was stirred at room temperature for 10 minutes, and to the above mixture was added ethyl succinoyl chloride (0.27 g, 1.6 mmol) and the mixture was stirred at room temperature. The reaction mixture was concentrated in vacuo, the residue was dissolved in acetonitrile, filtered, and the filtrate was concentrated in vacuo. The above product was dissolved in acetonitrile and passed through DOWEX® 1x20-200-$Cl^-$ column to afford 0.14 g of 6,11-ethano-12, 12-di(3-furyl)-10-(3-ethoxycarbonyl)propionyloxy-6,11-dihydrobenzo-[b]quinolizinium chloride (Formula I: $R^1$=$R^2$=$R^3$=$R^4$=H; $R^5$=$R^6$=3-furyl; $R^7$=10-OC(O)($CH_2$)$_2CO_2Et$; $X^-$=$Cl^-$) as a solid, m.p. 120°–124° C.

EXAMPLE 167

(a)

A mixture of ethyl maleic acid (50 g, 0.31 mol) and thionyl chloride (50 ml) was heated at 100° C. for 3 hours and the excess thionyl chloride was removed in vacuo. The residue was distilled to afford 45 g (79.4%) of ethyl maleic chloride as an oil, b.p. 71° C./10mm.

(b)

To a solution of 0.57 g (1.25 mmol) of 6,11-ethano-12, 12-di(3-furyl)-10-hydroxy-6,11-dihydrobenzo[b] quinolizinium perchlorate in 25 ml of acetonitrile was added $CS_2CO_3$ (0.45 g, 1.38 mmol) and the solution was stirred at room temperature for 10 minutes. To the above mixture was added ethyl maleic chloride (0.3 g, 1.38 mmol) and the mixture was stirred at room temperature for 20 hours. The reaction mixture was filtered and concentrated in vacuo, the residue was triturated in water, and filtered. The above product was washed with ether and dried to afford 0.4 g of 6,11-ethano-12,12-di(3-furyl)-10-(ethoxycarbonylethenylcarbonyloxy)-6,11-dihydrobenzo[b] quinolizinium perchlorate (Formula I: $R^1$=$R^2$=$R^3$=$R^4$=H; $R^5$=$R^6$=3-furyl; $R^7$=10-OC(O)CH=CH $CO_2Et$; $X^-$=$ClO_4^-$) as a solid.

(c)

6,11-Ethano-12,12-di(3-furyl)-10-(ethoxycarbonylethenylcarbonyloxy)-6,11-dihydrobenzo[b] quinolizinium perchlorate (0.4 g) was convened to the corresponding chloride by passing the salt through DOWEX® 1x2-200-$Cl^-$ (water/acetonitrile, 7.3) to afford 0.14 g (40%) of 6,11-ethano-12,12-di(3-furyl)-10-(OC(O) CH=CHCO$_2$Et)-6,11-dihydrobenzo[b]quinolizinium perchlorate (Formula I: $R^1$=$R^2$=$R^3$=$R^4$=H; $R^5$=$R^6$=3-furyl; $R^7$=OC(O)CH=CHCO$_2$Et; $X^-$=$Cl^-$), as a solid.

EXAMPLE 168

(a)

A mixture of 1-methoxybenzo[b]quinolizinium perchlorate (1.4 g; 6.1 mmol) in 30 ml of 48% HBr was heated at 100° C. for 16 hour. The reaction mixture was poured into 100 ml of water and 50 ml of sodium perchlorate was added with stirring. The resulting solid was filtered and dried to afford 1.6 g (88.8%) of 1-hydroxybenzo[b]quinolizinium perchlorate (Formula II: $R^1$=1-OH; $R^2$=$R^3$=H; $X^-$=$ClO_4^-$) as a solid.

(b)

A reaction mixture containing 1-hydroxybenzo[b] quinolizinium perchlorate (1.5 g; 5.07 mmol) and 1,1-di(3- furyl)-ethylene (1.5 g, 9.3 mol) in 50 ml of acetonitrile was allowed to reflux under nitrogen with stirring for 10 hour. The reaction mixture was concentrated in vacuo, the residue was dissolved in methanol, and filtered. The filtrate was concentrated in vacuo and the residue was crystallized from ether/methylene chloride (100 ml, 2:1 ). The solid product was filtered and dried to afford 1.7 g (73.9%) of 6,11-ethano-12,12-di(3-furyl)-1-hydroxy-6,11-dihydrobenzo[b]-quinolizinium perchlorate (Formula I: $R^1$=1-OH; $R^2$=$R^3$=$R^4$=$R^7$=H; $R^5$=$R^6$=3-furyl; $X^-$=$ClO_4^-$) as a solid.

(c)

6,11-Ethano-12,12-di(3-furyl)-1-hydroxy-6,11-dihydrobenzo-[b]quinolizinium perchlorate (1.2 g, 2.6 mmol) was converted to the corresponding chloride salt by passing the above salt through DOWEX® 1x2-200-Cl⁻ after placing the salt in acetonitrile. The chloride residue was dried in vacuo to afford 0.82 g (75.9%) of 6,11-ethano-12,12-di(3-furyl)-1-hydroxy-6,11-dihydrobenzo[b]quinolizinium chloride (Formula I: $R^1$=1—OH; $R^2$=$R^3$=$R^4$=$R^7$=H; $R^5$=$R^6$=3-furyl; $X^-$=$Cl^-$) as a solid.

EXAMPLE 169

A mixture of 0.5 g (1.1 mmol) of 6,11-ethano-12,12-di(3-furyl)-10-hydroxy-6,11-dihydrobenzo[b]quinolizinium perchlorate and $CS_2CO_3$ (0.39 g, 1.2 mmol) in 20 ml of acetonitrile was stirred at room temperature for 10 minutes, and to the above mixture was added acetyl chloride (0.13 g, 1.6 mmol) and the mixture was stirred at room temperature overnight. The reaction mixture was concentrated in vacuo, the residue was dissolved in acetonitrile, filtered, and the filtrate was concentrated in vacuo. The above product was dissolved in acetonitrile and passed through DOWEX® 1x2-200-Cl⁻ column to afford 0.27 g of 6,11-ethano-12,12-di(3-furyl)-10-acetyloxy-6,11-dihydrobenzo-[b]quinolizinium chloride (Formula I: $R^1$=$R^2$=$R^3$=$R^4$=H; $R^5$=$R^6$=3-furyl; $R^7$=OC(O)$CH_3$; $X^-$=$Cl^-$) as a solid, m.p. 75°–82° C.

EXAMPLE 170

A mixture of 0.4 g (1 mmol) of 6,11-ethano-12,12-di(3-furyl)-1-hydroxy-6,11-dihydrobenzo[b]quinolizinium perchlorate and $CS_2CO_3$ (0.31 g, 1 mmol) in 20 ml of acetonitrile was stirred at room temperature for 5 minutes. To the above mixture was added acetyl chloride (0.1 g) and the mixture was stirred at room temperature. The reaction mixture was concentrated in vacuo, the residue was triturated in ether, and the solid was filtered. The above product was dissolved in acetonitrile and passed through DOWEX® 1x2-200-Cl⁻ column to afford 0.14 g of 6,11-ethano-12,12-di(3-furyl-1-acetyloxy-6,11-dihydrobenzo-[b]quinolizinium chloride (Formula I: $R^1$=$R^2$=$R^3$=$R^4$=H; $R^5$=$R^6$=3-furyl; $R^7$=OC(O)$CH_3$; $X^-$=$Cl^-$)as a solid, m.p. 128°–132° C.

EXAMPLE 171

(a)

A solution of KCN (3g, 0.046 mol) in a minimum of water was added to a solution of benzo[b]quinolizinium bromide (10 g; 0.0385 mol) in 200 ml water. The resulting solid was extracted with an equal volume of methylene chloride. The above organic layer was heated and a solution of bromine (6.4 g) in methylene chloride was added. The resulting yellow solid was isolated, dissolved in ethanol/water, and the resulting solution was treated with sodium perchlorate solution. The perchlorate salt was filtered and recrystallized from ethanol to afford 2 g of 6-cyano-benzo[b]quinolizinium perchlorate (Formula II: $R^1$=$R^7$=H; $R^2$=CN; $X^-$=$ClO_4^-$) as a solid.

(b)

A reaction mixture containing 6-cyano-benzo[b]quinolizinium perchlorate (1.45 g; 7.07 mmol) and 1,1-di(3-furyl)-ethylene (3 g) in 20 ml of acetonitrile and 40 ml of ethanol was heated to reflux under nitrogen while stirring overnight. The reaction mixture was concentrated in vacuo, the residue was dissolved in methylene chloride and purified by silica gel column 30 chromatography (70% ethyl acetate/30% (55/20/25 pyridine/acetic acid water)). Evaporation gave a brown oil which crystallized from methanol and was converted to the corresponding chloride salt by passing the compound through DOWEX® 1x2-200-Cl⁻ ion-exchange resin. The chloride residue was dried in vacuo and recrystallized from 2-propanol to afford 0.377 g (13.1%) of 6,11-ethano-12,12-di(3-furyl)-6-cyano-6,11-dihydrobenzo[b]quinolizinium chloride (Formula I: $R^1$=$R^3$=$R^4$=$R^7$=H; $R^2$=CN; $R^5$=$R^6$=3-furyl; $X^-$=$Cl^-$) as a solid, m.p. 168° C. softens.

EXAMPLE 172

To a solution of 0.45 g (1 mmol) of 6,11-ethano-12,12-di(3-furyl)-10-hydroxy-6,11-dihydrobenzo[b]quinolizinium perchlorate in 10 ml of DMF was added $CS_2CO_3$ (0.65 g, 2 mmol) under nitrogen and the mixture was stirred at room temperature for 10 minutes. To the above mixture was added octyl bromide (0.4 g) and the mixture was stirred at room temperature overnight. The reaction mixture was concentrated in vacuo, the residue was disssolved in acetonitrile and filtered. The filtrate was concentrated in vacuo, the resulting solid was dissolved in 50 ml of methanol/water/acetonitrile (1:1:1) and treated with sodium perchlorate (8 g). The mixture was concentrated in vacuo, the solid was washed with hexane and ether, and crystallized from acetonitrile/methanol/ether to afford 0.36 g (63.2%) of 6,11-ethano-12,12-di(3-furyl-10-octyloxy-6,11-dihydrobenzo-[b]quinolizinium perchlorate (Formula I: $R^1$=$R^2$=$R^3$=$R^4$=H; $R^5$=$R^6$=3-furyl; $R^7$=O($CH_2$)$_7CH_3$; $X^-$=$ClO_4^-$) as a solid, m.p. 143°–145° C.

EXAMPLE 173

(a)

To a cooled (−78° C.) solution of 1-(p-methoxyphenyl) methyl-imidazole (9.4 g, 0.05 mol) in 200 ml of ether/THF (1:1) was added in portions, 22 ml (0.055 mol) of n-butyllithium (2.5M) over a 1 hour period, and the mixture was stirred at −78° C. for 1.5 h. To the above mixture was added at −78° C. N-methyl-N-methoxy-urethane (3.325 g, 0.025 mol), the mixture was stirred for 1 h at −78° C., and then was allowed to warm to −10° C. The mixture was quenched with saturated ammonium chloride solution and stirred overnight. The organic layer was dried over sodium sulfate, concentrated in vacuo, and the residue was purified by HPLC to afford 10.3 g of 1,1-di[1-(p-methoxyphenyl) methylimidazol-2-yl]ketone.

(b)

To a solution of potassium t-butoxide (3.56 g, 0.032 mol) in 15 ml of THF cooled at 0° C. was added methyltriphenylphosphonium bromide (1.143 g; 0.03 mol) and the resulting mixture was allowed to warm to room temperature with stirring for 1 hour. To the above mixture was added 1,1-di

[1-(p-methoxyphenyl)methylimidazol-2-yl]ketone (8.5 g, 21 mmol) in 30 ml of THF, followed by stirring for 2 hours at room temperature. The above mixture was quenched with saturated ammonium chloride solution, stirred, and filtered through a pad of SUPERCEL®. The filtrate was concentrated in vacuo and the residue was purified by chromatography on silica (ethyl acetate, 5 ethyl acetate/ether/methanol) to afford 3 g (35%) of 1,1-di[1-(p-methoxyphenylmethylimidazol-2-yl)]ethylene (Formula III: $R^3=R^4=H$; $R^5=R^6=$

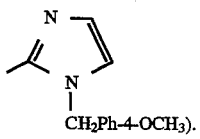

CH$_2$Ph-4-OCH$_3$).

(c)

A reaction mixture containing benzo[b]quinolizinium hexafluorophosphate (1.53 g; 5 mmol) and 1,1-di[1-(p-methoxyphenyl)methyl-imidazol-2-yl)]ethylene (3 g; 7.5 mmol) in 25 ml of acetonitrile was refluxed for 54 h under argon. The reaction solvent was 15 replaced with nitromethane and the mixture was refluxed for 4 days. The mixture was concentrated in vacuo, the residue was purified by silica gel column chromatography (methylene chloride/methanol, 20:1) to afford 2.1 g (59%) of 6,11-ethano-12,12-di [1-(p-methoxy-phenyl)methylimidazol-2-yl]-6,11-dihydrobenzo[b]quinolizinium hexafluorophosphate (Formula I: $R^1=R^2=R^3=R^4=R^7=H$; $R^5=R^6=$

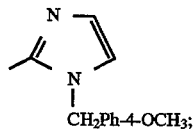

CH$_2$Ph-4-OCH$_3$;

$X^-=PF_6^-$).

(d)

A solution of 2.1 g (3 mmol) of 6,11-ethano-12,12-di[1-(p-methoxyphenyl)methylimidazol-2-yl]-6,11-dihydrobenzo[b]quinolizinium hexafluorophosphate in 15 ml of trifluoroacetic acid was refluxed under nitrogen for 24 h. The mixture was concentrated in vacuo, the residue was dissolved in methanol/water and filtered, and the filtrate was concentrated in vacuo to afford 2 g of 6,11-ethano-12,12-di-(imidazol-2-yl)-6,11-dihydrobenzo[b]quinolizinium trifluoroacetate (Formula I: $R^1=R^2=R^3=R^4=R^7=H$; $R^5=R^6=$

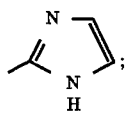

$X^-=OC(O)CF_3$), as a solid.

(e)

6,11-Ethano-12,12-di-(imidazol-2-yl)-6,11-dihydrobenzo[b]quinolinium trifluoroacetate (2 g) in acetonitrile/water (1:1) was converted to the corresponding chloride by passing the salt through DOWEX® 1x2-200-Cl$^{13}$(water/acetonitrile, 7:3) to afford 0.9 g of 6,11-ethano-12,12-di (imidazol-2-yl)-6,11-dihydrobenzo[b]quinolizinium chloride (Formula I: $R^1=R^2=R^3=R^4=R^7=H$; $R^5=R^6=$

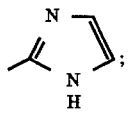

$X^-=Cl^-$), as a solid.

EXAMPLE 174

A mixture of 0.5 g (2.9 mmol) of 6,11-ethano-12,12-di (3-furyl)-10-hydroxy-6,11-dihydrobenzo[b]quinolizinium perchlorate and $CS_2CO_3$ (1.1214 g, 3.2 mmol) in 20 ml of acetonitrile was stirred at room temperature for 10 minutes. To the above mixture was added trimethylacetyl chloride (0.52 g, 4.4 mmol) and the mixture was stirred at room temperature. The reaction mixture was concentrated in vacuo, the residue was triturated in ether and water respectively, and filtered. The above product was dissolved in acetonitrile and passed through DOWEX® 1x2-200-Cl$^-$ column to afford 0.27 g of 6,11-ethano-12,12-di(3-furyl)-10-trimethylacetyloxy-6,11-dihydrobenzo-[b]quinolizinium chloride (Formula I: $R^1=R^2=R^3=R^4=H$; $R^5=R^6=$3-furyl; $R^7=OC(O)C(CH_3)_3$; $X^-=Cl^-$) as a solid, m.p. 128°–131° C.

EXAMPLE 175

(a)

A reaction mixture containing 10-hydroxy-benzo[b] quinolizinium perchlorate (1.42 g; 5 mmol) and 1,1-di[3-(2-p-methoxy-benzyl)-pyrazolyl-3-yl]ethylene (2.6 g; 6.5 mmol) in 50 ml of nitromethane was refluxed for 16 h under nitrogen. The reaction mixture was concentrated in vacuo, the residue was triturated in ether and filtered, and the solid was purified by silica gel column chromatography (methylene chloride/ether 9:1) to afford 3.4 g of 6,11-ethano-12,12-di[3-(2-p-methoxybenzyl)-pyrazolyl-3-yl]-6,11-dihydrobenzo[b]-quinolinium perchlorate (Formula I: $R^1=R^2=R^3=R^4=H$; $R^5=R^6=$

CH$_2$Ph-4-OCH$_3$;

$R^7=10OH$; $X^-=ClO_4^-$), as a solid.

(b)

A solution of 3.4 g (4.9 mmol) of 6,11-ethano-12,12-di [3-(2-p-methoxybenzyl)-pyrazolyl-3-yl]-6,11-dihydrobenzo[b]quinolizinium perchlorate in 50 ml of trifluoroacetic acid was refluxed under nitrogen for 24 h. The mixture was concentrated in vacuo, the residue triturated in methanol-water (1:1), and filtered. The filtrate was concentrated in vacuo and the solid product was converted to the corresponding chloride by passing the salt through DOWEX®1x2-200-Cl$^-$(water/acetonitrile, 1:1)) to afford 2.8 g of a crude product. The crude product was purified by repeating the above process of trifluoroacetic acid treatment followed by ion exchange chromatography to afford 2.0 g of 6,11-ethano-12,12-di-[pyrazolyl-3-yl]-6,11-dihydrobenzo [b]quinolizinium chloride (Formula I: $R^1=R^2=R^3=R^4=H$; $R^5=R^6=$

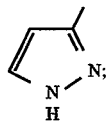

$R^7$=10-OH; $X^-$=Cl$^-$) as a solid, m.p. 308°–310° C.

EXAMPLE 176

(a)

A reaction mixture of 3.02 g (20 mmol) of 2-(1,3-dioxolan-2-yl)pyridine and 4.58 g (20 mmol) of methyl a-bromophenyl- acetate was stirred at room temperature for 4 days. The mixture was triturated in ether/ethyl acetate and filtered to afford 5.7 g of 1-[(a-phenyl)methoxycarbonylmethyl]-2-(1,3-dioxolan-2-yl)pyridiniumium bromide, (Formula VI: $R^1$=H; $R^2$=CO$_2$CH$_3$; $R^7$=H; $Z^-$=Br$^-$).

(b)

A mixture of 1-[(a-phenyl)methoxycarbonylmethyl]-2-(1,3-dioxalan-2-yl)pyridiniumium bromide (5.6 g, 14.74 mmol) and 60 g of PPA was heated at 120° C. under nitrogen for 8 hours. The excess PPA was decomposed by the addition of ice, the reaction mixture was stirred and filtered through a SUPERCEL® pad, and to the filtrate was added sodium perchlorate solution. The resulting solid was filtered, washed with water, and dried to afford 3 g (68%) of 6-methoxycarbonyl-benzo[b]quinolizinium perchlorate (Formula II: $R^1$=$R^7$=H; $R^2$=CO$_2$CH$_3$; $X^-$=ClO$_4^-$) as a solid.

(c)

A reaction mixture containing 6-methoxycarbonyl-benzo[b]quinolinizium perchlorate (2.8 g; 8.3 mmol) and 1,1-di(3-furyl)-ethylene (1.73 g) in 75 ml of acetonitrile was allowed to reflux under argon with stirring for 24 hours. The reaction mixture was concentrated in vacuo, the residue was recrystallized from acetone/methylene chloride to afford 2.5 g of 6,11-ethano-12,12-di(3-furyl)-6-methoxycarbonyl-6,11-dihydrobenzo[b]quinolizinium perchlorate (Formula I: $R^1$=$R^3$=$R^4$=$R^7$=H; $R^2$=CO$_2$CH$_3$; $R^5$=$R^6$=3-furyl; $X^-$=ClO$_4^-$) as a solid.

(d)

6,11-Ethano-12,12-di(3-furyl)-6-methoxycarbonyl-6,11-dihydrobenzo[b]quinolizinium perchlorate (1.21 g, 2.8 mmol) was converted to the corresponding chloride salt by passing the above salt through DOWEX® 1x2-200-Cl$^-$ after placing the salt in acetonitrile. The product was recrystallized from methylene chloride/acetone to afford 0.55 g (13.1%) of 6,11-ethano-12,12-di(3-furyl)-6-methoxycarbonyl-6,11-dihydrobenzo[b]-quinolizinium chloride (Formula I: $R^1$=$R^3$=$R^4$=$R^7$=H; $R^2$=CO$_2$CH$_3$; $R^5$=$R^6$=3-furyl; $X^-$=Cl$^-$) as a solid, m.p. 210°–212° C.

EXAMPLE 177

A mixture of 6,11-ethano-12,12-di(m-methoxyphenyl)-6,11-dihydrobenzo[b]quinolizinium perchlorate (3.5 g) in 50 ml of 48% HBr/acetic acid (1:1) was refluxed overnight. The reaction mixture was concentrated in vacuo, the residue was triturated with 100 ml of water and filtered. The solid residue was dissolved in methanol and treated with 0.9 g of sodium perchlorate in 100 ml of water. The organic solvent was removed in vacuo and the solid product was filtered and dried to afford 2.7 g (88%) of 6,11-ethano-12,12-di(m-hydroxyphenyl)-6,11-dihydrobenzo [b]quinolizinium perchlorate (Formula I: $R^1$=$R^2$=$R^3$=$R^4$=$R^7$=H; $R^5$=$R^6$=3-hydroxyphenyl; $X^-$=ClO$_4^-$) as a solid, m.p. 150°–160° C.

EXAMPLE 178

(a)

To a suspension of NaH (0.98 g, 0.039 mol) in THF was added ethanol (1.8 g, 0.039 mol) followed by 1,1-dimethylsuccinic anhydride (5 g, 0.037 mol), and the mixture was stirred at room temperature for 2 hour and then poured into 1 N HCl solution. The mixture was extracted with ethyl acetate, the organic layer was dried and concentrated in vacuo. The residue was crystallized from hexane to afford 1.8 g of 3-ethoxycarbonyl-3,3-dimethylpropionic acid as a solid.

(b)

A mixture of 3-ethoxycarbonyl-3,3-dimethylpropionic acid (1 g) and 3 ml of thionyl chloride was stirred at room temperature for 20 hours. The excess thionyl chloride was removed in vacuo to afford 1,1 g of 3-ethoxycarbonyl-3,3-dimethylpropionyl chloride.

(c)

To a solution of 1,3 g (2.8 mmol) of 6,11-ethano-12,12-di(3-furyl)-10-hydroxy-6,11-dihydrobenzo[b]quinolizinium perchlorate in 50 ml of acetonitrile was added CS$_2$CO$_3$ (1.86 g, 5.7 mmol) and the reaction mixture was stirred for 10 minutes. To the above mixture was added 1.1 g (5.7 mmol) of 3-ethoxycarbonyl-3,3-dimethylpropionyl chloride in 3 ml of methylene chloride and the mixture was stirred at room temperature under nitrogen for 30 20 hours. The reaction mixture was filtered and the filtrate was concentrated in vacuo. The residue was crystallized from methylene chloride/ethyl acete/methanol (7:2:1) and purified by triturating in ethyl acetate to afford 0.85 g (50%) of 6,11-ethano-12,12-di(3-furyl)-10-(OC(O)C(CH$_3$)$_2$CH$_2$CO$_2$Et)-6,11-dihydrobenzo[b]quinolizinium perchlorate (Formula I: $R^1$=$R^2$=$R^3$=$R^4$=H; $R^5$=$R^6$=3-furyl; $R^7$=10-OC(O)C(CH$_3$)$_2$CH$_2$CO$_2$Et; $X^-$=ClO$_4^-$).

(d)

The above 6,11-ethano-12,12-di(3-furyl)-10-(OC(O)C (CH$_3$)$_2$CH$_2$CO$_2$Et)-6,11-dihydrobenzo[b]quinolizinium perchlorate (0.8 g) was converted to the corresponding chloride salt by dissolving in acetonitrile and passing through DOWEX® 1x2-200-Cl$^-$ column to afford 0.57 g of 6,11-ethano -12,12-di(3-furyl)-10-(OC(O)C(CH$_3$)$_2$CH$_2$CO$_2$Et)-6,11-dihydrobenzo[b]quinolizinium chloride (Formula I: $R^1$=$R^2$=$R^3$=$R^4$=H; $R^5$=$R^6$=3-furyl; $R^7$=10-OC(O)C(CH$_3$)2CH$_2$CO$_2$Et; $X^-$=Cl$^-$).

EXAMPLE 179

(a)

A reaction mixture containing 10-methoxy-benzo[b]quinolizinium 5 perchlorate (0.774 g; 2.5 mmol) and 1,1-di[3-(1-p-methoxybenzyl)-pyrazolyl-3-yl]ethylene (1.2 g; 3 mmol) in 25 ml of nitromethane was refluxed for 14 h under nitrogen. The reaction mixture was concentrated in vacuo, the residue was triturated in ether, and the solid product was recrystallized from ether/methanol/methylene chloride to afford 1.7 g (95%) of 6,11-ethano-12,12-di[(1-p-methoxybenzyl)-pyrazolyl-3-yl]-10-methoxy-6,11-dihydrobenzo[b]quinolizinium perchlorate (Formula I: $R^1=R^2=R^3=R^4=H$; $R^5=R^6=$

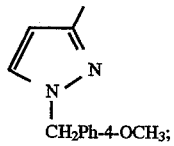

CH$_2$Ph-4-OCH$_3$;

$R^7$=10-OCH$_3$; $X^-$=ClO$_4^-$), as a solid.

(b)

A mixture of 1.65 g (2.32 mmol) of 6,11-ethano-12,12-di[(1-p-methoxybenzyl)-pyrazolyl-3-yl-10-methoxy-6,11-dihydrobenzo[b]quinolizinium perchlorate in 20 ml of trifluoroacetic acid was refluxed with stirring under argon for 48 h. The mixture was concentrated in vacuo, the residue dissolved in methanol/water (50%), filtered, and the filtrate was concentrated. The residual perchlorate salt was convened to the corresponding chloride salt by dissolving in acetonitrile and passing through DOWEX® 1x2-200-Cl$^-$ column and crystallized from isopropanol/water to afford 0.8 g (85%) of 6,11-ethano-12,12-di(pyrazolyl-3-yl]-10-methoxy-6,11-dihydrobenzo[b]quinolizinium chloride (Formula I: $R^1=R^2=R^3=R^4=H$;

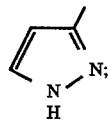

$R^5=R^6=H$ ; $R^2$=10-OCH$_3$; $X^-$=Cl$^-$), as a solid.

EXAMPLE 180

(a)

A mixture of 1-isoquinolinecarboxylic acid (25 g.0.14 mol), 25 g of AMBERLYST®-15 (H+), and 300 ml of methanol was refluxed for 3 days. The reaction mixture was cooled, filtered, and the filtrate was concentrated in vacuo to afford 13.6 g (50%) of 1-isoquinolinecarboxylic acid methyl ester.

(b)

1-Isoquinolinecarboxaldehyde (7.3 g, 64 %) was prepared from 1-isoquinolinecarboxylic acid methyl ester (13.6 g, 0.073 mol) and 1M LAH (36.6 ml in THF) in 300 ml of dry THF (J. Org. Chem., vol 28, p 1898, 1963) to afford 7.3 g (64%) of 1-isoquinolinecarboxaldehyde.

(c)

A mixture of 1-isoquinolinecarboxaldehyde (7.2 g, 46 mmol), 5.7 g (92 mmol) of ethylene glycol, 200 ml of toluene and 2.3 g (12 mmol) of p-toluenesulfonic acid under argon in a 3 neck-flask equipped with a Dean-Stark Trap was refluxed for 6 h separating the water. The mixture was cooled to room temperature, and poured into an ice-cold 10% sodium carbonate solution. The aqueous layer was extracted with ether, the combined organic layer was washed with brine, dried over sodium sulfate, and concentrated in vacuo to afford 9.3 g of 1-(1,3-dioxolan-2-yl)isoquinoline.

(d)

A reaction mixture of 9.5 g (46 mmol) of 1-(1,3-dioxolan-2-yl)isoquinoline and 7.91 g (46 mmol) of benzyl bromide was stirred for 72 hours. The mixture was cooled to room temperature, triturated with ethyl acetate, filtered, and the solid was washed with ether and dried to afford 15.2 g (88%) of 1-(1,3-dioxolan-2-yl)-2-benzylisoquinolium bromide (Formula VI: $R^1$ is a benzene ring fused at the 3,4-positions; $R^2=R^7=H$; $Z^-$=Br).

(e)

A mixture of 1-(1,3-dioxolan-2-yl)-2-benzylisoquinolium bromide (15.1 g, 21 mmol) and 200 ml of 48% HBr was refluxed with stirring for 24 hours. The mixture was cooled to room temperature, concentrated in vacuo, and the resulting brown residue was redissolved in water. The aqueous solution was filtered and the the filtrate was treated with KPF6 solution. The precipitated product was filtered, washed with water, dried in vacuo, and recrystallized from acetone to afford 6.9 g (45 %) of dibenzo[a,g]quinolizinium hexafluorophosphate (Formula II: $R^1$=a benzene ring fused to the 1,2-position; $R^3=R^7=H$; $X^-$=PF$_6^-$).

(f)

A reaction mixture containing dibenzo[a,g]quinolizinium hexafluorophosphate (2.5 g; 6.6 mmol) and 1,1-di(3-furyl) ethylene (1.28' g; 8 mmol) in 70 ml of acetonitrile was allowed to reflux under argon with stirring for 24 h. The reaction mixture was concentrated in vacuo, the residue was recrystallized from methylene chloride/ether to afford 3.3 g of 14,14-di(3-furyl)-8,13-ethano-8,13-dihydrodibenzo[a,g] quinolizinium hexafluorophosphate (Formula I: $R^1$=a benzene ring fused at the 1,2-position; $R^2=R^3=R^4=R^7=H$; $R^5=R^6$=3-furyl; $X^-$=PF$_6^-$).

(g)

14,14-Di(3-furyl)-8,13-ethano-8,13-dihydrodibenzo[a,g] quinolizinium hexafluorophosphate (3.2 g, 6.34 mmol) in acetonitrile was converted to the corresponding chloride by passing the salt through DOWEX® 1x2-200-Cl$^-$ (water/acetonitrile, 7:3) to afford 2.4 g (94%) of 14,14-di(3-furyl)-8,13-ethano-8,13-dihydrodibenzo[a,g]quinolizinium chloride (Formula I: $R^1$=a benzene ring fused at the 1,2-position; $R^2=R^3=R^4=R^7=H$; $R^5=R^6$=3-furyl; $X^-$=Cl$^-$) as a solid, m.p. 235°–237° C.

EXAMPLE 181

(a)

To a solution of 1,1-di(3-furyl)ketone (36.7 g, 0.226 mol) in 400 ml of THF at 0° C. was added ethylmagnesium bromide (3M in ether, 98.1 ml, 0.294 mol) and the resulting mixture was allowed to warm to room temperature in 30 minutes. The mixture was cooled to 0° C., quenched with 300 ml of ammonium chloride solution, and the resulting mixture was extracted with ethyl acetate (3x250ml). The organic layer was dried over sodium sulfate and concentrated in vacuo to afford 43 g of 1,1-di(3-furyl)propanol as an oil.

(b)

A mixture of 1,1-di(3-furyl)propanol (43 g) and 1 g of p-toluenesulfonic acid in 300 ml of toluene was allowed to react at room temperature and the resulting mixture was concentrated in vacuo. The residual red oil was purified by silica gel column chromatography (methylene chloride) and kugelrohr distillation (50°–80° C. at 0.25 mmHg) to afford 4 g of 1,1-di(3-furyl-1-propene (Formula III: $R^3$=$CH_3$; $R^4$=H; $R^5$=$R^6$=3-furyl) as an oil, b.p. 50°–80° C. (0.25 mm).

(c) & (d)

A reaction mixture containing benzo[b]quinolizinium hexafluorophosphate (5.8 g; 19.1 mmol) and 1,1-di(3-furyl)-1-propene (4 g; 22.9 mmol) in 300 ml of nitromethane was refluxed for 12 h under nitrogen. The reaction mixture was decanted, the liquid was concentrated in vacuo, the residue was triturated in ether (200 ml), and filtered. The solid product was purified by silica gel chromatography (1:1 ethylacetate/PAW) and preparative HPLC (C-18, Waters 4000, 55% MEOH, 45% $H_2O$ 10 mM $KPF_6$) to afford two isomers:

Isomer 1; 6,11-ethano-12,12-di(3-furyl)-13-methyl-6,11-dihydrobenzo[b]quinolizinium hexafluorophosphate (Example 181 (c) Formula I: $R^1$=$R^2$=$R^4$=$R^7$=H; $R^3$=$CH_3$; $R^5$=$R^6$=3-furyl; $X^-$=$PF_6^-$); 42 mg.

Isomer 2; 6,11-ethano-12,12-di(3-furyl)-13-methyl-6,11-dihydrobenzo[b]quinolizinium hexafluorophosphate (Example 181 (d) Formula I: $R^1$=$R^2$=$R^3$=$R^7$-H; $R^4$=$CH_3$; $R^5$=$R^6$=3-furyl; $X^-$=$PF_6^-$); 128 mg.

EXAMPLE 182

(a)

To a solution of 2,6-di(tetrahydro-2H-2-pyranyloxymethyl)-phenyl bromide (15.5 g, 39 mmol) in ether at –30° C. was added n-BuLi (2.5M, 16.4 ml, 41 mmol) and the mixture was allowed to warm to room temperature and stirred for 1.5 hours. The mixture was cooled to 0° C., and TMEDA (4.56 g, 37 mmol) was added, and the resulting mixture was cooled to –50° C. After stirring for 20 minutes, 2-pyridylcarboxaldehyde (6.31 g, 58 mmol) was added. The above mixture was warmed to room temperature over a period of 2 hours, quenched with saturated sodium bicarbonate, and diluted with ethyl acetate with stirring. The organic layer was washed with brine and concentrated in vacuo to afford 11.7 g (73%) of 1-(2-pyridyl)-1-[2,6-di(tetrahydro-2H-2-pyranyloxymethyl)phenyl]-methanol as an oil.

(b)

A solution of 1 g (2.42 mmol) of 1-(2-pyridyl)-1-[2,6-di(tetrahydro-2H-2-pyranyloxymethyl)phenyl]-methanol in 14 ml of acetic acid/THF/water (4:2:1) was heated at 100° C. under nitrogen for 6 hours. The mixture was concentrated in vacuo, the residue was dissolved in ethyl acetate and concentrated in vacuo. The residual solid was triturated with ether to afford 0.26 g of 1-(2-pyridyl)-1-[2,6-di(hydroxymethyl)-phenyl]methanol (Formula X: $R^1$=$R^2$=H; $R^7$=6-hydroxymethyl) as a solid.

(c)

A mixture of 0.6 g (2.5 mmol) of 1-(2-pyridyl)-1-[2,6-di(hydroxymethyl)-phenyl]methanol and 10 ml of $POCl_3$ was refluxed with 30 stirring for 4 hours. The mixture was cooled, poured onto ice, stirred and treated with a 20% sodium perchlorate solution. The resulting mixture was filtered, the resulting solid was washed with water, and dried to afford 0.58 g of 10-chloromethyl-benzo[b]quinolizinium perchlorate (Formula II: $R^1$=$R^2$=H; $R^7$=10-$CH_2Cl$; $X^-$=$ClO_4^-$).

(d)

A reaction mixture containing 10-chloromethyl-benzo[b]quinolizinium perchlorate (0.58 g; 1.8 mmol) and 1,1-di(3-furyl)-ethylene (1 g, 6.1 mmol) in 50 ml of acetonitrile was refluxed under nitrogen for 10 hours. The reaction mixture was concentrated in vacuo and the residue was crystallized from methanol/isopropanol (3:1) to afford 0.75 g of 6,11-ethano-12,12-di(3-furyl)-10-chloromethyl-6,11-dihydrobenzo[b]quinolizinium perchlorate (Formula I: $R^1$=$R^2$=$R^3$=$R^4$=H; $R^5$=$R^6$=3-furyl; $R^7$=10-$CH_2Cl$; $X^-$=$ClO_4^-$) as a solid.

(e)

To a solution of 6,11-ethano-12,12-di(3-furyl)-10-chloromethyl-6,11-dihydrobenzo[b]quinolizinium perchlorate (0.5 g) in 65 ml of acetone was added NaI (0.3 g, 2 equiv), and the mixture was heated at 50°–60° C. for 5 hours. The mixture was filtered and the filtrate was concentrated in vacuo to afford 0.8 g of the iodide. To a solution of the iodide in 150 ml of acetone/water (1:1) was added 0.5 g of sodium carbonate and the mixture was refluxed under nitrogen for 16 hours. The solvent was removed in vacuo and the residue was treated with a 10% sodium perchlorate solution. The resulting solids were collected by filtration and crystallized from acetonitrile to afford 0.18 g of 6,11-ethano-12,12-di(3-furyl)-10-hydroxymethyl-6,11-dihydrobenzo[b]quinolizinium perchlorate (Formula I: $R^1$=$R^2$=$R^3$=$R^4$=H; $R^5$=$R^6$=3-furyl; $R^7$=$CH_2OH$; $X^-$=$ClO_4^-$) as a solid, m.p. 224°–226° C.

EXAMPLE 183

(a)

A mixture of 9 g (35 mmol) of 1-(2-pyridyl)-1-[(2-hydroxymethyl)-5,6-methylenedioxyphenyl]methanol and 30 ml of $POCl_3$ was refluxed with stirring for 6 hours, the mixture was cooled to room temperature, and poured into ice/water. The mixture was treated with $KPF_6$ solution, the resulting solid was filtered, and washed with water, and dried to afford 6.3 g of 9,10-methylenedioxy-benzo[b]quinolizinium hexafluorophosphate (Formula II: $R^1$=$R^2$=H; $R^7$=9,10-$OCH_2O$-; $X^-$=$PF_6^-$).

(b)

A reaction mixture containing 9,10-methylenedioxybenzo[b]quinolizinium hexafluorophosphate (1.85 g; 5 mmol) and 1,1-di(3-furyl)-ethylene (1 g, 6.25 mmol) in 25 ml of acetonitrile was allowed to reflux under nitrogen with stirring for 18 hours. The reaction mixture was concentrated in vacuo and the residue was purified by silica gel column chromatography (methylene chloride/methanol, 9:1) to afford 1.5 g (56%) of 6,11-ethanol-12,12-di(3-furyl)-9,10-methylenedioxy-6,11-dihydrobenzo[b]quinolizinium hexafluoro-phosphate (Formula I: $R^1$=$R^2$=$R^3$=$R^4$=H; $R^5$=$R^6$=3-furyl; $R^7$=9,10-$OCH_2O$-; $X^-$=$PF_6^-$) as a solid.

(c)

6,11-Ethano-12,12-di(3-furyl)-9,10-methylenedioxy-6,11-dihydrobenzo[b]quinolizinium hexafluorophosphate (1.5 g) was converted to the corresponding chloride salt by passing the above salt through DOWEX® 1x2-200-Cl– after placing the salt in acetonitrile. The chloride residue obtained was recrystallized from water and dried in vacuo to afford 1.0 g (47%) of 6,11-ethano-12,12-di(3-furyl)-9,10 methylenedioxy-6,11-dihydrobenzo[b]quinolizinium chloride (Formula I: $R^1=R^2=R^3=R^4=H$; $R^5=R^6$=3-furyl; $R^7$=9,10-$OCH_2O$-; $X^-=PF_6^-$) as a solid, m.p. 198°–200° C.

EXAMPLE 184

(a)

To a cooled (–78° C.) solution of 1-(p-toluenesulfonyl)-pyrazole (18.2 g, 0.082 mol) in 400 ml of THF was added at –78° C. in portions 53.1 ml (0.0903 mol) of t-butyllithium (2.5M) and the mixture was stirred at –78° C. for 10 minutes. To the above mixture was added at –78° C. 3-(N-methyl-N-methoxycarbamoyl)furan (14 g, 0.0903 mol) and the mixture was stirred for 1 h at –78° C., and then was allowed to warm to room temperature. The mixture was poured into 1N HCl solution, extracted with ethyl acetate (3×150ml), the organic layer was dried over sodium sulfate, concentrated in vacuo, and the residue was purified by silica gel column chromatography (ether:hexane, 2:1). The residue was taken up in ether, filtered and the filtrate was concentrated in vacuo to afford 6.9 g of 1-(3-furyl)-1-[1-(p-toluenesulfonyl)pyrazol-5-yl]ketone.

(b)

To a solution of methyltriphenyl-phosphonium bromide (7.71 g; 21.5 mmol) in 100 ml of ether cooled to –30° C. was added n-BuLi (8.6 ml, 2.5M hexane, 21.5 mmol). The resulting mixture was allowed to warm to room temperature with stirring for 1 hour. To the above mixture was added 1-(3-furyl)-1-[1-(p-toluenesulfonyl)pyrazol-5-yl]ketone (6.5 g, 20 mmol) in 25 ml of THF, then the mixture was refluxed for 1 hour. The above mixture was cooled, filtered, and the filtrate was concentrated in vacuo. The residue was purified by chromatography on silica (hexane/methylene chloride, 1:1) to afford 3.51 g of 1-(3-furyl)-1-[1-(p-toluenesulfonyl)pyrazol-5-yl]ethylene (Formula III: $R^3=R^4=H$; $R^5$=3-furyl; $R^6$=

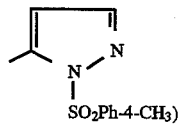

as a yellow oil.

(c) & (d)

A reaction mixture containing benzo[b]quinolizinium bromide (2.3 g; 8.86 mmol) and 1-(3-furyl)-1-[1-(p-toluenesulfonyl)-pyrazol-5-yl]ethylene (3.2 g; 10.19 mmol) in 75 ml of nitromethane was refluxed for 2 h under nitrogen. The reaction mixture was concentrated in vacuo, the residue was 20 triturated with ether and filtered to yield a tan solid. The solid was purified by silica gel column chromatography (10% methanol in methylene chloride) to afford:

Isomer 1 6,11-ethano-12-(3-furyl)-12-[1-(p-toluenesulfonyl)pyrazol-5-yl]-6,11-dihydrobenzo[b]quinolizinium bromide (138 mg; Example 184(c) Formula I: $R^1=R^2=R^3=R^4=R^7$=H; $R^5$=

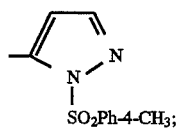

$R^6$=3-furyl; $X^-=Br^-$). m.p. 158°–163° C.

Isomer 2 6,11-ethano-12-(3-furyl)-12-[1-(p-toluenesulfonyl)pyrazol-5-yl]-6,11-dihydrobenzo[b]quinolizinium bromide (104 mg; Formula I: $R^1=R^2=R^3=R^4=R^7$=H; $R^5$=3-furyl; $R^6$=

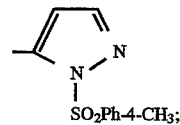

$X^-=Br^-$). m.p. 205°–211° C.

EXAMPLE 185

(a)

To a solution of 6,11-ethano-12-(3-furyl)-12-[1-(p-toluenesulfonyl)pyrazol-5-yl]-6,11-dihydrobenzo[b]quinolizinium bromide (2.03 g, 35 mmol; Example 184(c)) in 20 ml of ethanol was added NaOMe (0.094 g, 3.5 mmol) and the mixture was stirred for 4 hours. The mixture was concentrated in vacuo, and the residue was purified by silica gel chromatography (10% methanol in methylene chloride). The product (bromide) was treated with a sodium perchlorate solution, filtered and the solid was recrystallized from isopropanol to afford 1.44 g of 6,11-ethano-12-(3-furyl)-12-(5-pyrazolyl]-6,11-dihydrobenzo[b]quinolizinium perchlorate (Formula I: $R^1=R^2=R^3=R^4=R^7$=H; $R^5$=5-pyrazolyl; $R^6$=3-furyl; $X^-=ClO_4^-$), m.p. 122°–130° C.

(b)

To a solution of 6,11-ethano-12-(3-furyl)-12-[1-(p-toluenesulfonyl)pyrazol-5-yl]-6,11-dihydrobenzo[b]quinolizinium bromide (0.6 g, 10 mmol; Example 184(d)) in 25 ml of ethanol was added NaOMe (0.094 g, 3.5 mmol) and the mixture was stirred for 4 hours. The mixture was concentrated in vacuo, the residue was dissolved in 5 ml of methanol and 20 ml of water and was treated with a sodium perchlorate solution, and filtered. The solid product was recrystallized from isopropanol and methylene chloride to afford 98.3 mg of 6,11-ethano-12-(3-furyl)-12-(5-pyrazolyl]-6,11-dihydrobenzo[b]quinolizinium perchlorate (Formula I: $R^1=R^2=R^3=R^4=R^7$=H; $R^5$=3-furyl; $R^6$=pyrazolyl; $X^-=ClO_4^-$), m.p. 142° C.

EXAMPLE 186

(a)

To a solution of 3-amino-4-methylbenzoic acid methyl ester (25 g, 0.15 mol) in 1 L of acetic acid cooled to 0° C. was added a solution of $NaNO_2$ (12.5 g, 0.182 mol) in 50 ml of water and the mixture was warmed to room temperature with stirring over 4 hours. The solution was concentrated in vacuo, the residue was triturated with water, the solid was filtered and washed with water and hexane to afford 19 g (71.6%) of methyl indazole-6-carboxylate.

(b)

To a solution of methyl indazole-6-carboxylate (19 g, 0.107 mol) in 100 ml of DMF was added NaH (3.3 g, 0.135 mol) and the mixture was stirred at room temperature for 1 hour. To the above mixture cooled to 0° C. was added trimethylsilyl-ethoxymethyl chloride (22.4 g, 0.135 mol), and the mixture was stirred at room temperature for 3 hours. The mixture was poured into 300 ml of water, and the resulting mixture was extracted with ether. The organic layer was washed with water and brine, dried, and concentrated in vacuo to afford 3.7 g (52.5%) of methyl 1-(trimethylsilylethoxymethyl)-indazole-6-carboxylate.

(c)

To a mixture of LAH (5.73 g, 0.15 mol) in 200 ml of ether was added a solution of methyl 1-(trimethylsilylethoxymethyl)-indazole-6-carboxylate in 200 ml of ether over a 30 minutes period and the mixture was stirred for 1 hour. The resulting mixture was quenched with water(6 ml), 1N NaOH (15 ml) and water (6 ml), diluted with ethyl acetate with stirring and filtered. The filtrate was concentrated in vacuo, and the residue was crystallized from hexane/ethyl acetate (2:1) to afford 18.1 g (87%) of 1-(trimethylsilyl-ethoxymethyl)indazolyl-6-methanol.

(d)

A mixture of 1-(trimethylsilylethoxymethyl)indazolyl-6-methanol (18.1 g, 65 mmol) in 400 ml of 50% aqueous acetic acid and n-bromosuccinimide (NBS) (12.6 g, 71 mmol) was stirred at room temperature for 20 minutes. The resulting solid was filtered, washed with water and hexane, and dried to afford 16.8 g (72.1%) of 1-(trimethylsilylethoxymethyl)-5-bromoindazol-yl-6-methanol.

(e)

A mixture of 1-(trimethylsilylethoxymethyl)-5-bromoindazol-yl-6-methanol (16.8 g, 47 mmol), triphenylphosphine (15 g, 56 mmol), and carbon tetrabromide (18.6 g, 56 mmol) in 500 ml of methylene chloride was stirred under nitrogen overnight. The mixture was concentrated in vacuo and the solid was crystallized from hexane/ethyl acetate 9:1) to afford 5.1 g (25.8%) of 1-(trimethylsilylethoxymethyl-5-bromo-6-bromo-methyl-indazole.

(f)

A mixture of 1-(trimethylsilylethoxymethyl)-5-bromo-6-bromo-methylindazole (5.1 g, 12 mmol) and 1-[2-(1,3-dioxolanyl)]-pyridine (1.9 g, 12.7 mmol) was stirred at room temperature under nitrogen for 48 hours. The mixture was triturated with ether and decanted. The residue was dissolved in warm water, filtered, and the filtrate was treated with a KPF$_6$ (1.5 g) solution with stirring. The solid product was filtered and dried to afford 5.8 g (75.3%) of 1-[1-(trimethylsilylethoxy-methyl)-5-bromolindazol-6-ylmethyl-2-(1,3-dioxolanyl)-pyridinium hexafluoro-phosphate.

(g)

To a mixture of polyphosphoric acid (125 ml) and methanesulfonic acid (25 ml) at 100° C. was added 5.8 g (9.1 mmol) of 1-[1-(trimethylsilylethoxymethyl)-5-bromolindazol-6-yl-methyl-2-(1,3-dioxolanyl)pyridinium hexafluorophosphate and the mixture was allowed to react at 100° C. for 5 hours. The mixture was cooled to room temperature, diluted with 125 ml of warm water and 800 ml of methanol, and the resulting mixture was treated with a 30% KPF$_6$ solution. The solid was filtered, dissolved in 500 ml of acetonitrile and filtered. The filtrate was concentrated in vacuo, the residue was filtered and washed with ether to afford 2.3 g (57%) of 7-bromo-9,10-pyrazolo-benzo[b] quinolizinium hexafluorophosphate (Formula II: $R^1=R^2=H$; $R^7=7$-Br;

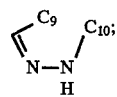

$X^-=PF_6^-$).

(h)

A reaction mixture containing 7-bromo-9,10-pyrazolobenzo[b]quinolizinium hexafluorophosphate (2.5 g; 5.2 mmol) and 1,1-di(3-furyl)ethylene (1.26 g; 7.8 mmol) in 75 ml of acetonitrile was allowed to reflux under nitrogen with stirring for 8 h. The reaction mixture was concentrated in vacuo, the residue was crystallized from methanol to afford 2.3 g (73.4%) of 12,12-di(3-furyl)-7-bromo-6,11-ethano-6,11-dihydro-9,10-pyrazolobenzo[b]quinolizinium hexafluoro-phosphate (Formula I: $R^1=R^2=R^3=R^4=H$; $R^5=R^6=3$-furyl; $R^7=7$-Br;

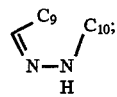

$X^-=PF_6^-$).

(i)

To a solution of 12,12-di(3-furyl)-7-bromo-6,11-ethano-6,11-dihydro-9,10-pyrazolobenzo[b]quinolizinium hexafluorophosphate (2.2 g, 3.6 mmol) in methanol/acetonitrile (150 ml, 5:1) was added 1 g of 5% Pd/CaCO$_3$ and the 10 mixture was hydrogenated at 50 psi for 3 hours. The mixture was filtered, the filtrate was concentrated, and the residue was purified by column chromatography (methylene chloride/ethyl acetate/methanol, 7:2:1). The above solid was recrystallized from isopropanol/ethyl acetate/methanol (1:4: 1) to afford 1.2 g (62.8%) of 12,12-di(3-furyl)-6,11-ethano-6,11-dihydro-9,10-pyrazolobenzo[b]quinolizinium hexafluorophosphate (Formula I: $R^1=R^2=R^3=R^4=H$; $R^5=R^6=3$-furyl; $R^7=$

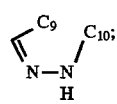

$C^-=PF_6^-$).

(j)

12,12-Di(3-furyl)-6,11-ethano-6,11-dihydro-9,10-pyrazolobenzo[b]quinolizinium hexafluorophosphate (1.2 g, 2.3 mmol) in acetonitrile/water (1:1) was converted to the corresponding chloride by passing the salt through DOWEX® 1x2-200-Cl-(water/acetonitrile, 7.3) to afford 0.61 g (64.2%) of 12,12-di(3-furyl)-6,11-ethano-6,11-dihydro-9,10-pyrazolobenzo[b]quinolizinium chloride (Formula I: $R^1=R^2=R^3=R^4=H$; $R^5=R^6=3$-furyl; $R^7=$ $X^-=Cl^-$), as a solid.

EXAMPLE 187

(a)

To a solution of 3-hydroxy-4-chlorotoluene (25 g, 0.175 mol) in 400 ml of acetone was added 30.11 g (0.22 mol) of milled potassium carbonate and 31.22 g (0.22 mol) of methyl iodide, and the mixture was refluxed with stirring for 16 hours. The mixture was cooled, filtered, and the filtrate was concentrated in vacuo. The residue was dissolved in ether, washed with water, and the organic layer was dried over sodium sulfate and concentrated in vacuo to afford 25.6 g of 3-methoxy-4-chlorotoluene as a solid.

(b)

A mixture of 3-methoxy-4-chlorotoluene (25.5 g, 0.163 mol) and $KMnO_4$ (62 g, 0.392 mol) in 1.2 L of water was refluxed with stirring for 16 hours. The mixture was filtered, the filtrate was neutralized with conc. HCl solution (to pH=2), and the resulting solid was filtered, washed with water, and dried to afford 3-methoxy-4-chlorobenzoic acid (17.5 g, 58%).

(c)

To 30.6 ml of $BH_3.THF$ was added a solution of 3-methoxy-4-chlorobenzoic acid (35 g, 0.187 mol) in 450 ml of THF, and the mixture was refluxed with stirring under argon for 3 hours. The mixture was quenched 25 with THF/water (1:1,300 ml), concentrated in vacuo, and the residue was partitioned between methylene chloride/water. The organic layer was dried over sodium sulfate and concentrated in vacuo to afford 29.4 g (90%) of 3-methoxy-4-chlorophenylmethanol.

(d)

To a solution of 29 g (0.168 mol) of 3-methoxy-4-chlorophenylmethanol in 600 ml of ether cooled to $-20°$ C. was added dropwise 142 ml (0.353 mol) of 2.5M n-butyllithium in hexane and the resulting mixture was stirred at room temperature for 2 hours. The reaction mixture was cooled to $0°$ C., 19.52 g (0.168 mol) of TMEDA was added. The above reaction mixture was cooled to $-30°$ C., 26.96 g (0.252 mol) of pyridine-2-carboxaldehyde in 30 ml of THF was added, and the resulting reaction mixture was allowed to warm to $0°$ C. and quenched with 10 ml of water. The resulting diol was filtered, and filtrate was extracted with ethyl acetate, dried over sodium sulfate, and the solvent was removed in vacuo. The combined residue was triturated with ether to afford 35.3 g (75%) of 2-[1-hydroxy-(2'-hydroxymethyl-5-chloro-6-methoxy)benzyl]pyridine (Formula X: $R^1=R^2=H$; $R^7=5$-Cl, 6-$OCH_3$).

(e)

A mixture of 35 g (0.125 mol) of 2-[1-hydroxy-(2'-hydroxymethyl-5-chloro-6-methoxy)benzyl]pyridine and 150 ml of $POCl_3$ was refluxed with stirring for 2 h. The mixture was cooled, poured into ice, filtered, and the filtrate was treated with sodium perchlorate solution. The resulting mixture was filtered, the solid was washed with water, dried and recrystallized from acetonitrile to afford 35.1 g (81%) of 9-chloro-10-methoxy-benzo[b]quinolizinium perchlorate (Formula II: $R^1=R^2=H$; $R^7=9$-Cl, 10-$OCH_3$; $X^-=ClO_4^-$) as a solid, m.p. $234°-237°$ C.

(f)

A reaction mixture containing 9-chloro-10-methoxybenzo[b]quinolizinium perchlorate (2 g; 5.81 mmol) and 1,1-di (3-furyl)-ethylene (1.11 g, 7 mmol) in 50 ml of acetonitrile was allowed to reflux under nitrogen with stirring for 6 hours. The reaction mixture was concentrated in vacuo and the residue was crystallized from methylene chloride/ethyl acetate/methanol (7:2:1). The solid product was purified by silica gel chromatography (9:1 methylene chloride/methanol) to afford 3.1 g of 6,11-ethano-12,12-di(3-furyl)-9-chloro-10-methoxy-6,11-dihydrobenzo[b]quinolizinium perchlorate (Formula I: $R^1=R^2=R^3=R^4=H$; $R^5=R^6=3$-furyl; $R^7=9$-Cl, 10-$OCH_3$; $X^-=ClO_4^-$)) as a solid.

(g)

6,11-Ethano-12,12-di(3-furyl)-9-chloro-10-methoxy-6,11-dihydrobenzo-[b]quinolizinium perchlorate (3 g, 5.95 mmol) was converted to the corresponding chloride salt by passing the above salt through DOWEX® 1x20-200-Cl$^-$ after placing the salt in acetonitrile. The chloride residue obtained was dried in vacuo and recrystallized from methylene chloride/ether to afford 1.83 g (71%) of 6,11-ethanol-12,12-di(3-furyl)-9-chloro-10-methoxy-6,11-dihydrobenzo[b]quinolizinium chloride (Formula I: $R^1=R^2=R^3=R^4=H$; $R^5=R^6=3$-furyl; $R^7=$Cl; 10-$OCH_3$; $X^-=Cl^-$) as a solid.

EXAMPLE 188

(a)

A reaction mixture containing 9-chloro-10-methoxybenzo[b]quinolizinium perchlorate (5 g; 14.83 mmol) and 48% HBr (50 ml) was refluxed with stirring for 18 hours. The mixture was concentrated in vacuo, the residue was redissolved in water, filtered, and the filtrate was treated with a sodium perchlorate solution with stirring for 40 minutes. The solid was filtered and recrystallized from acetone/ether (1:1) to afford 3.8 g (79%) of 9-chloro-10-hydroxy-benzo[b]quinolizinium perchlorate (Formula II: $R^1=R^2=H$; $R^7=9$-Cl; 10-OH; $X^-=ClO_4^-$), m.p. $203°-205°$ C.

(b)

A reaction mixture containing 8-chloro-9-hydroxybenzo[b]quinolizinium perchlorate (3.3 g; 10 mmol) and 1,1-di (3-furyl)ethylene (1.76 g, 11 mmol) in 50 ml of acetonitrile was allowed to reflux under nitrogen with stirring for 6 hours. The reaction mixture was concentrated in vacuo and the residue was crystallized from methylene chloride/ethyl acetate/methanol (7:2:1). The solid product was purified by silica gel chromatography (9:1 methylene chloride/methanol) to afford 3.3 g of 6,11-ethano-12,12-di(3-furyl)-9-chloro-10-hydroxy-6,11-dihydrobenzorb]quinolizinium perchlorate (Formula I: $R^1=R^2=R^3=R^4=H$; $R^5=R^6=3$-furyl; $R^7=9$-Cl; 10-OH; $X^-=ClO_4^-$) as a solid.

(c)

6,11-Ethano-12,12-di(3-furyl)-9-chloro-10-hydroxy-6,11-dihydrobenzo[b]quinolizinium perchlorate (3.1 g) was converted to the corresponding chloride salt by passing the above salt through DOWEX® 1x20-200-Cl$^-$ after placing the salt in acetonitrile. The chloride residue obtained was dried in vacuo and recrystallized from acetonitrile to afford 1.0 g (71%) of 6,11-ethano-12,12-di(3-furyl)-9-chloro-10-hydroxy-6,11-dihydrobenzo[b]quinolizinium chloride (Formula I: $R^1=R^2=R^3=R^4=H$; $R^5=R^6=3$-furyl; $R^7=9$-Cl; 10-OH; $X^-=Cl^-$) as a solid, m.p. $256°-258°$ C.

EXAMPLE 189

(a)

A reaction mixture containing 8-chloro-benzo[b] quinolizinium bromide (0.5 g; 1.7 mmol) and 1,1-di[(1-p-methoxybenzyl)-pyrazol-5-yl]-ethylene (0.748 g; 1.87 mmol) in 10 ml of nitromethane was refluxed for 2 h under nitrogen. The reaction mixture was concentrated in vacuo, the residue was purified by flash chromatography on silica (10% methanol in methylene chloride) and treated with 10 ml of saturated sodium perchlorate solution. The resulting solid was recrystallized from isopropanol to afford 0.68 g (56.6%) of 6-11-ethano-12,12-di[(1-p-methoxy-benzyl) -pyrazol-5-yl]-9-chloro-6,11-dihydrobenzo[b]quinolizinium perchlorate (Formula I: $R^1=R^2=R^3=R^4=H$; $R^5=R^6=$

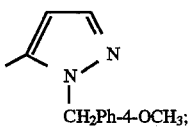

$R^7$=9-Cl; $X^-=ClO_4^-$), as a solid.

(b)

A solution of 680 mg (0.95 mmol) of 6,11-ethano-12,12-di[(1-p-methoxy-benzyl)-pyrazol-5-yl]-9-chloro-6,11-dihydrobenzo-[b]quinolizinium perchlorate in 10 ml of trifluoroacetic acid was refluxed under nitrogen for 12 h. The mixture was concentrated in vacuo, the residue was dissolved in 50% methanol in water, and filtered. The aqueous layer was concentrated in vacuo to remove methanol and the residue was treated with saturated sodium perchlorate in water. The resulting solid product was filtered and triturated in isopropanol/methylene chloride to afford 305 mg (67.7%) of 6,11-ethano-12,12-di-(pyrazol-5-yl)]-9-Chloro-6,11-dihydrobenzo[b]quinolizinium perchlorate (Formula I: $R^1=R^2=R^3=R^4=H$; $R^5=R^6=$

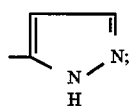

$R^7$=9-Cl; $X^-=ClO_4^-$), as a solid.

EXAMPLE 190

(a)

A reaction mixture containing 9-hydroxy-benzo[b] quinolizinium perchlorate (2.4 g; 8.2 mmol) and 1,1-di[3-(1-triisopropyl-silyl)-pyrrolyl]ethylene (5 g; 10.6 mmol) in 100 ml of acetonitrile was refluxed overnight under nitrogen. The reaction mixture was filtered, the filtrate was concentrated in vacuo, and the residue was triturated with ether to afford 2.3 g (36%) of 6,11-ethano-12,12-di [3-(1-trii sopropylsilyl)-pyrrolyl]-10-hydroxy-6,11-dihydrobenzo[b] quinolizinium perchlorate (Formula I: $R^1=R^2=R^3=R^4=H$; $R^5=R^6=$

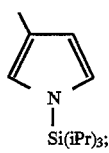

$R^7$=10-OH; $X^-=ClO_4^-$), as a yellow solid.

(b)

To a solution of 2.2 g (2.9 mmol) of 6,11-ethano-12,12-di[3-(1-triisopropylsilyl)pyrrolyl]-10-hydroxy-6,11-dihydrobenzo[b]quinolizinium perchlorate in 50 ml of methylene chloride was added tetrabutylammonium fluoride (2.9 ml, 2.7 mmol, 1.0M) and the mixture was stirred at room temperature under nitrogen overnight. The solid precipitate was converted to the corresponding chloride salt by passing the above salt through DOWEX® 1x2-200-Cl⁻ after placing the salt in methanol. The chloride residue obtained was dried in vacuo and the solid was washed with methylene chloride, and dried to afford 0.39 g of 6,11-ethano-12,12-di(3-pyrrolyl)-10-hydroxy-6,11-dihydrobenzo[b]quinolizinium chloride (Formula I: $R^1=R^2=R^3=R^4=H$; $R^5=R^6$=3-pyrrolyl; $R^7$=10-OH; $X^-=Cl^-$), as a solid, m.p. 190°–195° C.

EXAMPLE 191

(a)

3-Isoquinolinecarboxaldehyde (7 g, 84%) was prepared by reduction of 3-isoquinolinecarboxylic acid methyl ester (10 g, 52 mmol) with 1M LAH (27 ml in THF,27 mmol) in 300 ml of dry THF at −78° C. for 30 minutes. The mixture was quenched with 7 ml of acetic acid, concentrated in vacuo, and the residue was purified by silica gel column chromatography (hexane/ethyl acetate, 2:1) to afford 7 g (84%) of 3-iso-quinolinecarboxaldehyde.

(b)

A mixture of 3-isoquinolinecarboxaldehyde (7 g, 44.5 mmol), 5.5 g (88 mmol) of ethylene glycol, 400 ml of toluene and 1.1 g (4.4 mmol) of p-toluenesulfonic acid was refluxed for 16 h while separating the water formed. The mixture was cooled to room temperature and washed with sodium bicarbonate solution, water, and brine. The organic layer was dried over sodium sulfate, and concentrated in vacuo to afford 8 g (89.9%) of 3-(1,3-dioxolan-2-yl) isoquinoline (Formula XII: $R^2=R^7=H$).

(c)

A reaction mixture of 8 g (39.7 mmol) of 3-(1,3-dioxolan-2-yl)isoquinoline and 8 g (86.4 mmol) of chloroacetone in acetone was stirred at room temperature for 20 hours. To the mixture was added 5 g of KBr and the resulting mixture was stirred. The resulting mixture was filtered, the residual solid was stirred in 350 ml of acetonitrile and filtered. The above filtrate was concentrated in vacuo, and the residue was triturated in ethyl acetate to afford 8.6 g (64.7%) of 3-(1,3-dioxolan-2-yl)-2-(2-oxopropyl)isoquinolium bromide (Formula XIV: $R^2=R^7=H$; $Z^-=Br^-$).

(d)

A mixture of 3-(1,3-dioxolan-2-yl)-2-(2-oxopropyl) isoquinolium bromide (8.6 g, 25.5 mmol) and 75 ml of 48% HBr was refluxed with stirring for 3 hours. The mixture was cooled to room temperature, diluted with water 30 and filtered. The residue was dissolved in hot water and treated with 100 ml of 25% sodium perchlorate solution. The precipitated product was filtered, washed with hexane, ether, and ethyl acetate and dried in vacuo to afford 6.4 g (85.3%) of 3-hydroxybenzo [b]quinolizinium perchlorate (Formula II: $R^1$=3-OH; $R^2$=$R^7$=H; $X^-$=$ClO_4^-$).

(c)

A reaction mixture containing 3-hydroxy-benzo[b] quinolizinium perchlorate (1 g; 3.4 mmol) and 1,1-di(3-furyl)ethylene (1 g; 6.2 mmol) in 50 ml of acetonitrile was allowed to reflux under nitrogen with stirring for 16 h. The reaction mixture was concentrated in vacuo, the residue was triturated in 50 ml of methylene chloride/ether (1:2) and filtered. The solid was retriturated in ethyl acetate, filtered, the resulting solid was washed with ether to afford 1.35 g (87%) of 12,12-di(3-furyl-3-hydroxy-6,11-ethano-6,11-dihydrobenzo[b]-quinolizinium perchlorate (Formula I: $R^1$=3-OH; $R^2$=$R^3$=$R^4$=$R^7$=H; $R^5$=$R^6$=3-furyl; $X^-$=$ClO_4^-$).

(f)

12,12-Di(3-furyl)-3-hydroxy-6,11-ethano-6,11-dihydrobenzo[b]-quinolizinium perchlorate (1.35 g, 2.9 mmol) in acetonitrile was converted to the corresponding chloride by passing the salt through DOWEX® 1x2-200-Cl-(water/acetonitrile, 7.3). The salt was filtered, washed with cold water, and dried to afford 0.27 g (23.7%) of 12,12-di(3-furyl)-3-hydroxy-6,11-ethano-6,11-dihydrobenzo[b]quinolizinium chloride (Formula I: $R^1$=3-OH; $R^2$=$R^3$=$R^4$=$R^7$=H; $R^5$=$R^6$=3-furyl; $X^-$=$Cl^-$) as a solid.

EXAMPLE 192

(a)

A mixture of 75.0 g furyl-3-carboxylic acid (0.669 mol), 53.8 ml thionyl chloride (0.737 mol), and 325 ml toluene was heated to reflux while stirring overnight. Then the volume of the mixture was reduced by distilling 150 ml. The mixture was cooled and 500 ml methylene chloride, 71.9 g (0.737 mol) of N,O-dimethylhydroxylamine hydrochloride and 0.15 g of 4-dimethylaminopyridine was added. The mixture was cooled to 0° C. and 120 ml of pyridine was added dropwise. The mixture was allowed to warm to room temperature and stirred overnight. The solids that formed were filtered, rinsed with 600 ml methylene chloride, then discarded. The filtrate was extracted twice with 600 ml portions of 2N HCL then twice with 600 ml water. The methylene chloride layer was dried over magnesium sulfate, filtered and concentrated in vacuo. The resulting dark oil was distilled through a 15 cm glass Vigreaux column, bp 115°–125° C. at 0.4 mm Hg. Upon cooling the distillate crystallized, affording 68.5 g (66%) of 3-(N-methyl-N-methoxycarbamoyl) furan as a white solid, mp 39°–42° C.

(b)

A solution of n-BuLi in hexane (155 ml, 2.5M, 0.39 moles) and ether (908.5 ml) was cooled to –78° C. under nitrogen. 3-bromofuran (57.3 g, 0.39 mol) in ether (113.6 ml) was added dropwise while maintaining the temperature of the mixture below -70° C. The mixture was stirred at –78° C. for 1 hour then 56.6 g (0.365 mol) of 3-(N-methyl-N-methoxycarbamoyl)furan in 167 ml of ether was added dropwise over a period of 20 minutes. The mixture was stirred overnight and allowed to warm to room temperature. The mixture was quenched with 440 ml of water, and filtered. The filtrate was extracted with methylene chloride. The organic layer was concentrated in vacuo, the residue was crystallized from t-butylmethyl ether (175 ml) and washed with hexane to afford 41.85 g (65.3%) of 1,1-di(3-furyl)ketone as an off-white colored solid.

(c)

To a solution of 1,1-di(3-furyl)ketone (41.85 g) in 440 ml of THF cooled to 0° C. under nitrogen with stirring was added dropwise 129.4 ml (0.38 mol) of 3M methylmagnesium bromide in ether at below 10° C. The mixture was allowed to warm to room temperature, and stirred for 4 hours. The above mixture was cooled to 0° C., quenched with a saturated ammonium chloride solution and stirred for 30 minutes. The aqueous layer was extracted with THF (440 ml), the combined organic layer was dried over magnesium sulfate, and concentrated in vacuo (to 440 ml). The above layer was treated with 0.25 g of p-toluenesulfonic acid and heated to reflux for 2 hours. The solution was washed with a saturated sodium bicarbonate solution, dried over magnesium sulfate and distilled (15 cm Vigreux column bp 60° C. at 0.2 mm Hg) to afford 34.35 g of 1,1-di(3-furyl)ethylene (Formula III: $R^3$=$R^4$=H; $R^5$=$R^6$=3-furyl) as a clear oil.

(d)

To a solution of 2,6-dibromoypyridine (53.9 g, 0.2275 mol) in THF (144 ml)/ether (288 ml)/hexane (144 ml) at –78° C. was added dropwise n-BuLi (100 ml, 2.5M, 0.25 mol) in hexane. The mixture was stirred for 10 minutes, and then DMF (36.5 g, 0.5 mol) was added. The reaction mixture was allowed to warm to –50° C., quenched with 270 ml of methanol, and then ethyl acetate (1 L) and 60 ml of water were added at room temperature with stirring. The layers were separated and the organic layer was extracted with 2×60 ml of water. The organic layer was washed with brine, dried over magnesium sulfate, concentrated in vacuo, and the residue was purified by silica gel chromatography (10% ether in hexane) to afford 6-bromo-2-pyridylcarboxaldehyde (Formula IX: $R^1$=6-Br) as an oil.

(e)

To a solution of 28.4 g (0.152 mol) of 2-bromobenzyl alcohol and 22.9 ml (0.152 mol) of TMEDA in 550 ml ether cooled to –30° C. was added dropwise 133.6 ml (0.152.mol) of 2.5M n-butyl lithium in hexanes. Stirred for 30 minutes at –30° C., then at room temperature for 1 hour. The reaction mixture was cooled to –20° C. and 25.7 g (0.138 mol) of 6-bromopyridine-2-carboxaldehyde in 550 ml of ether was added. The reaction mixture was stirred for 1 hour. The solution was allowed to warm to room temperature while stirring overnight. The mixture was quenched with 200 ml saturated ammonium chloride solution, and 600 ml of ethyl acetate and 200 ml of methylene chloride were added. The layers were seperated and the aqueous layer was extracted with 200 ml ethyl acetate. The combined organic layers were dried over magnesium sulfate, filtered and evaporated in vacuo. The residue was purified by chromatography on silica-gel with ethyl acetate-hexane (gradient) affording 12.76 g of 2-[1-hydroxy-(2'-hydroxy-methyl)benzyl]-6-bromopyridine (Formula X: $R^1$=6-Br; $R^2$=$R^7$=H) as a solid, m.p. 123°–125° C.

(f)

A mixture of 12.75 g (0.0434 mol) of 2-[1-hydroxy-(2'-hydroxymethyl)benzyl]-6-bromopyridine and 75 ml of POCl$_3$ was heated at 110° C. while stirring for 4 h. The mixture was cooled, concentrated in vacuo, and the residue was dissolved in water. A solution of excess sodium perchlorate was added and the precipitate filtered. The solid was washed with water, and was purified by silica gel chromatography (9/1 methylene chloride/methanol) to afford 1.7 g of 4-chloro-benzo[b]quinolizinium perchlorate (Formula II: R$^1$=4-Cl; R$^2$=R$^7$=H; ClO$_4^-$).

(g)

A reaction mixture containing 4-chloro-benzo[b] quinolizinium perchlorate (1.13 g; 3.6 mmol) and 1,1-di(3-furyl)-ethylene (0.757 g, 4.73 mmol) in 50 ml of nitromethane was heated to reflux under nitrogen while stirring for 3 hours. The reaction mixture was concentrated in vacuo and the residue was purified by chromatography on silica gel (2/8 2-propanol-methylene chloride) to afford 1.36 g (83.4%) of 6,11-ethano-12,12-di(3-furyl)-4-chloro-6,11-dihydrobenzo[b]-quinolizinium perchlorate (Formula I: R$^1$=4-Cl; R$^2$=R$^3$=R$^4$=R$^7$=H; R$^5$=R$^6$=3-furyl; X$^-$=ClO$_4^-$) as a solid.

EXAMPLE 193

A reaction mixture containing 9-hydroxy-benzo-[b] quinolizinium perchlorate (1.4 g; 4.8 mmol) and 1,1-di(3-furyl)-ethylene (1 g, 6.2 mmol) in 25 ml of acetonitrile was allowed to reflux under argon with stirring for 3 hour. The reaction mixture was concentrated in vacuo, the residue was triturated in methanol/water (2:1), and concentrated in vacuo. The residual salt was convened to the corresponding chloride by passing the salt through DOWEX® 1x2-200-Cl$^-$ (water/acetonitrile, 7.3). The salt was filtered, washed with cold water, and dried to afford 0.31 g (15%) of 12,12-di(3-furyl)-9-hydroxy-6,11-ethano-6,11-dihydrobenzo[b] quinolizinium chloride (Formula I: R$^1$=R$^2$=R$^3$=R$^4$=H; R$^5$=R$^6$=3-furyl; R$^7$=9-OH; X$^-$=Cl$^-$) as a solid, m.p. 263°–265° C.

EXAMPLE 194

(a)

Bromoacetyl bromide (20 g, 99.1 mmol) was added to a solution of 1-octanol (12.9 g, 99.1 mmol) and 10 ml of pyridine in 100 ml of methylene chloride at 0° C. After 10 minutes, the mixture was quenched with 100 ml of ice/water, and the aqueous layer was extracted with methylene chloride, and the combined organic layer was washed with 1N HCl (3×100 ml) and brine. The organic layer was dried over magnesium sulfate, concentrated in vacuo, and the product was distilled under high vacuum to afford 6 g of 1-octyl bromoacetate as an oil, b.p. 93° C.

(b)

To a mixture of lithium diisopropylamide (prepared from 4.8 g, (47.8 mmol) of diisopropylamine and 19.1 ml, (2.5M, 47.8 mmol) of n-BuLi) in 50 ml of THF was added isobutyric acid (2.2 ml, 23.9 mmol) at 0° C. and the mixture was allowed to warm to 45° C. with stirring. To the mixture cooled to −78° C., was added 4.3 g (23.9 mmol) of HMPA followed by a solution of 1-octyl bromoacetate (6 g, 23.9 mmol) in 50 ml of THF under argon at −78° C. The mixture was quenched with 1N HCl, warmed to room temperature, and extracted with ether (3×50ml). The organic layer was dried over magnesium sulfate, concentrated in vacuo, and purified by flash chromatography (10% methanol/ethyl acetate) to afford 0.8 g of 3-(1-octyloxycarbonyl)-2,2-dimethylbutyric acid.

(c)

3-(1-Octyloxycarbonyl)-2,2-dimethylbutyric acid (0.4 g) was treated with thionyl chloride (20 ml) and the excess thionyl chloride was removed in vacuo to afford 0.33 g of 3-(1-octyloxycarbonyl)-2,2-dimethylbutyric acid chloride.

(d)

To a solution of 0.36 g (0.8 mmol) of 6,11-ethano-12,12-di(3-furyl)-10-hydroxy-6,11-dihydrobenzo[b]quinolizinium perchlorate in 20 ml of acetonitrile was added CS$_2$CO$_3$ (0.27 g, 0.8 mmol) and the reaction mixture was stirred for 10 minutes. To the above mixture was added 0.33 g (1.2 mmol) of 3-(1-octyloxycarbonyl)-2,2-dimethylbutyric acid chloride in methylene chloride and the mixture was stirred at room temperature under nitrogen. The reaction mixture was filtered and the filtrate was concentrated in vacuo. The residue was purified by flash chromatography (10% methanol/methylene chloride) and the resulting salt was converted to the corresponding chloride by passing the salt through DOWEX® 1x2-200-Cl$^-$ (water/acetonitrile, 7/3). The salt was filtered, washed with cold water, and dried to afford 0.26 g (51%) of 12,12-di(3-furyl)-10-(OC(O)C(CH$_3$)$_2$CH$_2$C(O)OOctyl-6,11-ethano-6,11-dihydrobenzo[b]quinolinizium chloride (Formula I: R$^1$=R$^2$=R$^3$=R$^4$=H; R$^5$=R$^6$=3-furyl; R$^7$=10-OC(O)C(CH$_3$)$_2$CH$_2$C(O)OOctyl; X$^-$=Cl$^-$) as a solid, m.p. 60°–65° C.

EXAMPLE 195

(a)

A reaction mixture containing 9-hydroxy-benzo[b] quinolizinium perchlorate (1 g; 3.4 mmol) and 1,1-di[(1-p-methoxybenzyl)-pyrazol-3-yl]ethylene (2 g; 5.1 mmol) in 75 ml of aceto-nitrile/ethanol (8:1) was refluxed for 16 h under nitrogen. The reaction mixture was filtered, the filtrate was concentrated in vacuo, the residue was triturated in methanol to afford 0.75 g (32.5%) of 6,11-ethano-12,12-di[(1-p-methoxy-benzyl)pyrazol-3-yl]-9-hydroxy-6,11-dihydrobenzo[b]quinolizinium perchlorate (Formula I: R$^1$=R$^2$=R$^3$=R$^4$=H; R$^5$=R$^6$=

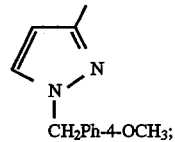

R$^7$=9OH; X$^-$=ClO$_4^-$), as a solid.

(b)

A solution of 750 mg (1.1 mmol) of 6,11-ethano-12,12-di[(2-p-methoxy-benzyl)-pyrazol-3-yl]-9-hydroxy-6,11-dihydrobenzo-[b]quinolizinium perchlorate in 60 ml of trifluoroacetic acid was refluxed under nitrogen for 24 h. The mixture was concentrated in vacuo, the residue dissolved in 50 ml of methanol and the solvent was removed in vacuo. The resulting residue was triturated in methanol/water (300 ml, 1:1), the aqueous layer was filtered, and the filtrate was concentrated in vacuo to afford 500 mg of 6,11-ethano-12,12-di-(pyrazol-3-yl)-9-hydroxy-6,11-dihydrobenzo-[b] quinolizinium perchlorate (Formula I: R$^1$=R$^2$=R$^3$=R$^4$=H; R$^5$=R$^6$=

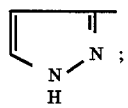

$R^7$=9-OH; $X^-$=$ClO_4^-$), as a solid.

(c)

6,11-Ethano-12,12-di-(pyrazol-3-yl)]-9-hydroxy-6,11-dihydrobenzo[b]quinolizinium perchlorate (0.5 g, 1.1 mmol) was converted to the corresponding chloride by passing the salt through DOWEX® 1x2-200-Cl⁻ (water/acetonitrile, 7/3). The salt was dissolved in 50 ml of boiling methanol/water, filtered and the filtrate was concentrated in vacuo to afford 0.15 g (34.8%) of 12,12-di(pyrazol-3-yl)-9-hydroxy-6,11-ethano-6,11-dihydrobenzo[b]quinolizinium chloride (Formula I: $R^1$=$R^2$=$R^3$=$R^4$=H; $R^5$=$R^6$=

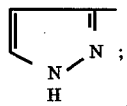

$R^7$=9-OH; $X^-$=Cl⁻) as a solid.

EXAMPLE 196

(a)

mixture of 3.9 g (26 mmol) of 2-(1,3-dioxolan-2-yl)pyridine and 5 g (26 mmol) of 4-fluorobenzyl bromide was stirred at room temperature overnight and the resulting mixture was triturated in ether. The white solid was filtered and washed with ether to afford 8.1 g (91%) of 2-(1,3-dioxolan-2-yl)-1-(p-fluorobenzylpyridinium bromide (Formula VI: $R^1$=$R^2$=H; $R^7$=4-F; $Z^-$=Br⁻).

(b)

A mixture of 8.1 g (24 mmol) of 2-(1,3-dioxolan-2-yl)-1-(p-fluorobenzyl)pyridinium bromide in 100 ml of 48% HBr solution was refluxed for 18 hours. The mixture was heated in vacuo to remove HBr solution. The dry residue was dissolved in water, treated with an excess sodium perchlorate solution. The solid was filtered, washed with water, and dried in vacuo to afford 3 g (41%) of 9-fluorobenzo[b]quinolizinium perchlorate (Formula II: $R^1$=$R^2$=H; $R^7$=9-F; $X^-$=$ClO_4^-$).

(c)

A reaction mixture containing 9-fluorobenzo[b]quinolizinium perchlorate (0.6 g; 2 mmol) and 1,1-di(3-furyl)-ethylene (0.32 g, 6.2 mmol) in 20 ml of acetonitrile was allowed to reflux under argon with stirring for 3 hour. The reaction mixture was concentrated in vacuo, the residue was triturated in ether, redissolved in acetonitrile, treated with activated charcoal and filtered. The filtrate was concentrated in vacuo and the residue was crystallized from methanol to afford 0.67 g of J2.12-di(3-furyl)-9-fluoro-6,11-ethano-6,11-dihydrobenzo[b]quinolizinium perchlorate (Formula I: $R^1$=$R^2$=$R^3$=$R^4$=H; $R^5$=$R^6$=3-furyl; $R^7$=9-F; $X^-$=$ClO_4^-$) as a solid, m.p. 256°–258° C.

EXAMPLE 197

(a)

To a mixture of DABCO™ (5.72 g, 51 mmol) in 200 ml of ether at −20° C. was added dropwise 2.5M n-BuLi (51 mmol) and the mixture was stirred at −20° C. for 1 hour. The above mixture was cooled to −78° C., a solution of 3-fluoropyridine (5 g, 51 mmol) in ether (25 ml) was added at −78° C., and the mixture was stirred at −60° C. for 1 hour. The above reaction mixture was cooled to −78° C., DMF (4.2 g, 56 mmol) was added and the mixture was stirred at this temperature for 2 hours. The reaction mixture was allowed to warm to −10° C., quenched with 50 ml of water and saturated ammonium chloride solution. The aqueous layer was extracted with ethyl acetate (3×100 ml) and the combined organic layer was dried over magnesium sulfate, concentrated in vacuo, and the residue was purified by silica gel chromatography (1:1 ether/hexane) to afford 1.5 g (23.5%) 3-fluoro-2-pyridylcarboxaldehyde (Formula IX: $R^1$=3-F).

(b)

To a solution of 2 g (10.6 mmol) of 2-bromobenzyl alcohol and TMEDA (1.24 g, 10.6 mmol) in ether (100 ml) cooled to −30° C. was added in portions 9 ml (22 mmol) of 2.5 M n-butyllithium in hexane with stirring for 30 minutes and the resulting mixture was stirred at room temperature for 1 hour. The reaction mixture was cooled to −20° C., 1.3 g (10.4 mmol) of 3-fluoropyridine-2-carboxaldehyde in 50 ml of ether with stirring for 1 hour. The resulting reaction mixture was allowed to warm to room temperature and stirred overnight and quenched with water. The resulting diol was filtered, and filtrate was extracted with ethyl acetate, the organic layer was washed with brine, dried over magnesium sulfate, and the solvent was removed in vacuo. The combined residue was purified by silica gel chromatography (ethyl acetate) to afford 0.5 g of 2-[1-hydroxy-(2'-hydroxymethyl)benzyl]-3-fluoropyridine (Formula X: $R^1$=3-F; $R^2$=$R^7$=H) as a solid.

(c)

A mixture of 0.5 g (2.1 mmol) of 2-[1-hydroxy-(2'-hydroxy-methyl)benzyl]-3-fluoropyridine and 25 ml of $POCl_3$ was heated at 110° C. with stirring for 1 h. The mixture was cooled, poured into ice/water with stirring, and sodium perchlorate (10 g) solution was added. The resulting mixture was filtered, the solid was washed with water and ether to afford 0.4 g (64%) of 1-fluoro-benzo[b]quinolizinium perchlorate (Formula II: $R^1$=1-F; $R^2$=R 7=H; $X^-$=$ClO_4^-$).

(d)

A reaction mixture containing 1-fluoro-benzo[b]quinolizinium perchlorate (0.35 g; 1.2 mmol) and 1,1-di(3-furyl)ethylene (0.32 g, 2 mmol) in 25 ml of acetonitrile was allowed to reflux under nitrogen with stirring for 18 hours. The reaction mixture was concentrated in vacuo and the residue was triturated in methanol, filtered, and washed with ethyl acetate and ether to afford 0.4 g (72.7%) of 6,11-ethano-12,12-di(3-furyl)-1-fluoro-6,11-dihydrobenzo[b]quinolizinium perchlorate (Formula I: $R^1$=1-F; $R^2$=$R^3$=$R^4$=$R^7$=H; $R^5$=$R^6$=3-furyl; $X^-$=$ClO_4^-$) as a solid, m.p. 213°–214° C.

EXAMPLE 198

(a)

A reaction mixture containing 9-fluoro-benzo[b]quinolizinium perchlorate (0.69 g; 2 mmol) and 1,1-di[(1-p-methoxybenzyl)-pyrazol-3-yl]ethylene (0.8 g; 2 mmol) in 25 ml of aceto-nitrile was refluxed for 2 h under nitrogen.

The reaction mixture was filtered, the filtrate was concentrated in vacuo, and the residue was triturated in methanol. The solid product was purified by silica gel column chromatography (methylene chloride/methanol, 9:1) to afford 0.92 g (32.5%) of 6,11-ethano-12,12-di[(1-p-methoxybenzyl)pyrazol-3-yl]-9-fluoro-6,11-dihydrobenzo[b]quinolizinium perchlorate (Formula I: $R^1=R^2=R^3=R^4=H$; $R^5=R^6=$

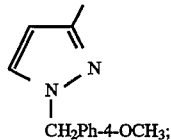

CH₂Ph-4-OCH₃;

$R^7$=9-F; $X^-$=ClO₄⁻), as a solid.

(b)

A solution of 900 mg (1.3 mmol) of 6,11-ethano-12,12-di[(1-p-methoxy-benzyl)-pyrazol-3-yl]-9-fluoro-6,11-dihydrobenzo[b]quinolizinium perchlorate in 25 ml of trifluoroacetic acid was refluxed under nitrogen for 24 h. The mixture was concentrated in vacuo and the residue dissolved in methanol/water. The aqueous layer was filtered, the filtrate was concentrated in vacuo, and the product was convened to the corresponding chloride by passing the salt through DOWEX® 1x2-200-Cl-(water/acetonitrile, 7/3). The salt was recrystallized from acetonitrile to afford 250 mg of 6,11-ethano-12,12-di-(pyrazol-3-yl)]-9-fluoro-6,11-dihydrobenzo-[b]quinolizinium chloride (Formula I: $R^1=R^2=R^3=R^4=H$; $R^5=R^6=$

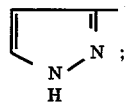

$R^2$=9-F; $X^-$=Cl⁻) as a solid, m.p. >300° C.(d).

EXAMPLE 199

(a) & (b)

A reaction mixture containing 10-hydroxy-benzo[b] quinolizinium perchlorate (2.54 g; 8.6 mmol) and 1-(3-furyl)-1-[1-(p-toluenesulfonyl)-pyrazol-5-yl]ethylene (3 g; 9.5 mmol) in 100 ml of nitromethane was refluxed for 3 h under nitrogen. The reaction mixture was concentrated in vacuo, and the solid was purified by silica gel column chromatography (40% paw in ethyl acetate) and crystallization of each isomer from isopropanol to afford: Isomer 1: 6,11-ethano-12-(3-furyl)-12-[1-(p-toluenesulfonyl)-pyrazol-5-yl]-10-hydroxy-6,11-dihydrobenzo[b]quinolizinium perchlorate (1.2 g; Example 199(a); Formula I: $R^1=R^2=R^3=R^4=H$; $R^5=$

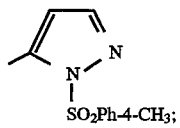

SO₂Ph-4-CH₃;

$R^6$=3-furyl; $R^7$=10-OH; $X^-$=ClO₄⁻), m.p.154°–158° C. Isomer 2: 6,11-ethano-12-(3-furyl)-12-[1-(p-toluenesulfonyl)pyrazol-5-yl]-10-hydroxy-6,11-dihydrobenzo[b] quinolizinium perchlorate (1.4 g; Example 199(b); Formula I: $R^1=R^2=R^3=R^4=H$; $R^5$=3-furyl; $R^6=$

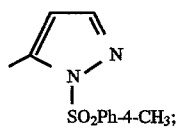

SO₂Ph-4-CH₃;

$R^7$=10-OH; $X^-$=ClO₄⁻), m.p. 230°–262° C.

EXAMPLE 200

To a solution of 700 mg (1.1 mmol) of 6,11-ethano-12-(3-furyl)-12-[1-(p-toluenesulfonyl)-pyrazol-5-yl]-10-hydroxy-6,11-dihydrobenzo[b]quinolizinium perchlorate (Example 199(a)) in 50 ml of methanol was added 1.5 ml (1.5 mmol) of 1M t-BuOK in THF and the mixture was stirred for 3 hours. The mixture was filtered, the filtrate was concentrated in vacuo, and the residue was convened to the corresponding chloride by passing the salt through DOWEX® 1x2-200-Cl-(water/acetonitrile, 7/3). The salt was crystallized from methanol to afford 390 mg of 6,11-ethano-12-(3-furyl-12-(pyrazol-5-yl-10-hydroxy-6,11-dihydro-benzo[b]quinolizinium chloride (Formula I: $R^1=R^2=R^3=R^4=H$; $R^5$=5-pyrazolyl; $R^6$-3-furyl; $R^7$=10-OH; $X^-$=Cl⁻) as a solid, m.p. 142°–148° C.

EXAMPLE 201

(a, b)

To a solution of 300 ml of nitric acid/sulfuric acid (1:1) cooled to −10° C. was added benzo[b]quinolizinium bromide (15 g; 57 mmol) over a 10 minute period, and then the mixture was stirred for 25 minutes and poured into ice. The mixture was filtered and the filtrate was treated with 200 ml of 35% sodium perchlorate solution. The product was filtered and dried to afford a mixture of 10-nitro-benzo[b] quinolizinium perchlorate (Ex.201b) and 7-nitro-benzo[b] quinolizinium perchlorate (Ex 201 a)

(c, d)

A reaction mixture containing a mixture (1 g, 3.08 mmol) of 10-nitrobenzo[b]quinolizinium perchlorate (Ex.201b) and 7-nitro-benzo[b]quinolizinium perchlorate (Ex 201a) and 1,1-di(3-furyl)ethylene (0.5 g, 3.09 mmol) in 20 ml of acetonitrile was allowed to reflux under argon with stirring for 2 hours. The reaction mixture was concentrated in vacuo and the residue was triturated in ether to yield 1.43 g of a solid mixture. The solid mixture was chromatographically separated using C-18 Waters Delta pack (55 ml/min; inj vol=0.5 ml, det; 270 nm, mobile phase=60% 0.01M sodium perchlorate in water and 40% methanol) to afford:

Isomer A: 6,11-ethano-12,12-di(3-furyl)-7-nitro-6,11-dihydrobenzo[b]quinolizinium perchlorate (53 mg; Example 201 (c), Formula I: $R^1=R^2=R^3=R^4=H$; $R^5=R^6$=3-furyl; $R^7$=7-NO₂; $X^-$=ClO₄⁻) as a solid, m.p. 260° C.

Isomer B: 6,11-ethano-12,12-di(3-furyl-10-nitro-6,11-dihydrobenzo[b]quinolizinium perchlorate (116 mg; Example 20 1 (d), Formula I: $R^1=R^2=R^3=R^4=H$; $R^5=R^6$=3-furyl; $R^7$=10-NO2; $X^-$=ClO₄⁻) as a solid, m.p. 208° C.

EXAMPLE 202

It is contemplated that treatment of 6,11-ethano-12,12-di (3-furanyl)-1-hydroxy-6,11-dihydrobenzo[b]quinolizinium chloride of Example 168(c) with an excess of ClC(O)(CH₂)

$_7$CH=CH(CH$_2$)$_7$CH$_3$ in the presence of pyridine and 1,8-diazabicyclic [5.4.0]undec-7ene (DBU) will afford (6,11-ethano-12,12-di(3-furanyl)-1-[OC(OC(O)CH$_2$)$_7$CH=CH(CH$_2$)$_7$CH$_3$]-6,11-dihydrobenzo[b]quinolizinium chloride (Formula I: R$^1$=1-[OC(O)(CH$_2$)$_7$CH=CH(CH$_2$)$_7$CH$_3$]; R$^2$=R$^3$=R$^4$=R$^7$=H; R$^5$=R$^6$=3-furanyl, X$^-$=Cl$^-$).

EXAMPLE 203

It is contemplated that treatment of 6,11-ethano-12,12-di(3-furanyl)-1-hydroxy-6,11-dihydrobenzo[b]quinolizinium chloride of Example 168(c) with an excess of ClC(O)CH=CHCO$_2$CH$_2$CH$_3$ in acetonitrile in the presence of cesium carbonate will afford 6,11-ethano-12,12-di(3-furanyl)-1-[OC(O)CH=CHCO$_2$CH$_2$CH$_3$]-6,11-dihydrobenzo[b]quinolizinium chloride (Formula I: R$^1$=1-[OC(O)CH=CHCO$_2$CH$_2$CH$_3$]; R$^2$=R$^3$=R$^4$=R$^7$=H; R$^5$=R$^6$=3-furanyl; X$^-$=Cl$^-$).

EXAMPLE 204

It is contemplated that treatment of 6,11-ethano-12,12-di(3-furanyl)-3-hydroxy-6,11-dihydrobenzo[b]quinolizinium chloride of Example 191 (f) with an excess of octylbromide in dimethylformamide in the presence of cesuim carbonate will afford 6,11-ethano-12,12-di(3-furanyl)-3-n-octyloxy-6,11-dihydrobenzo[b]quinolizinium chloride (Formula I: R$^1$=3-O(CH$_2$)$_7$CH$_3$; R$^2$=R$^3$=R$^4$=R$^7$=H; R$^5$=R$^6$=3-furanyl; X$^-$=Cl$^-$).

EXAMPLE 205

It is contemplated that treatment of 6,11-ethano-12,12-di(3-furanyl)-3-hydroxy-6,11-dihydrobenzo[b]quinolizinium chloride of Example 191 (f) with an excess of ClC(O)C(CH$_3$)$_2$CH$_2$C(O)O(CH$_2$)$_7$CH$_3$ of example 194(c) in acetonitrile in the presence of cesium carbonate will afford 6,11-ethano-12,12-di(3-furanyl)-3-[OC(O)C(CH$_3$)$_2$CH$_2$C(O)O(CH2)$_7$CH$_3$]-6,11-dihydrobenzo[b]quinolizinium chloride (Formula I: R$^1$=3-[OC(O)C(CH$_3$)$_2$CH$_2$C(O)O(CH$_2$)$_7$CH$_3$]; R$^2$=R$^3$=R$^4$=R 7=H; R$^5$=R$^6$=3-furanyl; X$^-$=Cl$^-$).

EXAMPLE 206

(a)

Following a procedure similar to that described in Example 164(b) but substituting 3-nitropyridine-2-carboxaldehyde for 3-methoxypyridine-2-carboxyaldehyde it is contemplated that there can be prepared 2-[1-hydroxy-(2'-hydroxymethylbenzyl]-3-nitropyridine (Formula X: R$^1$=3-NO$_2$; R$^2$=R$^7$=H).

(b)

Following a procedure similar to that described in Example 164(c) but substituting 2-[1-hydroxy-(2'-hydroxymethyl)benzyl]-3-nitropyridine for 2-[1-hydroxy-(2'-hydroxymethyl)benzyl]-3-methoxypyridine it is contemplated that there can be prepared 1-nitrobenzo[b]quinolizinium perchlorate (Formula II: R$^1$=1-NO$_2$; R$^2$=R$^7$=H; X$^-$=ClO$_4^-$).

(c)

Following a procedure similar to that described in Example 164(d) but 25 substituting 1-nitrobenzo[b]quinolizinium perchlorate for 1-methoxybenzo[b]quinolizinium perchlorate, it is contemplated that there can be prepared 6,11-ethano-12,12-di(3-furanyl)-1-nitro-6,11-dihydrobenzo[b]quinolizinium perchlorate.

(d)

It is contemplated that treatment of 6,11-ethano-12,12-di(3-furanyl)-1-nitro-6,11-dihydrobenzo[b]quinolizinium perchlorate with stannous chloride and aqueous hydrochloric acid, followed by treatment of the 1-amino derivative thus formed with methanesulfonyl chloride will afford 6,11-ethano-12,12-di(3-furanyl)-1-methylsulfonylamino-6,11-dihydrobenzo[b]quinolizinium perchlorate (Formula I: R$^1$=1-NHSO$_2$CH$_3$; R$^2$=R$^3$=R$^4$=R$^7$=H; R$^5$=R$^6$=3-furanyl; X$^-$=ClO$_4^-$).

EXAMPLE 207

It is contemplated that treatment of 6,11-ethano-12,12-di(3-furanyl)-10-nitro-6,11-dihydrobenzo[b]quinolizinium perchlorate with stannous chloride and aqueous hydrochloric acid, followed by treatment of the resulting 10-amino derivative with methanesulfonyl chloride will afford 6,11-ethano-12,12-di(3-furanyl)-10-methylsulfonylamino-6,11-dihydrobenzo[b]quinolizinium perchlorate (Formula I: R$^1$=R$^2$=R$^3$=R$^4$=H; R$^5$=R$^6$=3-furanyl; R$^7$=10-NHSO$_2$CH$_3$; X$^-$=ClO$_4^-$).

BIOLOGICAL TEST RESULTS

Representative examples of the compounds of the invention have been found to possess valuable pharmacological properties. In particular, they have been found to bind to the PCP receptor and are thus non-competitive blockers (antagonists) of the effects which excitatory amino acids, such as glutamate, have upon the NMDA receptor. The compounds of the invention are thus useful in the treatment or prevention of neurodegenerative disorders such as Huntington's disease, Alzheimer's disease, amyotrophic lateral sclerosis, Down's Syndrome, senile dementia, glutaric acidaemia type I, multi-infarct dementia, Parkinson's disease, viral encephalopathies (which include, but are not limited thereto, dementia associated with HIV infections) and neuronal damage associated with uncontrolled seizures, as well as in the treatment or prevention of neurotoxic injuries associated with ischemic, hypoxic or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, spinal or head trauma, coronary artery bypass graft, neonatal anoxic trauma, and perinatal asphyxia.

The compounds of the invention are particularly useful in the treatment or prevention of neurotoxic injuries associated with ischemic, hypoxic or hypoglycemic conditions, and especially ischemic, hypoxic, or hypoglycemic conditions which are associated with stroke.

The pharmacological properties of representative examples of the compounds of the invention was demonstrated by conventional in vitro and in vivo biological test procedures such as the following:

[$^3$H] TCP Radioreceptor Assay

[$^3$H]TCP binding to PCP recognition sites was performed as described by Vignon et al. Brain Research 1983, 280, 194–197. Male Sprague-Dawley rats were sacrificed by decapitation, and whole brains were homogenized in 10 volumes (wt/vol) of cold Tris-HCl buffer (50 mM, pH 7.7) using a Brinkmann Polytron (setting 6, 30 sec). The homogenate was centrifuged at 40,000×g for 10 min at 4° C. The supernatant was decanted, and the homogenization and centrifugation steps were repeated twice as described above.

Following this, the pellet was resuspended in Tris-HCl (5 mM, pH 7.7) at a tissue concentration of 0.5–0.75 g/mL, and one mL aliquots were frozen at −70° C. until use. The binding characteristics for PCP recognition sites were not altered by the freezing of membrane suspensions.

On the day of the assay, membrane aliquots were thawed, resuspended in fresh 5 mM Tris-HCl buffer at a tissue concentration of 1 mg/mL, and stored on ice until use. Each assay tube contained 100 gl of [$^3$H]TCP at a final concentration of approximately 1 nM, 100 μL of various concentrations of the compounds of interest, 500 μL of the tissue suspension and 300 μL of buffer to a final assay volume of 1 mL and a final protein concentration of 0.5 mg/tube. Non-specific binding was defined by addition of a final concentration of 100 μM PCP to blank tubes. All tubes were incubated at room temperature for 25 min before termination of the reaction by rapid filtration over Whatman GF/B glass fiber filters that had been presoaked in a solution of 0.5% polyethylenimine for at least 1 hr prior to use. Filters were washed with three 4 mL volumes of cold Tris buffer. Following addition of scintillation cocktail, the amount of bound radioactivity was determined by liquid scintillation spectrometry using a Beckman LS 5000TA liquid scintillation counter with an efficiency for tritium of approximately 55%. Inhibition constants ($K_i$ values) were calculated using the EBDA/LIGAND program (McPherson, J. Pharmacol. Meth. 1985, 14, 213–228), purchased from Elsevier/Biosoft, Inc. Results are reported as the $K_i$ values (in nM) which are expressed as the mean of at least two separate determinations; or as a percent (%) inhibition of binding at 10 μM.

Antagonism of NMDA-induced Neurotoxicity in Cultured Neurons

Preparation of Cultured Conical Neurons

Pregnant, Swiss-Webster mice were obtained from Taconic Farms (Germantown, New York) and sacrificed 16 days post conception. Fetuses were removed and placed in a sterile dish containing Hank's balanced salt solution CHBSS), pH 7.4. Brain cortices were dissected, meninges were removed, the tissue was minced and placed into a solution of HBSS containing 0.25% (w/v) trypsin at 37° C. for 15 minutes. Tissue was then triturated with a sterile pasteur pipet, diluted with minimal essential media (Gibco 330-1430), pH 7.4, supplemented with 10% horse serum, 10% fetal calf serum, 2 mM 1-glutamine, 21 mM d-glucose, 2.2 g/L sodium bicarbonate, 1000 U/mL penicillin, and 1,000 μg/mL streptomycin. Cells were plated onto Falcon primaria 96 well plates at a final density of 50,000 cells/well and incubated at 37° C. in the presence of 5% (v/v) carbon dioxide. After 5 days, plating media was replaced with maintenance media containing minimal essential media (Gibco 330-1430), pH 7.4, supplemented with 10% horse serum, 10% 1-glutamine, 21 mM d-glucose, 2.2 g/L sodium bicarbonate, 1,000 U/mL penicillin, 1,000 gg/mL streptomycin, and 10 gM cytosine arabinoside. On days 7 and 10, media was replaced with maintenance media as above lacking the cytosine arabinoside. Experiments were conducted on day 13.

Neuroprotection Assessment

Day 13 cultured cortical neurons were washed twice with minimal essential media, pH 7.4 and then exposed for 30 minutes to 500 RM N-methyl-D-aspartic acid (NMDA) with or without varying concentrations of test agents. Dizocilpine (MK-801) at a final concentration of 10 gM MK-801 was routinely included as a positive control. MK-801 and test agents were prepared in minimal essential media supplemented with 21 mM d-glucose and 2.2 g/L sodium bicarbonate (MEM). After 30 minutes, media was replaced with MEM alone. Exposure of neurons to test agents was limited to the NMDA treatment period. Twenty-four hours after removal of NMDA, an aliquot of media from each well was removed for assessment of cell injury by determining lactate dehydrogenase (LDH) activity by the method of Wroblewski and LaDue Proc. Soc. Exp. Biol. Med. 1955, 90, 210–213. The results are expressed as an $IC_{50}$ (in nM) value (concentration causing 50% inhibition) for the antagonism of NMDA-induced neurotoxicity.

Table 3 summarizes the results obtained from the testing of representative compounds of the invention in the [$^3$H] TCP radioreceptor assay as well as in the antagonism of NMDA-induced neurotoxicity in cultured neurons.

TABLE 3

| Example Number | [$^3$H]TCP $K_i$(nM) or Percent inhibition @ 10 μM | Antagonism of NMDA-induced neurotoxicity ($IC_{50}$ in nM) |
|---|---|---|
| 1F | 7.58 | — |
| 2(a) | 123 | — |
| 2(b) | 262 | — |
| 3(d) | 14.1 | — |
| 4(E) | 5868 | — |
| 5(c) | 13.3 | — |
| 5(d) | 22 | — |
| 6(c) | 1.19 | — |
| 6(d) | 1.2 | 244 |
| 7(b) | 1.38 | 7.6 |
| 7(c) | 1.1 | — |
| 8(c) | 117 | — |
| 9(b) | 5.9 | — |
| 10(c) | 1100 | — |
| 10(c-G) | 4447 | — |
| 10(c-k) | 696 | — |
| 11(d) | 26 | — |
| 11(F) | 73 | 2550 |
| 11(g) | 18 | 2005 |
| 12(b) | 253 | — |
| 13(a) | 19 | — |
| 13(b) | 45 | — |
| 14(c) | 4.9 | — |
| 15(c) | 1.4 | — |
| 17(b) | 8.18 | 197 |
| 18 | 19.5 | — |
| 19(b) | 6.8 | 102 |
| 20(h) | 7.15 | — |
| 21 | 13.0 | — |
| 22(b) | 9.07 | — |
| 23(c) | 22% | — |
| 24(b) | 8.39 | — |
| 25(c) | 39.3 | — |
| 26 | 32.7 | — |
| 27(E) | 10.4 | — |
| 28(c) | 11.7 | — |
| 29(c) | 31% | — |
| 30(c) | 22% | — |
| 31(c) | 2207 | — |
| 32(F) | 468 | — |
| 33(c) | 1144 | — |
| 34(c) | 21.9 | — |
| 35(c) | 41.0 | — |
| 36(c) | 185 | — |
| 37(E) | 36.7 | — |
| 38(c) | 16.6 | — |
| 39(c) | 1.79 | 45.4 |
| 40(b) | 1.66 | 20 |
| 42(E) | 2267 | — |
| 43(b) | 45% | — |
| 44(b) | 28122 | — |
| 45(E) | 491 | — |
| 46(c) | 31% | — |
| 47(d) | 2.11 | 40 |
| 48(b) | 2.08 | 23 |

TABLE 3-continued

| Example Number | [³H]TCP K₁(nM) or Percent inhibition @ 10 μM | Antagonism of NMDA-induced neurotoxicity (IC₅₀ in nM) |
|---|---|---|
| 49(E) | 54% | — |
| 50(b) | 1.24 | 22 |
| 51(c) | 22.3 | 83 |
| 52(F) | 1.82 | 39 |
| 53(g) | 93 | — |
| 54(E) | 52 | — |
| 55(b) | 104 | — |
| 56 | 56 | — |
| 57(d) | 1.9 | 36 |
| 58(c) | 32% | >1,000 |
| 59(c) | 3908 | — |
| 60(e) | 345 | — |
| 61(c) | 17 | — |
| 62(c) | 120 | — |
| 63(c) | 64% | — |
| 63(d) | 10 | 1629 |
| 64(f) | 13 | 360 |
| 65(c) | 2.8 | — |
| 66(g) | 6 | — |
| 67(e) | 80 | — |
| 67(g) | 1481 | — |
| 68(c) | 1.5 | — |
| 69(c) | 0.9 | — |
| 70(F) | 3832 | — |
| 71(F) | 3.1 | — |
| 111(a) | 6.07 | — |
| 111(b) | 37.8 | — |
| 158(f) | 632 | — |
| 159(h) | 31% | — |
| 160(d) | 453 | — |
| 161(d) | 3676 | — |
| 162(d) | 2.31 | — |
| 163 | 7.54 | — |
| 164(e) | 18.9 | — |
| 165 | 31.3 | — |
| 166 | 61.1 | — |
| 167(c) | 7.68 | — |
| 168(c) | 306 | — |
| 169 | 3.58 | — |
| 170 | 232 | — |
| 171(b) | 10.2 | 26.5 |
| 172 | 3377 | — |
| 173(e) | 1670 | — |
| 174 | 23.7 | — |
| 175(b) | 119 | — |
| 176(d) | 39.4 | — |
| 177 | 13.8 | — |
| 178(d) | 1430 | — |
| 179(b) | 259 | — |
| 180(g) | 19.9 | — |
| 181(c) | 6.36 | 11.4 |
| 181(4) | 6.15 | 55 |
| 182(e) | 159 | — |
| 183(c) | 2.72 | — |
| 184(c) | 12914 | — |
| 184(d) | 53% | — |
| 185(a) | 4.55 | 32.6 |
| 185(b) | 6.29 | 53 |
| 186(g) | 122 | — |
| 187(g) | 63.7 | — |
| 188(c) | 23.6 | — |
| 189(b) | 22.5 | — |
| 190(b) | 10.7 | — |
| 191(f) | 1530 | — |
| 192(g) | 633 | — |
| 193 | 2.13 | 11.8 |
| 194(d) | 71.3 | — |
| 195(c) | 12.6 | 30.8 |
| 196(c) | 4.11 | 80 |
| 197(d) | 13.8 | — |
| 198(b) | 11.7 | — |
| 199(a) | 27% | — |
| 200 | 11.5 | — |
| 201(c) | 3433 | — |
| 201(d) | 49.2 | — |

Middle Cerebral Artery Occlusion (MCAO) Model with Reperfusion

A 3-vessel rat ischemia model similar to those that have been extensively described in the literature (e.g. Stroke 17,738–743 (1986), Stroke 20, 513–518 (1989)) was utilized. Under isoflurane anesthesia the right middle cerebral artery (via an approach through the temporalis muscle) and both common carotid arteries were reversibly occluded for varying durations between minutes and 120 minutes. Both male Long Evans hooded rats and male Sprague-Dawley rats weighing between 300 and 420 grams were used. The animals' temperature was maintained throughout the study with heat lamps. A 15 femoral vein and the ipsilateral femoral artery were cannulated for intravenous infusion and arterial blood pressure measurements and blood samples. Infusions of the test compounds were initiated 30 minutes prior to occlusion at a rate of 40 microliters per minute. After reinitiation of blood flow the animals were allowed to regain consciousness. Six hours post-initiation of ischemia the animals were sacrificed and the extent of neuronal damage was quantified with TTC staining. The results are expressed as a percent inhibition (±SEM) of infarct and penumbra region.

Table 4 summarizes the results obtained from the testing of representative compounds of the invention in the MCAO model.

TABLE 4

| Example Number | Dose (mg Test Compound/ kg/min) | % Inhibition (+/− SEM) |
|---|---|---|
| 39(c) | 0.03 | 20 +/− 7 |
|  | 0.1 | 34 +/− 6 |
| 40(b) | 0.01 | 1 +/− 31 |
|  | 0.03 | 49 +/− 25 |
|  | 0.1 | 47 +/− 18 |
| 68(c) | 0.1 | 34 +/− 14 |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula

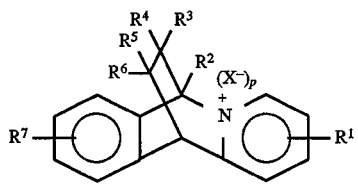

wherein:

$R^1$ is hydrogen, or from one to four, the same or different, substituents in any of the 1-,2-, 3- or 4-positions selected from the group consisting of lower-alkoxy, lower-alkyl, halogen, hydroxy, OC(O)alkyl-CH=CH-alkyl, OCO(O)alkyl, OC(O)-lower-alkenyl-C(O)Oalkyl, alkocy, OC(O)alkylC(O)alkyl, hydroxymethyl, nitro, amino and lower-alkylsulfonylamino or $R^1$ is a fused benzene ring;

$R^2$ is hydrogen, lower-alkyl, cyano or lower-alkoxycarbonyl;

$R^3$ and $R^4$ is independently hydrogen, or lower-alkyl; or $R^3$ and $R^4$ together form a cycloalkyl ring, or a lower alkylidene group;

$R^5$ and $R^6$ are independently a 5-membered heterocyclic ring system (or said 5-membered heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl, trilower-alkylsilyl, lower-alkylphenylsulfonyl, or trilower-alkylsilyl-lower-alkoxy-lower-alkyl);

or $R^3$ and $R^5$, and/or $R^4$ and $R^6$ taken together with the carbon atoms to which they are attached form a bicyclic ring system of the formula A:

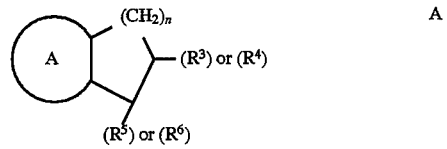

wherein A is a 5-membered heterocyclic ring system and n is one (or said A ring substituted on any available carbon atom thereof by lower-alkoxy, or lower-alkyl);

$R^7$ is hydrogen, or from one to four, the same or different, substituents in any of the 7-, 8-,9-, or 10-positions selected from the group consisting of lower-alkyl, lower-alkanolyloxy, halogen, nitro, hydroxy, lower-alkoxy, methylenedioxy, polyfluorolower-alkyl, OCO$(CH_2)_mC(O)$Oalkyl, OC(O)alkyl, C(O)Oalkyl, $CO_2^-$, carboxy, sulfo, $SO_3^-$, $PO_3H$; $PO_3^-$cyano, polychlorolower-alkyl, OC(O)alkyl-CH=CH-alkyl, OC(O)-lower-alkenyl-C(O)Oalkyl, alkoxy, OC(O)alkylC(O)Oalkyl, halomethyl, hydroxymethyl, amino and lower-alkylsulfonylamino wherein m is an integer from one to four and/or $R^7$ is a fused pyrazole ring; alkylsulfonylamino wherein m is an integer from one to four and/or $R^7$ is a fused pyrazole ring;

$X^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; with the following provisos: a) at least one of $R^5$ and $R^6$ when taken individually must be a substituted or unsubstituted 5-membered heterocyclic ring system and b) $R^5$ and $R^6$ cannot be furanyl.

2. A compound according to claim 1 wherein:

$R^1$ is hydrogen, or from one to four, the same or different, substituents in any of the 1-,2-, 3- or 4-positions selected from the group consisting of lower-alkoxy, lower-alkyl and halogen;

$R^2$ is hydrogen or lower-alkyl;

$R^3$ and $R^4$ are independently hydrogen, or lower-alkyl; or $R^3$ and $R^4$ together form a cycloalkyl ring, or a lower alkylidene group;

$R^5$ and $R^6$ are independently a 5-membered heterocyclic ring system (or said 5-membered heterocyclic ring system substituted on any available carbon atom thereof by lower-alkyl, oxo, nitro, halogen, or lower-alkoxy; or on any available nitrogen atom thereof by lower-alkyl, phenyl-lower-alkyl, trilower-alkylsilyl, or trilower-alkylsilyl-lower-alkoxy-lower-alkyl);

or $R^3$ and $R^5$, and/or $R^5$ and $R^6$ taken together with the carbon atoms to which they are attached form a bicyclic ring system of the formula A:

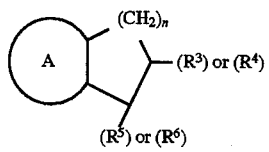

wherein A is a 5-membered heterocyclic ring system and n is one (or said A ring substituted on any available carbon atom thereof by lower-alkoxy, or lower-alkyl);

$R^7$ is hydrogen, or from one to four, the same or different, substituents in any of the 7-, 8-,9-, or 10-positions selected from the group consisting of lower-alkyl, lower-alkanolyloxy, halogen, nitro, hydroxy, lower-alkoxy, methylenedioxy, polyfluorolower-alkyl, OCO $(CH_2)_mC(O)$Oalkyl, OC(O)alkyl, C(O)Oalkyl, $CO_2^-$, carboxy, sulfo, $SO_3^-$, $PO_3H$; $PO_3^-$cyano, polychlorolower-alkyl, wherein m is an integer from one to four;

$X^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; with the following provisos: a) at least one of $R^5$ and $R^6$ when taken individually must be a substituted or unsubstituted 5-membered heterocyclic ring system and b) $R^5$ and $R^6$ cannot be furanyl.

3. A compound according to claim 2 wherein $R^5$ and $R^6$ are independently a 5-membered heterocyclic ring system (or said 5-membered heterocyclic ring system substituted on any available carbon atom thereof by lower-alkyl, oxo, or lower-alkoxy; or on any available nitrogen atom thereof by lower-alkyl, phenyl-lower-alkyl, trilower-alkylsilyl, or trilower-alkylsilyl-lower-alkoxy-lower-alkyl); and $R^7$ is hydrogen, or from one to four, the same or different, substituents in any of the 7-,8-,9- or 10-membered positions selected from the group consisting of lower-alkyl, lower-alkanoyloxy, halogen, nitro, hydroxy, lower-alkoxy, methylenedroxy, polyfluorolower-alkyl, $SO_3$-, and polychlorolower-alkyl.

4. A compound according to claim 2 wherein $R^5$ and $R^6$ are independently a 5-membered heterocyclic ring system (or said 5-membered heterocyclic ring system substituted on any available carbon atom thereof by lower-alkyl, oxo, or lower-alkoxy; or on any available nitrogen atom thereof by lower-alkoxyphenyl-lower-alkyl, trilower-alkylsilyl, or trilower-alkylsilyl-lower-alkoxy-lower-alkyl), and wherein A is a 5-membered heterocyclic ring system and n is one (or said A ring substituted on any available carbon atom thereof by lower-alkoxy, or lower-alkyl).

5. A compound according to claim 4 wherein $R^1$ is hydrogen, or one lower-alkyl substituent in any of the 1-,2-,3- or 4-positions; and $R^7$ is hydrogen, or from one to two, the same or different, substituents in any of the 7-,8-,9- or 10-positions selected from the group consisting of halogen, hydroxy, lower-alkoxy $SO_3^-$ and polyfluorolower-alkyl.

6. A compound according to claim 5 wherein $R^5$ and $R^6$ are independently a 5-membered heterocyclic ring system selected from the group consisting of thienyl, oxazolyl, thiazolyl, pyrazolyl, triazolyl and pyrrolyl (or said 5-membered heterocyclic ring system substituted on any available carbon atom thereof by lower-alkyl, oxo, or lower-alkoxy; or any available nitrogen atom thereof by lower-alkoxyphenyl-lower-alkyl, trilower-alkylsilyl, or tri-lower-alkylsilyl-lower-alkoxy-lower-alkyl); and A is a 5-membered heterocyclic ring system selected form the group consisting of isoxazolyl and thienyl (or said A ring substituted on any available carbon atom thereof by lower-alkoxy, or lower-alkyl).

7. A compound according to claim 6 wherein $R^5$ and $R^6$ are independently a 5-membered heterocyclic ring system selected from the group consisting of 2-thienyl, 3-thienyl, 4-oxazolyl, 2-thiazolyl, 5-thiazolyl, 5-pyrazolyl, 5-(1,2,3-triazolyl) and 3-pyrrolyl (or said 5-membered heterocyclic ring system substituted on any available carbon atom thereof by methyl, oxo, or methoxy; or any available nitrogen atom thereof by methoxyphenylmethyl, triisopropylsilyl, or $(CH_3)_3Si(CH_2)_2OCH_2)$, ethoxy or ethynyl and A is a 5-membered heterocyclic ring system selected from the group consisting of isoxazolyl and thienyl (or said A ring substituted on any available carbon atom thereof by methoxy, or methyl).

8. A compound according to claim 7 wherein $R^1$ is hydrogen or 1-lower-alkyl; and $R^7$ is hydrogen, or from one to two, the same or different, substituents in any of the 7-,8-,9- or 10-positions selected from the group consisting of bromine, fluorine, hydroxy, methoxy, isopropyoxy, $SO_3^-$ and trifluoromethyl.

9. A compound according to claim 8 wherein $R^1$ is hydrogen or 1-methyl; and $R^2$ is hydrogen, methyl, or butyl; and $R^3$ and $R^4$ are independently hydrogen, or methyl; or $R^3$ and $R^4$ together form a cyclopropyl ring, or a methylidene group.

10. A compound according to claim 9 selected from the group consisting of:

6,11-ethano-6-methyl-12,12-di(2-thienyl)-6,11-dihydrobenzo[b]quinolizinium $X^-$;

6,11-ethano-12,12-di(2-thienyl)-6,11-dihydrobenzo[b]quinolizinium $X^-$; and 6,11-ethano-12,12-di(3-thienyl)-6,11-dihydrobenzo[b]quinolizinium $X^-$.

11. A compound according to claim 10 selected from the group consisting of:

6,11-ethano-6-methyl-12,12-di(2-thienyl)-6,11-dihydrobenzo[b]quinolizinium chloride;

6,11-ethano-12,12-di(2-thienyl)-6,11-dihydrobenzo[b]quinolizinium chloride; and 6,11-ethano-12,12-di(3-thienyl)-6,11-dihydrobenzo[b]quinolizinium chloride.

12. A compound according to claim 9 which is selected from the group consisting of:

6,11-ethano-12,12-di(3-pyrrolyl)-6,11-dihydrobenzo[b]quinolizinium chloride.

13. A compound according to claim 2 wherein $R^5$ and $R^6$ are independently a 5-membered heterocyclic ring system selected from the group consisting of pyrazolyl, triazolyl, imidazolyl and pyrrolyl (or said 5-membered heterocyclic ring system substituted on any available carbon atom thereof by lower-alkoxy; or any available nitrogen atom thereof by lowre-alkyl, lower-alkoxyphenyllower-alkyl, or trilower-alkylsilyl; $R^1$ is hydrogen or one or lower-alkoxy or halogen substituent in any of the 1-,2-, 3- or 4-positions; and $R^7$ is hydrogen, or from one to two, the same or different, substituents in any of the 7-, 8-, 9- or 10- positions selected from the group consisting of OC(O)alkyl, $OC(O)(CH_2)_mC(O)$ Oalkyl, hydroxy, lower-alkoxy, methylenedioxy, halogen and nitro.

14. A compound according to claim 13 wherein $R^5$ and $R^6$ are independently a 5-membered heterocyclic ring system selected from the group consisting of 3-, 4- and 5-pyrazolyl, 5-(1,2,4-triazolyl), 2-imidazolyl and 3-pyrrolyl (or said 5-membered heterocyclic ring system substituted on any available carbon atom thereof by methoxy, or on any available nitrogen atom thereof by methyl, methoxyphenylmethyl, or triisopropylsilyl); $R^1$ is hydrogen, 1-halogen, or 1-lower-alkoxy; and $R^7$ is hydrogen, or from one to two, the same or different, substituents in any of the 7-, 8-, 9- or 10- positions selected from the group consisting of $OC(O)(CH_2)_6CH_3$, $OCO(CH_2)_2C(O)OCH_2CH_3$, $OC(O)CH_3$, $OC(O)t$-Bu, hydroxy, methoxy, methylenedioxy, chloro, fluoro and nitro.

15. A compound according to claim 14 wherein $R^1$ is hydrogen, 1-fluoro, or 1-methoxy; $R^2$ is hydrogen, or methyl; and $R^3$ and $R^4$ are independently hydrogen or methyl; or $R^3$ and $R^4$ together form a methylidene group.

16. 6,11-Ethano-12,12-di(3-pyrazolyl)-9-hydroxy-6,11-dihydrobenzo[b]quinoliziniuim chloride according to claim 15.

17. A compound according to claim 1 wherein $R^1$ is from one to four, the same or different, substituents in any of the 1-, 2-, 3- or 4-positions selected from the group consisting of hydroxy, OC(O)alkyl-CH=CH-alkyl, OC(O) alkyl, OC(O)-lower-alkenyl-C(O)Oalkyl, alkoxy, OC(O)alkylC(O)Oalkyl, hydroxymethyl, nitro, amino and lower-alkylsulfonylamino; or $R^1$ is a fused benzene ring.

18. A compound according to claim 17 wherein:

$R^1$ is one substituent in any of the 1-, 2-, 3-, or 4- positions selected from the group consisting of hydroxy, and OC(O)alkyl; or $R^1$ is a fused benzene ring;

$R^2$, $R^3$, $R^4$ and $R^7$ are hydrogen; and $R^5$ and $R^6$ are independently a 5-membered heterocyclic ring system selected from the group consisting of thienyl, oxazolyl, thiazolyl, pyrazolyl, triazolyl, pyrrolyl and imidazolyl.

19. A compound according to claim 18 wherein $R^1$ is 1-hydroxy, 1-OC(O)CH$_3$ or a fused benzene ring.

20. A compound according to claim 1 wherein $R^2$ is cyano or lower alkoxycarbonyl.

21. A compound according to claim 20 wherein: $R^1$, $R^3$, $R^4$ and $R^7$ are hydrogen; and $R^5$ and $R^6$ are independently selected from the group consisting of thienyl, oxazolyl, thiazolyl, pyrazolyl, triazolyl, pyrrolyl and imidazolyl.

22. A compound according to claim 1 wherein $R^7$ is from one to four, the same or different, substituents in any of the 7-, 8-, 9- or 10-positions selected from the group consisting of OC(O)alkyl-CH=CH-alkyl, OC(O)-lower-alkenyl-C(O) Oalkyl, alkoxy, OC(O)alkylC(O)Oalkyl, halomethyl, hydroxymethyl, amino and lower-alkylsulfonylamino and/or $R^7$ is a fused pyrazole ring.

23. A compound according to claim 22 wherein: $R^1$, $R^2$, $R^3$, and $R^4$ are hydrogen; and $R^5$ and $R^6$ are independently a 5-membered heterocyclic ring system selected from the group consisting of thienyl, oxazolyl, thiazolyl, pyrazolyl, triazolyl, pyrrolyl and imidazolyl.

24. A compound according to claim 23 wherein $R^7$ is one substituent selected from the group consisting of OC(O)(CH$_2$)$_7$HC=CH-(CH$_2$)$_7$CH$_3$, OC(O)-CH=CH-C(O)OCH$_2$CH$_3$, O(CH$_2$)$_7$CH$_3$, OC(O)C(CH$_3$)2CH$_2$C(O)OCH$_2$CH$_3$, chloromethyl, hydroxymethyl, and OC(O)C(CH$_3$)$_2$CH$_2$C(O)O(CH$_2$)$_7$CH$_3$; and/or $R^7$ is a fused pyrazole ring.

25. A pharmaceutical composition which comprises a compound of the formula:

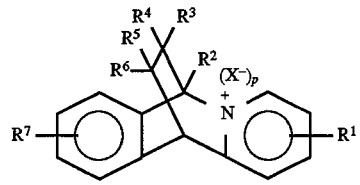

wherein:

$R^1$ is hydrogen, or from one to four, the same or different, substituents in any of the 1-,2-, 3- or 4- positions selected from the group consisting of lower-alkoxy, lower-alkyl, halogen, hydroxy, OC(O)alkyl-CH=CH-alkyl, OC(O)alkyl, OC(O)-lower-alkenyl-C(O)Oalkyl, alkoxy, OC(O)alkylC(O)Oalkyl, hydroxymethyl, nitro, amino and lower-alkylsulfonylamino or $R^1$ is a fused benzene ring;

$R^2$ is hydrogen, lower-alkyl, cyano or lower-alkoxycarbonyl;

$R^3$ and $R^4$ are independently hydrogen, or lower-alkyl; or $R^3$ and $R^4$ together form a cycloalkyl ring, or a lower alkylidene group;

$R^5$ and $R^6$ are independently a 5-membered heterocyclic ring system or said 5-membered heterocyclic ring system substituted on any available carbon atom thereof by hydroxy, lower-alkyl, oxo, nitro, halogen, or lower-alkoxy; or on any available nitrogen atom thereof by loweralkyl, phenyl-lower-alkyl trilower-alkylsilyl, lower-alkylphenylsulfonyl, or trilower-alkylsilyl-lower-alkoxy-lower-alkyl;

or $R^3$ and $R^5$, and/or $R^4$ and $R^6$ taken together with the cabon atoms to which they are attached form a bicyclic ring system of the formula A:

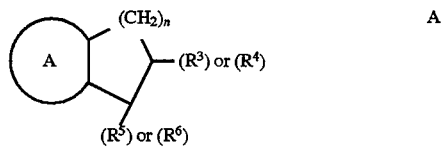

wherein A is a 5-membered heterocyclic ring system and n is one (or said A ring substituted on any available carbon atom thereof by lower-alkoxy, or lower-alkyl);

$R^7$ is hydrogen, or from one to four, the same or different, substituents in any of the 7-, 8-,9-, or 10- positions selected from the group consisting of lower-alkyl, lower-alkanoyloxy, halogen, nitro, hydroxy, lower-alkoxy, methylenedioxy, polyfluorolower-alkyl, OCO(CH$_2$)$_m$C(O)Oalkyl, OC(O)alkyl, C(O)Oalkyl, CO$_2^-$, carboxy, sulfo, SO$_3^-$, PO$_3$H; PO$_3^-$ cyano, polychlorolower-alkyl, OC(O)alkyl-CH=CH-alkyl, OC(O)-lower-alkenyl-C(O)Oalkyl, alkoxy, OC(O)alkylC(O)Oalkyl, halomethyl, hydroxymethyl, amino and lower-alkylsulfonylamino wherein m is an integer from one to four and/or $R^7$ is a fused pyrazole ring;

X$^-$ is an anion; and p is zero when $R^7$ is a negatively charged radical and p is one when $R^7$ is other than a negatively charged radical; or a pharmaceutically acceptable acid-addition salt of basic members thereof; or a solvate thereof; or a stereoisomer thereof; together with a pharmaceutically acceptable carrier, adjuvant, diluent or vehicle, with the proviso that at least one of $R^5$ and $R^6$ when taken individually must be a substituted or unsubstituted 5-membered heterocyclic ring system and R⁵ and R⁶ cannot be furanyl.

26. A method for the treatment or prevention of neurotoxic injuries which comprises administering to a patient in need of such treatment an effective amount of a compound of the formula:

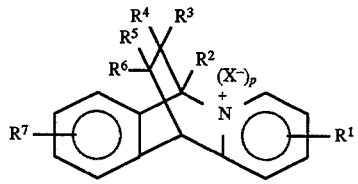

wherein:

R¹ is hydrogen, or from one to four, the same or different, substituents in any of the 1-,2-, 3- or 4- positions selected from the group consisting of lower-alkoxy, lower-alkyl, halogen, hydroxy, OC(O)alkyl-CH=CH-alkyl, OC(O)alkyl, OC(O)-lower-alkenyl-C(O)Oalkyl, alkoxy, OC(O)alkylC(O)Oalkyl, hydroxymethyl, nitro, amino and lower-alkylsulfonylamino or R¹ is a fused benzene ring;

R² is hydrogen, lower-alkyl, cyano or lower-alkoxycarbonyl;

R³ and R⁴ are independently hydrogen, or lower-alkyl; or R³ and R⁴ together form a cycloalkyl ring, or a lower alkylidene group;

R⁵ and R⁶ are independently a 5- membered heterocyclic ring system or said 5-membered heterocyclic ring system substituted on any available carbon atom thereof by hydroxy, lower-alkyl, oxo, nitro, halogen, or lower-alkoxy; or on any available nitrogen atom thereof by lower-alkyl, phenyl-lower-alkyl, trilower-alkylsilyl, lower-alkylphenylsulfonyl, or trilower-alkylsilyl-lower-alkoxy-lower-alkyl;

or R³ and R⁵, and/or R⁴ and R⁶ taken together with the carbon atoms to which they are attached form a bicyclic ring system of the formula A:

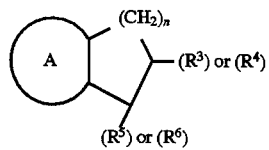

wherein A is a 5-membered heterocyclic ring system and n is one (or said A ring substituted on any available carbon atom thereof by lower-alkoxy, or lower-alkyl);

R⁷ is hydrogen, or from one to four, the same or different, substituents in any of the 7-, 8-,9-, or 10-positions selected from the group consisting of lower-alkyl, lower-alkanoyloxy, halogen, nitro, hydroxy, lower-alkoxy, methylenedioxy, polyfluorolower-alkyl, OCO$(CH_2)_m$C(O)Oalkyl, OC(O)alkyl, C(O)Oalkyl, $CO_2^-$, carboxy, sulfo, $SO_3^-$, $PO_3H$; $PO_3^-$ cyano, polychlorolower-alkyl, OC(O)alkyl-CH=CH-alkyl, OC(O)-lower-alkenyl-C(O)Oalkyl, alkoxy, OC(O)alkylC(O)Oalkyl, halomethyl, hydroxymethyl, amino and lower-alkylsulfonylamino wherein m is an integer from one to four and/or R⁷ is a fused pyrazole ring;

X⁻ is an anion; and p is zero when R⁷ is a negatively charged radical and p is one when R⁷ is other than a negatively charged radical; or a pharmaceutically acceptable acid-addition salt of basic members thereof; or a solvate thereof; or a stereoisomer thereof; together with a pharmaceutically acceptable carrier, adjuvant, diluent or vehicle, with the proviso that at least one of R⁵ and R⁶ when taken individually must be a substituted or unsubstituted 5-membered heterocyclic ring system and R⁵ and R⁶ cannot be furanyl.

* * * * *